(12) United States Patent
Kozlowski et al.

(10) Patent No.: US 8,680,263 B2
(45) Date of Patent: Mar. 25, 2014

(54) CARBOHYDRATE-BASED DRUG DELIVERY POLYMERS AND CONJUGATES THEREOF

(75) Inventors: Antoni Kozlowski, Huntsville, AL (US); Samuel P. McManus, Huntsville, AL (US); Xiaoming Shen, Madison, AL (US)

(73) Assignee: Nektar Therapeutics, San Francisco, CA (US)

( * ) Notice: Subject to any disclaimer, the term of this patent is extended or adjusted under 35 U.S.C. 154(b) by 222 days.

(21) Appl. No.: 13/119,276

(22) PCT Filed: Sep. 17, 2009

(86) PCT No.: PCT/US2009/005233
§ 371 (c)(1),
(2), (4) Date: Mar. 16, 2011

(87) PCT Pub. No.: WO2010/033240
PCT Pub. Date: Mar. 25, 2010

(65) Prior Publication Data
US 2011/0171716 A1 Jul. 14, 2011

Related U.S. Application Data

(60) Provisional application No. 61/192,672, filed on Sep. 19, 2008, provisional application No. 61/208,089, filed on Feb. 18, 2009, provisional application No. 61/153,966, filed on Feb. 19, 2009.

(51) Int. Cl.
*C08B 37/02* (2006.01)

(52) U.S. Cl.
USPC .......................................................... 536/51

(58) Field of Classification Search
None
See application file for complete search history.

(56) References Cited

U.S. PATENT DOCUMENTS

| | | | |
|---|---|---|---|
| 4,461,724 | A | 7/1984 | Konishi |
| 4,585,754 | A | 4/1986 | Meisner et al. |
| 5,288,708 | A | 2/1994 | Sikiric et al. |
| 5,470,831 | A | 11/1995 | Whitman et al. |
| 5,545,719 | A | 8/1996 | Shashoua |
| 5,672,662 | A | 9/1997 | Harris et al. |
| 5,888,762 | A | 3/1999 | Joliot et al. |
| 5,922,675 | A | 7/1999 | Baker et al. |
| 5,998,367 | A | 12/1999 | Gaeta et al. |
| 6,080,762 | A | 6/2000 | Allen et al. |
| 6,083,909 | A | 7/2000 | Sommermeyer et al. |
| 6,524,591 | B1 | 2/2003 | Schmid |
| 8,252,275 | B2 | 8/2012 | Bentley et al. |
| 2006/0121062 | A1 | 6/2006 | Eichner et al. |

FOREIGN PATENT DOCUMENTS

| | | |
|---|---|---|
| EP | 0 078 228 | 5/1983 |
| EP | 2 070 950 | 6/2009 |
| WO | WO 96/40749 | 12/1996 |
| WO | WO 00/01417 | 1/2000 |
| WO | WO 00/29427 | 5/2000 |
| WO | WO 2004/024761 | 3/2004 |
| WO | WO 2004024761 A1 * | 3/2004 |
| WO | WO 2005/014024 | 2/2005 |
| WO | WO 2005/016973 | 2/2005 |
| WO | WO 2006/077397 | 7/2006 |

OTHER PUBLICATIONS

Rohrling et al. Carbohydrate Research 337 (2002) 691-700.*
Abe, et al., "Versatile synthesis of oligosaccharide-containing fullerenes," Tetrahedron: Asymmetry, vol. 16, pp. 15-19, (2005).
Baudys, et al., "Extending Insulin Action in Vivo by Conjugation to Carboxylmethyl Dextran," Bioconjugate Chemistry, vol. 9, pp. 176-183, (1998).
Cervigni, et al., "Synthesis of Glycopeptides and Lipopeptides by Chemoselective Ligation," Angew. Chem. Int. Ed. Engl., vol. 35, No. 11, pp. 1230-1232, (1996).
Filpula, et al., "Releasable PEGylation of proteins with customized linkers," Advanced Drug Delivery Reviews, vol. 60, pp. 29-49, (2008).
Harris, et al., "Effect of Pegylation on Pharmaceuticals," Nature, vol. 2, pp. 214-221, (Mar. 2003).
Harris, "Laboratory Synthesis of Polyethylene Glycol Derivatives," JMS-Rev. Macromol. Chem. Phys., vol. C25, No. 3, pp. 325-373, (1985).
Harris, et al., "Poly(ethylene glycol) Chemistry and Biological Applications", ACS Symposium Series, 11 pages, (1997).
Hatanaka, et al., "One-Step Synthesis of Biotinyl Photoprobes from Unprotected Carbohydrates," J. Org. Chem., vol. 65, pp. 5639-5643, (2000).
Leteux, et al., "Biotinyl-L-3-(2-naphthyl)-alanine hydrazide derivatives of N-glycan: . . . ," Glycobiology, vol. 8, No. 3, pp. 227-236, (1998).
Pasut, et al., "Protein, peptide and non-peptide drug PEGylation for therapeutic application," Expert Opin. Ther. Patents, vol. 14, No. 6, pp. 859-894, (2004).
Roberts, et al., "Chemistry for peptide and protein PEGylation," Advanced Drug Delivery Reviews, vol. 54, pp. 459-476, (2002).
Sadamoto, et al., "Control of Bacteria Adhesion by Cell-Wall Engineering," J. Am. Chem. Soc., vol. 126, pp. 3755-3761, (2004).
Shinohara, et al., "Bifunctional Labeling Reagent for Oligosaccharides to Incorporate Both Chromophore and Biotin Groups," Anal. Chem., vol. 68, pp. 2573-2579, (1996).
Spatola, "Peptide Backbone Modifications: . . . ," Chem. And Biochem. of Amino Acids, Peptides, and Proteins, Weinstein, Marcel Dekker, New York, pp. 267-357, (1983).
Zalipsky, et al., "Use of Functionalized Poly(Ethylene Glycol)s for Modification of Polypeptides", Poly(Ethylene Glycol) Chemistry: Biotechnical and Biomedical Applications, Eds. J.M. Harris, Plenum Press, New York, 13 pages, (1992).

(Continued)

*Primary Examiner* — Layla Bland
(74) *Attorney, Agent, or Firm* — Timothy A. Marquart

(57) ABSTRACT

Provided herein are water-soluble carbohydrate polymers which are monoderivatized at their reducing terminus, such that the carbohydrate polymers can be selectively conjugated at a single location. Also provided are methods of preparation and conjugation of the monoderivatized carbohydrate polymers.

20 Claims, 4 Drawing Sheets

(56) References Cited

OTHER PUBLICATIONS

Zhao, et al., "Novel Degradable Poly(ethylene glycol) Esters for Drug Delivery," Amer. Chem. Soc., Chapter 28, pp. 458-472, (1997).

Zhao, et al., "Rapid, sensitive structure analysis of oligosaccharides," Proc. Natl. Acad. Sci., vol. 94, pp. 1629-1633, (Mar. 1997).

PCT International Search Report and Written Opinion corresponding to PCT Application No. PCT/US2009/005233 date of mailing May 4, 2010.

PCT International Preliminary Report on Patentability corresponding to PCT Application No. PCT/US2009/005233 date of mailing Mar. 31, 2011.

Enzon Pharmaceuticals, Macromolecular Engineering Technologies, 16 pages, (2004).

NEKTAR™—Transforming Therapeutics, Nektar Molecule Engineering: Polyethylene Glycol and Derivatives for Advanced PEGylation, 24 pages, Catalog—2003, (Jul. 2003).

NEKTAR™—Transforming Therapeutics, Nektar Advanced PEGylation: Polyethylene Glycol and Derivatives for Advanced PEGylation, 27 pages, Catalog—2004, (Jul. 2004).

NEKTAR™—Transforming Therapeutics, Nektar Advanced PEGylation: Polyethylene Glycol and Derivatives for Advanced PEGylation, 33 pages, (Catalog 2005-2006).

NOF Corporation, PEG Derivatives, Phospholipid and Drug Delivery Materials for Pharmaceuticals, 46 pages, Catalogue 2003—$1^{st}$, (Jan. 2003).

NOF Corporation, PEG Derivatives, Phospholipid and Drug Delivery Materials for Pharmaceuticals, 27 pages, Catalogue 2003—$2^{nd}$, (Mar. 2004).

NOF Corporation, PEG Derivatives, Phospholipids and Drug Delivery Materials for Pharmaceutical Products and Formulations, 60 pages, Catalogue Ver. 8, (Apr. 2006).

Polypure Products, PEG amines; PEG acids and amino acids; PEG thiols and disulfides; Biotins, 5 pages, (Apr. 2004).

Polypure Products, PEG amines; PEG acids and amino acids; PEG thiols and disulfides; Biotins, 5 pages, (Apr. 2005).

Quanta Biodesign, Labeling, Derivatization and Crosslinking Reagents for Biological and Related Materials with dPEG™, 38 pages, (Mar. 12, 2004).

Quanta Biodesign, Labeling, Modification and Crosslinking Reagents incorporating our unique monodispersed dPEG™ Technology, 31 pages, (Nov. 5, 2004).

Quanta Biodesign, Ltd., Leading innovator, producer and provider of monodisperse discrete PEG™ (dPEG™) derivatives, (Product Catalog), 26 pages, (Updated: Jul. 18, 2005).

Quanta Biodesign, Ltd., Leading innovator, producer and provider of monodisperse discrete PEG™ (dPEG™) derivatives, (Product Catalog), 26 pages, (Updated: Nov. 17, 2005).

Shearwater Polymers, Inc., Polyethylene Glycol Derivatives, 50 pages, Catalog—(Mar. 1995).

Shearwater Polymers, Inc., Polyethylene Glycol Derivatives, 55 pages, Catalog 1997-1998, (Jul. 1997).

Shearwater Polymers, Inc., Polyethylene Glycol and Derivatives: Functionalized Biocompatible Polymers for Research and Pharmaceuticals, 50 pages, Catalog—(Jan. 2000).

Shearwater Corporation, Polyethylene Glycol and Derivatives for Biomedical Applications, 20 pages, Catalog—(Jul. 2001).

* cited by examiner

SEQUENCE LISTING

```
<160> NUMBER OF SEQ ID NOS: 301

<210> SEQ ID NO 1
<211> LENGTH: 28
<212> TYPE: PRT
<213> ORGANISM: Homo sapiens

<400> SEQUENCE: 1

Ser Leu Arg Arg Ser Ser Cys Phe Gly Gly Arg Met Asp Arg Ile Gly
1               5                   10                  15

Ala Gln Ser Gly Leu Gly Cys Asn Ser Phe Arg Tyr
            20                  25

<210> SEQ ID NO 2
<211> LENGTH: 10
<212> TYPE: PRT
<213> ORGANISM: Homo sapiens

<400> SEQUENCE: 2

Tyr Gly Gly Phe Leu Arg Lys Tyr Pro Lys
1               5                   10

<210> SEQ ID NO 3
<211> LENGTH: 110
<212> TYPE: PRT
<213> ORGANISM: Homo sapiens

<400> SEQUENCE: 3

Met Ala Leu Trp Met Arg Leu Leu Pro Leu Leu Ala Leu Leu Ala Leu
1               5                   10                  15

Trp Gly Pro Asp Pro Ala Ala Ala Phe Val Asn Gln His Leu Cys Gly
            20                  25                  30

Ser His Leu Val Glu Ala Leu Tyr Leu Val Cys Gly Glu Arg Gly Phe
        35                  40                  45

Phe Tyr Thr Pro Lys Thr Arg Arg Glu Ala Glu Asp Leu Gln Val Gly
    50                  55                  60

Gln Val Glu Leu Gly Gly Gly Pro Gly Ala Gly Ser Leu Gln Pro Leu
65                  70                  75                  80

Ala Leu Glu Gly Ser Leu Gln Lys Arg Gly Ile Val Glu Gln Cys Cys
                85                  90                  95

Thr Ser Ile Cys Ser Leu Tyr Gln Leu Glu Asn Tyr Cys Asn
            100                 105                 110
```

```
<210> SEQ ID NO 4
<211> LENGTH: 70
<212> TYPE: PRT
<213> ORGANISM: Homo sapiens

<400> SEQUENCE: 4

Met Ala Leu Trp Met Arg Leu Leu Pro Leu Leu Ala Leu Leu Ala Leu
1               5                   10                  15

Trp Gly Pro Asp Pro Ala Ala Ala Phe Val Asn Gln His Leu Cys Gly
            20                  25                  30

Ser His Leu Val Glu Ala Leu Tyr Leu Val Cys Gly Glu Arg Gly Phe
        35                  40                  45

Phe Tyr Thr Pro Lys Thr Arg Arg Glu Ala Glu Asp Leu Gln Val Gly
    50                  55                  60

Gln Val Glu Leu Gly Gly
65                  70

<210> SEQ ID NO 5
<211> LENGTH: 40
<212> TYPE: PRT
<213> ORGANISM: Homo sapiens

<400> SEQUENCE: 5

Gly Pro Gly Ala Gly Ser Leu Gln Pro Leu Ala Leu Glu Gly Ser Leu
1               5                   10                  15

Gln Lys Arg Gly Ile Val Glu Gln Cys Cys Thr Ser Ile Cys Ser Leu
            20                  25                  30

Tyr Gln Leu Glu Asn Tyr Cys Asn
        35                  40

<210> SEQ ID NO 6
<211> LENGTH: 82
<212> TYPE: PRT
<213> ORGANISM: Homo sapiens

<400> SEQUENCE: 6

Gly Ser Gly Leu Thr Asn Ile Lys Thr Glu Glu Ile Ser Glu Val Lys
1               5                   10                  15

Met Asp Ala Glu Phe Arg His Asp Ser Gly Tyr Glu Val His His Gln
            20                  25                  30

Lys Leu Val Phe Phe Ala Glu Asp Val Gly Ser Asn Lys Gly Ala Ile
        35                  40                  45

Ile Gly Leu Met Val Gly Gly Val Val Ile Ala Thr Val Ile Ile Ile
    50                  55                  60

Thr Leu Val Met Leu Lys Lys Gln Tyr Thr Ser Asn His His Gly Val
65                  70                  75                  80

Val Glu

<210> SEQ ID NO 7
<211> LENGTH: 434
<212> TYPE: PRT
<213> ORGANISM: Homo sapiens

<400> SEQUENCE: 7

Met Glu Ser Glu Ser Glu Ser Gly Ala Ala Ala Asp Thr Pro Pro Leu
1               5                   10                  15

Glu Thr Leu Ser Phe His Gly Asp Glu Glu Ile Ile Glu Val Val Glu
            20                  25                  30

Leu Asp Pro Gly Pro Pro Asp Pro Asp Asp Leu Ala Gln Glu Met Glu
```

```
                    35                  40                  45
Asp Val Asp Phe Glu Glu Glu Glu Glu Gly Asn Glu Gly
                50                  55                  60

Trp Val Leu Glu Pro Gln Glu Val Val Gly Ser Met Gly Pro
65                  70                  75                  80

Asp Asp Ser Glu Val Thr Phe Ala Leu His Ser Ala Ser Val Phe Cys
                85                  90                  95

Val Ser Leu Asp Pro Lys Thr Asn Thr Leu Ala Val Thr Gly Gly Glu
                100                 105                 110

Asp Asp Lys Ala Phe Val Trp Arg Leu Ser Asp Gly Glu Leu Leu Phe
                115                 120                 125

Glu Cys Ala Gly His Lys Asp Ser Val Thr Cys Ala Gly Phe Ser His
                130                 135                 140

Asp Ser Thr Leu Val Ala Thr Gly Asp Met Ser Gly Leu Leu Lys Val
                145                 150                 155                 160

Trp Gln Val Asp Thr Lys Glu Glu Val Trp Ser Phe Glu Ala Gly Asp
                165                 170                 175

Leu Glu Trp Met Glu Trp His Pro Arg Ala Pro Val Leu Leu Ala Gly
                180                 185                 190

Thr Ala Asp Gly Asn Thr Trp Met Trp Lys Val Pro Asn Gly Asp Cys
                195                 200                 205

Lys Thr Phe Gln Gly Pro Asn Cys Pro Ala Thr Cys Gly Arg Val Leu
                210                 215                 220

Pro Asp Gly Lys Arg Ala Val Val Gly Tyr Glu Asp Gly Thr Ile Arg
225                 230                 235                 240

Ile Trp Asp Leu Lys Gln Gly Ser Pro Ile His Val Leu Lys Gly Thr
                245                 250                 255

Glu Gly His Gln Gly Pro Leu Thr Cys Val Ala Ala Asn Gln Asp Gly
                260                 265                 270

Ser Leu Ile Leu Thr Gly Ser Val Asp Cys Gln Ala Lys Leu Val Ser
                275                 280                 285

Ala Thr Thr Gly Lys Val Val Gly Val Phe Arg Pro Glu Thr Val Ala
                290                 295                 300

Ser Gln Pro Ser Leu Gly Glu Gly Glu Glu Ser Glu Ser Asn Ser Val
305                 310                 315                 320

Glu Ser Leu Gly Phe Cys Ser Val Met Pro Leu Ala Ala Val Gly Tyr
                325                 330                 335

Leu Asp Gly Thr Leu Ala Ile Tyr Asp Leu Ala Thr Gln Thr Leu Arg
                340                 345                 350

His Gln Cys Gln His Gln Ser Gly Ile Val Gln Leu Leu Trp Glu Ala
                355                 360                 365

Gly Thr Ala Val Val Tyr Thr Cys Ser Leu Asp Gly Ile Val Arg Leu
                370                 375                 380

Trp Asp Ala Arg Thr Gly Arg Leu Leu Thr Asp Tyr Arg Gly His Thr
385                 390                 395                 400

Ala Glu Ile Leu Asp Phe Ala Leu Ser Lys Asp Ala Ser Leu Val Val
                405                 410                 415

Thr Thr Ser Gly Asp His Lys Ala Lys Val Phe Cys Val Gln Arg Pro
                420                 425                 430

Asp Arg

<210> SEQ ID NO 8
<211> LENGTH: 39
<212> TYPE: PRT
```

```
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 8

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser
        35

<210> SEQ ID NO 9
<211> LENGTH: 25
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: misc_feature
<222> LOCATION: (1)..(1)
<223> OTHER INFORMATION: /note="N-term acetylated"
<220> FEATURE:
<221> NAME/KEY: misc_feature
<222> LOCATION: (25)..(25)
<223> OTHER INFORMATION: /note="C-term amidated"

<400> SEQUENCE: 9

Ala Thr Gln Arg Leu Ala Asn Glu Leu Val Arg Leu Gln Thr Tyr Pro
1               5                   10                  15

Arg Thr Asn Val Gly Ser Asn Thr Tyr
            20                  25

<210> SEQ ID NO 10
<211> LENGTH: 267
<212> TYPE: PRT
<213> ORGANISM: Homo sapiens

<400> SEQUENCE: 10

Met Pro Arg Ser Cys Cys Ser Arg Ser Gly Ala Leu Leu Leu Ala Leu
1               5                   10                  15

Leu Leu Gln Ala Ser Met Glu Val Arg Gly Trp Cys Leu Glu Ser Ser
            20                  25                  30

Gln Cys Gln Asp Leu Thr Thr Glu Ser Asn Leu Leu Glu Cys Ile Arg
        35                  40                  45

Ala Cys Lys Pro Asp Leu Ser Ala Glu Thr Pro Met Phe Pro Gly Asn
    50                  55                  60

Gly Asp Glu Gln Pro Leu Thr Glu Asn Pro Arg Lys Tyr Val Met Gly
65                  70                  75                  80

His Phe Arg Trp Asp Arg Phe Gly Arg Arg Asn Ser Ser Ser Ser Gly
                85                  90                  95

Ser Ser Gly Ala Gly Gln Lys Arg Glu Asp Val Ser Ala Gly Glu Asp
            100                 105                 110

Cys Gly Pro Leu Pro Glu Gly Gly Pro Glu Pro Arg Ser Asp Gly Ala
        115                 120                 125

Lys Pro Gly Pro Arg Glu Gly Lys Arg Ser Tyr Ser Met Glu His Phe
    130                 135                 140

Arg Trp Gly Lys Pro Val Gly Lys Lys Arg Arg Pro Val Lys Val Tyr
145                 150                 155                 160
```

```
Pro Asn Gly Ala Glu Asp Glu Ser Ala Glu Ala Phe Pro Leu Glu Phe
                165                 170                 175

Lys Arg Glu Leu Thr Gly Gln Arg Leu Arg Glu Gly Asp Gly Pro Asp
            180                 185                 190

Gly Pro Ala Asp Asp Gly Ala Gly Ala Gln Ala Asp Leu Glu His Ser
        195                 200                 205

Leu Leu Val Ala Ala Glu Lys Lys Asp Glu Gly Pro Tyr Arg Met Glu
    210                 215                 220

His Phe Arg Trp Gly Ser Pro Pro Lys Asp Lys Arg Tyr Gly Gly Phe
225                 230                 235                 240

Met Thr Ser Glu Lys Ser Gln Thr Pro Leu Val Thr Leu Phe Lys Asn
                245                 250                 255

Ala Ile Ile Lys Asn Ala Tyr Lys Lys Gly Glu
                260                 265

<210> SEQ ID NO 11
<211> LENGTH: 35
<212> TYPE: PRT
<213> ORGANISM: Human immunodeficiency virus type 1

<400> SEQUENCE: 11

Cys Thr Arg Pro Ser Asn Asn Thr Arg Lys Ser Ile Pro Val Gly Pro
1               5                   10                  15

Gly Lys Ala Leu Tyr Ala Thr Gly Ala Ile Ile Gly Asn Ile Arg Gln
            20                  25                  30

Ala His Cys
        35

<210> SEQ ID NO 12
<211> LENGTH: 508
<212> TYPE: PRT
<213> ORGANISM: Human immunodeficiency virus type 1

<400> SEQUENCE: 12

Met Gly Ala Arg Ala Ser Val Leu Ser Gly Gly Lys Leu Asp Lys Trp
1               5                   10                  15

Glu Lys Ile Arg Leu Arg Pro Gly Gly Lys Lys Thr Tyr Gln Leu Lys
            20                  25                  30

His Ile Val Trp Ala Ser Arg Glu Leu Glu Arg Phe Ala Val Asn Pro
        35                  40                  45

Gly Leu Leu Glu Thr Gly Gly Cys Lys Gln Ile Leu Val Gln Leu
    50                  55                  60

Gln Pro Ser Leu Gln Thr Gly Ser Glu Glu Leu Lys Ser Leu Tyr Asn
65                  70                  75                  80

Ala Val Ala Thr Leu Tyr Cys Val His Gln Gly Ile Glu Val Arg Asp
                85                  90                  95

Thr Lys Glu Ala Leu Asp Lys Ile Glu Glu Glu Gln Asn Lys Ser Lys
            100                 105                 110

Lys Lys Ala Gln Gln Ala Ala Ala Asp Thr Gly Asn Ser Ser Gln Val
        115                 120                 125

Ser Gln Asn Tyr Pro Ile Val Gln Asn Leu Gln Gly Gln Met Val His
    130                 135                 140

Gln Ala Ile Ser Pro Arg Thr Leu Asn Ala Trp Val Lys Val Ile Glu
145                 150                 155                 160

Glu Lys Ala Phe Ser Pro Glu Val Ile Pro Met Phe Ser Ala Leu Ser
                165                 170                 175
```

Glu Gly Ala Thr Pro Gln Asp Leu Asn Thr Met Leu Asn Thr Val Gly
            180                 185                 190

Gly His Gln Ala Ala Met Gln Met Leu Lys Glu Thr Ile Asn Glu Glu
        195                 200                 205

Ala Ala Glu Trp Asp Arg Leu His Pro Ala His Ala Gly Pro Asn Ala
210                 215                 220

Pro Gly Gln Met Arg Glu Pro Arg Gly Ser Asp Ile Ala Gly Thr Thr
225                 230                 235                 240

Ser Thr Leu Gln Glu Gln Ile Gly Trp Met Thr Ser Asn Pro Pro Val
            245                 250                 255

Pro Val Gly Glu Ile Tyr Lys Arg Trp Ile Ile Leu Gly Leu Asn Lys
        260                 265                 270

Ile Val Arg Met Tyr Ser Pro Val Ser Ile Leu Asp Ile Arg Gln Gly
    275                 280                 285

Pro Lys Glu Pro Phe Arg Asp Tyr Val Asp Arg Phe Tyr Lys Thr Leu
290                 295                 300

Arg Ala Glu Gln Ala Ser Gln Asp Val Lys Asn Trp Met Thr Glu Thr
305                 310                 315                 320

Leu Leu Val Gln Asn Ala Asn Pro Asp Cys Lys Thr Ile Leu Lys Ala
            325                 330                 335

Leu Gly Pro Ala Ala Thr Leu Glu Glu Met Met Thr Ala Cys Gln Gly
        340                 345                 350

Val Gly Gly Pro Ser His Lys Ala Arg Ile Leu Ala Glu Ala Met Ser
    355                 360                 365

Gln Val Thr Ser Pro Ala Asn Ile Met Met Gln Arg Gly Asn Phe Arg
    370                 375                 380

Asn Gln Arg Lys Thr Ile Lys Cys Phe Asn Cys Gly Lys Glu Gly His
385                 390                 395                 400

Leu Ala Arg His Cys Arg Ala Pro Arg Lys Lys Gly Cys Trp Lys Cys
            405                 410                 415

Gly Arg Glu Gly His Gln Met Lys Asp Cys Thr Glu Arg Gln Ala Asn
        420                 425                 430

Phe Leu Gly Lys Ile Trp Pro Ser His Lys Gly Arg Pro Gly Asn Phe
    435                 440                 445

Leu Gln Ser Arg Pro Glu Pro Thr Ala Pro Pro Glu Glu Ser Phe Arg
450                 455                 460

Phe Gly Glu Glu Thr Thr Thr Pro Pro Gln Lys Gln Glu Pro Leu Pro
465                 470                 475                 480

Ser Gln Lys Gln Glu Thr Ile Asp Lys Asp Leu Tyr Pro Leu Ala Ser
            485                 490                 495

Leu Lys Ser Leu Phe Gly Asn Asp Pro Ser Leu Gln
        500                 505

<210> SEQ ID NO 13
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 13

Asn Leu Arg Ile Ala Leu Arg
1               5

<210> SEQ ID NO 14

```
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 14

Arg Leu Ala Ile Arg Leu Asn
1               5

<210> SEQ ID NO 15
<211> LENGTH: 40
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 15

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val
        35                  40

<210> SEQ ID NO 16
<211> LENGTH: 42
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 16

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val Ile Ala
        35                  40

<210> SEQ ID NO 17
<211> LENGTH: 202
<212> TYPE: PRT
<213> ORGANISM: Homo sapiens

<400> SEQUENCE: 17

Met Lys Val Leu Ala Ala Gly Val Val Pro Leu Leu Leu Val Leu His
1               5                   10                  15

Trp Lys His Gly Ala Gly Ser Pro Leu Pro Ile Thr Pro Val Asn Ala
            20                  25                  30

Thr Cys Ala Ile Arg His Pro Cys His Asn Asn Leu Met Asn Gln Ile
        35                  40                  45

Arg Ser Gln Leu Ala Gln Leu Asn Gly Ser Ala Asn Ala Leu Phe Ile
    50                  55                  60

Leu Tyr Tyr Thr Ala Gln Gly Glu Pro Phe Pro Asn Asn Leu Asp Lys
65                  70                  75                  80

Leu Cys Gly Pro Asn Val Thr Asp Phe Pro Pro Phe His Ala Asn Gly
                85                  90                  95
```

```
Thr Glu Lys Ala Lys Leu Val Glu Leu Tyr Arg Ile Val Val Tyr Leu
            100                 105                 110

Gly Thr Ser Leu Gly Asn Ile Thr Arg Asp Gln Lys Ile Leu Asn Pro
        115                 120                 125

Ser Ala Leu Ser Leu His Ser Lys Leu Asn Ala Thr Ala Asp Ile Leu
    130                 135                 140

Arg Gly Leu Leu Ser Asn Val Leu Cys Arg Leu Cys Ser Lys Tyr His
145                 150                 155                 160

Val Gly His Val Asp Val Thr Tyr Gly Pro Asp Thr Ser Gly Lys Asp
                165                 170                 175

Val Phe Gln Lys Lys Leu Gly Cys Gln Leu Leu Gly Lys Tyr Lys
                180                 185                 190

Gln Ile Ile Ala Val Leu Ala Gln Ala Phe
            195                 200

<210> SEQ ID NO 18
<211> LENGTH: 382
<212> TYPE: PRT
<213> ORGANISM: Homo sapiens

<400> SEQUENCE: 18

Met Asp Phe Gly Leu Ala Leu Leu Ala Gly Leu Leu Gly Leu Leu
1               5                   10                  15

Leu Gly Gln Ser Leu Gln Val Lys Pro Leu Gln Val Glu Pro Pro Glu
            20                  25                  30

Pro Val Val Ala Val Ala Leu Gly Ala Ser Arg Gln Leu Thr Cys Arg
        35                  40                  45

Leu Ala Cys Ala Asp Arg Gly Ala Ser Val Gln Trp Arg Gly Leu Asp
    50                  55                  60

Thr Ser Leu Gly Ala Val Gln Ser Asp Thr Gly Arg Ser Val Leu Thr
65                  70                  75                  80

Val Arg Asn Ala Ser Leu Ser Ala Ala Gly Thr Arg Val Cys Val Gly
                85                  90                  95

Ser Cys Gly Gly Arg Thr Phe Gln His Thr Val Gln Leu Leu Val Tyr
            100                 105                 110

Ala Phe Pro Asp Gln Leu Thr Val Ser Pro Ala Ala Leu Val Pro Gly
        115                 120                 125

Asp Pro Glu Val Ala Cys Thr Ala His Lys Val Thr Pro Val Asp Pro
    130                 135                 140

Asn Ala Leu Ser Phe Ser Leu Leu Val Gly Gly Gln Glu Leu Glu Gly
145                 150                 155                 160

Ala Gln Ala Leu Gly Pro Glu Val Gln Glu Glu Glu Glu Pro Gln
                165                 170                 175

Gly Asp Glu Asp Val Leu Phe Arg Val Thr Glu Arg Trp Arg Leu Pro
            180                 185                 190

Pro Leu Gly Thr Pro Val Pro Pro Ala Leu Tyr Cys Gln Ala Thr Met
        195                 200                 205

Arg Leu Pro Gly Leu Glu Leu Ser His Arg Gln Ala Ile Pro Val Leu
    210                 215                 220

His Ser Pro Thr Ser Pro Glu Pro Pro Asp Thr Thr Ser Pro Glu Ser
225                 230                 235                 240

Pro Asp Thr Thr Ser Pro Glu Ser Pro Asp Thr Thr Ser Gln Glu Pro
                245                 250                 255

Pro Asp Thr Thr Ser Pro Glu Pro Pro Asp Lys Thr Ser Pro Glu Pro
            260                 265                 270
```

```
Ala Pro Gln Gln Gly Ser Thr His Thr Pro Arg Ser Pro Gly Ser Thr
            275                 280                 285

Arg Thr Arg Arg Pro Glu Ile Ser Gln Ala Gly Pro Thr Gln Gly Glu
        290                 295                 300

Val Ile Pro Thr Gly Ser Ser Lys Pro Ala Gly Asp Gln Leu Pro Ala
305                 310                 315                 320

Ala Leu Trp Thr Ser Ser Ala Val Leu Gly Leu Leu Leu Ala Leu
            325                 330                 335

Pro Thr Tyr His Leu Trp Lys Arg Cys Arg His Leu Ala Glu Asp Asp
            340                 345                 350

Thr His Pro Pro Ala Ser Leu Arg Leu Leu Pro Gln Val Ser Ala Trp
            355                 360                 365

Ala Gly Leu Arg Gly Thr Gly Gln Val Gly Ile Ser Pro Ser
            370                 375                 380

<210> SEQ ID NO 19
<211> LENGTH: 74
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 19

Asp Thr Thr Val Ser Glu Pro Ala Pro Ser Cys Val Thr Leu Tyr Gln
1               5                   10                  15

Ser Trp Arg Tyr Ser Gln Ala Asp Asn Gly Cys Ala Glu Thr Val Thr
            20                  25                  30

Val Lys Val Val Tyr Glu Asp Asp Thr Glu Gly Leu Cys Tyr Ala Val
        35                  40                  45

Ala Pro Gly Gln Ile Thr Thr Val Gly Asp Gly Tyr Ile Gly Ser His
    50                  55                  60

Gly His Ala Arg Tyr Leu Ala Arg Cys Leu
65                  70

<210> SEQ ID NO 20
<211> LENGTH: 151
<212> TYPE: PRT
<213> ORGANISM: Homo sapiens

<400> SEQUENCE: 20

Met Ser Ser Phe Ser Thr Thr Thr Val Ser Phe Leu Leu Leu Leu Ala
1               5                   10                  15

Phe Gln Leu Leu Gly Gln Thr Arg Ala Asn Pro Met Tyr Asn Ala Val
            20                  25                  30

Ser Asn Ala Asp Leu Met Asp Phe Lys Asn Leu Leu Asp His Leu Glu
        35                  40                  45

Glu Lys Met Pro Leu Glu Asp Glu Val Val Pro Pro Gln Val Leu Ser
    50                  55                  60

Asp Pro Asn Glu Glu Ala Gly Ala Ala Leu Ser Pro Leu Pro Glu Val
65                  70                  75                  80

Pro Pro Trp Thr Gly Glu Val Ser Pro Ala Gln Arg Asp Gly Gly Ala
            85                  90                  95

Leu Gly Arg Gly Pro Trp Asp Ser Ser Asp Arg Ser Ala Leu Leu Lys
            100                 105                 110

Ser Lys Leu Arg Ala Leu Leu Thr Ala Pro Arg Ser Leu Arg Arg Ser
            115                 120                 125
```

Ser Cys Phe Gly Gly Arg Met Asp Arg Ile Gly Ala Gln Ser Gly Leu
    130                 135                 140

Gly Cys Asn Ser Phe Arg Tyr
145                 150

<210> SEQ ID NO 21
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 21

Thr Thr Ser Gln Val Arg Pro Arg
1               5

<210> SEQ ID NO 22
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 22

Val Lys Thr Thr Ser Gln Val Arg Pro Arg
1               5                   10

<210> SEQ ID NO 23
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 23

Ser Gln Val Arg Pro Arg
1               5

<210> SEQ ID NO 24
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 24

Val Arg Pro Arg
1

<210> SEQ ID NO 25
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 25

Thr Thr Ser Gln Val Arg Pro Arg His Ile Thr

-continued

<210> SEQ ID NO 26
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 26

Thr Thr Ser Gln Val
1               5

<210> SEQ ID NO 27
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 27

Thr Ser Gln Val Arg
1               5

<210> SEQ ID NO 28
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 28

Thr Thr Ser Gly Ile His Pro Lys
1               5

<210> SEQ ID NO 29
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 29

Glu Gly Pro Trp Leu Glu Glu Glu Glu
1               5

<210> SEQ ID NO 30
<211> LENGTH: 84
<212> TYPE: PRT
<213> ORGANISM: Hirudinaria manillensis

<400> SEQUENCE: 30

Met Phe Ser Leu Lys Leu Phe Val Val Phe Leu Ala Val Cys Ile Cys
1               5                   10                  15

Val Ser Gln Ala Val Ser Tyr Thr Asp Cys Thr Glu Ser Gly Gln Asn
            20                  25                  30

Tyr Cys Leu Cys Val Gly Gly Asn Leu Cys Gly Gly Gly Lys His Cys
        35                  40                  45

Glu Met Asp Gly Ser Gly Asn Lys Cys Val Asp Gly Glu Gly Thr Pro

-continued

```
    50                  55                  60

Lys Pro Lys Ser Gln Thr Glu Gly Asp Phe Glu Glu Ile Pro Asp Glu
65                  70                  75                  80

Asp Ile Leu Asn

<210> SEQ ID NO 31
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 31

Tyr Ala Gly Ala Val Val Asn Asp Leu
1               5

<210> SEQ ID NO 32
<211> LENGTH: 100
<212> TYPE: PRT
<213> ORGANISM: Homo sapiens

<400> SEQUENCE: 32

Met Lys Leu Leu Ala Ala Thr Val Leu Leu Leu Thr Ile Cys Ser Leu
1               5                   10                  15

Glu Gly Ala Leu Val Arg Arg Gln Ala Lys Glu Pro Cys Val Glu Ser
            20                  25                  30

Leu Val Ser Gln Tyr Phe Gln Thr Val Thr Asp Tyr Gly Lys Asp Leu
        35                  40                  45

Met Glu Lys Val Lys Ser Pro Glu Leu Gln Ala Glu Ala Lys Ser Tyr
    50                  55                  60

Phe Glu Lys Ser Lys Glu Gln Leu Thr Pro Leu Ile Lys Lys Ala Gly
65                  70                  75                  80

Thr Glu Leu Val Asn Phe Leu Ser Tyr Phe Val Glu Leu Gly Thr His
                85                  90                  95

Pro Ala Thr Gln
            100

<210> SEQ ID NO 33
<211> LENGTH: 338
<212> TYPE: PRT
<213> ORGANISM: Mycobacterium bovis

<400> SEQUENCE: 33

Met Gln Leu Val Asp Arg Val Arg Gly Ala Val Thr Gly Met Ser Arg
1               5                   10                  15

Arg Leu Val Val Gly Ala Val Gly Ala Ala Leu Val Ser Gly Leu Val
            20                  25                  30

Gly Ala Val Gly Gly Thr Ala Thr Ala Gly Ala Phe Ser Arg Pro Gly
        35                  40                  45

Leu Pro Val Glu Tyr Leu Gln Val Pro Ser Pro Ser Met Gly Arg Asp
    50                  55                  60

Ile Lys Val Gln Phe Gln Ser Gly Gly Ala Asn Ser Pro Ala Leu Tyr
65                  70                  75                  80

Leu Leu Asp Gly Leu Arg Ala Gln Asp Asp Phe Ser Gly Trp Asp Ile
                85                  90                  95

Asn Thr Pro Ala Phe Glu Trp Tyr Asp Gln Ser Gly Leu Ser Val Val
            100                 105                 110
```

```
Met Pro Val Gly Gly Gln Ser Phe Tyr Ser Asp Trp Tyr Gln Pro
        115                 120                 125

Ala Cys Gly Lys Ala Gly Cys Gln Thr Tyr Lys Trp Glu Thr Phe Leu
130                 135                 140

Thr Ser Glu Leu Pro Gly Trp Leu Gln Ala Asn Arg His Val Lys Pro
145                 150                 155                 160

Thr Gly Ser Ala Val Val Gly Leu Ser Met Ala Ala Ser Ser Ala Leu
                165                 170                 175

Thr Leu Ala Ile Tyr His Pro Gln Gln Phe Val Tyr Ala Gly Ala Met
                180                 185                 190

Ser Gly Leu Leu Asp Pro Ser Gln Ala Met Gly Pro Thr Leu Ile Gly
        195                 200                 205

Leu Ala Met Gly Asp Ala Gly Gly Tyr Lys Ala Ser Asp Met Trp Gly
210                 215                 220

Pro Lys Glu Asp Pro Ala Trp Gln Arg Asn Asp Pro Leu Leu Asn Val
225                 230                 235                 240

Gly Lys Leu Ile Ala Asn Asn Thr Arg Val Trp Val Tyr Cys Gly Asn
                245                 250                 255

Gly Lys Pro Ser Asp Leu Gly Gly Asn Asn Leu Pro Ala Lys Phe Leu
        260                 265                 270

Glu Gly Phe Val Arg Thr Ser Asn Ile Lys Phe Gln Asp Ala Tyr Asn
        275                 280                 285

Ala Gly Gly His Asn Gly Val Phe Asp Phe Pro Asp Ser Gly Thr
        290                 295                 300

His Ser Trp Glu Tyr Trp Gly Ala Gln Leu Asn Ala Met Lys Pro Asp
305                 310                 315                 320

Leu Gln Arg Ala Leu Gly Ala Thr Pro Asn Thr Gly Pro Ala Pro Gln
                325                 330                 335

Gly Ala

<210> SEQ ID NO 34
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (3)..(3)
<223> OTHER INFORMATION: (NH(CH2)4CO)2-Asp

<400> SEQUENCE: 34

Phe Pro Asp Phe Glu Pro Ile Pro Leu
1               5

<210> SEQ ID NO 35
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: Pyro-Glu
<220> FEATURE:
<221> NAME/KEY: misc_feature
<222> LOCATION: (14)..(14)
<223> OTHER INFORMATION: /note="C-term amidated"
```

```
<400> SEQUENCE: 35

Glu Gln Arg Leu Gly Asn Gln Trp Ala Val Gly His Leu Leu
1               5                   10

<210> SEQ ID NO 36
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 36

Leu Asp Val Pro
1

<210> SEQ ID NO 37
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (2)..(2)
<223> OTHER INFORMATION: Alpha-Glu
<220> FEATURE:
<221> NAME/KEY: MOD_RES
<222> LOCATION: (10)..(11)
<223> OTHER INFORMATION: Alpha-Asp

<400> SEQUENCE: 37

Gly Glu Pro Pro Pro Gly Lys Pro Ala Asp Asp Ala Gly Leu
1               5                   10

<210> SEQ ID NO 38
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: 5-oxo-Pro
<220> FEATURE:
<221> NAME/KEY: misc_feature
<222> LOCATION: (14)..(14)
<223> OTHER INFORMATION: /note="C-term amidated"

<400> SEQUENCE: 38

Pro Gln Arg Leu Gly Asn Gln Trp Ala Val Gly His Leu Met
1               5                   10

<210> SEQ ID NO 39
<211> LENGTH: 32
<212> TYPE: PRT
<213> ORGANISM: Homo sapiens

<400> SEQUENCE: 39

Ser Pro Lys Met Val Gln Gly Ser Gly Cys Phe Gly Arg Lys Met Asp
1               5                   10                  15

Arg Ile Ser Ser Ser Ser Gly Leu Gly Cys Lys Val Leu Arg Arg His
            20                  25                  30
```

```
<210> SEQ ID NO 40
<211> LENGTH: 37
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 40

Gly Leu Ser Lys Gly Cys Phe Gly Leu Lys Leu Asp Arg Ile Gly Ser
1               5                   10                  15

Met Ser Gly Leu Gly Cys Pro Ser Leu Arg Asp Pro Arg Pro Asn Ala
            20                  25                  30

Pro Ser Thr Ser Ala
        35

<210> SEQ ID NO 41
<211> LENGTH: 31
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 41

Glu Ala Glu Asp Leu Gln Val Gly Gln Val Glu Leu Gly Gly Gly Pro
1               5                   10                  15

Gly Ala Gly Ser Leu Gln Pro Leu Ala Leu Glu Gly Ser Leu Gln
            20                  25                  30

<210> SEQ ID NO 42
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 42

Asn Leu Gly Val
1

<210> SEQ ID NO 43
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: Tyr(SO3)

<400> SEQUENCE: 43

Tyr Met Gly Trp Met Asp
1               5

<210> SEQ ID NO 44
<211> LENGTH: 12
<212> TYPE: PRT
<213> ORGANISM: Artificial Sequence
<220> FEATURE:
```

```
<221> NAME/KEY: source
<223> OTHER INFORMATION: /note="Description of Artificial Sequence:
      Synthetic peptide"

<400> SEQUENCE: 44

Thr Tyr Ile Cys Glu Val Glu Asp Gln Lys Glu Glu
1               5                   10

<210> SEQ ID NO 45
<211> LENGTH: 180
<212> TYPE: PRT
<213> ORGANISM: Homo sapiens

<400> SEQUENCE: 45

Met Gly Ile Pro Met Gly Lys Ser Met Leu Val Leu Leu Thr Phe Leu
1               5                   10                  15

Ala Phe Ala Ser Cys Cys Ile Ala Ala Tyr Arg Pro Ser Glu Thr Leu
                20                  25                  30

Cys Gly Gly Glu Leu Val Asp Thr Leu Gln Phe Val Cys Gly Asp Arg
            35                  40                  45

Gly Phe Tyr Phe Ser Arg Pro Ala Ser Arg Val Ser Arg Arg Ser Arg
        50                  55                  60

Gly Ile Val Glu Glu Cys Cys Phe Arg Ser Cys Asp Leu Ala Leu Leu
65                  70                  75                  80

Glu Thr Tyr Cys Ala Thr Pro Ala Lys Ser Glu Arg Asp Val Ser Thr
                85                  90                  95

Pro Pro Thr Val Leu Pro Asp Asn Phe Pro Arg Tyr Pro Val Gly Lys
            100                 105                 110

Phe Phe Gln Tyr Asp Thr Trp Lys Gln Ser Thr Gln Arg Leu Arg Arg
        115                 120                 125

Gly Leu Pro Ala Leu Leu Arg Ala Arg Arg Gly His Val Leu Ala Lys
130                 135                 140

Glu Leu Glu Ala Phe Arg Glu Ala Lys Arg His Arg Pro Leu Ile Ala
145                 150                 155                 160

Leu Pro Thr Gln Asp Pro Ala His Gly Gly Ala Pro Pro Glu Met Ala
                165                 170                 175

Ser Asn Arg Lys
            180

<210> SEQ ID NO 46
<211> LENGTH: 37
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: misc_feature
<222> LOCATION: (37)..(37)
<223> OTHER INFORMATION: /note="C-term amidated"

<400> SEQUENCE: 46

Ala Cys Asp Thr Ala Thr Cys Val Thr His Arg Leu Ala Gly Leu Leu
1               5                   10                  15

Ser Arg Ser Gly Gly Val Val Lys Asn Asn Phe Val Pro Thr Asn Val
                20                  25                  30

Gly Ser Lys Ala Phe
            35

<210> SEQ ID NO 47
```

```
<211> LENGTH: 622
<212> TYPE: PRT
<213> ORGANISM: Homo sapiens

<400> SEQUENCE: 47
```

| | | | | | | | | | | | | | | |
|---|---|---|---|---|---|---|---|---|---|---|---|---|---|---|
| Met | Ala | His | Val | Arg | Gly | Leu | Gln | Leu | Pro | Gly | Cys | Leu | Ala | Leu |
| 1 | | | | 5 | | | | | 10 | | | | | 15 |
| Ala | Ala | Leu | Cys | Ser | Leu | Val | His | Ser | Gln | His | Val | Phe | Leu | Ala | Pro | Gln |
| | | | 20 | | | | | 25 | | | | | 30 | | | |
| Gln | Ala | Arg | Ser | Leu | Leu | Gln | Arg | Val | Arg | Arg | Ala | Asn | Thr | Phe | Leu |
| | | 35 | | | | | 40 | | | | | 45 | | | |
| Glu | Glu | Val | Arg | Lys | Gly | Asn | Leu | Glu | Arg | Glu | Cys | Val | Glu | Glu | Thr |
| 50 | | | | | 55 | | | | | 60 | | | | | |
| Cys | Ser | Tyr | Glu | Glu | Ala | Phe | Glu | Ala | Leu | Glu | Ser | Ser | Thr | Ala | Thr |
| 65 | | | | | 70 | | | | | 75 | | | | | 80 |
| Asp | Val | Phe | Trp | Ala | Lys | Tyr | Thr | Ala | Cys | Glu | Thr | Ala | Arg | Thr | Pro |
| | | | | 85 | | | | | 90 | | | | | 95 | |
| Arg | Asp | Lys | Leu | Ala | Ala | Cys | Leu | Glu | Gly | Asn | Cys | Ala | Glu | Gly | Leu |
| | | | 100 | | | | | 105 | | | | | 110 | | |
| Gly | Thr | Asn | Tyr | Arg | Gly | His | Val | Asn | Ile | Thr | Arg | Ser | Gly | Ile | Glu |
| | | 115 | | | | | 120 | | | | | 125 | | | |
| Cys | Gln | Leu | Trp | Arg | Ser | Arg | Tyr | Pro | His | Lys | Pro | Glu | Ile | Asn | Ser |
| 130 | | | | | 135 | | | | | 140 | | | | | |
| Thr | Thr | His | Pro | Gly | Ala | Asp | Leu | Gln | Glu | Asn | Phe | Cys | Arg | Asn | Pro |
| 145 | | | | | 150 | | | | | 155 | | | | | 160 |
| Asp | Ser | Ser | Thr | Thr | Gly | Pro | Trp | Cys | Tyr | Thr | Thr | Asp | Pro | Thr | Val |
| | | | | 165 | | | | | 170 | | | | | 175 | |
| Arg | Arg | Gln | Glu | Cys | Ser | Ile | Pro | Val | Cys | Gly | Gln | Asp | Gln | Val | Thr |
| | | | 180 | | | | | 185 | | | | | 190 | | |
| Val | Ala | Met | Thr | Pro | Arg | Ser | Glu | Gly | Ser | Ser | Val | Asn | Leu | Ser | Pro |
| | | 195 | | | | | 200 | | | | | 205 | | | |
| Pro | Leu | Glu | Gln | Cys | Val | Pro | Asp | Arg | Gly | Gln | Gln | Tyr | Gln | Gly | Arg |
| 210 | | | | | 215 | | | | | 220 | | | | | |
| Leu | Ala | Val | Thr | Thr | His | Gly | Leu | Pro | Cys | Leu | Ala | Trp | Ala | Ser | Ala |
| 225 | | | | | 230 | | | | | 235 | | | | | 240 |
| Gln | Ala | Lys | Ala | Leu | Ser | Lys | His | Gln | Asp | Phe | Asn | Ser | Ala | Val | Gln |
| | | | | 245 | | | | | 250 | | | | | 255 | |
| Leu | Val | Glu | Asn | Phe | Cys | Arg | Asn | Pro | Asp | Gly | Asp | Glu | Glu | Gly | Val |
| | | | 260 | | | | | 265 | | | | | 270 | | |
| Trp | Cys | Tyr | Val | Ala | Gly | Lys | Pro | Gly | Asp | Phe | Gly | Tyr | Cys | Asp | Leu |
| | | 275 | | | | | 280 | | | | | 285 | | | |
| Asn | Tyr | Cys | Glu | Glu | Ala | Val | Glu | Glu | Glu | Thr | Gly | Asp | Gly | Leu | Asp |
| | 290 | | | | | 295 | | | | | 300 | | | | |
| Glu | Asp | Ser | Asp | Arg | Ala | Ile | Glu | Gly | Arg | Thr | Ala | Thr | Ser | Glu | Tyr |
| 305 | | | | | 310 | | | | | 315 | | | | | 320 |
| Gln | Thr | Phe | Phe | Asn | Pro | Arg | Thr | Phe | Gly | Ser | Gly | Glu | Ala | Asp | Cys |
| | | | | 325 | | | | | 330 | | | | | 335 | |
| Gly | Leu | Arg | Pro | Leu | Phe | Glu | Lys | Lys | Ser | Leu | Glu | Asp | Lys | Thr | Glu |
| | | | 340 | | | | | 345 | | | | | 350 | | |
| Arg | Glu | Leu | Leu | Glu | Ser | Tyr | Ile | Asp | Gly | Arg | Ile | Val | Glu | Gly | Ser |
| | | 355 | | | | | 360 | | | | | 365 | | | |
| Asp | Ala | Glu | Ile | Gly | Met | Ser | Pro | Trp | Gln | Val | Met | Leu | Phe | Arg | Lys |
| | 370 | | | | | 375 | | | | | 380 | | | | |
| Ser | Pro | Gln | Glu | Leu | Leu | Cys | Gly | Ala | Ser | Leu | Ile | Ser | Asp | Arg | Trp |
| 385 | | | | | 390 | | | | | 395 | | | | | 400 |

```
Val Leu Thr Ala Ala His Cys Leu Leu Tyr Pro Pro Trp Asp Lys Asn
            405                 410                 415

Phe Thr Glu Asn Asp Leu Leu Val Arg Ile Gly Lys His Ser Arg Thr
            420                 425                 430

Arg Tyr Glu Arg Asn Ile Glu Lys Ile Ser Met Leu Glu Lys Ile Tyr
            435                 440                 445

Ile His Pro Arg Tyr Asn Trp Arg Glu Asn Leu Asp Arg Asp Ile Ala
            450                 455                 460

Leu Met Lys Leu Lys Lys Pro Val Ala Phe Ser Asp Tyr Ile His Pro
465                 470                 475                 480

Val Cys Leu Pro Asp Arg Glu Thr Ala Ala Ser Leu Leu Gln Ala Gly
            485                 490                 495

Tyr Lys Gly Arg Val Thr Gly Trp Gly Asn Leu Lys Glu Thr Trp Thr
            500                 505                 510

Ala Asn Val Gly Lys Gly Gln Pro Ser Val Leu Gln Val Val Asn Leu
            515                 520                 525

Pro Ile Val Glu Arg Pro Val Cys Lys Asp Ser Thr Arg Ile Arg Ile
            530                 535                 540

Thr Asp Asn Met Phe Cys Ala Gly Tyr Lys Pro Asp Glu Gly Lys Arg
545                 550                 555                 560

Gly Asp Ala Cys Glu Gly Asp Ser Gly Gly Pro Phe Val Met Lys Ser
            565                 570                 575

Pro Phe Asn Asn Arg Trp Tyr Gln Met Gly Ile Val Ser Trp Gly Glu
            580                 585                 590

Gly Cys Asp Arg Asp Gly Lys Tyr Gly Phe Tyr Thr His Val Phe Arg
            595                 600                 605

Leu Lys Lys Trp Ile Gln Lys Val Ile Asp Gln Phe Gly Glu
            610                 615                 620

<210> SEQ ID NO 48
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (8)..(8)
<223> OTHER INFORMATION: Alpha-Asp
<220> FEATURE:
<221> NAME/KEY: MOD_RES
<222> LOCATION: (14)..(14)
<223> OTHER INFORMATION: Alpha-Glu

<400> SEQUENCE: 48

Leu Gln Asn Arg Arg Gly Leu Asp Leu Leu Phe Leu Lys Glu Gly Gly
1               5                   10                  15

<210> SEQ ID NO 49
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 49

Thr Thr Ser Gln Val Arg Pro
1               5
```

```
<210> SEQ ID NO 50
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (7)..(7)
<223> OTHER INFORMATION: Penicillaminyl-Thr

<400> SEQUENCE: 50

Phe Cys Tyr Trp Arg Thr Thr
1               5

<210> SEQ ID NO 51
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 51

Cys Val Phe Met
1

<210> SEQ ID NO 52
<211> LENGTH: 32
<212> TYPE: PRT
<213> ORGANISM: Homo sapiens

<400> SEQUENCE: 52

Cys Gly Asn Leu Ser Thr Cys Met Leu Gly Thr Tyr Thr Gln Asp Phe
1               5                   10                  15

Asn Lys Phe His Thr Phe Pro Gln Thr Ala Ile Gly Val Gly Ala Pro
            20                  25                  30

<210> SEQ ID NO 53
<211> LENGTH: 32
<212> TYPE: PRT
<213> ORGANISM: Salmo salar
<220> FEATURE:
<221> NAME/KEY: misc_feature
<222> LOCATION: (32)..(32)
<223> OTHER INFORMATION: /note="C-term amidated"

<400> SEQUENCE: 53

Cys Ser Asn Leu Ser Thr Cys Val Leu Gly Lys Leu Ser Gln Glu Leu
1               5                   10                  15

His Lys Leu Gln Thr Tyr Pro Arg Thr Asn Thr Gly Ser Gly Thr Pro
            20                  25                  30

<210> SEQ ID NO 54
<211> LENGTH: 60
<212> TYPE: PRT
<213> ORGANISM: Dendroaspis polylepis polylepis

<400> SEQUENCE: 54

Arg Ile Cys Tyr Ile His Lys Ala Ser Leu Pro Arg Ala Thr Lys Thr
1               5                   10                  15

Cys Val Glu Asn Thr Cys Tyr Lys Met Phe Ile Arg Thr Gln Arg Glu
            20                  25                  30
```

Tyr Ile Ser Glu Arg Gly Cys Gly Cys Pro Thr Ala Met Trp Pro Tyr
                35                  40                  45

Gln Thr Glu Cys Cys Lys Gly Asp Arg Cys Asn Lys
 50                  55                  60

<210> SEQ ID NO 55
<211> LENGTH: 320
<212> TYPE: PRT
<213> ORGANISM: Homo sapiens

<400> SEQUENCE: 55

Met Ala Gln Val Leu Arg Gly Thr Val Thr Asp Phe Pro Gly Phe Asp
 1               5                  10                  15

Glu Arg Ala Asp Ala Glu Thr Leu Arg Lys Ala Met Lys Gly Leu Gly
                20                  25                  30

Thr Asp Glu Glu Ser Ile Leu Thr Leu Leu Thr Ser Arg Ser Asn Ala
            35                  40                  45

Gln Arg Gln Glu Ile Ser Ala Ala Phe Lys Thr Leu Phe Gly Arg Asp
 50                  55                  60

Leu Leu Asp Asp Leu Lys Ser Glu Leu Thr Gly Lys Phe Glu Lys Leu
65                  70                  75                  80

Ile Val Ala Leu Met Lys Pro Ser Arg Leu Tyr Asp Ala Tyr Glu Leu
                85                  90                  95

Lys His Ala Leu Lys Gly Ala Gly Thr Asn Glu Lys Val Leu Thr Glu
            100                 105                 110

Ile Ile Ala Ser Arg Thr Pro Glu Glu Leu Arg Ala Ile Lys Gln Val
        115                 120                 125

Tyr Glu Glu Glu Tyr Gly Ser Ser Leu Glu Asp Asp Val Val Gly Asp
130                 135                 140

Thr Ser Gly Tyr Tyr Gln Arg Met Leu Val Val Leu Leu Gln Ala Asn
145                 150                 155                 160

Arg Asp Pro Asp Ala Gly Ile Asp Glu Ala Gln Val Glu Gln Asp Ala
                165                 170                 175

Gln Ala Leu Phe Gln Ala Gly Glu Leu Lys Trp Gly Thr Asp Glu Glu
            180                 185                 190

Lys Phe Ile Thr Ile Phe Gly Thr Arg Ser Val Ser His Leu Arg Lys
        195                 200                 205

Val Phe Asp Lys Tyr Met Thr Ile Ser Gly Phe Gln Ile Glu Glu Thr
    210                 215                 220

Ile Asp Arg Glu Thr Ser Gly Asn Leu Glu Gln Leu Leu Leu Ala Val
225                 230                 235                 240

Val Lys Ser Ile Arg Ser Ile Pro Ala Tyr Leu Ala Glu Thr Leu Tyr
                245                 250                 255

Tyr Ala Met Lys Gly Ala Gly Thr Asp Asp His Thr Leu Ile Arg Val
            260                 265                 270

Met Val Ser Arg Ser Glu Ile Asp Leu Phe Asn Ile Arg Lys Glu Phe
        275                 280                 285

Arg Lys Asn Phe Ala Thr Ser Leu Tyr Ser Met Ile Lys Gly Asp Thr
    290                 295                 300

Ser Gly Asp Tyr Lys Lys Ala Leu Leu Leu Leu Cys Gly Glu Asp Asp
305                 310                 315                 320

<210> SEQ ID NO 56
<211> LENGTH: 31
<212> TYPE: PRT
<213> ORGANISM: Sus scrofa

```
<400> SEQUENCE: 56

Ser Trp Leu Ser Lys Thr Ala Lys Lys Leu Glu Asn Ser Ala Lys Lys
1               5                   10                  15

Arg Ile Ser Glu Gly Ile Ala Ile Ala Ile Gln Gly Gly Pro Arg
            20                  25                  30

<210> SEQ ID NO 57
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (3)..(3)
<223> OTHER INFORMATION: N-methyl-Val
<220> FEATURE:
<221> NAME/KEY: misc_feature
<222> LOCATION: (5)..(5)
<223> OTHER INFORMATION: /note="C-term amidated"

<400> SEQUENCE: 57

Val Val Val Pro Pro
1               5

<210> SEQ ID NO 58
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: Pyro-Glu
<220> FEATURE:
<221> NAME/KEY: MOD_RES
<222> LOCATION: (4)..(4)
<223> OTHER INFORMATION: Tyr(SO3H)
<220> FEATURE:
<221> NAME/KEY: misc_feature
<222> LOCATION: (10)..(10)
<223> OTHER INFORMATION: /note="C-term amidated"

<400> SEQUENCE: 58

Glu Gln Asp Tyr Thr Gly Trp Met Asp Phe
1               5                   10

<210> SEQ ID NO 59
<211> LENGTH: 41
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 59

Ser Gln Glu Pro Pro Ile Ser Leu Asp Leu Thr Phe His Leu Leu Arg
1               5                   10                  15

Glu Val Leu Glu Met Thr Lys Ala Asp Gln Leu Ala Gln Gln Ala His
            20                  25                  30

Ser Asn Arg Lys Leu Leu Asp Ile Ala
                35                  40
```

```
<210> SEQ ID NO 60
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: Beta-Ala

<400> SEQUENCE: 60

Ala Arg Gly Phe Phe
1               5

<210> SEQ ID NO 61
<211> LENGTH: 41
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: MOD_RES
<222> LOCATION: (26)..(26)
<223> OTHER INFORMATION: Alph-Glu

<400> SEQUENCE: 61

Met Thr Leu Thr Val Gln Ala Arg Gln Leu Leu Ser Gln Ile Val Gln
1               5                   10                  15

Gln Gln Asn Asn Leu Leu Arg Ala Ile Glu Ala Gln Gln His Leu Leu
            20                  25                  30

Gln Leu Thr Val Trp Gly Ile Lys Gln
        35                  40

<210> SEQ ID NO 62
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 62

Arg Gly Asp Ser
1

<210> SEQ ID NO 63
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 63

Tyr Gly Gly Phe Leu Arg Arg Ile Arg Pro Lys Leu Lys Trp Asp Asn
1               5                   10                  15

Gln

<210> SEQ ID NO 64
<211> LENGTH: 94
<212> TYPE: PRT
```

<213> ORGANISM: Homo sapiens

<400> SEQUENCE: 64

Met Arg Thr Leu Ala Ile Leu Ala Ala Ile Leu Val Ala Leu Gln
1               5                   10                  15

Ala Gln Ala Glu Pro Leu Gln Ala Arg Ala Asp Glu Val Ala Ala
            20                  25                  30

Pro Glu Gln Ile Ala Ala Asp Ile Pro Glu Val Val Val Ser Leu Ala
        35                  40                  45

Trp Asp Glu Ser Leu Ala Pro Lys His Pro Gly Ser Arg Lys Asn Met
    50                  55                  60

Asp Cys Tyr Cys Arg Ile Pro Ala Cys Ile Ala Gly Glu Arg Arg Tyr
65                  70                  75                  80

Gly Thr Cys Ile Tyr Gln Gly Arg Leu Trp Ala Phe Cys Cys
                85                  90

<210> SEQ ID NO 65
<211> LENGTH: 60
<212> TYPE: PRT
<213> ORGANISM: Ornithodoros moubata

<400> SEQUENCE: 65

Ser Asp Asp Lys Cys Gln Gly Arg Pro Met Tyr Gly Cys Arg Glu Asp
1               5                   10                  15

Asp Asp Ser Val Phe Gly Trp Thr Tyr Asp Ser Asn His Gly Gln Cys
            20                  25                  30

Trp Lys Gly Ser Tyr Cys Lys His Arg Arg Gln Pro Ser Asn Tyr Phe
        35                  40                  45

Ala Ser Gln Gln Glu Cys Arg Asn Thr Cys Gly Ala
    50                  55                  60

<210> SEQ ID NO 66
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (7)..(7)
<223> OTHER INFORMATION: N2-methyl-Arg

<400> SEQUENCE: 66

Tyr Gly Gly Phe Leu Arg Arg
1               5

<210> SEQ ID NO 67
<211> LENGTH: 60
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 67

Glu Ala Met His Ser Phe Cys Ala Phe Lys Ala Asp Asp Gly Pro Cys
1               5                   10                  15

Arg Ala Ala His Pro Arg Trp Phe Phe Asn Ile Phe Thr Arg Gln Cys
            20                  25                  30

Glu Glu Phe Ile Tyr Gly Gly Cys Glu Gly Asn Gln Asn Arg Phe Glu

```
                35                  40                  45
Ser Leu Glu Glu Cys Lys Lys Met Cys Thr Arg Asp
     50                  55                  60

<210> SEQ ID NO 68
<211> LENGTH: 21
<212> TYPE: PRT
<213> ORGANISM: Homo sapiens

<400> SEQUENCE: 68

Met Arg Ala Ser Ser Phe Leu Ile Val Val Phe Leu Ile Ala Gly
1               5                   10                  15

Thr Leu Val Leu Glu
            20

<210> SEQ ID NO 69
<211> LENGTH: 57
<212> TYPE: PRT
<213> ORGANISM: Homo sapiens

<400> SEQUENCE: 69

Ala Gln Glu Pro Val Lys Gly Pro Val Ser Thr Lys Pro Gly Ser Cys
1               5                   10                  15

Pro Ile Ile Leu Ile Arg Cys Ala Met Leu Asn Pro Pro Asn Arg Cys
            20                  25                  30

Leu Lys Asp Thr Asp Cys Pro Gly Ile Lys Lys Cys Cys Glu Gly Ser
        35                  40                  45

Cys Gly Met Ala Cys Phe Val Pro Gln
    50                  55

<210> SEQ ID NO 70
<211> LENGTH: 31
<212> TYPE: PRT
<213> ORGANISM: Homo sapiens
<220> FEATURE:
<221> NAME/KEY: misc_feature
<222> LOCATION: (31)..(31)
<223> OTHER INFORMATION: /note="C-term amidated"

<400> SEQUENCE: 70

Ser Asn Leu Ser Thr Asn Val Leu Gly Lys Ser Gln Glu Leu His
1               5                   10                  15

Lys Leu Gln Thr Tyr Pro Arg Thr Asn Val Gly Ala Gly Thr Pro
            20                  25                  30

<210> SEQ ID NO 71
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: 5-oxo-Pro
<220> FEATURE:
<221> NAME/KEY: misc_feature
<222> LOCATION: (12)..(12)
<223> OTHER INFORMATION: /note="C-term amidated"

<400> SEQUENCE: 71

Pro Pro Ser Lys Asp Ala Phe Ala Ile Gly Leu Met
1               5                   10
```

<210> SEQ ID NO 72
<211> LENGTH: 31
<212> TYPE: PRT
<213> ORGANISM: Homo sapiens

<400> SEQUENCE: 72

Tyr Gly Gly Phe Met Thr Ser Glu Lys Ser Gln Thr Pro Leu Val Thr
1               5                   10                  15

Leu Phe Lys Asn Ala Ile Ile Lys Asn Ala Tyr Lys Lys Gly Glu
            20                  25                  30

<210> SEQ ID NO 73
<211> LENGTH: 482
<212> TYPE: PRT
<213> ORGANISM: Homo sapiens

<400> SEQUENCE: 73

Met Ala Ala Leu Met Thr Pro Gly Thr Gly Ala Pro Pro Ala Pro Gly
1               5                   10                  15

Asp Phe Ser Gly Glu Gly Ser Gln Gly Leu Pro Asp Pro Ser Pro Glu
            20                  25                  30

Pro Lys Gln Leu Pro Glu Leu Ile Arg Met Lys Arg Asp Gly Gly Arg
        35                  40                  45

Leu Ser Glu Ala Asp Ile Arg Gly Phe Val Ala Ala Val Val Asn Gly
    50                  55                  60

Ser Ala Gln Gly Ala Gln Ile Gly Ala Met Leu Met Ala Ile Arg Leu
65                  70                  75                  80

Arg Gly Met Asp Leu Glu Glu Thr Ser Val Leu Thr Gln Ala Leu Ala
                85                  90                  95

Gln Ser Gly Gln Gln Leu Glu Trp Pro Glu Ala Trp Arg Gln Gln Leu
            100                 105                 110

Val Asp Lys His Ser Thr Gly Gly Val Gly Asp Lys Val Ser Leu Val
        115                 120                 125

Leu Ala Pro Ala Leu Ala Ala Cys Gly Cys Lys Val Pro Met Ile Ser
    130                 135                 140

Gly Arg Gly Leu Gly His Thr Gly Gly Thr Leu Asp Lys Leu Glu Ser
145                 150                 155                 160

Ile Pro Gly Phe Asn Val Ile Gln Ser Pro Glu Gln Met Gln Val Leu
                165                 170                 175

Leu Asp Gln Ala Gly Cys Cys Ile Val Gly Gln Ser Glu Gln Leu Val
            180                 185                 190

Pro Ala Asp Gly Ile Leu Tyr Ala Ala Arg Asp Val Thr Ala Thr Val
        195                 200                 205

Asp Ser Leu Pro Leu Ile Thr Ala Ser Ile Leu Ser Lys Lys Leu Val
    210                 215                 220

Glu Gly Leu Ser Ala Leu Val Val Asp Val Lys Phe Gly Gly Ala Ala
225                 230                 235                 240

Val Phe Pro Asn Gln Glu Gln Ala Arg Glu Leu Ala Lys Thr Leu Val
                245                 250                 255

Gly Val Gly Ala Ser Leu Gly Leu Arg Val Ala Ala Ala Leu Thr Ala
            260                 265                 270

Met Asp Lys Pro Leu Gly Arg Cys Val Gly His Ala Leu Glu Val Glu
        275                 280                 285

Glu Ala Leu Leu Cys Met Asp Gly Ala Gly Pro Pro Asp Leu Arg Asp
    290                 295                 300

Leu Val Thr Thr Leu Gly Gly Ala Leu Leu Trp Leu Ser Gly His Ala

-continued

```
            305                 310                 315                 320
Gly Thr Gln Ala Gln Gly Ala Ala Arg Val Ala Ala Leu Asp Asp
                325                 330                 335
Gly Ser Ala Leu Gly Arg Phe Glu Arg Met Leu Ala Ala Gln Gly Val
                340                 345                 350
Asp Pro Gly Leu Ala Arg Ala Leu Cys Ser Gly Ser Pro Ala Glu Arg
                355                 360                 365
Arg Gln Leu Leu Pro Arg Ala Arg Glu Gln Glu Leu Leu Ala Pro
                370                 375                 380
Ala Asp Gly Thr Val Glu Leu Val Arg Ala Leu Pro Leu Ala Leu Val
385                 390                 395                 400
Leu His Glu Leu Gly Ala Gly Arg Ser Arg Ala Gly Glu Pro Leu Arg
                405                 410                 415
Leu Gly Val Gly Ala Glu Leu Leu Val Asp Val Gly Gln Arg Leu Arg
                420                 425                 430
Arg Gly Thr Pro Trp Leu Arg Val His Arg Asp Gly Pro Ala Leu Ser
                435                 440                 445
Gly Pro Gln Ser Arg Ala Leu Gln Glu Ala Leu Val Leu Ser Asp Arg
                450                 455                 460
Ala Pro Phe Ala Ala Pro Ser Pro Phe Ala Glu Leu Val Leu Pro Pro
465                 470                 475                 480

Gln Gln

<210> SEQ ID NO 74
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: misc_feature
<222> LOCATION: (5)..(5)
<223> OTHER INFORMATION: /note="C-term amidated"

<400> SEQUENCE: 74

Gly Asp Trp Pro Cys
1               5

<210> SEQ ID NO 75
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 75

Gln His Asn Pro Arg
1               5

<210> SEQ ID NO 76
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 76
```

```
Gly Arg Gly Asp Ser
1               5
```

<210> SEQ ID NO 77
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 77

```
Tyr Tyr Trp Ile Gly Ile Arg
1               5
```

<210> SEQ ID NO 78
<211> LENGTH: 92
<212> TYPE: PRT
<213> ORGANISM: Homo sapiens

<400> SEQUENCE: 78

```
Met Lys Pro Ile Gln Lys Leu Leu Ala Gly Leu Ile Leu Leu Thr Trp
1               5                   10                  15

Cys Val Glu Gly Cys Ser Ser Gln His Trp Ser Tyr Gly Leu Arg Pro
            20                  25                  30

Gly Gly Lys Arg Asp Ala Glu Asn Leu Ile Asp Ser Phe Gln Glu Ile
        35                  40                  45

Val Lys Glu Val Gly Gln Leu Ala Glu Thr Gln Arg Phe Glu Cys Thr
    50                  55                  60

Thr His Gln Pro Arg Ser Pro Leu Arg Asp Leu Lys Gly Ala Leu Glu
65                  70                  75                  80

Ser Leu Ile Glu Glu Thr Gly Gln Lys Lys Ile
                85                  90
```

<210> SEQ ID NO 79
<211> LENGTH: 44
<212> TYPE: PRT
<213> ORGANISM: Homo sapiens

<400> SEQUENCE: 79

```
Met Pro Leu Trp Val Phe Phe Phe Val Ile Thr Leu Ser Asn Ser Ser
1               5                   10                  15

Ser His Cys Ser Pro Pro Pro Leu Thr Leu Arg Met Arg Arg Tyr
            20                  25                  30

Ala Asp Ala Ile Phe Thr Asn Ser Tyr Arg Lys Val
        35                  40
```

<210> SEQ ID NO 80
<211> LENGTH: 107
<212> TYPE: PRT
<213> ORGANISM: Homo sapiens

<400> SEQUENCE: 80

```
Met Pro Leu Trp Val Phe Phe Phe Val Ile Thr Leu Ser Asn Ser Ser
1               5                   10                  15

Ser His Cys Ser Pro Pro Pro Leu Thr Leu Arg Met Arg Arg Tyr
            20                  25                  30

Ala Asp Ala Ile Phe Thr Asn Ser Tyr Arg Lys Val Leu Gly Gln Leu
        35                  40                  45

Ser Ala Arg Lys Leu Leu Gln Asp Ile Met Ser Arg Gln Gln Gly Glu
    50                  55                  60
```

```
Ser Asn Gln Glu Arg Gly Ala Arg Ala Arg Leu Gly Arg Gln Val Asp
 65                  70                  75                  80

Ser Met Trp Ala Glu Gln Lys Gln Met Glu Leu Glu Ser Ile Leu Val
                 85                  90                  95

Ala Leu Leu Gln Lys His Arg Asn Ser Gln Gly
            100                 105

<210> SEQ ID NO 81
<211> LENGTH: 123
<212> TYPE: PRT
<213> ORGANISM: Homo sapiens

<400> SEQUENCE: 81

Met Ala Arg Gly Ser Ala Leu Leu Ala Ser Leu Leu Ala Ala
 1               5                  10                  15

Ala Leu Ser Ala Ser Ala Gly Leu Trp Ser Pro Ala Lys Glu Lys Arg
             20                  25                  30

Gly Trp Thr Leu Asn Ser Ala Gly Tyr Leu Leu Gly Pro His Ala Val
         35                  40                  45

Gly Asn His Arg Ser Phe Ser Asp Lys Asn Gly Leu Thr Ser Lys Arg
     50                  55                  60

Glu Leu Arg Pro Glu Asp Asp Met Lys Pro Gly Ser Phe Asp Arg Ser
 65                  70                  75                  80

Ile Pro Glu Asn Asn Ile Met Arg Thr Ile Ile Glu Phe Leu Ser Phe
                 85                  90                  95

Leu His Leu Lys Glu Ala Gly Ala Leu Asp Arg Leu Leu Asp Leu Pro
            100                 105                 110

Ala Ala Ala Ser Ser Glu Asp Ile Glu Arg Ser
        115                 120

<210> SEQ ID NO 82
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: misc_feature
<222> LOCATION: (7)..(7)
<223> OTHER INFORMATION: /note="C-term amidated"

<400> SEQUENCE: 82

Glu Ala Tyr Gly Tyr Met Asp
 1               5

<210> SEQ ID NO 83
<211> LENGTH: 180
<212> TYPE: PRT
<213> ORGANISM: Homo sapiens

<400> SEQUENCE: 83

Met Lys Ser Ile Tyr Phe Val Ala Gly Leu Phe Val Met Leu Val Gln
 1               5                  10                  15

Gly Ser Trp Gln Arg Ser Leu Gln Asp Thr Glu Glu Lys Ser Arg Ser
             20                  25                  30

Phe Ser Ala Ser Gln Ala Asp Pro Leu Ser Asp Pro Asp Gln Met Asn
         35                  40                  45

Glu Asp Lys Arg His Ser Gln Gly Thr Phe Thr Ser Asp Tyr Ser Lys
     50                  55                  60
```

```
Tyr Leu Asp Ser Arg Arg Ala Gln Asp Phe Val Gln Trp Leu Met Asn
 65                  70                  75                  80

Thr Lys Arg Asn Arg Asn Ile Ala Lys Arg His Asp Glu Phe Glu
                 85                  90                  95

Arg His Ala Glu Gly Thr Phe Thr Ser Asp Val Ser Ser Tyr Leu Glu
            100                 105                 110

Gly Gln Ala Ala Lys Glu Phe Ile Ala Trp Leu Val Lys Gly Arg Gly
        115                 120                 125

Arg Arg Asp Phe Pro Glu Glu Val Ala Ile Val Glu Glu Leu Gly Arg
    130                 135                 140

Arg His Ala Asp Gly Ser Phe Ser Asp Glu Met Asn Thr Ile Leu Asp
145                 150                 155                 160

Asn Leu Ala Ala Arg Asp Phe Ile Asn Trp Leu Ile Gln Thr Lys Ile
                165                 170                 175

Thr Asp Arg Lys
            180

<210> SEQ ID NO 84
<211> LENGTH: 29
<212> TYPE: PRT
<213> ORGANISM: Homo sapiens

<400> SEQUENCE: 84

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr
            20                  25

<210> SEQ ID NO 85
<211> LENGTH: 92
<212> TYPE: PRT
<213> ORGANISM: Homo sapiens

<400> SEQUENCE: 85

Met Lys Pro Ile Gln Lys Leu Leu Ala Gly Leu Ile Leu Leu Thr Trp
1               5                   10                  15

Cys Val Glu Gly Cys Ser Ser Gln His Trp Ser Tyr Gly Leu Arg Pro
            20                  25                  30

Gly Gly Lys Arg Asp Ala Glu Asn Leu Ile Asp Ser Phe Gln Glu Ile
        35                  40                  45

Val Lys Glu Val Gly Gln Leu Ala Glu Thr Gln Arg Phe Glu Cys Thr
    50                  55                  60

Thr His Gln Pro Arg Ser Pro Leu Arg Asp Leu Lys Gly Ala Leu Glu
65                  70                  75                  80

Ser Leu Ile Glu Glu Glu Thr Gly Gln Lys Lys Ile
                85                  90

<210> SEQ ID NO 86
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: 5-oxo-His
<220> FEATURE:
<221> NAME/KEY: misc_feature
```

<222> LOCATION: (9)..(9)
<223> OTHER INFORMATION: /note="C-term amidated"

<400> SEQUENCE: 86

His Trp Ser Tyr Gly Leu Arg Pro Gly
1               5

<210> SEQ ID NO 87
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 87

Arg Gly Gly Leu Cys Tyr Cys Arg Gly Arg Phe Cys Val Cys Val Gly
1               5                   10                  15

<210> SEQ ID NO 88
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (2)..(2)
<223> OTHER INFORMATION: (4R)-4-hydroxy-Pro

<400> SEQUENCE: 88

Phe Pro Arg Gly
1

<210> SEQ ID NO 89
<211> LENGTH: 140
<212> TYPE: PRT
<213> ORGANISM: Homo sapiens

<400> SEQUENCE: 89

Met Gly Phe Gln Lys Phe Ser Pro Phe Leu Ala Leu Ser Ile Leu Val
1               5                   10                  15

Leu Leu Gln Ala Gly Ser Leu His Ala Ala Pro Phe Arg Ser Ala Leu
            20                  25                  30

Glu Ser Ser Pro Ala Asp Pro Ala Thr Leu Ser Glu Asp Glu Ala Arg
        35                  40                  45

Leu Leu Leu Ala Ala Leu Val Gln Asp Tyr Val Gln Met Lys Ala Ser
    50                  55                  60

Glu Leu Glu Gln Glu Gln Glu Arg Glu Gly Ser Ser Leu Asp Ser Pro
65                  70                  75                  80

Arg Ser Lys Arg Cys Gly Asn Leu Ser Thr Cys Met Leu Gly Thr Tyr
                85                  90                  95

Thr Gln Asp Phe Asn Lys Phe His Thr Phe Pro Gln Thr Ala Ile Gly
            100                 105                 110

Val Gly Ala Pro Gly Lys Lys Arg Asp Met Ser Ser Asp Leu Glu Arg
        115                 120                 125

Asp His Arg Pro His Val Ser Met Pro Gln Ala Asn
    130                 135                 140

<210> SEQ ID NO 90
<211> LENGTH: 5

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 90

Arg Met Phe Arg Tyr
1               5

<210> SEQ ID NO 91
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (6)..(6)
<223> OTHER INFORMATION: (3S,4S)-4-amino-5-cyclohexyl-3-hydroxypentanoic
      acid
<220> FEATURE:
<221> NAME/KEY: misc_feature
<222> LOCATION: (8)..(8)
<223> OTHER INFORMATION: /note=C-term amidated"

<400> SEQUENCE: 91

Val His Pro Phe His Xaa Leu Phe
1               5

<210> SEQ ID NO 92
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (3)..(3)
<223> OTHER INFORMATION: Alpha-Asp

<400> SEQUENCE: 92

Phe Leu Asp Val Pro Ala Ala Lys
1               5

<210> SEQ ID NO 93
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 93

Pro Val Thr Lys Pro Gln
1               5

<210> SEQ ID NO 94
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
```

```
<221> NAME/KEY: misc_feature
<222> LOCATION: (6)..(6)
<223> OTHER INFORMATION: /note="C-term amidated"

<400> SEQUENCE: 94

Ser Ile Lys Val Ala Val
1               5

<210> SEQ ID NO 95
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 95

Tyr Ile Gly Ser Arg
1               5

<210> SEQ ID NO 96
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 96

Ile Leu Arg Trp Pro Trp Trp Pro Trp Arg Arg
1               5                   10

<210> SEQ ID NO 97
<211> LENGTH: 304
<212> TYPE: PRT
<213> ORGANISM: Homo sapiens

<400> SEQUENCE: 97

Met Gly Asn His Ala Gly Lys Arg Glu Leu Asn Ala Glu Lys Ala Ser
1               5                   10                  15

Thr Asn Ser Glu Thr Asn Arg Gly Glu Ser Glu Lys Lys Arg Asn Leu
            20                  25                  30

Gly Glu Leu Ser Arg Thr Thr Ser Glu Asp Asn Glu Val Phe Gly Glu
        35                  40                  45

Ala Asp Ala Asn Gln Asn Asn Gly Thr Ser Ser Gln Asp Thr Ala Val
    50                  55                  60

Thr Asp Ser Lys Arg Thr Ala Asp Pro Lys Asn Ala Trp Gln Asp Ala
65                  70                  75                  80

His Pro Ala Asp Pro Gly Ser Arg Pro His Leu Ile Arg Leu Phe Ser
            85                  90                  95

Arg Asp Ala Pro Gly Arg Glu Asp Asn Thr Phe Lys Asp Arg Pro Ser
        100                 105                 110

Glu Ser Asp Glu Leu Gln Thr Ile Gln Glu Asp Ser Ala Ala Thr Ser
    115                 120                 125

Glu Ser Leu Asp Val Met Ala Ser Gln Lys Arg Pro Ser Gln Arg His
130                 135                 140

Gly Ser Lys Tyr Leu Ala Thr Ala Ser Thr Met Asp His Ala Arg His
145                 150                 155                 160

Gly Phe Leu Pro Arg His Arg Asp Thr Gly Ile Leu Asp Ser Ile Gly
                165                 170                 175
```

```
Arg Phe Phe Gly Gly Asp Arg Gly Ala Pro Lys Arg Gly Ser Gly Lys
            180                 185                 190

Asp Ser His His Pro Ala Arg Thr Ala His Tyr Gly Ser Leu Pro Gln
            195                 200                 205

Lys Ser His Gly Arg Thr Gln Asp Glu Asn Pro Val Val His Phe Phe
            210                 215                 220

Lys Asn Ile Val Thr Pro Arg Thr Pro Pro Ser Gln Gly Lys Gly
225                 230                 235                 240

Arg Gly Leu Ser Leu Ser Arg Phe Ser Trp Gly Ala Glu Gly Gln Arg
            245                 250                 255

Pro Gly Phe Gly Tyr Gly Gly Arg Ala Ser Asp Tyr Lys Ser Ala His
            260                 265                 270

Lys Gly Phe Lys Gly Val Asp Ala Gln Gly Thr Leu Ser Lys Ile Phe
            275                 280                 285

Lys Leu Gly Gly Arg Asp Ser Arg Ser Gly Ser Pro Met Ala Arg Arg
            290                 295                 300
```

<210> SEQ ID NO 98
<211> LENGTH: 197
<212> TYPE: PRT
<213> ORGANISM: Homo sapiens

<400> SEQUENCE: 98

```
Met Gly Asn His Ala Gly Lys Arg Glu Leu Asn Ala Glu Lys Ala Ser
1               5                   10                  15

Thr Asn Ser Glu Thr Asn Arg Gly Glu Ser Glu Lys Lys Arg Asn Leu
            20                  25                  30

Gly Glu Leu Ser Arg Thr Thr Ser Glu Asp Asn Glu Val Phe Gly Glu
        35                  40                  45

Ala Asp Ala Asn Gln Asn Asn Gly Thr Ser Ser Gln Asp Thr Ala Val
    50                  55                  60

Thr Asp Ser Lys Arg Thr Ala Asp Pro Lys Asn Ala Trp Gln Asp Ala
65                  70                  75                  80

His Pro Ala Asp Pro Gly Ser Arg Pro His Leu Ile Arg Leu Phe Ser
            85                  90                  95

Arg Asp Ala Pro Gly Arg Glu Asp Asn Thr Phe Lys Asp Arg Pro Ser
            100                 105                 110

Glu Ser Asp Glu Leu Gln Thr Ile Gln Glu Asp Ser Ala Ala Thr Ser
            115                 120                 125

Glu Ser Leu Asp Val Met Ala Ser Gln Lys Arg Pro Ser Gln Arg His
        130                 135                 140

Gly Ser Lys Tyr Leu Ala Thr Ala Ser Thr Met Asp His Ala Arg His
145                 150                 155                 160

Gly Phe Leu Pro Arg His Arg Asp Thr Gly Ile Leu Asp Ser Ile Gly
            165                 170                 175

Arg Phe Phe Gly Gly Asp Arg Gly Ala Pro Lys Arg Gly Ser Gly Lys
            180                 185                 190

Val Ser Ser Glu Glu
        195
```

<210> SEQ ID NO 99
<211> LENGTH: 197
<212> TYPE: PRT
<213> ORGANISM: Homo sapiens

<400> SEQUENCE: 99

Met Ala Ser Gln Lys Arg Pro Ser Gln Arg His Gly Ser Lys Tyr Leu

```
                1               5                  10                  15
Ala Thr Ala Ser Thr Met Asp His Ala Arg His Gly Phe Leu Pro Arg
                20                  25                  30

His Arg Asp Thr Gly Ile Leu Asp Ser Ile Gly Arg Phe Phe Gly Gly
            35                  40                  45

Asp Arg Gly Ala Pro Lys Arg Gly Ser Gly Lys Val Pro Trp Leu Lys
50                  55                  60

Pro Gly Arg Ser Pro Leu Pro Ser His Ala Arg Ser Gln Pro Gly Leu
65                  70                  75                  80

Cys Asn Met Tyr Lys Asp Ser His His Pro Ala Arg Thr Ala His Tyr
                85                  90                  95

Gly Ser Leu Pro Gln Lys Ser His Gly Arg Thr Gln Asp Glu Asn Pro
                100                 105                 110

Val Val His Phe Phe Lys Asn Ile Val Thr Pro Arg Thr Pro Pro Pro
                115                 120                 125

Ser Gln Gly Lys Gly Arg Gly Leu Ser Leu Ser Arg Phe Ser Trp Gly
                130                 135                 140

Ala Glu Gly Gln Arg Pro Gly Phe Gly Tyr Gly Gly Arg Ala Ser Asp
145                 150                 155                 160

Tyr Lys Ser Ala His Lys Gly Phe Lys Gly Val Asp Ala Gln Gly Thr
                165                 170                 175

Leu Ser Lys Ile Phe Lys Leu Gly Gly Arg Asp Ser Arg Ser Gly Ser
                180                 185                 190

Pro Met Ala Arg Arg
        195
```

<210> SEQ ID NO 100
<211> LENGTH: 22
<212> TYPE: PRT
<213> ORGANISM: Homo sapiens

<400> SEQUENCE: 100

```
Met Ala Ser Gln Lys Arg Pro Ser Gln Arg His Gly Ser Lys Tyr Leu
1               5                   10                  15

Ala Thr Ala Ser Thr Met
            20
```

<210> SEQ ID NO 101
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 101

```
Gly Pro Leu Ala
1
```

<210> SEQ ID NO 102
<211> LENGTH: 4
<212> TYPE: PRT
<213> ORGANISM: Homo sapiens

<400> SEQUENCE: 102

```
Asn Ala Gly Ala
1
```

<210> SEQ ID NO 103

<211> LENGTH: 487
<212> TYPE: PRT
<213> ORGANISM: Homo sapiens

<400> SEQUENCE: 103

```
Met Arg Glu Asn Met Ala Arg Gly Pro Cys Asn Ala Pro Arg Trp Ala
1               5                   10                  15

Ser Leu Met Val Leu Val Ala Ile Gly Thr Ala Val Thr Ala Ala Val
            20                  25                  30

Asn Pro Gly Val Val Arg Ile Ser Gln Lys Gly Leu Asp Tyr Ala
        35                  40                  45

Ser Gln Gln Gly Thr Ala Ala Leu Gln Lys Glu Leu Lys Arg Ile Lys
50                  55                  60

Ile Pro Asp Tyr Ser Asp Ser Phe Lys Ile Lys His Leu Gly Lys Gly
65                  70                  75                  80

His Tyr Ser Phe Tyr Ser Met Asp Ile Arg Glu Phe Gln Leu Pro Ser
                85                  90                  95

Ser Gln Ile Ser Met Val Pro Asn Val Gly Leu Lys Phe Ser Ile Ser
            100                 105                 110

Asn Ala Asn Ile Lys Ile Ser Gly Lys Trp Lys Ala Gln Lys Arg Phe
        115                 120                 125

Leu Lys Met Ser Gly Asn Phe Asp Leu Ser Ile Glu Gly Met Ser Ile
130                 135                 140

Ser Ala Asp Leu Lys Leu Gly Ser Asn Pro Thr Ser Gly Lys Pro Thr
145                 150                 155                 160

Ile Thr Cys Ser Ser Cys Ser Ser His Ile Asn Ser Val His Val His
                165                 170                 175

Ile Ser Lys Ser Lys Val Gly Trp Leu Ile Gln Leu Phe His Lys Lys
            180                 185                 190

Ile Glu Ser Ala Leu Arg Asn Lys Met Asn Ser Gln Val Cys Glu Lys
        195                 200                 205

Val Thr Asn Ser Val Ser Ser Glu Leu Gln Pro Tyr Phe Gln Thr Leu
210                 215                 220

Pro Val Met Thr Lys Ile Asp Ser Val Ala Gly Ile Asn Tyr Gly Leu
225                 230                 235                 240

Val Ala Pro Pro Ala Thr Thr Ala Glu Thr Leu Asp Val Gln Met Lys
                245                 250                 255

Gly Glu Phe Tyr Ser Glu Asn His His Asn Pro Pro Phe Ala Pro
            260                 265                 270

Pro Val Met Glu Phe Pro Ala Ala His Asp Arg Met Val Tyr Leu Gly
        275                 280                 285

Leu Ser Asp Tyr Phe Phe Asn Thr Ala Gly Leu Val Tyr Gln Glu Ala
290                 295                 300

Gly Val Leu Lys Met Thr Leu Arg Asp Asp Met Ile Pro Lys Glu Ser
305                 310                 315                 320

Lys Phe Arg Leu Thr Thr Lys Phe Phe Gly Thr Phe Leu Pro Glu Val
                325                 330                 335

Ala Lys Lys Phe Pro Asn Met Lys Ile Gln Ile His Val Ser Ala Ser
            340                 345                 350

Thr Pro Pro His Leu Ser Val Gln Pro Thr Gly Leu Thr Phe Tyr Pro
        355                 360                 365

Ala Val Asp Val Gln Ala Phe Ala Val Leu Pro Asn Ser Ser Leu Ala
370                 375                 380

Ser Leu Phe Leu Ile Gly Met His Thr Thr Gly Ser Met Glu Val Ser
385                 390                 395                 400
```

Ala Glu Ser Asn Arg Leu Val Gly Glu Leu Lys Leu Asp Arg Leu Leu
                405                 410                 415

Leu Glu Leu Lys His Ser Asn Ile Gly Pro Phe Pro Val Glu Leu Leu
            420                 425                 430

Gln Asp Ile Met Asn Tyr Ile Val Pro Ile Leu Val Leu Pro Arg Val
            435                 440                 445

Asn Glu Lys Leu Gln Lys Gly Phe Pro Leu Pro Thr Pro Ala Arg Val
450                 455                 460

Gln Leu Tyr Asn Val Val Leu Gln Pro His Gln Asn Phe Leu Leu Phe
465                 470                 475                 480

Gly Ala Asp Val Val Tyr Lys
                485

<210> SEQ ID NO 104
<211> LENGTH: 31
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: Alpha-Glu
<220> FEATURE:
<221> NAME/KEY: MOD_RES
<222> LOCATION: (9)..(9)
<223> OTHER INFORMATION: Alpha-Asp
<220> FEATURE:
<221> NAME/KEY: MOD_RES
<222> LOCATION: (15)..(15)
<223> OTHER INFORMATION: Alpha-Glu
<220> FEATURE:
<221> NAME/KEY: MOD_RES
<222> LOCATION: (20)..(20)
<223> OTHER INFORMATION: N6-N-(1-oxohexadecyl)-gamma-Glu
<220> FEATURE:
<221> NAME/KEY: MOD_RES
<222> LOCATION: (22)..(22)
<223> OTHER INFORMATION: Alpha-Glu

<400> SEQUENCE: 104

His Ala Glu Gly Thr Phe Thr Ser Asp Val Ser Ser Tyr Leu Glu Gly
1               5                   10                  15

Gln Ala Ala Glu Lys Glu Phe Ile Ala Trp Leu Val Arg Gly Arg
            20                  25                  30

<210> SEQ ID NO 105
<211> LENGTH: 70
<212> TYPE: PRT
<213> ORGANISM: Homo sapiens

<400> SEQUENCE: 105

Ser Phe Lys Ile Lys His Leu Gly Lys Gly His Tyr Ser Phe Tyr Ser
1               5                   10                  15

Met Asp Ile Arg Glu Phe Gln Leu Pro Ser Ser Gln Ile Ser Met Val
            20                  25                  30

Pro Asn Val Gly Leu Lys Phe Ser Ile Ser Asn Ala Asn Ile Lys Ile
            35                  40                  45

Ser Gly Lys Trp Lys Ala Gln Lys Arg Phe Leu Lys Met Ser Gly Asn
50                  55                  60

Phe Asp Leu Ser Ile Glu
65                  70

<210> SEQ ID NO 106
<211> LENGTH: 70
<212> TYPE: PRT

<213> ORGANISM: Homo sapiens

<400> SEQUENCE: 106

Gly Met Ser Ile Ser Ala Asp Leu Lys Leu Gly Ser Asn Pro Thr Ser
1               5                   10                  15

Gly Lys Pro Thr Ile Thr Cys Ser Ser Cys Ser Ser His Ile Asn Ser
            20                  25                  30

Val His Val His Ile Ser Lys Ser Lys Val Gly Trp Leu Ile Gln Leu
        35                  40                  45

Phe His Lys Lys Ile Glu Ser Ala Leu Arg Asn Lys Met Asn Ser Gln
    50                  55                  60

Val Cys Glu Lys Val Thr
65                  70

<210> SEQ ID NO 107
<211> LENGTH: 21
<212> TYPE: PRT
<213> ORGANISM: Homo sapiens

<400> SEQUENCE: 107

Cys Leu Gly Val Gly Ser Cys Asn Asp Phe Ala Gly Cys Gly Tyr Ala
1               5                   10                  15

Ile Val Cys Phe Trp
            20

<210> SEQ ID NO 108
<211> LENGTH: 70
<212> TYPE: PRT
<213> ORGANISM: Homo sapiens

<400> SEQUENCE: 108

Asn Ser Val Ser Ser Glu Leu Gln Pro Tyr Phe Gln Thr Leu Pro Val
1               5                   10                  15

Met Thr Lys Ile Asp Ser Val Ala Gly Ile Asn Tyr Gly Leu Val Ala
            20                  25                  30

Pro Pro Ala Thr Thr Ala Glu Thr Leu Asp Val Gln Met Lys Gly Glu
        35                  40                  45

Phe Tyr Ser Glu Asn His His Asn Pro Pro Pro Phe Ala Pro Pro Val
    50                  55                  60

Met Glu Phe Pro Ala Ala
65                  70

<210> SEQ ID NO 109
<211> LENGTH: 70
<212> TYPE: PRT
<213> ORGANISM: Homo sapiens

<400> SEQUENCE: 109

His Asp Arg Met Val Tyr Leu Gly Leu Ser Tyr Phe Phe Asn Thr
1               5                   10                  15

Ala Gly Leu Val Tyr Gln Glu Ala Gly Val Leu Lys Met Thr Leu Arg
            20                  25                  30

Asp Asp Met Ile Pro Lys Glu Ser Lys Phe Arg Leu Thr Thr Lys Phe
        35                  40                  45

Phe Gly Thr Phe Leu Pro Glu Val Ala Lys Lys Phe Pro Asn Met Lys
    50                  55                  60

Ile Gln Ile His Val Ser
65                  70

```
<210> SEQ ID NO 110
<211> LENGTH: 70
<212> TYPE: PRT
<213> ORGANISM: Homo sapiens

<400> SEQUENCE: 110

Ala Ser Thr Pro Pro His Leu Ser Val Gln Pro Thr Gly Leu Thr Phe
1               5                   10                  15

Tyr Pro Ala Val Asp Val Gln Ala Phe Ala Val Leu Pro Asn Ser Ser
            20                  25                  30

Leu Ala Ser Leu Phe Leu Ile Gly Met His Thr Thr Gly Ser Met Glu
        35                  40                  45

Val Ser Ala Glu Ser Asn Arg Leu Val Gly Glu Leu Lys Leu Asp Arg
    50                  55                  60

Leu Leu Leu Glu Leu Lys
65                  70

<210> SEQ ID NO 111
<211> LENGTH: 67
<212> TYPE: PRT
<213> ORGANISM: Homo sapiens

<400> SEQUENCE: 111

His Ser Asn Ile Gly Pro Phe Pro Val Glu Leu Leu Gln Asp Ile Met
1               5                   10                  15

Asn Tyr Ile Val Pro Ile Leu Val Leu Pro Arg Val Asn Glu Lys Leu
            20                  25                  30

Gln Lys Gly Phe Pro Leu Pro Thr Pro Ala Arg Val Leu Tyr Asn
        35                  40                  45

Val Val Leu Gln Pro His Gln Asn Phe Leu Leu Phe Gly Ala Asp Val
    50                  55                  60

Val Tyr Lys
65

<210> SEQ ID NO 112
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 112

Gly Glu Pro Pro Pro Gly Lys Pro Ala Asp Asp Ala Gly Leu Val
1               5                   10                  15

<210> SEQ ID NO 113
<211> LENGTH: 6
<212> TYPE: PRT
<213> ORGANISM: Homo sapiens

<400> SEQUENCE: 113

Asp Leu Gln Val Phe Val
1               5

<210> SEQ ID NO 114
<211> LENGTH: 5
<212> TYPE: PRT
<213> ORGANISM: Homo sapiens

<400> SEQUENCE: 114

Gly Glu Lys Lys Asp
```

```
1               5

<210> SEQ ID NO 115
<211> LENGTH: 5
<212> TYPE: PRT
<213> ORGANISM: Homo sapiens

<400> SEQUENCE: 115

Ala Thr His Glu Ser
1               5

<210> SEQ ID NO 116
<211> LENGTH: 6
<212> TYPE: PRT
<213> ORGANISM: Homo sapiens

<400> SEQUENCE: 116

Cys Leu Pro Val Ser Gly
1               5

<210> SEQ ID NO 117
<211> LENGTH: 6
<212> TYPE: PRT
<213> ORGANISM: Homo sapiens

<400> SEQUENCE: 117

Leu Pro Val Ser Gly Ser
1               5

<210> SEQ ID NO 118
<211> LENGTH: 6
<212> TYPE: PRT
<213> ORGANISM: Homo sapiens

<400> SEQUENCE: 118

Pro Cys His Ala Pro Pro
1               5

<210> SEQ ID NO 119
<211> LENGTH: 8
<212> TYPE: PRT
<213> ORGANISM: Homo sapiens

<400> SEQUENCE: 119

Gly Gly His Asp Leu Glu Ser Gly
1               5

<210> SEQ ID NO 120
<211> LENGTH: 6
<212> TYPE: PRT
<213> ORGANISM: Homo sapiens

<400> SEQUENCE: 120

Asp Asp Leu Gln Val Phe
1               5

<210> SEQ ID NO 121
<211> LENGTH: 5
<212> TYPE: PRT
<213> ORGANISM: Homo sapiens

<400> SEQUENCE: 121

Pro Leu Thr Ser Gly
1               5
```

```
<210> SEQ ID NO 122
<211> LENGTH: 8
<212> TYPE: PRT
<213> ORGANISM: Homo sapiens

<400> SEQUENCE: 122

Leu Ile His Phe Glu Glu Gly Val
1               5

<210> SEQ ID NO 123
<211> LENGTH: 7
<212> TYPE: PRT
<213> ORGANISM: Homo sapiens

<400> SEQUENCE: 123

Gly Glu Phe Ser Tyr Asp Ser
1               5

<210> SEQ ID NO 124
<211> LENGTH: 7
<212> TYPE: PRT
<213> ORGANISM: Homo sapiens

<400> SEQUENCE: 124

His Ala Pro Pro Leu Thr Ser
1               5

<210> SEQ ID NO 125
<211> LENGTH: 7
<212> TYPE: PRT
<213> ORGANISM: Homo sapiens

<400> SEQUENCE: 125

Asp Leu Glu Ser Gly Glu Phe
1               5

<210> SEQ ID NO 126
<211> LENGTH: 8
<212> TYPE: PRT
<213> ORGANISM: Homo sapiens

<400> SEQUENCE: 126

Gly Glu Phe Ser Val Cys Asp Ser
1               5

<210> SEQ ID NO 127
<211> LENGTH: 10
<212> TYPE: PRT
<213> ORGANISM: Homo sapiens

<400> SEQUENCE: 127

Lys Lys Gly Glu Phe Ser Val Ala Asp Ser
1               5                   10

<210> SEQ ID NO 128
<211> LENGTH: 9
<212> TYPE: PRT
<213> ORGANISM: Homo sapiens

<400> SEQUENCE: 128

Lys Lys Gly Glu Phe Tyr Cys Ser Arg
1               5

<210> SEQ ID NO 129
<211> LENGTH: 13
<212> TYPE: PRT
```

<213> ORGANISM: Homo sapiens

<400> SEQUENCE: 129

Gly Leu Arg Val Arg Val Trp Asn Gly Lys Phe Pro Lys
1               5                   10

<210> SEQ ID NO 130
<211> LENGTH: 16
<212> TYPE: PRT
<213> ORGANISM: Homo sapiens

<400> SEQUENCE: 130

Gly Val Ala Phe Glu Glu Ala Pro Asp Asp His Ser Phe Phe Leu Phe
1               5                   10                  15

<210> SEQ ID NO 131
<211> LENGTH: 7
<212> TYPE: PRT
<213> ORGANISM: Homo sapiens

<400> SEQUENCE: 131

Gly Gly His Asp Leu Ser Gly
1               5

<210> SEQ ID NO 132
<211> LENGTH: 8
<212> TYPE: PRT
<213> ORGANISM: Homo sapiens

<400> SEQUENCE: 132

Gly Gly His Asp Leu Glu Ser Gly
1               5

<210> SEQ ID NO 133
<211> LENGTH: 14
<212> TYPE: PRT
<213> ORGANISM: Homo sapiens

<400> SEQUENCE: 133

Gly Gly His Asp Leu Glu Ser Gly Glu Phe Ser Tyr Asp Ser
1               5                   10

<210> SEQ ID NO 134
<211> LENGTH: 14
<212> TYPE: PRT
<213> ORGANISM: Homo sapiens

<400> SEQUENCE: 134

Gly Gly Ser Asp Leu Ser Gly Glu Phe Ser Val Cys Asp Ser
1               5                   10

<210> SEQ ID NO 135
<211> LENGTH: 15
<212> TYPE: PRT
<213> ORGANISM: Homo sapiens

<400> SEQUENCE: 135

Gly Gly Ser Asp Leu Ser Gly Gly Glu Phe Ser Val Cys Asp Ser
1               5                   10                  15

<210> SEQ ID NO 136
<211> LENGTH: 15
<212> TYPE: PRT
<213> ORGANISM: Homo sapiens

<400> SEQUENCE: 136

Gly Gly Ser Asp Leu Ser Gly Gly Glu Phe Ser Val Ala Asp Ser
1               5                   10                  15

<210> SEQ ID NO 137
<211> LENGTH: 14
<212> TYPE: PRT
<213> ORGANISM: Homo sapiens

<400> SEQUENCE: 137

Gly Gly Ser Asp Leu Ser Gly Glu Phe Ser Val Ala Asp Ser
1               5                   10

<210> SEQ ID NO 138
<211> LENGTH: 6
<212> TYPE: PRT
<213> ORGANISM: Homo sapiens

<400> SEQUENCE: 138

Glu Thr Leu Gln Phe Arg
1               5

<210> SEQ ID NO 139
<211> LENGTH: 8
<212> TYPE: PRT
<213> ORGANISM: Homo sapiens

<400> SEQUENCE: 139

Lys Lys Glu Thr Leu Gln Phe Arg
1               5

<210> SEQ ID NO 140
<211> LENGTH: 8
<212> TYPE: PRT
<213> ORGANISM: Homo sapiens

<400> SEQUENCE: 140

Glu Thr Leu Gln Phe Arg Lys Lys
1               5

<210> SEQ ID NO 141
<211> LENGTH: 9
<212> TYPE: PRT
<213> ORGANISM: Homo sapiens

<400> SEQUENCE: 141

Lys Ala Ser Thr Thr Thr Asn Tyr Thr
1               5

<210> SEQ ID NO 142
<211> LENGTH: 13
<212> TYPE: PRT
<213> ORGANISM: Homo sapiens

<400> SEQUENCE: 142

Ala Leu Lys Arg Gln Gly Arg Thr Leu Tyr Gly Phe Gly
1               5                   10

<210> SEQ ID NO 143
<211> LENGTH: 8
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: Sarcosine

```
<400> SEQUENCE: 143

Xaa Arg Val Tyr Val His Pro Ala
1               5

<210> SEQ ID NO 144
<211> LENGTH: 60
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 144

Arg Lys Arg Gly Arg Gln Thr Tyr Thr Arg Tyr Gln Thr Leu Glu Leu
1               5                   10                  15

Glu Lys Glu Phe His Phe Asn Arg Tyr Leu Thr Arg Arg Arg Arg Ile
            20                  25                  30

Glu Ile Ala His Ala Leu Cys Leu Thr Glu Arg Gln Ile Lys Ile Trp
        35                  40                  45

Phe Gln Asn Arg Arg Met Lys Trp Lys Lys Glu Asn
    50                  55                  60

<210> SEQ ID NO 145
<211> LENGTH: 38
<212> TYPE: PRT
<213> ORGANISM: Homo sapiens

<400> SEQUENCE: 145

Arg Arg Arg Pro Arg Pro Pro Tyr Leu Pro Arg Pro Arg Pro Pro Pro
1               5                   10                  15

Phe Phe Pro Pro Arg Leu Pro Pro Arg Ile Pro Pro Gly Phe Pro Pro
            20                  25                  30

Arg Phe Pro Pro Arg Phe
        35

<210> SEQ ID NO 146
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: Alpha-Glu
<220> FEATURE:
<221> NAME/KEY: MOD_RES
<222> LOCATION: (5)..(5)
<223> OTHER INFORMATION: Alpha-Asp
<220> FEATURE:
<221> NAME/KEY: MOD_RES
<222> LOCATION: (7)..(7)
<223> OTHER INFORMATION: S-(acetylamino)methyl-Cys
<220> FEATURE:
<221> NAME/KEY: MOD_RES
<222> LOCATION: (8)..(8)
<223> OTHER INFORMATION: Alpha-Glu
<220> FEATURE:
<221> NAME/KEY: MOD_RES
<222> LOCATION: (10)..(10)
<223> OTHER INFORMATION: S-(acetylamino)methyl-Cys
<220> FEATURE:
<221> NAME/KEY: MOD_RES
<222> LOCATION: (12)..(12)
<223> OTHER INFORMATION: S-(acetylamino)methyl-Cys
<220> FEATURE:
```

<221> NAME/KEY: MOD_RES
<222> LOCATION: (14)..(14)
<223> OTHER INFORMATION: Alpha-Glu

<400> SEQUENCE: 146

Glu Trp Gln Thr Asp Asn Cys Glu Thr Cys Thr Cys Tyr Glu
1               5                   10

<210> SEQ ID NO 147
<211> LENGTH: 116
<212> TYPE: PRT
<213> ORGANISM: Homo sapiens

<400> SEQUENCE: 147

Met Leu Ser Cys Arg Leu Gln Cys Ala Leu Ala Ala Leu Ser Ile Val
1               5                   10                  15

Leu Ala Leu Gly Cys Val Thr Gly Ala Pro Ser Asp Pro Arg Leu Arg
            20                  25                  30

Gln Phe Leu Gln Lys Ser Leu Ala Ala Ala Gly Lys Gln Glu Leu
        35                  40                  45

Ala Lys Tyr Phe Leu Ala Glu Leu Leu Ser Glu Pro Asn Gln Thr Glu
50                  55                  60

Asn Asp Ala Leu Glu Pro Glu Asp Leu Ser Gln Ala Ala Glu Gln Asp
65                  70                  75                  80

Glu Met Arg Leu Glu Leu Gln Arg Ser Ala Asn Ser Asn Pro Ala Met
                85                  90                  95

Ala Pro Arg Glu Arg Lys Ala Gly Cys Lys Asn Phe Phe Trp Lys Thr
            100                 105                 110

Phe Thr Ser Cys
        115

<210> SEQ ID NO 148
<211> LENGTH: 176
<212> TYPE: PRT
<213> ORGANISM: Homo sapiens

<400> SEQUENCE: 148

Met Gln Arg Arg Leu Val Gln Gln Trp Ser Val Ala Val Phe Leu Leu
1               5                   10                  15

Ser Tyr Ala Val Pro Ser Cys Gly Arg Ser Val Glu Gly Leu Ser Arg
            20                  25                  30

Arg Leu Lys Arg Ala Val Ser Glu His Gln Leu Leu His Asp Lys Gly
        35                  40                  45

Lys Ser Ile Gln Asp Leu Arg Arg Arg Phe Phe Leu His His Leu Ile
50                  55                  60

Ala Glu Ile His Thr Ala Glu Ile Arg Ala Thr Ser Glu Val Ser Pro
65                  70                  75                  80

Asn Ser Lys Pro Ser Pro Asn Thr Lys Asn His Pro Val Phe Gly Ser
                85                  90                  95

Asp Asp Glu Gly Arg Tyr Leu Thr Gln Glu Thr Asn Lys Val Glu Thr
            100                 105                 110

Tyr Lys Glu Gln Pro Leu Lys Thr Pro Gly Lys Lys Lys Gly Lys
        115                 120                 125

Pro Gly Lys Arg Lys Glu Gln Glu Lys Lys Arg Arg Thr Arg Ser
        130                 135                 140

Ala Trp Leu Asp Ser Gly Val Thr Gly Ser Gly Leu Glu Gly Asp His
145                 150                 155                 160

Leu Ser Asp Thr Ser Thr Thr Ser Leu Glu Leu Asp Ser Arg Arg His

<210> SEQ ID NO 149
<211> LENGTH: 34
<212> TYPE: PRT
<213> ORGANISM: Homo sapiens

<400> SEQUENCE: 149

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe

<210> SEQ ID NO 150
<211> LENGTH: 35
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: misc_feature
<222> LOCATION: (1)..(1)
<223> OTHER INFORMATION: /note="N-term acetlyated"
<220> FEATURE:
<221> NAME/KEY: MOD_RES
<222> LOCATION: (10)..(11)
<223> OTHER INFORMATION: Alpha-Glu
<220> FEATURE:
<221> NAME/KEY: MOD_RES
<222> LOCATION: (17)..(17)
<223> OTHER INFORMATION: Alpha-Glu
<220> FEATURE:
<221> NAME/KEY: MOD_RES
<222> LOCATION: (20)..(20)
<223> OTHER INFORMATION: Alpha-Glu
<220> FEATURE:
<221> NAME/KEY: MOD_RES
<222> LOCATION: (22)..(22)
<223> OTHER INFORMATION: Alpha-Glu
<220> FEATURE:
<221> NAME/KEY: MOD_RES
<222> LOCATION: (25)..(25)
<223> OTHER INFORMATION: Alpha-Glu
<220> FEATURE:
<221> NAME/KEY: MOD_RES
<222> LOCATION: (27)..(27)
<223> OTHER INFORMATION: Alpha-Asp

<400> SEQUENCE: 150

Tyr Thr Ser Leu Ile His Ser Leu Ile Glu Glu Ser Gln Asn Gln Gln
1               5                   10                  15

Glu Lys Asn Glu Gln Glu Leu Leu Glu Leu Asp Lys Trp Ala Ser Leu
            20                  25                  30

Trp Asn Trp
        35

<210> SEQ ID NO 151
<211> LENGTH: 5
<212> TYPE: PRT
<213> ORGANISM: Homo sapiens

<400> SEQUENCE: 151

Ala Arg Pro Ala Lys
1               5

<210> SEQ ID NO 152

```
<211> LENGTH: 37
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 152

Lys Cys Asn Thr Ala Thr Cys Ala Thr Gln Arg Leu Ala Asn Phe Leu
1               5                   10                  15

Val His Ser Ser Asn Asn Phe Gly Ala Ile Leu Ser Ser Thr Asn Val
                20                  25                  30

Gly Ser Asn Thr Tyr
            35

<210> SEQ ID NO 153
<211> LENGTH: 30
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: misc_feature
<222> LOCATION: (1)..(1)
<223> OTHER INFORMATION: /note="N-term acetylated"
<220> FEATURE:
<221> NAME/KEY: MOD_RES
<222> LOCATION: (3)..(3)
<223> OTHER INFORMATION: Alpha-Asp
<220> FEATURE:
<221> NAME/KEY: MOD_RES
<222> LOCATION: (8)..(8)
<223> OTHER INFORMATION: Alpha-Glu
<220> FEATURE:
<221> NAME/KEY: MOD_RES
<222> LOCATION: (17)..(17)
<223> OTHER INFORMATION: Norleu
<220> FEATURE:
<221> NAME/KEY: MOD_RES
<222> LOCATION: (25)..(25)
<223> OTHER INFORMATION: Alpha-Asp

<400> SEQUENCE: 153

His Ser Asp Ala Val Phe Thr Glu Asn Tyr Thr Lys Leu Arg Lys Gln
1               5                   10                  15

Leu Ala Ala Lys Lys Tyr Leu Asn Asp Leu Lys Lys Gly Gly
                20                  25                  30

<210> SEQ ID NO 154
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 154

Leu Lys Arg Met Pro
1               5

<210> SEQ ID NO 155
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
```

```
                              Synthetic peptide"
<220> FEATURE:
<221> NAME/KEY: MOD_RES
<222> LOCATION: (1)..(1)
<223> OTHER INFORMATION: Pyro-Glu

<400> SEQUENCE: 155

Glu Glu Asp Cys Lys
1               5

<210> SEQ ID NO 156
<211> LENGTH: 43
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: MOD_RES
<222> LOCATION: (4)..(4)
<223> OTHER INFORMATION: Alpha-Glu
<220> FEATURE:
<221> NAME/KEY: MOD_RES
<222> LOCATION: (13)..(13)
<223> OTHER INFORMATION: Alpha-Glu
<220> FEATURE:
<221> NAME/KEY: MOD_RES
<222> LOCATION: (26)..(26)
<223> OTHER INFORMATION: Alpha-Glu

<400> SEQUENCE: 156

Met Phe Leu Glu Ala Ile Pro Met Ser Ile Pro Pro Glu Val Lys Phe
1               5                   10                  15

Asn Lys Pro Phe Val Phe Leu Met Ile Glu Gln Asn Thr Lys Ser Pro
            20                  25                  30

Leu Phe Met Gly Lys Val Val Asn Pro Thr Gln
        35                  40

<210> SEQ ID NO 157
<211> LENGTH: 7
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: Isoval
<220> FEATURE:
<221> NAME/KEY: MOD_RES
<222> LOCATION: (3)..(3)
<223> OTHER INFORMATION: Norleu
<220> FEATURE:
<221> NAME/KEY: MOD_RES
<222> LOCATION: (4)..(4)
<223> OTHER INFORMATION: Statin residue
<220> FEATURE:
<221> NAME/KEY: MOD_RES
<222> LOCATION: (6)..(6)
<223> OTHER INFORMATION: Statin residue

<400> SEQUENCE: 157

Val Phe Leu Xaa Ala Xaa Lys
1               5

<210> SEQ ID NO 158
<211> LENGTH: 32
<212> TYPE: PRT
<213> ORGANISM: Salmo salar

<400> SEQUENCE: 158

Cys Ser Asn Leu Ser Thr Cys Val Leu Gly Lys Leu Ser Gln Glu Leu
```

```
                      1               5                  10                 15
His Lys Leu Gln Thr Tyr Pro Arg Thr Asn Thr Gly Ser Gly Thr Pro
                    20                  25                 30

<210> SEQ ID NO 159
<211> LENGTH: 29
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: misc_feature
<222> LOCATION: (29)..(29)
<223> OTHER INFORMATION: /note="C-term amidated"

<400> SEQUENCE: 159

Tyr Ala Asp Ala Ile Phe Thr Asn Ser Tyr Arg Lys Val Leu Gly Gln
1               5                   10                  15

Leu Ser Ala Arg Lys Leu Leu Gln Asp Ile Met Ser Arg
                20                  25

<210> SEQ ID NO 160
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 160

His Ser Asp Gly Thr Phe
1               5

<210> SEQ ID NO 161
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 161

Lys Leu Leu Leu Leu Lys Leu Leu Leu Lys Leu Leu Leu Leu Lys
1               5                   10                  15

Leu Leu Leu Leu
                20

<210> SEQ ID NO 162
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 162

Trp Ala Gly Gly Asp Ala Ser Gly Glu
1               5

<210> SEQ ID NO 163
<211> LENGTH: 108
<212> TYPE: PRT
<213> ORGANISM: Homo sapiens
```

-continued

<400> SEQUENCE: 163

Met Pro Leu Trp Val Phe Phe Phe Val Ile Leu Thr Leu Ser Asn Ser
1               5                   10                  15

Ser His Cys Ser Pro Pro Pro Leu Thr Leu Arg Met Arg Arg Tyr
            20                  25                  30

Ala Asp Ala Ile Phe Thr Asn Ser Tyr Arg Lys Val Leu Gly Gln Leu
            35                  40                  45

Ser Ala Arg Lys Leu Leu Gln Asp Ile Met Ser Arg Gln Gln Gly Glu
        50                  55                  60

Ser Asn Gln Glu Arg Gly Ala Arg Ala Arg Leu Gly Arg Gln Val Asp
65                  70                  75                  80

Ser Met Trp Ala Glu Gln Lys Gln Met Glu Leu Glu Ser Ile Leu Val
                85                  90                  95

Ala Leu Leu Gln Lys His Ser Arg Asn Ser Gln Gly
                100                 105

<210> SEQ ID NO 164
<211> LENGTH: 70
<212> TYPE: PRT
<213> ORGANISM: Homo sapiens

<400> SEQUENCE: 164

Met Pro Leu Trp Val Phe Phe Phe Val Ile Leu Thr Leu Ser Asn Ser
1               5                   10                  15

Ser His Cys Ser Pro Pro Pro Leu Thr Leu Arg Met Arg Arg Tyr
            20                  25                  30

Ala Asp Ala Ile Phe Thr Asn Ser Tyr Arg Lys Val Leu Gly Gln Leu
            35                  40                  45

Ser Ala Arg Lys Leu Leu Gln Asp Ile Met Ser Arg Gln Gln Gly Glu
        50                  55                  60

Ser Asn Gln Glu Arg Gly
65                  70

<210> SEQ ID NO 165
<211> LENGTH: 38
<212> TYPE: PRT
<213> ORGANISM: Homo sapiens

<400> SEQUENCE: 165

Ala Arg Ala Arg Leu Gly Arg Gln Val Asp Ser Met Trp Ala Glu Gln
1               5                   10                  15

Lys Gln Met Glu Leu Glu Ser Ile Leu Val Ala Leu Leu Gln Lys His
            20                  25                  30

Ser Arg Asn Ser Gln Gly
            35

<210> SEQ ID NO 166
<211> LENGTH: 200
<212> TYPE: PRT
<213> ORGANISM: Homo sapiens

<400> SEQUENCE: 166

Met Ala Ser Leu Tyr Val Gly Asp Leu His Pro Glu Val Thr Glu Ala
1               5                   10                  15

Met Leu Tyr Glu Lys Phe Ser Pro Ala Gly Pro Ile Leu Ser Ile Arg
            20                  25                  30

Ile Cys Arg Asp Lys Ile Thr Arg Arg Ser Leu Gly Tyr Ala Tyr Val
            35                  40                  45

Asn Tyr Gln Gln Pro Val Asp Ala Lys Arg Ala Leu Glu Thr Leu Asn
    50                  55                  60

Phe Asp Val Ile Lys Gly Arg Pro Val Arg Ile Met Trp Ser Gln Arg
65                  70                  75                  80

Asp Pro Ser Leu Arg Lys Ser Gly Val Gly Asn Val Phe Ile Lys Asn
                85                  90                  95

Leu Gly Lys Thr Ile Asp Asn Lys Ala Leu Tyr Asn Ile Phe Ser Ala
            100                 105                 110

Phe Gly Asn Ile Leu Ser Cys Lys Val Ala Cys Asp Glu Lys Gly Pro
        115                 120                 125

Lys Gly Tyr Gly Phe Val His Phe Gln Lys Gln Glu Ser Ala Glu Arg
    130                 135                 140

Ala Ile Asp Val Met Asn Gly Met Phe Leu Asn Tyr Arg Lys Ile Phe
145                 150                 155                 160

Val Gly Arg Phe Lys Ser His Lys Glu Arg Glu Ala Glu Arg Gly Ala
                165                 170                 175

Trp Ala Arg Gln Ser Thr Ser Ala Asp Val Lys Asp Phe Glu Glu Asp
            180                 185                 190

Thr Asp Glu Glu Ala Thr Leu Arg
        195                 200

<210> SEQ ID NO 167
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 167

Arg Arg Trp Cys Tyr Arg Lys Cys Tyr Lys Gly Tyr Cys Tyr Arg Lys
1               5                   10                  15

Cys

<210> SEQ ID NO 168
<211> LENGTH: 8
<212> TYPE: PRT
<213> ORGANISM: Homo sapiens

<400> SEQUENCE: 168

Leu Glu Asp Gly Pro Lys Phe Leu
1               5

<210> SEQ ID NO 169
<211> LENGTH: 30
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 169

Lys Ser Ser Gln Tyr Ile Lys Ala Asn Ser Lys Phe Ile Gly Ile Thr
1               5                   10                  15

Glu Ala Ala Ala Phe Leu Pro Ser Asp Phe Phe Pro Ser Val
            20                  25                  30

<210> SEQ ID NO 170
<211> LENGTH: 8

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (6)..(6)
<223> OTHER INFORMATION: Alpha-Asp
<220> FEATURE:
<221> NAME/KEY: MOD_RES
<222> LOCATION: (7)..(7)
<223> OTHER INFORMATION: O-methyl-Tyr

<400> SEQUENCE: 170

Cys Asn Pro Arg Gly Asp Tyr Arg
1               5

<210> SEQ ID NO 171
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 171

Gly Gly Gly Lys
1

<210> SEQ ID NO 172
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: misc_feature
<222> LOCATION: (12)..(12)
<223> OTHER INFORMATION: /note="C-term amidated"

<400> SEQUENCE: 172

Gly Gly Gly Cys Tyr Phe Gln Asn Cys Pro Lys Gly
1               5                   10

<210> SEQ ID NO 173
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 173

Gln Glu Asp Leu Ile Asp Val
1               5

<210> SEQ ID NO 174
<211> LENGTH: 214
<212> TYPE: PRT
<213> ORGANISM: Mus musculus

<400> SEQUENCE: 174

Met Glu Pro Gly Leu Trp Leu Leu Leu Gly Leu Thr Val Thr Ser Ala
1               5                   10                  15
```

Ala Gly Leu Val Pro Cys Pro Gln Ser Gly Asp Ser Gly Arg Ala Ser
                20                  25                  30

Val Ser Gln Gly Pro Pro Glu Ala Gly Ser Glu Arg Gly Cys Glu Glu
            35                  40                  45

Thr Val Ala Gly Pro Gly Glu Arg Ile Val Ser Pro Thr Val Ala Leu
        50                  55                  60

Pro Ala Gln Pro Glu Ser Ala Gly Gln Glu Arg Ala Pro Gly Arg Ser
65                  70                  75                  80

Gly Lys Gln Glu Asp Lys Gly Leu Pro Ala His His Arg Pro Arg Arg
                85                  90                  95

Cys Thr Cys Phe Thr Tyr Lys Asp Lys Glu Cys Val Tyr Tyr Cys His
            100                 105                 110

Leu Asp Ile Ile Trp Ile Asn Thr Pro Glu Gln Thr Val Pro Tyr Gly
        115                 120                 125

Leu Ser Asn Tyr Arg Glu Ser Leu Arg Gly Lys Arg Ser Leu Gly Pro
130                 135                 140

Val Pro Glu Ser Ser Gln Pro Ser Pro Trp Thr Arg Leu Arg Cys Thr
145                 150                 155                 160

Cys Met Gly Ala Asp Lys Ala Cys Ala His Phe Cys Ala Arg Thr
                165                 170                 175

Arg Asp Val Thr Ser Tyr Ser Gly Arg Ala Glu Arg Pro Ala Ala Glu
        180                 185                 190

Glu Met Arg Glu Thr Gly Gly Pro Arg Gln Arg Leu Met Ser Arg Thr
            195                 200                 205

Asp Lys Ala His Arg Pro
        210

<210> SEQ ID NO 175
<211> LENGTH: 356
<212> TYPE: PRT
<213> ORGANISM: Homo sapiens

<400> SEQUENCE: 175

Met Ala Ala Glu Gly Trp Ile Trp Arg Trp Gly Trp Gly Arg Arg Cys
1               5                   10                  15

Leu Gly Arg Pro Gly Leu Leu Gly Pro Gly Pro Gly Thr Thr Pro
                20                  25                  30

Leu Phe Leu Leu Leu Leu Leu Gly Ser Val Thr Ala Asp Ile Thr Asp
            35                  40                  45

Gly Asn Ser Glu His Leu Lys Arg Glu His Ser Leu Ile Lys Pro Tyr
        50                  55                  60

Gln Gly Val Gly Ser Ser Ser Met Pro Leu Trp Asp Phe Gln Gly Ser
65                  70                  75                  80

Thr Met Leu Thr Ser Gln Tyr Val Arg Leu Thr Pro Asp Glu Arg Ser
                85                  90                  95

Lys Glu Gly Ser Ile Trp Asn His Gln Pro Cys Phe Leu Lys Asp Trp
            100                 105                 110

Glu Met His Val His Phe Lys Val His Gly Thr Gly Lys Lys Asn Leu
        115                 120                 125

His Gly Asp Gly Ile Ala Leu Trp Tyr Thr Arg Asp Arg Leu Val Pro
130                 135                 140

Gly Pro Val Phe Gly Ser Lys Asp Asn Phe His Gly Leu Ala Ile Phe
145                 150                 155                 160

Leu Asp Thr Tyr Pro Asn Asp Glu Thr Thr Glu Arg Val Phe Pro Tyr
                165                 170                 175

```
Ile Ser Val Met Val Asn Asn Gly Ser Leu Ser Tyr Asp His Ser Lys
            180                 185                 190

Asp Gly Arg Trp Thr Glu Leu Ala Gly Cys Thr Ala Asp Phe Arg Asn
            195                 200                 205

Arg Asp His Asp Thr Phe Leu Ala Val Arg Tyr Ser Arg Gly Arg Leu
    210                 215                 220

Thr Val Met Thr Asp Leu Glu Asp Lys Asn Glu Trp Lys Asn Cys Ile
225                 230                 235                 240

Asp Ile Thr Gly Val Arg Leu Pro Thr Gly Tyr Tyr Phe Gly Ala Ser
            245                 250                 255

Ala Gly Thr Gly Asp Leu Ser Asn His Asp Ile Ile Ser Met Lys
            260                 265                 270

Leu Phe Gln Leu Met Val Glu His Thr Pro Asp Glu Glu Ser Ile Asp
            275                 280                 285

Trp Thr Lys Ile Glu Pro Ser Val Asn Phe Leu Lys Ser Pro Lys Asp
            290                 295                 300

Asn Val Asp Asp Pro Thr Gly Asn Phe Arg Ser Gly Pro Leu Thr Gly
305                 310                 315                 320

Trp Arg Val Phe Leu Leu Leu Cys Ala Leu Leu Gly Ile Val Val
            325                 330                 335

Cys Ala Val Val Gly Ala Val Val Phe Gln Lys Arg Gln Glu Arg Asn
            340                 345                 350

Lys Arg Phe Tyr
        355

<210> SEQ ID NO 176
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: misc_feature
<222> LOCATION: (8)..(8)
<223> OTHER INFORMATION: /note="C-term amidated"

<400> SEQUENCE: 176

Thr Asp Ser Phe Val Gly Leu Met
1               5

<210> SEQ ID NO 177
<211> LENGTH: 8
<212> TYPE: PRT
<213> ORGANISM: Homo sapiens

<400> SEQUENCE: 177

Lys Pro Gly Glu Pro Gly Pro Lys
1               5

<210> SEQ ID NO 178
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 178

Gly Ser His Lys
1
```

```
<210> SEQ ID NO 179
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 179

Ala Ser His Lys
1

<210> SEQ ID NO 180
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 180

Leu Ser His Lys
1

<210> SEQ ID NO 181
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 181

Thr Ser His Lys
1

<210> SEQ ID NO 182
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 182

Tyr Ser His Lys
1

<210> SEQ ID NO 183
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 183

Pro Ser His Lys
1

<210> SEQ ID NO 184
<211> LENGTH: 4
<212> TYPE: PRT
```

```
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: Pyro-Glu

<400> SEQUENCE: 184

Glu Ser His Lys
1

<210> SEQ ID NO 185
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 185

Trp Ser His Lys
1

<210> SEQ ID NO 186
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (2)..(2)
<223> OTHER INFORMATION: Hydroxy-Pro

<400> SEQUENCE: 186

Pro Pro Gly Ala Gly
1               5

<210> SEQ ID NO 187
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 187

Trp Ala Ser Gly Asn
1               5

<210> SEQ ID NO 188
<211> LENGTH: 8
<212> TYPE: PRT
<213> ORGANISM: Homo sapiens

<400> SEQUENCE: 188

Asp Ala Asp Pro Arg Gln Tyr Ala
1               5

<210> SEQ ID NO 189
<211> LENGTH: 518
<212> TYPE: PRT
<213> ORGANISM: Homo sapiens
```

<400> SEQUENCE: 189

```
Met Ser Cys Val Lys Leu Trp Pro Ser Gly Ala Pro Ala Pro Leu Val
1               5                   10                  15
Ser Ile Glu Glu Leu Glu Asn Gln Glu Leu Val Gly Lys Gly Gly Phe
            20                  25                  30
Gly Thr Val Phe Arg Ala Gln His Arg Lys Trp Gly Tyr Asp Val Ala
        35                  40                  45
Val Lys Ile Val Asn Ser Lys Ala Ile Ser Arg Glu Val Lys Ala Met
50                  55                  60
Ala Ser Leu Asp Asn Glu Phe Val Leu Arg Leu Glu Gly Val Ile Glu
65                  70                  75                  80
Lys Val Asn Trp Asp Gln Asp Pro Lys Pro Ala Leu Val Thr Lys Phe
                85                  90                  95
Met Glu Asn Gly Ser Leu Ser Gly Leu Leu Gln Ser Gln Cys Pro Arg
            100                 105                 110
Pro Trp Pro Leu Leu Cys Arg Leu Leu Lys Glu Val Val Leu Gly Met
        115                 120                 125
Phe Tyr Leu His Asp Gln Asn Pro Val Leu Leu His Arg Asp Leu Lys
130                 135                 140
Pro Ser Asn Val Leu Leu Asp Pro Glu Leu His Val Lys Leu Ala Asp
145                 150                 155                 160
Phe Gly Leu Ser Thr Phe Gln Gly Gly Ser Gln Ser Gly Thr Gly Ser
                165                 170                 175
Gly Glu Pro Gly Gly Thr Leu Gly Tyr Leu Ala Pro Glu Leu Phe Val
            180                 185                 190
Asn Val Asn Arg Lys Ala Ser Thr Ala Ser Asp Val Tyr Ser Phe Gly
        195                 200                 205
Ile Leu Met Trp Ala Val Leu Ala Gly Arg Glu Val Glu Leu Pro Thr
210                 215                 220
Glu Pro Ser Leu Val Tyr Glu Ala Val Cys Asn Arg Gln Asn Arg Pro
225                 230                 235                 240
Ser Leu Ala Glu Leu Pro Gln Ala Gly Pro Glu Thr Pro Gly Leu Glu
                245                 250                 255
Gly Leu Lys Glu Leu Met Gln Leu Cys Trp Ser Ser Glu Pro Lys Asp
            260                 265                 270
Arg Pro Ser Phe Gln Glu Cys Leu Pro Lys Thr Asp Glu Val Phe Gln
        275                 280                 285
Met Val Glu Asn Asn Met Asn Ala Ala Val Ser Thr Val Lys Asp Phe
290                 295                 300
Leu Ser Gln Leu Arg Ser Ser Asn Arg Arg Phe Ser Ile Pro Glu Ser
305                 310                 315                 320
Gly Gln Gly Gly Thr Glu Met Asp Gly Phe Arg Arg Thr Ile Glu Asn
                325                 330                 335
Gln His Ser Arg Asn Asp Val Met Val Ser Glu Trp Leu Asn Lys Leu
            340                 345                 350
Asn Leu Glu Glu Pro Pro Ser Ser Val Pro Lys Lys Cys Pro Ser Leu
        355                 360                 365
Thr Lys Arg Ser Arg Ala Gln Glu Glu Gln Val Pro Gln Ala Trp Thr
370                 375                 380
Ala Gly Thr Ser Ser Asp Ser Met Ala Gln Pro Pro Gln Thr Pro Glu
385                 390                 395                 400
Thr Ser Thr Phe Arg Asn Gln Met Pro Ser Pro Thr Ser Thr Gly Thr
                405                 410                 415
```

Pro Ser Pro Gly Pro Arg Gly Asn Gln Gly Ala Glu Arg Gln Gly Met
            420                 425                 430

Asn Trp Ser Cys Arg Thr Pro Glu Pro Asn Pro Val Thr Gly Arg Pro
        435                 440                 445

Leu Val Asn Ile Tyr Asn Cys Ser Gly Val Gln Val Gly Asp Asn Asn
    450                 455                 460

Tyr Leu Thr Met Gln Gln Thr Thr Ala Leu Pro Thr Trp Gly Leu Ala
465                 470                 475                 480

Pro Ser Gly Lys Gly Arg Gly Leu Gln His Pro Pro Val Gly Ser
            485                 490                 495

Gln Glu Gly Pro Lys Asp Pro Glu Ala Trp Ser Arg Pro Gln Gly Trp
            500                 505                 510

Tyr Asn His Ser Gly Lys
            515

<210> SEQ ID NO 190
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 190

Gly Tyr Tyr Trp Ser Trp Ile Arg Gln Pro Pro Gly Lys Gly Glu Glu
1               5                   10                  15

Trp Ile Gly

<210> SEQ ID NO 191
<211> LENGTH: 82
<212> TYPE: PRT
<213> ORGANISM: Homo sapiens

<400> SEQUENCE: 191

Gly Ser Gly Leu Thr Asn Ile Lys Thr Glu Glu Ile Ser Glu Val Lys
1               5                   10                  15

Met Asp Ala Glu Phe Arg His Asp Ser Gly Tyr Glu Val His His Gln
            20                  25                  30

Lys Leu Val Phe Phe Ala Glu Asp Val Gly Ser Asn Lys Gly Ala Ile
        35                  40                  45

Ile Gly Leu Met Val Gly Gly Val Val Ile Ala Thr Val Ile Ile Ile
    50                  55                  60

Thr Leu Val Met Leu Lys Lys Gln Tyr Thr Ser Asn His His Gly Val
65                  70                  75                  80

Val Glu

<210> SEQ ID NO 192
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: misc_feature
<222> LOCATION: (10)..(10)
<223> OTHER INFORMATION: /note="C-term amidated"

<400> SEQUENCE: 192

```
Leu Arg Ala His Ala Val Asp Val Asn Gly
1               5                   10

<210> SEQ ID NO 193
<211> LENGTH: 9
<212> TYPE: PRT
<213> ORGANISM: Homo sapiens

<400> SEQUENCE: 193

Leu Leu Pro Gly Gly Arg Pro Tyr Arg
1               5

<210> SEQ ID NO 194
<211> LENGTH: 359
<212> TYPE: PRT
<213> ORGANISM: Homo sapiens

<400> SEQUENCE: 194

Met Ile Leu Asn Ser Ser Thr Glu Asp Gly Ile Lys Arg Ile Gln Asp
1               5                   10                  15

Asp Cys Pro Lys Ala Gly Arg His Asn Tyr Ile Phe Val Met Ile Pro
                20                  25                  30

Thr Leu Tyr Ser Ile Ile Phe Val Gly Ile Phe Gly Asn Ser Leu
            35                  40                  45

Val Val Ile Val Ile Tyr Phe Tyr Met Lys Leu Lys Thr Val Ala Ser
    50                  55                  60

Val Phe Leu Leu Asn Leu Ala Leu Ala Asp Leu Cys Phe Leu Leu Thr
65                  70                  75                  80

Leu Pro Leu Trp Ala Val Tyr Thr Ala Met Glu Tyr Arg Trp Pro Phe
                85                  90                  95

Gly Asn Tyr Leu Cys Lys Ile Ala Ser Ala Ser Val Ser Phe Asn Leu
            100                 105                 110

Tyr Ala Ser Val Phe Leu Leu Thr Cys Leu Ser Ile Asp Arg Tyr Leu
        115                 120                 125

Ala Ile Val His Pro Met Lys Ser Arg Leu Arg Arg Thr Met Leu Val
130                 135                 140

Ala Lys Val Thr Cys Ile Ile Ile Trp Leu Leu Ala Gly Leu Ala Ser
145                 150                 155                 160

Leu Pro Ala Ile Ile His Arg Asn Val Phe Phe Ile Glu Asn Thr Asn
                165                 170                 175

Ile Thr Val Cys Ala Phe His Tyr Glu Ser Gln Asn Ser Thr Leu Pro
            180                 185                 190

Ile Gly Leu Gly Leu Thr Lys Asn Ile Leu Gly Phe Leu Phe Pro Phe
        195                 200                 205

Leu Ile Ile Leu Thr Ser Tyr Thr Leu Ile Trp Lys Ala Leu Lys Lys
    210                 215                 220

Ala Tyr Glu Ile Gln Lys Asn Lys Pro Arg Asn Asp Asp Ile Phe Lys
225                 230                 235                 240

Ile Ile Met Ala Ile Val Leu Phe Phe Phe Ser Trp Ile Pro His
                245                 250                 255

Gln Ile Phe Thr Phe Leu Asp Val Leu Ile Gln Leu Gly Ile Ile Arg
            260                 265                 270

Asp Cys Arg Ile Ala Asp Ile Val Asp Thr Ala Met Pro Ile Thr Ile
        275                 280                 285

Cys Ile Ala Tyr Phe Asn Asn Cys Leu Asn Pro Leu Phe Tyr Gly Phe
    290                 295                 300

Leu Gly Lys Lys Phe Lys Arg Tyr Phe Leu Gln Leu Leu Lys Tyr Ile
```

```
                305                 310                 315                 320
Pro Pro Lys Ala Lys Ser His Ser Asn Leu Ser Thr Lys Met Ser Thr
                    325                 330                 335

Leu Ser Tyr Arg Pro Ser Asp Asn Val Ser Ser Ser Thr Lys Lys Pro
                    340                 345                 350

Ala Pro Cys Phe Glu Val Glu
                355

<210> SEQ ID NO 195
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 195

Ile Leu Arg Trp Pro Trp Trp Pro Trp Arg Arg
1               5                   10

<210> SEQ ID NO 196
<211> LENGTH: 109
<212> TYPE: PRT
<213> ORGANISM: Homo sapiens

<400> SEQUENCE: 196

Met Arg Gly Ala Leu Leu Val Leu Ala Leu Leu Val Thr Gln Ala Leu
1               5                   10                  15

Gly Val Lys Met Ala Glu Thr Cys Pro Ile Phe Tyr Asp Val Phe Phe
                20                  25                  30

Ala Val Ala Asn Gly Asn Glu Leu Leu Leu Asp Leu Ser Leu Thr Lys
            35                  40                  45

Val Asn Ala Thr Glu Pro Glu Arg Thr Ala Met Lys Lys Ile Gln Asp
        50                  55                  60

Cys Tyr Val Glu Asn Gly Leu Ile Ser Arg Val Leu Asp Gly Leu Val
65                  70                  75                  80

Met Thr Thr Ile Ser Ser Ser Lys Asp Cys Met Gly Glu Ala Val Gln
                85                  90                  95

Asn Thr Val Glu Asp Leu Lys Leu Asn Thr Leu Gly Arg
                100                 105

<210> SEQ ID NO 197
<211> LENGTH: 138
<212> TYPE: PRT
<213> ORGANISM: Homo sapiens

<400> SEQUENCE: 197

Met Asn Ser Leu Val Ser Trp Gln Leu Leu Leu Phe Leu Cys Ala Thr
1               5                   10                  15

His Phe Gly Glu Pro Leu Glu Lys Val Ala Ser Val Gly Asn Ser Arg
                20                  25                  30

Pro Thr Gly Gln Gln Leu Glu Ser Leu Gly Leu Leu Ala Pro Gly Glu
            35                  40                  45

Gln Ser Leu Pro Cys Thr Glu Arg Lys Pro Ala Ala Thr Ala Arg Leu
        50                  55                  60

Ser Arg Arg Gly Thr Ser Leu Ser Pro Pro Glu Ser Ser Gly Ser
65                  70                  75                  80

Pro Gln Gln Pro Gly Leu Ser Ala Pro His Ser Arg Gln Ile Pro Ala
                85                  90                  95
```

```
Pro Gln Gly Ala Val Leu Val Gln Arg Glu Lys Asp Leu Pro Asn Tyr
            100                 105                 110

Asn Trp Asn Ser Phe Gly Leu Arg Phe Gly Lys Arg Glu Ala Ala Pro
            115                 120                 125

Gly Asn His Gly Arg Ser Ala Gly Arg Gly
            130                 135

<210> SEQ ID NO 198
<211> LENGTH: 422
<212> TYPE: PRT
<213> ORGANISM: Homo sapiens

<400> SEQUENCE: 198

Met Ser Thr Ser Tyr Gly Cys Phe Trp Arg Phe Ile His Gly Ile
1               5                   10                  15

Gly Arg Ser Gly Asp Ile Ser Ala Val Gln Pro Lys Ala Ala Gly Ser
            20                  25                  30

Ser Leu Leu Asn Lys Ile Thr Asn Ser Leu Val Leu Asp Ile Ile Lys
            35                  40                  45

Leu Ala Gly Val His Thr Val Ala Asn Cys Phe Val Val Pro Met Ala
50                  55                  60

Thr Gly Met Ser Leu Thr Leu Cys Phe Leu Thr Leu Arg His Lys Arg
65                  70                  75                  80

Pro Lys Ala Lys Tyr Ile Ile Trp Pro Arg Ile Asp Gln Lys Ser Cys
                85                  90                  95

Phe Lys Ser Met Ile Thr Ala Gly Phe Glu Pro Val Val Ile Glu Asn
                100                 105                 110

Val Leu Glu Gly Asp Glu Leu Arg Thr Asp Leu Lys Ala Val Glu Ala
            115                 120                 125

Lys Val Gln Glu Leu Gly Pro Asp Cys Ile Leu Cys Ile His Ser Thr
130                 135                 140

Thr Ser Cys Phe Ala Pro Arg Val Pro Asp Arg Leu Glu Glu Leu Ala
145                 150                 155                 160

Val Ile Cys Ala Asn Tyr Asp Ile Pro His Ile Val Asn Asn Ala Tyr
                165                 170                 175

Gly Val Gln Ser Ser Lys Cys Met His Leu Ile Gln Gln Gly Ala Arg
            180                 185                 190

Val Gly Arg Ile Asp Ala Phe Val Gln Ser Leu Asp Lys Asn Phe Met
            195                 200                 205

Val Pro Val Gly Gly Ala Ile Ile Ala Gly Phe Asn Asp Ser Phe Ile
            210                 215                 220

Gln Glu Ile Ser Lys Met Tyr Pro Gly Arg Ala Ser Ala Ser Pro Ser
225                 230                 235                 240

Leu Asp Val Leu Ile Thr Leu Leu Ser Leu Gly Ser Asn Gly Tyr Lys
                245                 250                 255

Lys Leu Leu Lys Glu Arg Lys Glu Met Phe Ser Tyr Leu Ser Asn Gln
            260                 265                 270

Ile Lys Lys Leu Ser Glu Ala Tyr Asn Glu Arg Leu Leu His Thr Pro
            275                 280                 285

His Asn Pro Ile Ser Leu Ala Met Thr Leu Lys Thr Leu Asp Glu His
            290                 295                 300

Arg Asp Lys Ala Val Thr Gln Leu Gly Ser Met Leu Phe Thr Lys Gln
305                 310                 315                 320

Val Ser Gly Ala Arg Val Val Pro Leu Gly Ser Met Gln Thr Val Ser
                325                 330                 335
```

```
Gly Tyr Thr Phe Arg Gly Phe Met Ser His Thr Asn Asn Tyr Pro Cys
                340                 345                 350

Ala Tyr Leu Asn Ala Ala Ser Ala Ile Gly Met Lys Met Gln Asp Val
            355                 360                 365

Asp Leu Phe Ile Asn Arg Leu Asp Arg Cys Leu Lys Ala Val Arg Lys
        370                 375                 380

Glu Arg Ser Lys Glu Ser Asp Asp Asn Tyr Asp Lys Thr Glu Asp Val
385                 390                 395                 400

Asp Ile Glu Glu Met Ala Leu Lys Leu Asp Asn Val Leu Leu Asp Thr
                405                 410                 415

Tyr Gln Asp Ala Ser Ser
                420

<210> SEQ ID NO 199
<211> LENGTH: 246
<212> TYPE: PRT
<213> ORGANISM: Homo sapiens

<400> SEQUENCE: 199

Met Thr Leu Ile Glu Gly Val Gly Asp Glu Val Thr Val Leu Phe Ser
1               5                   10                  15

Val Leu Ala Cys Leu Leu Val Leu Ala Leu Ala Trp Val Ser Thr His
            20                  25                  30

Thr Ala Glu Gly Gly Asp Pro Leu Pro Gln Pro Ser Gly Thr Pro Thr
        35                  40                  45

Pro Ser Gln Pro Ser Ala Ala Met Ala Ala Thr Asp Ser Met Arg Gly
50                  55                  60

Glu Ala Pro Gly Ala Glu Thr Pro Ser Leu Arg His Arg Gly Gln Ala
65                  70                  75                  80

Ala Gln Pro Glu Pro Ser Thr Gly Phe Thr Ala Thr Pro Pro Ala Pro
                85                  90                  95

Asp Ser Pro Gln Glu Pro Leu Val Leu Arg Leu Lys Phe Leu Asn Asp
            100                 105                 110

Ser Glu Gln Val Ala Arg Ala Trp Pro His Asp Thr Ile Gly Ser Leu
        115                 120                 125

Lys Arg Thr Gln Phe Pro Gly Arg Glu Gln Gln Val Arg Leu Ile Tyr
130                 135                 140

Gln Gly Gln Leu Leu Gly Asp Asp Thr Gln Thr Leu Gly Ser Leu His
145                 150                 155                 160

Leu Pro Pro Asn Cys Val Leu His Cys His Val Ser Thr Arg Val Gly
                165                 170                 175

Pro Pro Asn Pro Pro Cys Pro Pro Gly Ser Glu Pro Gly Pro Ser Gly
            180                 185                 190

Leu Glu Ile Gly Ser Leu Leu Leu Pro Leu Leu Leu Leu Leu Leu Leu
        195                 200                 205

Leu Leu Trp Tyr Cys Gln Ile Gln Tyr Arg Pro Phe Phe Pro Leu Thr
210                 215                 220

Ala Thr Leu Gly Leu Ala Gly Phe Thr Leu Leu Leu Ser Leu Leu Ala
225                 230                 235                 240

Phe Ala Met Tyr Arg Pro
                245

<210> SEQ ID NO 200
<211> LENGTH: 39
<212> TYPE: PRT
<213> ORGANISM: Homo sapiens
```

```
<220> FEATURE:
<221> NAME/KEY: misc_feature
<222> LOCATION: (39)..(39)
<223> OTHER INFORMATION: /note="C-term amidated"

<400> SEQUENCE: 200

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 201
<211> LENGTH: 177
<212> TYPE: PRT
<213> ORGANISM: Homo sapiens

<400> SEQUENCE: 201

Met Gln Arg Arg Leu Val Gln Gln Trp Ser Val Ala Val Phe Leu Leu
1               5                   10                  15

Ser Tyr Ala Val Pro Ser Cys Gly Arg Ser Val Glu Gly Leu Ser Arg
            20                  25                  30

Arg Leu Lys Arg Ala Val Ser Glu His Gln Leu Leu His Asp Lys Gly
        35                  40                  45

Lys Ser Ile Gln Asp Leu Arg Arg Arg Phe Phe Leu His His Leu Ile
    50                  55                  60

Ala Glu Ile His Thr Ala Glu Ile Arg Ala Thr Ser Glu Val Ser Pro
65                  70                  75                  80

Asn Ser Lys Pro Ser Pro Asn Thr Lys Asn His Pro Val Arg Phe Gly
                85                  90                  95

Ser Asp Asp Glu Gly Arg Tyr Leu Thr Gln Glu Thr Asn Lys Val Glu
            100                 105                 110

Thr Tyr Lys Glu Gln Pro Leu Lys Thr Pro Gly Lys Lys Lys Lys Gly
        115                 120                 125

Lys Pro Gly Lys Arg Lys Glu Gln Glu Lys Lys Arg Arg Thr Arg
    130                 135                 140

Ser Ala Trp Leu Asp Ser Gly Val Thr Gly Ser Gly Leu Glu Gly Asp
145                 150                 155                 160

His Leu Ser Asp Thr Ser Thr Thr Ser Leu Glu Leu Asp Ser Arg Arg
                165                 170                 175

His

<210> SEQ ID NO 202
<211> LENGTH: 36
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: misc_feature
<222> LOCATION: (36)..(36)
<223> OTHER INFORMATION: /note="C-term amidated"

<400> SEQUENCE: 202

Met Cys Met Pro Cys Phe Thr Thr Asp His Gln Met Ala Arg Lys Cys
1               5                   10                  15

Asp Asp Cys Cys Gly Gly Lys Gly Arg Gly Lys Cys Tyr Gly Pro Gln
            20                  25                  30
```

```
Cys Leu Cys Arg
        35

<210> SEQ ID NO 203
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: misc_feature
<222> LOCATION: (1)..(1)
<223> OTHER INFORMATION: /note="N-term acetylated"
<220> FEATURE:
<221> NAME/KEY: misc_feature
<222> LOCATION: (12)..(12)
<223> OTHER INFORMATION: /note="C-term amidated"

<400> SEQUENCE: 203

Arg Tyr Tyr Arg Trp Lys Lys Lys Lys Lys Lys Lys
1               5                   10

<210> SEQ ID NO 204
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 204

Cys Thr Thr His Trp Gly Phe Thr Leu Cys
1               5                   10

<210> SEQ ID NO 205
<211> LENGTH: 97
<212> TYPE: PRT
<213> ORGANISM: Homo sapiens

<400> SEQUENCE: 205

Met Val Phe Val Arg Arg Pro Trp Pro Ala Leu Thr Thr Val Leu Leu
1               5                   10                  15

Ala Leu Leu Val Cys Leu Gly Ala Leu Val Asp Ala Tyr Pro Ile Lys
            20                  25                  30

Pro Glu Ala Pro Arg Glu Asp Ala Ser Pro Glu Glu Leu Asn Arg Tyr
        35                  40                  45

Tyr Ala Ser Leu Arg His Tyr Leu Asn Leu Val Thr Arg Gln Arg Tyr
    50                  55                  60

Gly Lys Arg Asp Gly Pro Asp Thr Leu Leu Ser Lys Thr Phe Phe Pro
65                  70                  75                  80

Asp Gly Glu Asp Arg Pro Val Arg Ser Arg Ser Glu Gly Pro Asp Leu
                85                  90                  95

Trp

<210> SEQ ID NO 206
<211> LENGTH: 8
<212> TYPE: PRT
<213> ORGANISM: Homo sapiens

<400> SEQUENCE: 206

Asn Ala Pro Val Ser Ile Pro Gln
1               5
```

<210> SEQ ID NO 207
<211> LENGTH: 711
<212> TYPE: PRT
<213> ORGANISM: Homo sapiens

<400> SEQUENCE: 207

Met Ala Glu Arg Glu Ser Gly Leu Gly Gly Gly Ala Ala Ser Pro
1               5                   10                  15

Pro Ala Ala Ser Pro Phe Leu Gly Leu His Ile Ala Ser Pro Pro Asn
            20                  25                  30

Phe Arg Leu Thr His Asp Ile Ser Leu Glu Glu Phe Glu Asp Glu Asp
        35                  40                  45

Leu Ser Glu Ile Thr Asp Glu Cys Gly Ile Ser Leu Gln Cys Lys Asp
50                  55                  60

Thr Leu Ser Leu Arg Pro Pro Arg Ala Gly Leu Leu Ser Ala Gly Gly
65                  70                  75                  80

Gly Gly Ala Gly Ser Arg Leu Gln Ala Glu Met Leu Gln Met Asp Leu
                85                  90                  95

Ile Asp Ala Thr Gly Asp Thr Pro Gly Ala Glu Asp Asp Glu Glu Asp
            100                 105                 110

Asp Asp Glu Glu Arg Ala Ala Arg Arg Pro Gly Ala Gly Pro Pro Lys
        115                 120                 125

Ala Glu Ser Gly Gln Glu Pro Ala Ser Arg Gly Gln Gly Ser Gln
130                 135                 140

Gly Gln Ser Gln Gly Pro Gly Ser Gly Asp Thr Tyr Arg Pro Lys Arg
145                 150                 155                 160

Pro Thr Thr Leu Asn Leu Phe Pro Gln Val Pro Arg Ser Gln Asp Thr
            165                 170                 175

Leu Asn Asn Asn Ser Leu Gly Lys Lys His Ser Trp Gln Asp Arg Val
        180                 185                 190

Ser Arg Ser Ser Ser Pro Leu Lys Thr Gly Glu Gln Thr Pro Pro His
    195                 200                 205

Glu His Ile Cys Leu Ser Asp Glu Leu Pro Pro Gln Ser Gly Pro Ala
    210                 215                 220

Pro Thr Thr Asp Arg Gly Thr Ser Thr Asp Ser Pro Cys Arg Arg Ser
225                 230                 235                 240

Thr Ala Thr Gln Met Ala Pro Pro Gly Gly Pro Ala Ala Pro Pro
            245                 250                 255

Gly Gly Arg Gly His Ser His Arg Asp Arg Ile His Tyr Gln Ala Asp
        260                 265                 270

Val Arg Leu Glu Ala Thr Glu Glu Ile Tyr Leu Thr Pro Val Gln Arg
    275                 280                 285

Pro Pro Asp Ala Ala Glu Pro Thr Ser Ala Phe Leu Pro Pro Thr Glu
    290                 295                 300

Ser Arg Met Ser Val Ser Ser Asp Pro Asp Pro Ala Ala Tyr Pro Ser
305                 310                 315                 320

Thr Ala Gly Arg Pro His Pro Ser Ile Ser Glu Glu Glu Gly Phe
            325                 330                 335

Asp Cys Leu Ser Ser Pro Glu Arg Ala Glu Pro Gly Gly Gly Trp
        340                 345                 350

Arg Gly Ser Leu Gly Glu Pro Pro Pro Arg Ala Ser Leu Ser
    355                 360                 365

Ser Asp Thr Ser Ala Leu Ser Tyr Asp Ser Val Lys Tyr Thr Leu Val
370                 375                 380

Val Asp Glu His Ala Gln Leu Glu Leu Val Ser Leu Arg Pro Cys Phe
385                 390                 395                 400

Gly Asp Tyr Ser Asp Glu Ser Asp Ser Ala Thr Val Tyr Asp Asn Cys
            405                 410                 415

Ala Ser Val Ser Ser Pro Tyr Glu Ser Ala Ile Gly Glu Glu Tyr Glu
            420                 425                 430

Glu Ala Pro Arg Pro Gln Pro Pro Ala Cys Leu Ser Glu Asp Ser Thr
            435                 440                 445

Pro Asp Glu Pro Asp Val His Phe Ser Lys Lys Phe Leu Asn Val Phe
            450                 455                 460

Met Ser Gly Arg Ser Arg Ser Ser Ser Ala Glu Ser Phe Gly Leu Phe
465                 470                 475                 480

Ser Cys Ile Ile Asn Gly Glu Glu Gln Glu Gln Thr His Arg Ala Ile
            485                 490                 495

Phe Arg Phe Val Pro Arg His Glu Asp Glu Leu Glu Leu Glu Val Asp
            500                 505                 510

Asp Pro Leu Leu Val Glu Leu Gln Ala Glu Asp Tyr Trp Tyr Glu Ala
            515                 520                 525

Tyr Asn Met Arg Thr Gly Ala Arg Gly Val Phe Pro Ala Tyr Tyr Ala
            530                 535                 540

Ile Glu Val Thr Lys Glu Pro Glu His Met Ala Ala Leu Ala Lys Asn
545                 550                 555                 560

Ser Asp Trp Val Asp Gln Phe Arg Val Lys Phe Leu Gly Ser Val Gln
            565                 570                 575

Val Pro Tyr His Lys Gly Asn Asp Val Leu Cys Ala Ala Met Gln Lys
            580                 585                 590

Ile Ala Thr Thr Arg Arg Leu Thr Val His Phe Asn Pro Pro Ser Ser
            595                 600                 605

Cys Val Leu Glu Ile Ser Val Arg Gly Val Lys Ile Gly Val Lys Ala
610                 615                 620

Asp Asp Ser Gln Glu Ala Lys Gly Asn Lys Cys Ser His Phe Phe Gln
625                 630                 635                 640

Leu Lys Asn Ile Ser Phe Cys Gly Tyr His Pro Lys Asn Asn Lys Tyr
            645                 650                 655

Phe Gly Phe Ile Thr Lys His Pro Ala Asp His Arg Phe Ala Cys His
            660                 665                 670

Val Phe Val Ser Glu Asp Ser Thr Lys Ala Leu Ala Glu Ser Val Gly
            675                 680                 685

Arg Ala Phe Gln Gln Phe Tyr Lys Gln Phe Val Glu Tyr Thr Cys Pro
            690                 695                 700

Thr Glu Asp Ile Tyr Leu Glu
705                 710

<210> SEQ ID NO 208
<211> LENGTH: 710
<212> TYPE: PRT
<213> ORGANISM: Homo sapiens

<400> SEQUENCE: 208

Met Ala Glu Arg Glu Ser Gly Gly Leu Gly Gly Gly Ala Ala Ser Pro
1               5                   10                  15

Pro Ala Ala Ser Pro Phe Leu Gly Leu His Ile Ala Ser Pro Pro Asn
            20                  25                  30

Phe Arg Leu Thr His Asp Ile Ser Leu Glu Glu Phe Glu Asp Glu Asp
            35                  40                  45

```
Leu Ser Glu Ile Thr Asp Glu Cys Gly Ile Ser Leu Gln Cys Lys Asp
    50                  55                  60

Thr Leu Ser Leu Arg Pro Arg Ala Gly Leu Leu Ser Ala Gly Gly
65                  70                  75                  80

Gly Gly Ala Gly Ser Arg Leu Gln Ala Glu Met Leu Gln Met Asp Leu
                85                  90                  95

Ile Asp Ala Thr Gly Asp Thr Pro Gly Ala Glu Asp Asp Glu Glu Asp
                100                 105                 110

Asp Asp Glu Glu Arg Ala Ala Arg Arg Pro Gly Ala Gly Pro Pro Lys
            115                 120                 125

Ala Glu Ser Gly Gln Glu Pro Ala Ser Arg Gly Gln Gly Gln Ser Gln
    130                 135                 140

Gly Gln Ser Gln Gly Pro Gly Ser Gly Asp Thr Tyr Arg Pro Lys Arg
145                 150                 155                 160

Pro Thr Thr Leu Asn Leu Phe Pro Gln Val Pro Arg Ser Gln Asp Thr
                165                 170                 175

Leu Asn Asn Asn Ser Leu Gly Lys Lys His Ser Trp Gln Asp Arg Val
                180                 185                 190

Ser Arg Ser Ser Ser Pro Leu Lys Thr Gly Glu Gln Thr Pro Pro His
    195                 200                 205

Glu His Ile Cys Leu Ser Asp Glu Leu Pro Pro Gln Ser Gly Pro Ala
    210                 215                 220

Pro Thr Thr Asp Arg Gly Thr Ser Thr Asp Ser Pro Cys Arg Arg Ser
225                 230                 235                 240

Thr Ala Thr Gln Met Ala Pro Pro Gly Gly Pro Ala Ala Pro Pro
                245                 250                 255

Gly Gly Arg Gly His Ser His Arg Asp Arg Ile His Tyr Gln Ala Asp
            260                 265                 270

Val Arg Leu Glu Ala Thr Glu Glu Ile Tyr Leu Thr Pro Val Gln Arg
    275                 280                 285

Pro Pro Asp Ala Ala Glu Pro Thr Ser Ala Phe Leu Pro Pro Thr Glu
    290                 295                 300

Ser Arg Met Ser Val Ser Ser Asp Pro Asp Pro Ala Ala Tyr Pro Ser
305                 310                 315                 320

Thr Ala Gly Arg Pro His Pro Ser Ile Ser Glu Glu Glu Glu Gly Phe
                325                 330                 335

Asp Cys Leu Ser Ser Pro Glu Arg Ala Glu Pro Pro Gly Gly Gly Trp
                340                 345                 350

Arg Gly Ser Leu Gly Glu Pro Pro Pro Pro Arg Ala Ser Leu Ser
            355                 360                 365

Ser Asp Thr Ser Ala Leu Ser Tyr Asp Ser Val Lys Tyr Thr Leu Val
    370                 375                 380

Val Asp Glu His Ala Gln Leu Glu Leu Val Ser Leu Arg Pro Cys Phe
385                 390                 395                 400

Gly Asp Tyr Ser Asp Glu Ser Asp Ser Ala Thr Val Tyr Asp Asn Cys
                405                 410                 415

Ala Ser Val Ser Ser Pro Tyr Glu Ser Ala Ile Gly Glu Glu Tyr Glu
                420                 425                 430

Glu Ala Pro Arg Pro Gln Pro Ala Cys Leu Ser Glu Asp Ser Thr
            435                 440                 445

Pro Asp Glu Pro Asp Val His Phe Ser Lys Lys Phe Leu Asn Val Phe
    450                 455                 460

Met Ser Gly Arg Ser Arg Ser Ser Ser Ala Glu Ser Phe Gly Leu Phe
```

-continued

```
                465                 470                 475                 480
Ser Cys Ile Ile Asn Gly Glu Glu Gln Glu Gln Thr His Arg Ala Ile
                    485                 490                 495

Phe Arg Phe Val Pro Arg His Glu Asp Glu Leu Glu Leu Glu Val Asp
                500                 505                 510

Asp Pro Leu Leu Val Glu Leu Gln Ala Glu Asp Tyr Trp Tyr Glu Ala
            515                 520                 525

Tyr Asn Met Arg Thr Gly Ala Arg Gly Val Phe Pro Ala Tyr Tyr Ala
        530                 535                 540

Ile Glu Val Thr Lys Glu Pro Glu His Met Ala Ala Leu Ala Lys Asn
545                 550                 555                 560

Ser Asp Trp Val Asp Gln Phe Arg Val Lys Phe Leu Gly Ser Val Gln
                565                 570                 575

Val Pro Tyr His Lys Gly Asn Asp Val Leu Cys Ala Ala Met Gln Lys
            580                 585                 590

Ile Ala Thr Thr Arg Arg Leu Thr Val His Phe Asn Pro Pro Ser Ser
        595                 600                 605

Cys Val Leu Glu Ile Ser Val Arg Gly Val Lys Gly Val Lys Ala Asp
    610                 615                 620

Asp Ser Gln Glu Ala Lys Gly Asn Lys Cys Ser His Phe Gln Leu
625                 630                 635                 640

Lys Asn Ile Ser Phe Cys Gly Tyr His Pro Lys Asn Asn Lys Tyr Phe
                645                 650                 655

Gly Phe Ile Thr Lys His Pro Ala Asp His Arg Phe Ala Cys His Val
            660                 665                 670

Phe Val Ser Glu Asp Ser Thr Lys Ala Leu Ala Glu Ser Val Gly Arg
        675                 680                 685

Ala Phe Gln Gln Phe Tyr Lys Gln Phe Val Glu Tyr Thr Cys Pro Thr
    690                 695                 700

Glu Asp Ile Tyr Leu Glu
705                 710

<210> SEQ ID NO 209
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 209

Tyr Gly Phe Gly Gly
1               5

<210> SEQ ID NO 210
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 210

Tyr Cys Trp Ser Gln Tyr Leu Cys Tyr
1               5

<210> SEQ ID NO 211
<211> LENGTH: 28
```

```
<212> TYPE: PRT
<213> ORGANISM: Homo sapiens

<400> SEQUENCE: 211

His Ser Asp Ala Val Phe Thr Asp Asn Tyr Thr Arg Leu Arg Lys Gln
1               5                   10                  15

Met Ala Val Lys Lys Tyr Leu Asn Ser Ile Leu Asn
            20                  25

<210> SEQ ID NO 212
<211> LENGTH: 9
<212> TYPE: PRT
<213> ORGANISM: Homo sapiens

<400> SEQUENCE: 212

Ser Ala Leu Leu Arg Ser Ile Pro Ala
1               5

<210> SEQ ID NO 213
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 213

Leu Glu Glu Lys Lys Gly Asn Tyr Val Val Thr Asp His Cys
1               5                   10

<210> SEQ ID NO 214
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 214

Asn Phe Gly Ala Ile Leu
1               5

<210> SEQ ID NO 215
<211> LENGTH: 312
<212> TYPE: PRT
<213> ORGANISM: Homo sapiens

<400> SEQUENCE: 215

Met Ala Lys Val Phe Ser Phe Ile Leu Val Thr Thr Ala Leu Thr Met
1               5                   10                  15

Gly Arg Glu Ile Ser Ala Leu Glu Asp Cys Ala Gln Glu Gln Met Arg
            20                  25                  30

Leu Arg Ala Gln Val Arg Leu Leu Glu Thr Arg Val Lys Gln Gln Gln
        35                  40                  45

Val Lys Ile Lys Gln Leu Leu Gln Glu Asn Glu Val Gln Phe Leu Asp
    50                  55                  60

Lys Gly Asp Glu Asn Thr Val Ile Asp Leu Gly Ser Lys Arg Gln Tyr
65                  70                  75                  80

Ala Asp Cys Ser Glu Ile Phe Asn Asp Gly Tyr Lys Leu Ser Gly Phe
                85                  90                  95

Tyr Lys Ile Lys Pro Leu Gln Ser Pro Ala Glu Phe Ser Val Tyr Cys
            100                 105                 110
```

```
Asp Met Ser Asp Gly Gly Trp Thr Val Ile Gln Arg Arg Ser Asp
            115                 120                 125

Gly Ser Glu Asn Phe Asn Arg Gly Trp Lys Asp Tyr Glu Asn Gly Phe
    130                 135                 140

Gly Asn Phe Val Gln Lys His Gly Glu Tyr Trp Leu Gly Asn Lys Asn
145                 150                 155                 160

Leu His Phe Leu Thr Thr Gln Glu Asp Tyr Thr Leu Lys Ile Asp Leu
                165                 170                 175

Ala Asp Phe Glu Lys Asn Ser Arg Tyr Ala Gln Tyr Lys Asn Phe Lys
            180                 185                 190

Val Gly Asp Glu Lys Asn Phe Tyr Glu Leu Asn Ile Gly Glu Tyr Ser
            195                 200                 205

Gly Thr Ala Gly Asp Ser Leu Ala Gly Asn Phe His Pro Glu Val Gln
    210                 215                 220

Trp Trp Ala Ser His Gln Arg Met Lys Phe Ser Thr Trp Asp Arg Asp
225                 230                 235                 240

His Asp Asn Tyr Glu Gly Asn Cys Ala Glu Glu Asp Gln Ser Gly Trp
                245                 250                 255

Trp Phe Asn Arg Cys His Ser Ala Leu Asn Gly Val Tyr Tyr Ser
            260                 265                 270

Gly Pro Tyr Thr Ala Lys Thr Asp Asn Gly Ile Val Trp Tyr Thr Trp
    275                 280                 285

His Gly Trp Trp Tyr Ser Leu Lys Ser Val Val Met Lys Ile Arg Pro
    290                 295                 300

Asn Asp Phe Ile Pro Asn Val Ile
305                 310

<210> SEQ ID NO 216
<211> LENGTH: 64
<212> TYPE: PRT
<213> ORGANISM: Homo sapiens

<400> SEQUENCE: 216

Met Ala Lys Val Phe Ser Phe Ile Leu Val Thr Thr Ala Leu Thr Met
1               5                   10                  15

Gly Arg Glu Ile Ser Ala Leu Glu Asp Cys Ala Gln Glu Gln Met Arg
            20                  25                  30

Leu Arg Ala Gln Val Arg Leu Leu Glu Thr Arg Val Lys Gln Gln Gln
        35                  40                  45

Val Lys Ile Lys Gln Leu Leu Gln Glu Asn Glu Val Gln Phe Leu Asp
    50                  55                  60

<210> SEQ ID NO 217
<211> LENGTH: 19
<212> TYPE: PRT
<213> ORGANISM: Vibrio cholerae

<400> SEQUENCE: 217

Asn Leu Ile Asp Cys Cys Glu Ile Cys Cys Asn Pro Ala Cys Phe Gly
1               5                   10                  15

Cys Leu Asn

<210> SEQ ID NO 218
<211> LENGTH: 83
<212> TYPE: PRT
<213> ORGANISM: Laticauda semifasciata

<400> SEQUENCE: 218
```

```
Met Lys Thr Leu Leu Thr Leu Val Val Thr Ile Val Cys Leu
1               5                   10                  15

Asp Leu Gly Tyr Thr Arg Ile Cys Phe Asn His Gln Ser Ser Gln Pro
                20                  25                  30

Gln Thr Thr Lys Thr Cys Ser Pro Gly Glu Ser Ser Cys Tyr Asn Lys
            35                  40                  45

Gln Trp Ser Asp Phe Arg Gly Thr Ile Ile Glu Arg Gly Cys Gly Cys
50                      55                  60

Pro Thr Val Lys Pro Gly Ile Lys Leu Ser Cys Cys Glu Ser Glu Val
65                  70                  75                  80

Cys Asn Asn

<210> SEQ ID NO 219
<211> LENGTH: 141
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 219

Met Ser Asn Lys Lys Ile Ile Lys Ile Ile Lys Leu Gln Ile Pro Gly
1               5                   10                  15

Gly Lys Ala Asn Pro Ala Pro Pro Ile Gly Pro Ala Leu Gly Ala Ala
                20                  25                  30

Gly Val Asn Ile Met Gly Phe Cys Lys Glu Phe Asn Ala Ala Thr Gln
            35                  40                  45

Asp Arg Pro Gly Asp Leu Leu Pro Val Val Ile Thr Val Tyr Ser Asp
50                      55                  60

Lys Thr Phe Ser Phe Val Met Lys Gln Ser Pro Val Ser Ser Leu Ile
65                  70                  75                  80

Lys Lys Ala Leu Gly Leu Glu Ser Gly Ser Lys Ile Pro Asn Arg Asn
                85                  90                  95

Lys Val Gly Lys Leu Thr Arg Ala Gln Ile Thr Val Ile Ala Glu Gln
            100                 105                 110

Lys Met Lys Asp Met Asp Val Val Leu Leu Glu Ser Ala Glu Arg Met
        115                 120                 125

Val Glu Gly Thr Ala Arg Ser Met Gly Val Asp Val Glu
    130                 135                 140

<210> SEQ ID NO 220
<211> LENGTH: 172
<212> TYPE: PRT
<213> ORGANISM: Mus musculus

<400> SEQUENCE: 220

Met Ser Val Pro Glu Pro Pro Pro Asp Gly Val Leu Thr Gly Pro
1               5                   10                  15

Ser Asp Ser Leu Glu Ala Gly Glu Pro Thr Pro Gly Leu Ser Asp Thr
                20                  25                  30

Ser Pro Asp Glu Gly Leu Ile Glu Asp Phe Pro Val Asp Asp Arg Ala
            35                  40                  45

Val Glu His Leu Val Gly Gly Leu Leu Ser His Tyr Leu Pro Asp Leu
50                      55                  60

Gln Arg Ser Lys Arg Ala Leu Gln Glu Leu Thr Gln Asn Gln Val Val
65                  70                  75                  80
```

```
Leu Leu Asp Thr Leu Glu Gln Glu Ile Ser Lys Phe Lys Glu Cys His
                85                  90                  95

Ser Met Leu Asp Ile Asn Ala Leu Phe Thr Glu Ala Lys His Tyr His
            100                 105                 110

Ala Lys Leu Val Thr Ile Arg Lys Glu Met Leu Leu Leu His Glu Lys
        115                 120                 125

Thr Ser Lys Leu Lys Lys Arg Ala Leu Lys Leu Gln Gln Lys Arg Gln
    130                 135                 140

Arg Glu Glu Leu Glu Arg Glu Gln Gln Arg Glu Lys Glu Phe Glu Arg
145                 150                 155                 160

Glu Lys Gln Leu Thr Ala Lys Pro Ala Lys Arg Thr
                165                 170
```

```
<210> SEQ ID NO 221
<211> LENGTH: 90
<212> TYPE: PRT
<213> ORGANISM: Human immunodeficiency virus type 1

<400> SEQUENCE: 221
```

```
Lys Leu Thr Pro Leu Cys Val Thr Leu Asn Cys Thr Asp Leu Asp Leu
1               5                   10                  15

Arg Asn Thr Thr Asn Asn Thr Thr Glu Glu Arg Gly Glu Met Lys
                20                  25                  30

Asn Cys Ser Phe Asn Ile Thr Thr Asn Ile Arg Asp Arg Tyr Gln Lys
            35                  40                  45

Glu Tyr Ala Leu Phe Tyr Lys Leu Asp Val Ile Pro Ile Lys Glu Asp
        50                  55                  60

Asn Thr Ser Asp Asn Thr Ser Tyr Arg Leu Ile Ser Cys Asn Thr Ser
65                  70                  75                  80

Val Ile Thr Gln Ala Cys Pro Lys Ile Ser
                85                  90
```

```
<210> SEQ ID NO 222
<211> LENGTH: 191
<212> TYPE: PRT
<213> ORGANISM: Bubalus bubalis

<400> SEQUENCE: 222
```

```
Ala Phe Pro Ala Met Ser Leu Ser Leu Phe Ala Asn Ala Val Leu
1               5                   10                  15

Arg Ala Gln His Leu His Gln Leu Ala Ala Asp Thr Phe Lys Glu Phe
                20                  25                  30

Glu Arg Thr Tyr Ile Pro Glu Gly Gln Arg Tyr Ser Ile Gln Asn Thr
            35                  40                  45

Gln Val Ala Phe Cys Phe Ser Glu Thr Ile Pro Ala Pro Thr Gly Lys
        50                  55                  60

Asn Glu Ala Gln Gln Lys Ser Asp Leu Glu Leu Leu Arg Ile Ser Leu
65                  70                  75                  80

Leu Leu Ile Gln Ser Trp Leu Gly Pro Leu Gln Phe Leu Ser Arg Val
                85                  90                  95

Phe Thr Asn Ser Leu Val Phe Gly Thr Ser Asp Arg Val Tyr Glu Lys
            100                 105                 110

Leu Lys Asp Leu Glu Glu Gly Ile Leu Ala Leu Met Arg Glu Leu Glu
        115                 120                 125

Asp Gly Thr Pro Arg Ala Gly Gln Ile Leu Lys Arg Thr Tyr Asp Lys
    130                 135                 140

Phe Asp Thr Asn Met Arg Ser Asp Asp Ala Leu Leu Lys Asn Tyr Gly
```

```
                        145                 150                 155                 160
Leu Leu Ser Cys Phe Arg Lys Asp Leu His Lys Thr Glu Thr Tyr Leu
                    165                 170                 175

Arg Val Met Lys Cys Arg Arg Phe Gly Glu Ala Ser Cys Ala Phe
                180                 185                 190

<210> SEQ ID NO 223
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 223

Leu Ser Glu Asn Asp Glu Trp Thr Gln Asp Arg Ala Lys Pro
1               5                   10

<210> SEQ ID NO 224
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 224

Asn Pro Phe Pro Thr Trp Arg Lys Arg Pro Gly
1               5                   10

<210> SEQ ID NO 225
<211> LENGTH: 134
<212> TYPE: PRT
<213> ORGANISM: Homo sapiens

<400> SEQUENCE: 225

Met Asp Pro Gln Thr Ala Pro Ser Arg Ala Leu Leu Leu Leu Leu Phe
1               5                   10                  15

Leu His Leu Ala Phe Leu Gly Gly Arg Ser His Pro Leu Gly Ser Pro
                20                  25                  30

Gly Ser Ala Ser Asp Leu Glu Thr Ser Gly Leu Gln Glu Gln Arg Asn
            35                  40                  45

His Leu Gln Gly Lys Leu Ser Glu Leu Gln Val Glu Gln Thr Ser Leu
        50                  55                  60

Glu Pro Leu Gln Glu Ser Pro Arg Pro Thr Gly Val Trp Lys Ser Arg
65                  70                  75                  80

Glu Val Ala Thr Glu Gly Ile Arg Gly His Arg Lys Met Val Leu Tyr
                85                  90                  95

Thr Leu Arg Ala Pro Arg Ser Pro Lys Met Val Gln Gly Ser Gly Cys
                100                 105                 110

Phe Gly Arg Lys Met Asp Arg Ile Ser Ser Ser Ser Gly Leu Gly Cys
            115                 120                 125

Lys Val Leu Arg Arg His
        130

<210> SEQ ID NO 226
<211> LENGTH: 87
<212> TYPE: PRT
<213> ORGANISM: Heloderma suspectum

<400> SEQUENCE: 226
```

```
Met Lys Ile Ile Leu Trp Leu Cys Val Phe Gly Leu Phe Leu Ala Thr
1               5                   10                  15

Leu Phe Pro Ile Ser Trp Gln Met Pro Val Glu Ser Gly Leu Ser Ser
            20                  25                  30

Glu Asp Ser Ala Ser Ser Glu Ser Phe Ala Ser Lys Ile Lys Arg His
        35                  40                  45

Gly Glu Gly Thr Phe Thr Ser Asp Leu Ser Lys Gln Met Glu Glu Glu
    50                  55                  60

Ala Val Arg Leu Phe Ile Glu Trp Leu Lys Asn Gly Gly Pro Ser Ser
65              70                  75                  80

Gly Ala Pro Pro Pro Ser Gly
                85
```

<210> SEQ ID NO 227
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 227

```
His Gly Val Ser Gly His Gly Gln His Gly Val His Gly
1               5                   10
```

<210> SEQ ID NO 228
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"
<220> FEATURE:
<221> NAME/KEY: misc_feature
<222> LOCATION: (1)..(1)
<223> OTHER INFORMATION: /note="N-term acetylated"
<220> FEATURE:
<221> NAME/KEY: misc_feature
<222> LOCATION: (9)..(9)
<223> OTHER INFORMATION: /note="C-term amidated"

<400> SEQUENCE: 228

```
Lys Trp Arg Arg Trp Val Arg Trp Ile
1               5
```

<210> SEQ ID NO 229
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 229

```
Lys Phe His Glu Lys His His Ser His Arg Gly Tyr
1               5                   10
```

<210> SEQ ID NO 230
<211> LENGTH: 51
<212> TYPE: PRT
<213> ORGANISM: Homo sapiens

<400> SEQUENCE: 230

```
Met Lys Phe Phe Val Phe Ala Leu Ile Leu Ala Leu Met Leu Ser Met
1               5                   10                  15

Thr Gly Ala Asp Ser His Ala Lys Arg His His Gly Tyr Lys Arg Lys
            20                  25                  30

Phe His Glu Lys His His Ser His Arg Gly Tyr Arg Ser Asn Tyr Leu
        35                  40                  45

Tyr Asp Asn
    50

<210> SEQ ID NO 231
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 231

Met Gln Cys Asn Ser
1               5

<210> SEQ ID NO 232
<211> LENGTH: 390
<212> TYPE: PRT
<213> ORGANISM: Homo sapiens

<400> SEQUENCE: 232

Met Pro Pro Ser Gly Leu Arg Leu Leu Pro Leu Leu Leu Pro Leu Leu
1               5                   10                  15

Trp Leu Leu Val Leu Thr Pro Gly Arg Pro Ala Ala Gly Leu Ser Thr
            20                  25                  30

Cys Lys Thr Ile Asp Met Glu Leu Val Lys Arg Lys Arg Ile Glu Ala
        35                  40                  45

Ile Arg Gly Gln Ile Leu Ser Lys Leu Arg Leu Ala Ser Pro Pro Ser
    50                  55                  60

Gln Gly Glu Val Pro Pro Gly Pro Leu Pro Glu Ala Val Leu Ala Leu
65                  70                  75                  80

Tyr Asn Ser Thr Arg Asp Arg Val Ala Gly Glu Ser Ala Glu Pro Glu
                85                  90                  95

Pro Glu Pro Glu Ala Asp Tyr Tyr Ala Lys Glu Val Thr Arg Val Leu
            100                 105                 110

Met Val Glu Thr His Asn Glu Ile Tyr Asp Lys Phe Lys Gln Ser Thr
        115                 120                 125

His Ser Ile Tyr Met Phe Phe Asn Thr Ser Glu Leu Arg Glu Ala Val
    130                 135                 140

Pro Glu Pro Val Leu Leu Ser Arg Ala Glu Leu Arg Leu Leu Arg Leu
145                 150                 155                 160

Lys Leu Lys Val Glu Gln His Val Glu Leu Tyr Gln Lys Tyr Ser Asn
                165                 170                 175

Asn Ser Trp Arg Tyr Leu Ser Asn Arg Leu Leu Ala Pro Ser Asp Ser
            180                 185                 190

Pro Glu Trp Leu Ser Phe Asp Val Thr Gly Val Val Arg Gln Trp Leu
        195                 200                 205

Ser Arg Gly Gly Glu Ile Glu Gly Phe Arg Leu Ser Ala His Cys Ser
    210                 215                 220

Cys Asp Ser Arg Asp Asn Thr Leu Gln Val Asp Ile Asn Gly Phe Thr
225                 230                 235                 240
```

```
Thr Gly Arg Arg Gly Asp Leu Ala Thr Ile His Gly Met Asn Arg Pro
            245                 250                 255
Phe Leu Leu Leu Met Ala Thr Pro Leu Glu Arg Ala Gln His Leu Gln
        260                 265                 270
Ser Ser Arg His Arg Arg Ala Leu Asp Thr Asn Tyr Cys Phe Ser Ser
    275                 280                 285
Thr Glu Lys Asn Cys Cys Val Arg Gln Leu Tyr Ile Asp Phe Arg Lys
290                 295                 300
Asp Leu Gly Trp Lys Trp Ile His Glu Pro Lys Gly Tyr His Ala Asn
305                 310                 315                 320
Phe Cys Leu Gly Pro Cys Pro Tyr Ile Trp Ser Leu Asp Thr Gln Tyr
                325                 330                 335
Ser Lys Val Leu Ala Leu Tyr Asn Gln His Asn Pro Gly Ala Ser Ala
            340                 345                 350
Ala Pro Cys Cys Val Pro Gln Ala Leu Glu Pro Leu Pro Ile Val Tyr
        355                 360                 365
Tyr Val Gly Arg Lys Pro Lys Val Glu Gln Leu Ser Asn Met Ile Val
    370                 375                 380
Arg Ser Cys Lys Cys Ser
385                 390

<210> SEQ ID NO 233
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 233

Cys Asn Gly Arg Cys Gly
1               5

<210> SEQ ID NO 234
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 234

Val Pro Val Asp
1

<210> SEQ ID NO 235
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 235

Val Pro Asp Pro Arg
1               5

<210> SEQ ID NO 236
<211> LENGTH: 348
<212> TYPE: PRT
<213> ORGANISM: Homo sapiens
```

<400> SEQUENCE: 236

```
Met Leu Gln Thr Lys Asp Leu Ile Trp Thr Leu Phe Phe Leu Gly Thr
1               5                   10                  15

Ala Val Ser Leu Gln Val Asp Ile Val Pro Ser Gln Gly Glu Ile Ser
            20                  25                  30

Val Gly Glu Ser Lys Phe Phe Leu Cys Gln Val Ala Gly Asp Ala Lys
        35                  40                  45

Asp Lys Asp Ile Ser Trp Phe Ser Pro Asn Gly Glu Lys Leu Thr Pro
    50                  55                  60

Asn Gln Gln Arg Ile Ser Val Val Trp Asn Asp Asp Ser Ser Ser Thr
65                  70                  75                  80

Leu Thr Ile Tyr Asn Ala Asn Ile Asp Asp Ala Gly Ile Tyr Lys Cys
                85                  90                  95

Val Val Thr Gly Glu Asp Gly Ser Glu Ser Glu Ala Thr Val Asn Val
            100                 105                 110

Lys Ile Phe Gln Lys Leu Met Phe Lys Asn Ala Pro Thr Pro Gln Glu
        115                 120                 125

Phe Arg Glu Gly Glu Asp Ala Val Ile Val Cys Asp Val Val Ser Ser
130                 135                 140

Leu Pro Pro Thr Ile Ile Trp Lys His Lys Gly Arg Asp Val Ile Leu
145                 150                 155                 160

Lys Lys Asp Val Arg Phe Ile Phe Leu Ser Asn Asn Tyr Leu Pro Ile
                165                 170                 175

Pro Gly Ile Lys Lys Thr Asp Glu Gly Thr Tyr Arg Cys Glu Gly Arg
            180                 185                 190

Ile Leu Ala Arg Gly Glu Ile Asn Phe Asn Asp Ile Gln Val Ile Val
        195                 200                 205

Asn Val Pro Pro Thr Ile Gln Ala Arg Gln Asn Ile Val Asn Ala Thr
    210                 215                 220

Ala Asn Leu Gly Gln Ser Val Thr Leu Val Cys Asp Ala Glu Gly Phe
225                 230                 235                 240

Pro Gly Pro Thr Met Ser Trp Thr Lys Asp Gly Glu Gln Ile Glu Gln
                245                 250                 255

Glu Glu His Asp Glu Lys Tyr Leu Phe Ser Asp Asp Ser Ser His Leu
            260                 265                 270

Thr Ile Lys Lys Val Asp Lys Asn His Glu Ala Glu Asn Ile Cys Ile
        275                 280                 285

Ala Glu Asn Lys Val Gly Glu Gln Asp Ala Thr Ile His Leu Lys Val
290                 295                 300

Phe Ala Lys Pro Gln Ile Thr Tyr Val Glu Asp Gln Thr Ala Met Glu
305                 310                 315                 320

Leu Ala Glu Gln Val Ile Leu Thr Val Glu Ala Ser Gly Asp His Ile
                325                 330                 335

Pro Tyr Ile Thr Trp Trp Thr Ser Thr Trp Gln Ile
            340                 345
```

<210> SEQ ID NO 237
<211> LENGTH: 153
<212> TYPE: PRT
<213> ORGANISM: Homo sapiens

<400> SEQUENCE: 237

```
Met Val Ala Thr Lys Thr Phe Ala Leu Leu Leu Ser Leu Phe Leu
1               5                   10                  15
```

```
Ala Val Gly Leu Gly Glu Lys Glu Gly His Phe Ser Ala Leu Pro
            20                  25                  30

Ser Leu Pro Val Gly Ser His Ala Lys Val Ser Ser Pro Gln Pro Arg
        35                  40                  45

Gly Pro Arg Tyr Ala Glu Gly Thr Phe Ile Ser Asp Tyr Ser Ile Ala
 50                  55                  60

Met Asp Lys Ile His Gln Gln Asp Phe Val Asn Trp Leu Leu Ala Gln
 65                  70                  75                  80

Lys Gly Lys Lys Asn Asp Trp Lys His Asn Ile Thr Gln Arg Glu Ala
                 85                  90                  95

Arg Ala Leu Glu Leu Ala Ser Gln Ala Asn Arg Lys Glu Glu Glu Ala
                100                 105                 110

Val Glu Pro Gln Ser Ser Pro Ala Lys Asn Pro Ser Asp Glu Asp Leu
            115                 120                 125

Leu Arg Asp Leu Leu Ile Gln Glu Leu Leu Ala Cys Leu Leu Asp Gln
        130                 135                 140

Thr Asn Leu Cys Arg Leu Arg Ser Arg
145                 150

<210> SEQ ID NO 238
<211> LENGTH: 24
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 238

Glu Leu Tyr Ser Ala Leu Ala Asn Lys Cys Cys His Val Gly Cys Thr
1               5                   10                  15

Lys Arg Ser Leu Ala Arg Phe Cys
            20

<210> SEQ ID NO 239
<211> LENGTH: 28
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 239

Asp Ser Trp Met Glu Glu Val Ile Lys Leu Cys Gly Arg Glu Leu Val
1               5                   10                  15

Arg Ala Gln Ile Ala Ile Cys Gly Met Ser Thr Ser
            20                  25

<210> SEQ ID NO 240
<211> LENGTH: 31
<212> TYPE: PRT
<213> ORGANISM: Homo sapiens

<400> SEQUENCE: 240

Glu Ala Glu Asp Leu Gln Val Gly Gln Val Glu Leu Gly Gly Gly Pro
1               5                   10                  15

Gly Ala Gly Ser Leu Gln Pro Leu Ala Leu Glu Gly Ser Leu Gln
            20                  25                  30

<210> SEQ ID NO 241
<211> LENGTH: 80
```

```
<212> TYPE: PRT
<213> ORGANISM: Homo sapiens

<400> SEQUENCE: 241

Met Asp Lys Phe Trp Trp His Ala Ala Trp Gly Leu Cys Leu Val Pro
1               5                   10                  15

Leu Ser Leu Ala Gln Ile Asp Leu Asn Ile Thr Cys Arg Phe Ala Gly
            20                  25                  30

Val Phe His Val Glu Lys Asn Gly Arg Tyr Ser Ile Ser Arg Thr Glu
        35                  40                  45

Ala Ala Asp Leu Cys Lys Ala Phe Asn Ser Thr Leu Pro Thr Met Ala
    50                  55                  60

Gln Met Glu Lys Ala Leu Ser Ile Gly Phe Glu Thr Cys Ser Ser Thr
65                  70                  75                  80

<210> SEQ ID NO 242
<211> LENGTH: 83
<212> TYPE: PRT
<213> ORGANISM: Bitis arietans

<400> SEQUENCE: 242

Ser Pro Pro Val Cys Gly Asn Lys Ile Leu Glu Gln Gly Glu Asp Cys
1               5                   10                  15

Asp Cys Gly Ser Pro Ala Asn Cys Gln Asp Arg Cys Cys Asn Ala Ala
            20                  25                  30

Thr Cys Lys Leu Thr Pro Gly Ser Gln Cys Asn Tyr Gly Glu Cys Cys
        35                  40                  45

Asp Gln Cys Arg Phe Lys Lys Ala Gly Thr Val Cys Arg Ile Ala Arg
    50                  55                  60

Gly Asp Trp Asn Asp Asp Tyr Cys Thr Gly Lys Ser Ser Asp Cys Pro
65                  70                  75                  80

Trp Asn His

<210> SEQ ID NO 243
<211> LENGTH: 50
<212> TYPE: PRT
<213> ORGANISM: Homo sapiens

<400> SEQUENCE: 243

Met Glu Cys Glu Ser Gly Pro Cys Cys Arg Asn Cys Lys Phe Leu Lys
1               5                   10                  15

Glu Gly Thr Ile Cys Lys Arg Ala Arg Gly Asp Asp Leu Asp Asp Tyr
            20                  25                  30

Cys Asn Gly Lys Thr Cys Asp Cys Pro Arg Asn Pro His Lys Gly Pro
        35                  40                  45

Ala Thr
    50

<210> SEQ ID NO 244
<211> LENGTH: 82
<212> TYPE: PRT
<213> ORGANISM: Homo sapiens

<400> SEQUENCE: 244

Glu Ala Ser Trp Lys Pro Arg Ser Gln Gln Pro Asp Ala Pro Leu Gly
1               5                   10                  15

Thr Gly Ala Asn Arg Asp Leu Glu Leu Pro Trp Leu Glu Gln Gln Gly
            20                  25                  30

Pro Ala Ser His His Arg Arg Gln Leu Gly Pro Gln Gly Pro Pro His
```

```
                    35                  40                  45
Leu Val Ala Asp Pro Ser Lys Lys Gln Gly Pro Trp Leu Glu Glu
 50                  55                  60

Glu Glu Ala Tyr Gly Trp Met Asp Phe Gly Arg Arg Ser Ala Glu Asp
 65                  70                  75                  80

Glu Asn

<210> SEQ ID NO 245
<211> LENGTH: 23
<212> TYPE: PRT
<213> ORGANISM: Human herpesvirus 1

<400> SEQUENCE: 245

Met Gly Gly Ala Ala Ala Arg Leu Gly Ala Val Ile Leu Phe Val Val
 1                   5                  10                  15

Ile Val Gly Leu His Gly Val
                 20

<210> SEQ ID NO 246
<211> LENGTH: 12
<212> TYPE: PRT
<213> ORGANISM: Homo sapiens

<400> SEQUENCE: 246

Leu Tyr Glu Asn Lys Pro Arg Arg Pro Tyr Ile Leu
 1                   5                  10

<210> SEQ ID NO 247
<211> LENGTH: 176
<212> TYPE: PRT
<213> ORGANISM: Homo sapiens

<400> SEQUENCE: 247

Met Lys Val Leu Leu Cys Asp Leu Leu Leu Ser Leu Phe Ser Ser
 1                   5                  10                  15

Val Phe Ser Ser Cys Gln Arg Asp Cys Leu Thr Cys Gln Glu Lys Leu
                 20                  25                  30

His Pro Ala Leu Asp Ser Phe Asp Leu Glu Val Cys Ile Leu Glu Cys
                 35                  40                  45

Glu Glu Lys Val Phe Pro Ser Pro Leu Trp Thr Pro Cys Thr Lys Val
 50                  55                  60

Met Ala Arg Ser Ser Trp Gln Leu Ser Pro Ala Ala Pro Glu His Val
 65                  70                  75                  80

Ala Ala Ala Leu Tyr Gln Pro Arg Ala Ser Glu Met Gln His Leu Arg
                 85                  90                  95

Arg Met Pro Arg Val Arg Ser Leu Phe Gln Glu Gln Glu Glu Pro Glu
                100                 105                 110

Pro Gly Met Glu Glu Ala Gly Glu Met Glu Gln Lys Gln Leu Gln Lys
                115                 120                 125

Arg Phe Gly Gly Phe Thr Gly Ala Arg Lys Ser Ala Arg Lys Leu Ala
                130                 135                 140

Asn Gln Lys Arg Phe Ser Glu Phe Met Arg Gln Tyr Leu Val Leu Ser
145                 150                 155                 160

Met Gln Ser Ser Gln Arg Arg Arg Thr Leu His Gln Asn Gly Asn Val
                165                 170                 175

<210> SEQ ID NO 248
<211> LENGTH: 37
<212> TYPE: PRT
```

<213> ORGANISM: Homo sapiens

<400> SEQUENCE: 248

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Lys Arg Asn
            20                  25                  30

Arg Asn Asn Ile Ala
        35

<210> SEQ ID NO 249
<211> LENGTH: 49
<212> TYPE: PRT
<213> ORGANISM: Sus scrofa

<400> SEQUENCE: 249

Gly Trp Pro Gln Ala Pro Ala Met Asp Gly Ala Gly Lys Thr Gly Ala
1               5                   10                  15

Glu Glu Ala Gln Pro Pro Glu Gly Lys Gly Ala Arg Glu His Ser Arg
            20                  25                  30

Gln Glu Glu Glu Glu Thr Ala Gly Ala Pro Gln Gly Leu Phe Arg
        35                  40                  45

Gly

<210> SEQ ID NO 250
<211> LENGTH: 185
<212> TYPE: PRT
<213> ORGANISM: Homo sapiens

<400> SEQUENCE: 250

Met Pro Arg Leu Phe Leu Phe His Leu Leu Glu Phe Cys Leu Leu Leu
1               5                   10                  15

Asn Gln Phe Ser Arg Ala Val Ala Ala Lys Trp Lys Asp Asp Val Ile
            20                  25                  30

Lys Leu Cys Gly Arg Glu Leu Val Arg Ala Gln Ile Ala Ile Cys Gly
        35                  40                  45

Met Ser Thr Trp Ser Lys Arg Ser Leu Ser Gln Glu Asp Ala Pro Gln
    50                  55                  60

Thr Pro Arg Pro Val Ala Glu Ile Val Pro Ser Phe Ile Asn Lys Asp
65                  70                  75                  80

Thr Glu Thr Ile Ile Ile Met Leu Glu Phe Ile Ala Asn Leu Pro Pro
                85                  90                  95

Glu Leu Lys Ala Ala Leu Ser Glu Arg Gln Pro Ser Leu Pro Glu Leu
            100                 105                 110

Gln Gln Tyr Val Pro Ala Leu Lys Asp Ser Asn Leu Ser Phe Glu Glu
        115                 120                 125

Phe Lys Lys Leu Ile Arg Asn Arg Gln Ser Glu Ala Ala Asp Ser Asn
    130                 135                 140

Pro Ser Glu Leu Lys Tyr Leu Gly Leu Asp Thr His Ser Gln Lys Lys
145                 150                 155                 160

Arg Arg Pro Tyr Val Ala Leu Phe Glu Lys Cys Cys Leu Ile Gly Cys
                165                 170                 175

Thr Lys Arg Ser Leu Ala Lys Tyr Cys
            180                 185

<210> SEQ ID NO 251
<211> LENGTH: 27
<212> TYPE: PRT

<213> ORGANISM: Homo sapiens

<400> SEQUENCE: 251

His Ser Asp Gly Thr Phe Thr Ser Glu Leu Ser Arg Leu Arg Glu Gly
1               5                   10                  15

Ala Arg Leu Gln Arg Leu Leu Gln Gly Leu Val
            20                  25

<210> SEQ ID NO 252
<211> LENGTH: 207
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 252

Met Ala Pro Phe Glu Pro Leu Ala Ser Gly Ile Leu Leu Leu Leu Trp
1               5                   10                  15

Leu Ile Ala Pro Ser Arg Ala Cys Thr Cys Val Pro Pro His Pro Gln
            20                  25                  30

Thr Ala Phe Cys Asn Ser Asp Leu Val Ile Arg Ala Lys Phe Val Gly
        35                  40                  45

Thr Pro Glu Val Asn Gln Thr Thr Leu Tyr Gln Arg Tyr Glu Ile Lys
    50                  55                  60

Met Thr Lys Met Tyr Lys Gly Phe Gln Ala Leu Gly Asp Ala Ala Asp
65                  70                  75                  80

Ile Arg Phe Val Tyr Thr Pro Ala Met Glu Ser Val Cys Gly Tyr Phe
                85                  90                  95

His Arg Ser His Asn Arg Ser Glu Glu Phe Leu Ile Ala Gly Lys Leu
            100                 105                 110

Gln Asp Gly Leu Leu His Ile Thr Thr Cys Ser Phe Val Ala Pro Trp
        115                 120                 125

Asn Ser Leu Ser Leu Ala Gln Arg Arg Gly Phe Thr Lys Thr Tyr Thr
    130                 135                 140

Val Gly Cys Glu Glu Cys Thr Val Phe Pro Cys Leu Ser Ile Pro Cys
145                 150                 155                 160

Lys Leu Gln Ser Gly Thr His Cys Leu Trp Thr Asp Gln Leu Leu Gln
                165                 170                 175

Gly Ser Glu Lys Gly Phe Gln Ser Arg His Leu Ala Cys Leu Pro Arg
            180                 185                 190

Glu Pro Gly Leu Cys Thr Trp Gln Ser Leu Arg Ser Gln Ile Ala
        195                 200                 205

<210> SEQ ID NO 253
<211> LENGTH: 74
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 253

Asp Thr Thr Val Ser Glu Pro Ala Pro Ser Cys Val Thr Leu Tyr Gln
1               5                   10                  15

Ser Trp Arg Tyr Ser Gln Ala Asp Asn Gly Cys Ala Gln Thr Val Thr
            20                  25                  30

Val Lys Val Val Tyr Glu Asp Asp Thr Glu Gly Leu Cys Tyr Ala Val

```
                35                  40                  45
Ala Pro Gly Gln Ile Thr Thr Val Gly Asp Gly Tyr Ile Gly Ser His
        50                  55                  60

Gly His Ala Arg Tyr Leu Ala Arg Cys Leu
65                  70
```

<210> SEQ ID NO 254
<211> LENGTH: 44
<212> TYPE: PRT
<213> ORGANISM: Homo sapiens

<400> SEQUENCE: 254

```
Met Ser Asp Lys Pro Asp Met Ala Glu Ile Glu Lys Phe Asp Lys Ser
1               5                   10                  15

Lys Leu Lys Lys Thr Glu Thr Gln Glu Lys Asn Pro Leu Pro Ser Lys
            20                  25                  30

Glu Thr Ile Glu Gln Glu Lys Gln Ala Gly Glu Ser
        35                  40
```

<210> SEQ ID NO 255
<211> LENGTH: 32
<212> TYPE: PRT
<213> ORGANISM: Rana tigrina

<400> SEQUENCE: 255

```
Thr Ala Pro Arg Ser Leu Arg Arg Ser Ser Cys Phe Gly Gly Arg Met
1               5                   10                  15

Asp Arg Ile Gly Ala Gln Ser Gly Leu Gly Cys Asn Ser Phe Arg Tyr
            20                  25                  30
```

<210> SEQ ID NO 256
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 256

```
Gly Ser Arg Ala His Ser Ser His Leu Lys
1               5                   10
```

<210> SEQ ID NO 257
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 257

```
Glu Leu Lys Cys Tyr Thr Cys Lys Glu Pro Met Thr Ser Ala Ala Cys
1               5                   10                  15
```

<210> SEQ ID NO 258
<211> LENGTH: 4
<212> TYPE: PRT
<213> ORGANISM: Homo sapiens

<400> SEQUENCE: 258

```
Asp Ala His Lys
1
```

```
<210> SEQ ID NO 259
<211> LENGTH: 38
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 259

Lys Met Val Gln Gly Ser Gly Cys Phe Gly Arg Lys Met Asp Ile Ser
1               5                   10                  15

Ser Ser Ser Gly Leu Gly Cys Pro Ser Leu Arg Asp Pro Arg Pro Asn
            20                  25                  30

Ala Pro Ser Thr Ser Ala
        35

<210> SEQ ID NO 260
<211> LENGTH: 54
<212> TYPE: PRT
<213> ORGANISM: Homo sapiens
<220> FEATURE:
<221> NAME/KEY: misc_feature
<222> LOCATION: (54)..(54)
<223> OTHER INFORMATION: /note="C-term amidated"

<400> SEQUENCE: 260

Gly Thr Ser Leu Ser Pro Pro Glu Ser Ser Gly Ser Pro Gln Gln
1               5                   10                  15

Pro Gly Leu Ser Ala Pro His Ser Arg Gln Ile Pro Ala Pro Gln Gly
            20                  25                  30

Ala Val Leu Val Gln Arg Glu Lys Asp Leu Pro Asn Tyr Asn Trp Asn
        35                  40                  45

Ser Phe Gly Leu Arg Phe
    50

<210> SEQ ID NO 261
<211> LENGTH: 14
<212> TYPE: PRT
<213> ORGANISM: Homo sapiens
<220> FEATURE:
<221> NAME/KEY: misc_feature
<222> LOCATION: (14)..(14)
<223> OTHER INFORMATION: /note="C-term amidated"

<400> SEQUENCE: 261

Asp Leu Pro Asn Tyr Asn Trp Asn Ser Phe Gly Leu Arg Phe
1               5                   10

<210> SEQ ID NO 262
<211> LENGTH: 13
<212> TYPE: PRT
<213> ORGANISM: Homo sapiens
<220> FEATURE:
<221> NAME/KEY: misc_feature
<222> LOCATION: (13)..(13)
<223> OTHER INFORMATION: /note="C-term amidated"

<400> SEQUENCE: 262

Leu Pro Asn Tyr Asn Trp Asn Ser Phe Gly Leu Arg Phe
1               5                   10

<210> SEQ ID NO 263
<211> LENGTH: 10
<212> TYPE: PRT
<213> ORGANISM: Homo sapiens
```

```
<220> FEATURE:
<221> NAME/KEY: misc_feature
<222> LOCATION: (10)..(10)
<223> OTHER INFORMATION: /note="C-term amidated"

<400> SEQUENCE: 263

Tyr Asn Trp Asn Ser Phe Gly Leu Arg Phe
1               5                   10

<210> SEQ ID NO 264
<211> LENGTH: 25
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: misc_feature
<222> LOCATION: (1)..(16)
<223> OTHER INFORMATION: /note="Disulfide bridge"
<220> FEATURE:
<221> NAME/KEY: misc_feature
<222> LOCATION: (8)..(20)
<223> OTHER INFORMATION: /note="Disulfide bridge"
<220> FEATURE:
<221> NAME/KEY: misc_feature
<222> LOCATION: (15)..(25)
<223> OTHER INFORMATION: /note="Disulfide bridge"
<220> FEATURE:
<221> NAME/KEY: misc_feature
<222> LOCATION: (25)..(25)
<223> OTHER INFORMATION: /note="C-term amidated"

<400> SEQUENCE: 264

Cys Lys Gly Lys Gly Ala Lys Cys Ser Arg Leu Met Tyr Asp Cys Cys
1               5                   10                  15
Thr Gly Ser Cys Arg Ser Gly Lys Cys
            20                  25

<210> SEQ ID NO 265
<211> LENGTH: 18
<212> TYPE: PRT
<213> ORGANISM: Sus scrofa
<220> FEATURE:
<221> NAME/KEY: misc_feature
<222> LOCATION: (18)..(18)
<223> OTHER INFORMATION: /note="C-term amidated"

<400> SEQUENCE: 265

Arg Gly Gly Arg Leu Cys Tyr Cys Arg Arg Arg Phe Cys Val Cys Val
1               5                   10                  15
Gly Arg

<210> SEQ ID NO 266
<211> LENGTH: 26
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: misc_feature
<222> LOCATION: (1)..(1)
<223> OTHER INFORMATION: /note="N-term acetylated"
<220> FEATURE:
<221> NAME/KEY: misc_feature
<222> LOCATION: (26)..(26)
<223> OTHER INFORMATION: /note="C-term amidated"

<400> SEQUENCE: 266
```

```
Lys Trp Lys Ser Phe Leu Lys Thr Phe Lys Ser Ala Val Lys Thr Val
1               5                   10                  15

Leu His Thr Ala Leu Lys Ala Ile Ser Ser
            20                  25

<210> SEQ ID NO 267
<211> LENGTH: 25
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 267

Lys Trp Lys Ser Phe Leu Lys Thr Phe Lys Ser Val Lys Thr Val Leu
1               5                   10                  15

His Thr Ala Leu Lys Ala Ile Ser Ser
            20                  25

<210> SEQ ID NO 268
<211> LENGTH: 26
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 268

Lys Trp Lys Ser Phe Leu Lys Thr Phe Lys Ser Ala Lys Lys Thr Val
1               5                   10                  15

Leu His Thr Ala Leu Lys Ala Ile Ser Ser
            20                  25

<210> SEQ ID NO 269
<211> LENGTH: 26
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 269

Lys Trp Lys Ser Phe Leu Lys Thr Phe Lys Ser Ala Lys Lys Lys Val
1               5                   10                  15

Leu His Thr Ala Leu Lys Ala Ile Ser Ser
            20                  25

<210> SEQ ID NO 270
<211> LENGTH: 33
<212> TYPE: PRT
<213> ORGANISM: Homo sapiens

<400> SEQUENCE: 270

His Ala Asp Gly Ser Phe Ser Asp Glu Met Asn Thr Ile Leu Asp Asn
1               5                   10                  15

Leu Ala Ala Arg Asp Phe Ile Asn Trp Leu Ile Gln Thr Lys Ile Thr
            20                  25                  30

Asp

<210> SEQ ID NO 271
<211> LENGTH: 33
```

```
<212> TYPE: PRT
<213> ORGANISM: Homo sapiens

<400> SEQUENCE: 271

His Gly Asp Gly Ser Phe Ser Asp Glu Met Asn Thr Ile Leu Asp Asn
1               5                   10                  15

Leu Ala Ala Arg Asp Phe Ile Asn Trp Leu Ile Gln Thr Lys Ile Thr
            20                  25                  30

Asp

<210> SEQ ID NO 272
<211> LENGTH: 34
<212> TYPE: PRT
<213> ORGANISM: Homo sapiens

<400> SEQUENCE: 272

His Gly Asp Gly Ser Phe Ser Asp Glu Met Asn Thr Ile Leu Asp Asn
1               5                   10                  15

Leu Ala Ala Arg Asp Phe Ile Asn Trp Leu Ile Gln Thr Lys Ile Thr
            20                  25                  30

Asp Cys

<210> SEQ ID NO 273
<211> LENGTH: 16
<212> TYPE: PRT
<213> ORGANISM: Homo sapiens

<400> SEQUENCE: 273

Leu Arg Ile Val Gln Cys Ala Ser Val Glu Gly Ser Cys Gly Phe Tyr
1               5                   10                  15

<210> SEQ ID NO 274
<211> LENGTH: 16
<212> TYPE: PRT
<213> ORGANISM: Homo sapiens
<220> FEATURE:
<221> NAME/KEY: misc_feature
<222> LOCATION: (1)..(1)
<223> OTHER INFORMATION: /note="N-term acetylated"

<400> SEQUENCE: 274

Leu Arg Ile Val Gln Cys Ala Lys Val Glu Gly Ser Cys Gly Phe Tyr
1               5                   10                  15

<210> SEQ ID NO 275
<211> LENGTH: 17
<212> TYPE: PRT
<213> ORGANISM: Homo sapiens
<220> FEATURE:
<221> NAME/KEY: misc_feature
<222> LOCATION: (1)..(1)
<223> OTHER INFORMATION: /note="N-term acetylated"

<400> SEQUENCE: 275

Leu Arg Ile Val Gln Cys Ala Ser Val Glu Gly Ser Cys Gly Phe Tyr
1               5                   10                  15

Lys

<210> SEQ ID NO 276
<211> LENGTH: 31
<212> TYPE: PRT
<213> ORGANISM: Homo sapiens

<400> SEQUENCE: 276
```

Glu Ala Glu Asp Leu Gln Val Gly Gln Val Glu Leu Gly Gly Gly Pro
1               5                   10                  15

Gly Ala Gly Ser Leu Gln Pro Leu Ala Leu Glu Gly Ser Leu Gln
            20                  25                  30

<210> SEQ ID NO 277
<211> LENGTH: 16
<212> TYPE: PRT
<213> ORGANISM: Sus scrofa

<400> SEQUENCE: 277

Arg Gly Gly Arg Leu Cys Tyr Cys Arg Arg Phe Cys Ile Cys Val
1               5                   10                  15

<210> SEQ ID NO 278
<211> LENGTH: 19
<212> TYPE: PRT
<213> ORGANISM: Sus scrofa

<400> SEQUENCE: 278

Arg Gly Gly Gly Leu Cys Tyr Cys Arg Arg Phe Cys Val Cys Val
1               5                   10                  15

Gly Arg Gly

<210> SEQ ID NO 279
<211> LENGTH: 19
<212> TYPE: PRT
<213> ORGANISM: Sus scrofa

<400> SEQUENCE: 279

Arg Gly Gly Arg Leu Cys Tyr Cys Arg Gly Trp Ile Cys Phe Cys Val
1               5                   10                  15

Gly Arg Gly

<210> SEQ ID NO 280
<211> LENGTH: 19
<212> TYPE: PRT
<213> ORGANISM: Sus scrofa

<400> SEQUENCE: 280

Arg Gly Gly Arg Leu Cys Tyr Cys Arg Pro Arg Phe Cys Val Cys Val
1               5                   10                  15

Gly Arg Gly

<210> SEQ ID NO 281
<211> LENGTH: 149
<212> TYPE: PRT
<213> ORGANISM: Sus scrofa

<400> SEQUENCE: 281

Met Glu Thr Gln Arg Ala Ser Leu Cys Leu Gly Arg Trp Ser Leu Trp
1               5                   10                  15

Leu Leu Leu Leu Gly Leu Val Val Pro Ser Ala Ser Ala Gln Ala Leu
            20                  25                  30

Ser Tyr Arg Glu Ala Val Leu Arg Ala Val Asp Arg Leu Asn Glu Gln
        35                  40                  45

Ser Ser Glu Ala Asn Leu Tyr Arg Leu Leu Glu Leu Asp Gln Pro Pro
    50                  55                  60

Lys Ala Asp Glu Asp Pro Gly Thr Pro Lys Pro Val Ser Phe Thr Val
65                  70                  75                  80

Lys Glu Thr Val Cys Pro Arg Pro Thr Arg Gln Pro Pro Glu Leu Cys

```
                       85                   90                   95
Asp Phe Lys Glu Asn Gly Arg Val Lys Gln Cys Val Gly Thr Val Thr
               100                 105                 110

Leu Asp Gln Ile Lys Asp Pro Leu Asp Ile Thr Cys Asn Glu Val Gln
           115                 120                 125

Gly Val Arg Gly Gly Arg Leu Cys Tyr Cys Arg Pro Arg Phe Cys Val
       130                 135                 140

Cys Val Gly Arg Gly
145

<210> SEQ ID NO 282
<211> LENGTH: 5
<212> TYPE: PRT
<213> ORGANISM: Homo sapiens

<400> SEQUENCE: 282

Glu Gly Ser Leu Cys
1               5

<210> SEQ ID NO 283
<211> LENGTH: 5
<212> TYPE: PRT
<213> ORGANISM: Homo sapiens

<400> SEQUENCE: 283

Tyr Gly Gly Phe Met
1               5

<210> SEQ ID NO 284
<211> LENGTH: 9
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: Tyr(SO3)
<220> FEATURE:
<221> NAME/KEY: MOD_RES
<222> LOCATION: (7)..(7)
<223> OTHER INFORMATION: Norleu

<400> SEQUENCE: 284

Arg Asp Tyr Thr Gly Trp Leu Asp Phe
1               5

<210> SEQ ID NO 285
<211> LENGTH: 13
<212> TYPE: PRT
<213> ORGANISM: Homo sapiens

<400> SEQUENCE: 285

Tyr Gly Gly Phe Leu Arg Arg Ile Arg Pro Lys Leu Lys
1               5                   10

<210> SEQ ID NO 286
<211> LENGTH: 25
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 286

Arg Ser Ser Cys Phe Gly Gly Arg Met Asp Arg Ile Gly Ala Gln Ser
1               5                   10                  15
```

```
Gly Leu Gly Cys Asn Ser Phe Arg Tyr
            20                  25

<210> SEQ ID NO 287
<211> LENGTH: 37
<212> TYPE: PRT
<213> ORGANISM: Homo sapiens

<400> SEQUENCE: 287

Glu Val Val Pro Pro Gln Val Leu Ser Asp Pro Asn Glu Glu Ala Gly
1               5                   10                  15

Ala Ala Leu Ser Pro Leu Pro Glu Val Pro Pro Trp Thr Gly Glu Val
            20                  25                  30

Ser Pro Ala Gln Arg
        35

<210> SEQ ID NO 288
<211> LENGTH: 65
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 288

Val Val Tyr Thr Asp Cys Thr Glu Ser Gly Gln Asn Leu Cys Leu Cys
1               5                   10                  15

Glu Gly Ser Asn Val Cys Gly Gln Gly Asn Lys Cys Ile Leu Gly Ser
            20                  25                  30

Asp Gly Glu Lys Asn Gln Cys Val Thr Gly Glu Gly Thr Pro Lys Pro
        35                  40                  45

Gln Ser His Asn Asp Gly Asp Phe Glu Glu Ile Pro Glu Glu Tyr Leu
    50                  55                  60

Gln
65

<210> SEQ ID NO 289
<211> LENGTH: 14
<212> TYPE: PRT
<213> ORGANISM: Homo sapiens

<400> SEQUENCE: 289

Ala Leu Lys Arg Gln Gly Arg Thr Leu Tyr Gly Phe Gly Gly
1               5                   10

<210> SEQ ID NO 290
<211> LENGTH: 5
<212> TYPE: PRT
<213> ORGANISM: Homo sapiens

<400> SEQUENCE: 290

Tyr Gly Phe Gly Gly
1               5

<210> SEQ ID NO 291
<211> LENGTH: 11
<212> TYPE: PRT
<213> ORGANISM: Homo sapiens
<220> FEATURE:
<221> NAME/KEY: misc_feature
<222> LOCATION: (1)..(1)
<223> OTHER INFORMATION: /note="N-term acetylated"
```

```
<400> SEQUENCE: 291

Ala Ser Gln Lys Arg Pro Ser Gln Arg His Gly
1               5                   10

<210> SEQ ID NO 292
<211> LENGTH: 11
<212> TYPE: PRT
<213> ORGANISM: Homo sapiens
<220> FEATURE:
<221> NAME/KEY: misc_feature
<222> LOCATION: (1)..(1)
<223> OTHER INFORMATION: /note="N-term acetylated"

<400> SEQUENCE: 292

Ala Ser Gln Tyr Arg Pro Ser Gln Arg His Gly
1               5                   10

<210> SEQ ID NO 293
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: Pyro-Glu
<220> FEATURE:
<221> NAME/KEY: misc_feature
<222> LOCATION: (10)..(10)
<223> OTHER INFORMATION: /note="C-term amidated"

<400> SEQUENCE: 293

Glu His Trp Ser Tyr Gly Leu Arg Pro Gly
1               5                   10

<210> SEQ ID NO 294
<211> LENGTH: 15
<212> TYPE: PRT
<213> ORGANISM: Phodopus sp.

<400> SEQUENCE: 294

Gly Leu His Asp Pro Ser His Gly Thr Leu Pro Asn Gly Ser Gly
1               5                   10                  15

<210> SEQ ID NO 295
<211> LENGTH: 41
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 295

Ile Val Leu Ser Leu Asp Val Pro Ile Gly Leu Leu Gln Ile Leu Leu
1               5                   10                  15

Glu Gln Ala Arg Ala Arg Ala Arg Glu Gln Ala Thr Thr Asn Ala
            20                  25                  30

Arg Ile Leu Ala Arg Val Gly His Cys
        35                  40

<210> SEQ ID NO 296
<211> LENGTH: 8
<212> TYPE: PRT
<213> ORGANISM: Artificial Sequence
```

```
<220> FEATURE:
<221> NAME/KEY: source
<223> OTHER INFORMATION: /note="Description of Artificial Sequence:
      Synthetic peptide"
<220> FEATURE:
<221> NAME/KEY: misc_feature
<222> LOCATION: (8)..(8)
<223> OTHER INFORMATION: /note="C-term amidated"

<400> SEQUENCE: 296

Lys Pro Ser Ser Pro Pro Glu Glu
1               5

<210> SEQ ID NO 297
<211> LENGTH: 23
<212> TYPE: PRT
<213> ORGANISM: Homo sapiens
<220> FEATURE:
<221> NAME/KEY: misc_feature
<222> LOCATION: (23)..(23)
<223> OTHER INFORMATION: /note="C-term amidated"

<400> SEQUENCE: 297

Phe Asn Ala Pro Phe Asp Val Gly Ile Lys Leu Ser Gly Val Gln Tyr
1               5                   10                  15

Gln Gln His Ser Gln Ala Leu
            20

<210> SEQ ID NO 298
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (2)..(2)
<223> OTHER INFORMATION: Lys(Et)

<400> SEQUENCE: 298

Gly Lys Pro Arg
1

<210> SEQ ID NO 299
<211> LENGTH: 22
<212> TYPE: PRT
<213> ORGANISM: Homo sapiens

<400> SEQUENCE: 299

Gly Leu Ser Lys Gly Cys Phe Gly Leu Lys Leu Asp Arg Ile Gly Ser
1               5                   10                  15

Met Ser Gly Leu Gly Cys
            20

<210> SEQ ID NO 300
<211> LENGTH: 49
<212> TYPE: PRT
<213> ORGANISM: Homo sapiens

<400> SEQUENCE: 300

Tyr Leu Tyr Gln Trp Leu Gly Ala Pro Val Pro Tyr Pro Asp Pro Leu
1               5                   10                  15

Glu Pro Arg Arg Glu Val Cys Glu Leu Asn Pro Asp Cys Asp Glu Leu
            20                  25                  30

Ala Asp His Ile Gly Phe Gln Glu Ala Tyr Arg Arg Phe Tyr Gly Pro
```

```
                 35                  40                  45
Val

<210> SEQ ID NO 301
<211> LENGTH: 31
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 301

Glu Ala Glu Asp Leu Gln Val Gly Gln Val Glu Leu Gly Gly Gly Pro
1               5                   10                  15

Gly Ala Gly Cys Leu Gln Pro Leu Ala Leu Glu Gly Ser Leu Gln
            20                  25                  30
```

CARBOHYDRATE-BASED DRUG DELIVERY POLYMERS AND CONJUGATES THEREOF

CROSS REFERENCE TO RELATED APPLICATIONS

This application is a 35 U.S.C. §371 application of International Application No. PCT/US2009/005233, filed 17 Sep. 2009, designating the United States, which claims the benefit of priority under 35 U.S.C. §119(e) to U.S. Provisional Patent Application Ser. No. 61/192,672, filed 19 Sep. 2008; U.S. Provisional Patent Application Ser. No. 61/208,089, filed 18 Feb. 2009; and U.S. Provisional Patent Application Ser. No. 61/153,966, filed 19 Feb. 2009 each of which are incorporated by reference in their entireties.

BACKGROUND OF THE INVENTION

In recent years, human therapeutics have expanded past traditional small molecule drugs and into the realm of biopharmaceuticals. The discovery of novel proteins and peptides has led to the development of numerous protein and polypeptide biopharmaceuticals. Unfortunately, proteins and polypeptides, when utilized as therapeutics, often exhibit properties that make them extremely difficult to formulate or administer, such as short circulating half lives, immunogenicity, proteolytic degradation, and low solubility.

There is significant interest in using naturally occurring biopolymers as drug delivery and/or conjugating agents, as they are generally safe and because they are biodegradable. Both of these factors are very significant in selecting a polymer for drug delivery, as polymer safety and clearance rank among the most important issues in selecting a delivery polymer. Solubility in serum and in aqueous media is often very important for drug manufacture and drug delivery. By far the most successful water soluble polymer in use for drug delivery is polyethylene glycol (PEG) (see e.g. Harris, J. M. (1985), "Laboratory Synthesis of Polyethylene Glycol Derivatives", *JMS-Rev. Macromol. Chem. Phys.* C25: 325-373; Harris, J. M. and Chess, R. B. (2003), "Effect of PEGylation on Pharmaceuticals", *Nature Reviews Drug Discovery* 2: 214-221; Roberts, M. J., Bentley, M. D., and Harris, J. M. (2002), "Chemistry for peptide and protein PEGylation", *Adv. Drug Del. Rev.* 54: 459-476; Pasut, G., Guiotto, A., and Veronese, F. M. (2004), "Protein, peptide and non-peptide drug PEGylation for therapeutic application", *Expert Opin. Ther. Patents* 14:1-36; Filpula, D. and Zhao, H. (2008), "Releasable PEGylation of proteins with customized linkers", *Adv. Drug Del. Rev.* 60: 29-49; Zhao, X and Harris, J. M. (1997), "Novel degradable poly(ethylene glycol) esters for drug delivery", In: Harris J. M. and Zalipsky S. (eds): *Poly (ethylene glycol) chemistry and biological applications*, American Chemical Society, Washington, D.C., 458-472.)

Attempts have also been made to use carbohydrates for conjugation with and delivery of drugs. The most prominent examples are hydroxyethyl starch (HES) and polysialic acid (PSA). HES, a derivative of naturally occurring starch (amylopectin & amylose), has been described as the polymer of choice as a polyfunctional carrier for oligopeptide-polymer conjugates. It is non-toxic and nonimmunogenic and is degraded by α-amylase in the body.

HES is recommended as a polyfunctional carrier, since it has a large number of functional groups (primarily hydroxyl groups), making monofunctionalization virtually impossible. Thus, activation of HES for attachment of drug moieties provides a polyfunctional polymer with a diversity of sites; i.e. some polymer molecules have more functional sites than other polymer molecules, and the overall result is a polydisperse distribution of reactive sites. This is often acceptable for smaller drug molecules, where several drug molecules per polymer strand may be acceptable, as long as biodistribution is not affected by the polydisperse character of the conjugate. However, it is undesirable for larger molecules such as proteins, where a single protein molecule per polymer moiety is highly desired. In fact, in many cases, e.g. with very large proteins like Factor VIII, multiple polymer molecules may be desired to protect the protein. While PEGs are very suitable for such applications, because they can readily be engineered to provide only one active group per polymer molecule, it is very difficult to selectively activate only one functional group of a carbohydrate polymer.

Polysialic acid (PSA) and hyaluronic acid (HA) are acid carbohydrates that have also been promoted for drug delivery. However, the very high biodegradability of HA is problematic, as it is generally inadequately stable in vivo to be a good delivery agent. HA also suffers from its strong targeting properties which consistently steer it toward certain biotargets. PSA has enjoyed more recent attention. Like HES, however, PSA is only reasonably useful when polyfunctionality is acceptable. Thus, to this point, polysaccharides have not presented a significant commercial threat to the use of PEGs (PEGylation) for modification of the pharmacological properties of drugs; i.e. relatively little product development activity has occurred, and there are no launched products.

Another issue that must be dealt with in employing carbohydrates for drug delivery is control of molecular weight. It is possible, for example, to manufacture PEG with fairly precise control of molecular weight and polydispersity. Thus, it is common to see commercially available PEGs having moderate molecular weights (i.e. 20-40 kD) with a polydispersity of 1.10 or less. Since carbohydrates are biologically derived, often with variable molecular weights, obtaining a specific molecular weight for drug delivery is difficult. With respect to molecular weight distribution, commercially available dextrans often have polydispersity values of 2.0 or greater, or around 1.25-1.35 for purified materials.

Thus, there remains a need to overcome these barriers of polyfunctionality and polydispersity in order to take advantage of the desirable properties of these naturally occurring polymers.

SUMMARY

In one aspect, the invention provides a method of selectively monoderivatizing a water-soluble carbohydrate polymer at its reductive terminus, wherein said reductive terminus comprises a hemiacetal or ketal group or the corresponding aldehyde or ketone functionality, the method comprising:

contacting said carbohydrate polymer with a heterobifunctional oxyamine or hydrazine reagent, effective to produce a monoderivatized carbohydrate derivative having a functional group, not selected from oxyamine and hydrazine, linked via an oxyimine or hydrazone moiety at said terminus.

The method may further comprise reducing the double bond of said oxyimine or hydrazone moiety. Thus, the monoderivatized carbohydrate polymer may have a structure $$POLY^1\text{-}C^\alpha HR^1\text{—}NR^3\text{—}X\text{-}L^1\text{-}G^1 \qquad (I)$$

where $POLY^1$ is said carbohydrate polymer and $C^\alpha$ is the anomeric carbon atom of said terminal hemiacetal or ketal group or corresponding aldehyde or ketone functionality;

$R^1$ is H or hydroxymethyl;

X is oxygen or $NR^2$, where $R^2$ is hydrogen, methyl, lower alkyl, cycloalkyl, or aryl, and is preferably H or methyl, and more preferably H;

$R^3$ is H or methyl, and is typically H;

$L^1$ is a linker group, and $G^1$ is an optionally protected functional group, not selected from oxyamine and hydrazine.

When the reduction step is not carried out, the 4. The method of claim 1, wherein the monoderivatized carbohydrate derivative monoderivatized carbohydrate polymer may have a structure $$POLY^1\text{-}C^\alpha(R^1)\!\!=\!\!N\text{-}X\text{-}L^1\text{-}G^1 \qquad (II)$$

where:

$POLY^1$ is said carbohydrate polymer and $C^\alpha$ is the anomeric carbon atom of said terminal hemiacetal or ketal group or corresponding aldehyde or ketone functionality;

$R^1$ is H or hydroxymethyl;

X is oxygen or $NR^2$, where $R^2$ is hydrogen, methyl, lower alkyl, cycloalkyl, or aryl, and is preferably H or methyl, and more preferably H;

$L^1$ is said linker group, and $G^1$ is said optionally protected functional group, not selected from oxyamine and hydrazine.

The heterobifunctional oxyamine or hydrazine reagent used for such monoderivatization typically has the structure $$R^3HN\text{---}X\text{-}L^1\text{-}G^1 \qquad (III)$$

where:

X is oxygen or $NR^2$, where $R^2$ is hydrogen, methyl, lower alkyl, cycloalkyl, or aryl, and is preferably H or methyl, and more preferably H;

$R^3$ is H or methyl, and is generally H;

$L^1$ is a linker group, and $G^1$ is an optionally protected functional group, not selected from oxyamine and hydrazine, which is unreactive under the conditions of said contacting.

In selected embodiments, X is oxygen (an oxyamine reagent) or $NR^2$, e.g. $NH_2$ (a hydrazine reagent). X may also be sulfur.

$R^1$ may be hydroxymethyl, when $POLY^1$ is a ketose, or hydrogen, when $POLY^1$ is an aldose, such as a dextran or a chitosan. $POLY^1$ generally has a molecular weight in the range of 200 Da to 2,000,000 Da. Molecular weights such as 5 KDa, 10 KDa, 20 KDa, 40 KDa, and 70 KDa, for example, are typical.

$L^1$ is a linker as defined further below. Preferably, $L^1$ consists of moieties selected from alkylene, $-CH_2CH_2O-$, amide, carbamate, and combinations thereof; more preferably, $L^1$ consists of alkylene moieties, $-CH_2CH_2O-$ moieties, and combinations thereof. Generally, $L^1$ is 1 to about 20 atoms in length, and may be 3-12, or 3-8 atoms in length.

The functional group $G^1$ may be selected from amine, hydroxy, thiol, carboxylic acid, carboxylic acid ester, imide ester, orthoester, carbonate, isocyanate, isothiocyanate, aldehyde, acetal, ketone, ketal, thione, alkenyl, acrylate, methacrylate, acrylamide, sulfone, maleimide, disulfide, iodo, epoxy, sulfonate, thiosulfonate, silane, alkoxysilane, halosilane, and phosphoramidate; and in selected embodiments is selected from amine, hydroxy, thiol, carboxylic acid, carboxylic acid ester, imide ester, orthoester, carbonate, isocyanate, aldehyde, acetal, ketone, ketal, and maleimide.

The preparation method may also include a step of purifying the carbohydrate polymer. In particular, when the heterobifunctional reagent comprises an oxyamine or hydrazine at one terminus and a carboxylic acid or amine group at the other terminus, effective to produce a monoderivatized water-soluble carbohydrate polymer having a single terminal carboxylic acid or amine group, the method may further comprise purifying the amine- or carboxylic acid-terminated carbohydrate polymer by ion exchange chromatography.

In a related aspect, the invention provides a monofunctional water-soluble carbohydrate-based reagent having the structure $$POLY^1\text{-}C^\alpha(H)_x(R^1)\overset{\cdots}{=\!=\!=}N(R^3)_x\text{---}X\text{-}L^1\text{-}G^1 \qquad (IV)$$

where:

$POLY^1$ is a water-soluble carbohydrate polymer having a terminal anomeric carbon atom, where $C^\alpha$ is said terminal anomeric carbon atom;

$\cdots$ represents a double bond when x=0 and a single bond when x=1;

$R^1$ is H or hydroxymethyl;

X is oxygen or $NR^2$, where $R^2$ is hydrogen, methyl, lower alkyl, cycloalkyl, or aryl, and is preferably H or methyl, and more preferably H;

$R^3$ is H or methyl, and is typically H;

$L^1$ is a linker group, and $G^1$ is a functional group, in reactive or protected form, not selected from oxyamine and hydrazine.

In selected embodiments, the carbohydrate reagent has a double bond represented by $\cdots$ such that x=0. In other embodiments, e.g. where the double bond is subjected to reduction, the carbohydrate reagent has a single bond represented by $\cdots$ such that x=1.

Selected embodiments of the components represented by X, $R^1$, $POLY^1$, $L^1$, and $G^1$ are as described above.

Exemplary carbohydrate reagents include the reagent having a structure designated herein as dextran-O-(carboxymethyl)oxyimine (2); the reagent having a structure designated herein as oxyimine-linked dextran-butanoic acid (7); the reagent having a structure designated herein as oxyimine-linked dextran(40K)-butyraldehyde (16); the reagent having a structure designated herein as oxyimine-linked chitosan tetra(ethylene glycol) maleimidopropionamide (22); and the reagent having a structure designated herein as oxyimine-linked chitosan butanoic acid (23). The carbohydrate component in any of these structures may have any of a variety of molecular weights. The reagents also include protected versions of the terminal functional groups.

In another aspect, the invention provides a method of preparing a water-soluble carbohydrate reagent having a single terminal carboxylic acid group, the method comprising oxidizing a water-soluble carbohydrate polymer, such as a dextran, having a terminal acetal or aldehyde group under mild conditions, effective to produce an oxidized carbohydrate having a single terminal carboxylic acid group and having substantially the same molecular weight as the carbohydrate prior to oxidation. Such conditions include reaction with iodine ($I_2$) and a hydroxide base as described herein.

The method may further comprise the step of purifying the carbohydrate reagent by ion exchange chromatography, such that the purified carbohydrate reagent is substantially free of unreacted carbohydrate and overoxidized byproducts. Such purification may also be effective to significantly reduce the polydispersity of the monocarboxylic acid reagent relative to that of the carbohydrate prior to oxidation.

In accordance with this method, the invention provides a water-soluble carbohydrate reagent, preferably a dextran, having a single terminal functional group which is a carboxylic acid. The carboxyl carbon of the carboxylic acid is the terminal anomeric carbon of the starting carbohydrate. Such carbohydrate monocarboxylic acids may have a molecular weight of 200 Da to 2,000,000 Da.

Also provided are the corresponding carboxylic acid derivatives, which can be readily prepared from the carbohydrate monocarboxylic acid. The carboxylic acid derivative may be selected from ester, activated ester, thioester, anhydride, amide, acid halide, nitrile, carbamate, carbonate, isocyanate, and isothiocyanate.

Also provided is a conjugate comprising the water-soluble carbohydrate monocarboxylic acid or derivative and a covalently attached biologically active molecule, which may be prepared by reaction of the carbohydrate monocarboxylic acid or derivative with a biologically active molecule having a suitable reactive group. In one embodiment, the biologically active molecule is a protein or peptide, where the reactive group is typically an amine.

In one embodiment, the biologically active molecule is insulin. Accordingly, the invention provides a method of reducing blood glucose levels in a diabetic subject, including a human subject, by administering a dextran monocarboxylic acid-insulin conjugate.

The invention also provides conjugates of a water-soluble carbohydrate reagent and a biologically active molecule, having the structure

$$POLY^1\text{-}C^{\alpha}(H)_x(R^1) \mathrel{\underline{\underline{\phantom{=}}}} N(H)_x\text{—}X\text{-}L^1\text{-}G^2\text{-}B \qquad (V)$$

where

POLY$^1$ is a water-soluble carbohydrate polymer having a terminal anomeric carbon atom, where $C^{\alpha}$ is said terminal anomeric carbon atom;

$\underline{\underline{\phantom{=}}}$ represents a double bond when x=0 and a single bond when x=1;

R$^1$ is H or hydroxymethyl;

X is oxygen or NR$^2$, where R$^2$ is hydrogen, methyl, lower alkyl, cycloalkyl, or aryl;

L$^1$ is a linker group, and

G$^2$ is a covalent bond comprising a residue or converted form of functional group G$^1$, not selected from oxyamine and hydrazine, following reaction with a corresponding functional group on biomolecule B.

Selected embodiments of the components represented by the variables in structure (V) include those disclosed for structure (IV) above.

In selected embodiments, POLY$^1$ is a chitosan. In further embodiments of this type, the biologically active molecule is an oligonucleotide, such as an RNA.

In other embodiments, POLY$^1$ is a dextran. Exemplary dextran conjugates include conjugates of proteins or peptides, such as conjugates of lysozyme, protegrin-1, C-peptide, and insulin as described herein. In one embodiment, the biologically active molecule is insulin, which may be a partially acetylated insulin. Such conjugates include having the structure disclosed herein as 20. The dextran component in this conjugate may vary in molecular weight. In a preferred embodiment, the carbohydrate is dextran(40 KDa).

In a related aspect, the invention provides a method of reducing blood glucose levels in a diabetic subject, including a human subject, by administering a dextran-insulin conjugate having the structure designated as 20 herein.

These and other aspects of the invention will become apparent upon review of the following description and accompanying figures.

DETAILED DESCRIPTION OF THE INVENTION

I. Definitions

Figure 1:
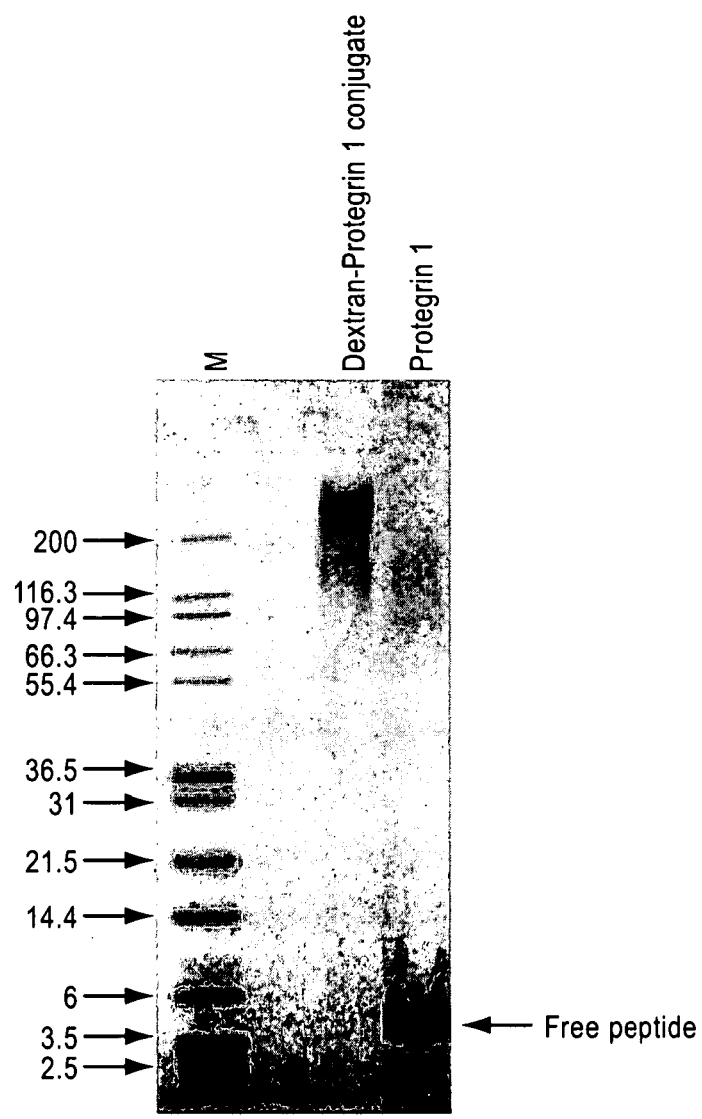
FIG. 1 shows gels produced by SDS-PAGE analysis (4-12% gel) of purified dextran-butryraldehyde-40K-protegrin-1, as described in Example 16. Dextran perturbs the gel migration of the dextran-peptide conjugate; the conjugate's band location is not indicative of its size. The marker (M) molecular weight unit is kDa.

Before describing the present invention in detail, it is to be understood that this invention is not limited to particular polymers, synthetic techniques, active agents, and the like, as such may vary.

As used in this specification and in the claims, the singular forms "a", "an", and "the" include plural referents unless the context clearly dictates otherwise. Thus, for example, reference to "a polymer" includes a single polymer as well as two or more of the same or different polymers, reference to "a conjugate" refers to a single conjugate as well as two or more of the same or different conjugates, reference to "an excipient" includes a single excipient as well as two or more of the same or different excipients, and the like.

"Optional" and "optionally" mean that the subsequently described circumstance may or may not occur, so that the description includes instances where the circumstance occurs and instances where it does not.

In describing and claiming the present invention, the following terminology will be used in accordance with the definitions described below.

As used herein, the terms "therapeutic peptide" and "therapeutic peptides" mean one or more peptides having demonstrated or potential use in treating, preventing, or ameliorating one or more diseases, disorders, or conditions in a subject in need thereof, as well as related peptides. These terms may be used to refer to therapeutic peptides prior to conjugation to a water-soluble polymer as well as following the conjugation. Therapeutic peptides include, but are not limited to, those disclosed herein, including in Table 1. Therapeutic peptides include peptides found to have use in treating, preventing, or ameliorating one or more diseases, disorders, or conditions after the time of filing of this application. Related peptides include fragments of therapeutic peptides, therapeutic peptide variants, and therapeutic peptide derivatives that retain some or all of the therapeutic activities of the therapeutic peptide. As will be known to one of skill in the art, as a general principle, modifications may be made to peptides that do not alter, or only partially abrogate, the properties and activities of those peptides. In some instances, modifications may be made that result in an increase in therapeutic activities. Thus, in the spirit of the invention, the terms "therapeutic peptide" or "therapeutic peptides" are meant to encompass modifications to the therapeutic peptides defined and/or disclosed herein that do not alter, only partially abrogate, or increase the therapeutic activities of the parent peptide.

The term "therapeutic activity" as used herein refers to a demonstrated or potential biological activity whose effect is consistent with a desirable therapeutic outcome in humans, or to desired effects in non-human mammals or in other species or organisms. A given therapeutic peptide may have one or more therapeutic activities, however the term "therapeutic activities" as used herein may refer to a single therapeutic activity or multiple therapeutic activities. "Therapeutic activity" includes the ability to induce a response in vitro, and may be measured in vivo or in vitro. For example, a desirable effect may be assayed in cell culture, or by clinical evaluation, $EC_{50}$ assays, $IC_{50}$ assays, or dose response curves. In vitro or cell culture assays, for example, are commonly available and known to one of skill in the art for many therapeutic peptides as defined and/or disclosed herein. Therapeutic activity includes treatment, which may be prophylactic or ameliorative, or prevention of a disease, disorder, or condition. Treatment of a disease, disorder or condition can include improvement of a disease, disorder or condition by any amount, including elimination of a disease, disorder or condition.

As used herein, the terms "peptide," "polypeptide," and "protein," refer to polymers comprised of amino acid monomers linked by amide bonds. Peptides may include the standard 20 α-amino acids that are used in protein synthesis by cells (i.e. natural amino acids), as well as non-natural amino acids (non-natural amino acids may be found in nature, but not used in protein synthesis by cells, e.g., ornithine, citrulline, and sarcosine, or may be chemically synthesized), amino acid analogs, and peptidomimetics. Spatola, (1983) in Chemistry and Biochemistry of Amino Acids, Peptides, and Proteins, Weinstein, ed., Marcel Dekker, New York, p. 267. The amino acids may be D- or L-optical isomers. Peptides may be formed by a condensation or coupling reaction between the α-carbon carboxyl group of one amino acid and the amino group of another amino acid. The terminal amino acid at one end of the chain (amino terminal) therefore has a free amino group, while the terminal amino acid at the other end of the chain (carboxy terminal) has a free carboxyl group. Alternatively, the peptides may be non-linear, branched peptides or cyclic peptides. Moreover, the peptides may optionally be modified or protected with a variety of functional groups or protecting groups, including on the amino and/or carboxy terminus.

Amino acid residues in peptides are abbreviated as follows: Phenylalanine is Phe or F; Leucine is Leu or L; Isoleucine is Ile or I; Methionine is Met or M; Valine is Val or V; Serine is Ser or S; Proline is Pro or P; Threonine is Thr or T; Alanine is Ala or A; Tyrosine is Tyr or Y; Histidine is His or H; Glutamine is Gln or Q; Asparagine is Asn or N; Lysine is Lys or K; Aspartic Acid is Asp or D; Glutamic Acid is Glu or E; Cysteine is Cys or C; Tryptophan is Trp or W; Arginine is Arg or R; and Glycine is Gly or G.

The terms "therapeutic peptide fragment" or "fragments of therapeutic peptides" refer to a polypeptide that comprises a truncation at the amino-terminus and/or a truncation at the carboxyl-terminus of a therapeutic peptide as defined herein. The terms "therapeutic peptide fragment" or "fragments of therapeutic peptides" also encompasses amino-terminal and/or carboxyl-terminal truncations of therapeutic peptide variants and therapeutic peptide derivatives. Therapeutic peptide fragments may be produced by synthetic techniques known in the art or may arise from in vivo protease activity on longer peptide sequences. It will be understood that therapeutic peptide fragments retain some or all of the therapeutic activities of the therapeutic peptides.

As used herein, the terms "therapeutic peptide variants" or "variants of therapeutic peptides" refer to therapeutic peptides having one or more amino acid substitutions, including conservative substitutions and non-conservative substitutions, amino acid deletions (either internal deletions and/or C- and/or N-terminal truncations), amino acid additions (either internal additions and/or C- and/or N-terminal additions, e.g., fusion peptides), or any combination thereof. Variants may be naturally occurring (e.g. homologs or orthologs), or non-natural in origin. The term "therapeutic peptide variants" may also be used to refer to therapeutic peptides incorporating one or more non-natural amino acids, amino acid analogs, and peptidomimetics. It will be understood that, in accordance with the invention, therapeutic peptide fragments retain some or all of the therapeutic activities of the therapeutic peptides.

The terms "therapeutic peptide derivatives" or "derivatives of therapeutic peptides" as used herein refer to therapeutic peptides, therapeutic peptide fragments, and therapeutic peptide variants that have been chemically altered other than through covalent attachment of a water-soluble polymer. It will be understood that, in accordance with the invention, therapeutic peptide derivatives retain some or all of the therapeutic activities of the therapeutic peptides.

"PEG", "polyethylene glycol" and "poly(ethylene glycol)" as used herein, are meant to encompass any water-soluble poly(ethylene oxide). Typically, PEGs comprise the following structure "—O(CH$_2$CH$_2$O)$_m$—" where (m) is 2 to 4000. As used herein, PEG also includes "—(CH$_2$CH$_2$O)$_m$—;" and "—CH$_2$CH$_2$—O(CH$_2$CH$_2$O)$_m$—CH$_2$CH$_2$—", depending upon whether or not the terminal oxygens have been displaced. When the PEG further comprises a spacer moiety (to be described in greater detail below), the atoms comprising the spacer moiety, when covalently attached to a water-soluble polymer segment, do not result in the formation of an oxygen-oxygen bond (i.e., an "—O—O—" or peroxide linkage). The term "PEG" includes structures having various terminal or "end capping" groups and so forth. The term "PEG" also means a polymer that contains a majority, that is to say, greater than 50%, of —CH$_2$CH$_2$O— monomeric subunits. With respect to specific forms, the PEG can take any number of a variety of molecular weights, as well as structures or geometries such as "branched," "linear," "forked," "multifunctional," "dendrimeric", and the like.

The terms "end-capped" or "terminally capped" are interchangeably used herein to refer to a terminal or endpoint of a polymer having an end-capping moiety. Typically, although not necessarily, the end-capping moiety comprises a hydroxy or $C_{1-20}$ alkoxy group. Thus, examples of end-capping moieties include alkoxy (e.g., methoxy, ethoxy and benzyloxy), as well as aryl, heteroaryl, cyclo, heterocyclo, and the like. In addition, saturated, unsaturated, substituted and unsubstituted forms of each of the foregoing are envisioned. Moreover, the end-capping group can also be a silane. The end-capping group can also advantageously comprise a detectable label. When the polymer has an end-capping group comprising a detectable label, the amount or location of the polymer and/or the moiety (e.g., active agent) of interest to which the polymer is coupled to can be determined by using a suitable detector. Such labels include, without limitation, fluorescers, chemiluminescers, moieties used in enzyme labeling, colorimetric (e.g., dyes), metal ions, radioactive moieties, and the like. Suitable detectors include photometers, films, spectrometers, and the like.

"Non-naturally occurring", with respect to a polymer or water-soluble polymer, indicates that the polymer in its entirety is not found in nature. A non-naturally occurring polymer or water-soluble polymer may, however, contain one or more subunits or portions of a subunit that are naturally occurring, so long as the overall polymer structure is not found in nature.

A "water-soluble polymer" is any polymer that is soluble in water at room temperature. Typically, a water-soluble polymer will transmit at least about 75%, more preferably at least about 95% of light, transmitted by the same solution after filtering. On a weight basis, a water-soluble polymer will preferably be at least about 35% (by weight) soluble in water, more preferably at least about 50% (by weight) soluble in water, still more preferably about 70% (by weight) soluble in water, and still more preferably about 85% (by weight) soluble in water. It is still more preferred, however, that the water-soluble polymer is about 95% (by weight) soluble in water and most preferred that the water-soluble polymer is completely soluble in water.

"Molecular weight", in the context of a water-soluble polymer of the invention, such as PEG, can be expressed as either a number average molecular weight or a weight average molecular weight. Unless otherwise indicated, all references to molecular weight herein refer to the weight average molecular weight. Both molecular weight determinations, number average and weight average, can be made using gel permeation chromatography or other liquid chromatography techniques. Other methods for measuring molecular weight can also be used, such as end-group analysis or colligative properties (e.g., freezing-point depression, boiling-point elevation, or osmotic pressure) to determine number average molecular weight, or light scattering techniques, ultracentrifugation or viscometry to determine weight average molecular weight. The polymers of the invention are typically polydisperse (i.e., number average molecular weight and weight average molecular weight of the polymers are not equal), possessing low polydispersity values of preferably less than about 1.2, more preferably less than about 1.15, still more preferably less than about 1.10, yet still more preferably less than about 1.05, and most preferably less than about 1.03.

An "organic radical" as used includes, for example, alkyl, substituted alkyl, alkenyl, substituted alkenyl, alkynyl, substituted alkynyl, aryl and substituted aryl.

"Alkyl" refers to a hydrocarbon chain, typically ranging from about 1 to 20 atoms in length. Such hydrocarbon chains are preferably but not necessarily saturated and may be branched or straight chain, although typically straight chain is preferred. Exemplary alkyl groups include ethyl, propyl, butyl, pentyl, isooctyl, decyl, 3-ethyl-3-pentyl, 2-methyl-1-hexyl, and the like. As used herein, "alkyl" includes cycloalkyl, when three or more carbon atoms are referenced, and lower alkyl. "Alkylene" refers to an unsaturated bivalent radical (e.g. —(CH$_2$)$_n$)—.

"Lower alkyl" refers to an alkyl group containing from 1 to 6 carbon atoms, preferably 1 to 4 carbon atoms, and may be straight chain or branched, as exemplified by methyl, ethyl, n-butyl, iso-butyl, and tert-butyl. When a group is defined as "alkyl" herein, lower alkyl is generally a preferred embodiment.

"Cycloalkyl" refers to a saturated or unsaturated cyclic hydrocarbon chain, including bridged, fused, or Spiro cyclic compounds, preferably made up of 3 to about 12 carbon atoms, more preferably 3 to about 8.

"Alkoxy" refers to an —O—R group, wherein R is alkyl or substituted alkyl, preferably C$_1$-C$_{20}$ alkyl (e.g., methoxy, ethoxy, propyloxy, benzyl, perfluorobutyl, etc.), preferably C$_1$-C$_7$ alkyl, more preferably C$_1$-C$_7$ alkyl. "Alkoxyalkyl" refers to an —R—O—R group, where R is as defined above, and is preferably unsubstituted C$_1$-C$_7$ alkyl.

"Aminoalkyl" refers to an —NHR or —NR$_2$ group, where R is alkyl as defined above, and is preferably unsubstituted C$_1$-C$_7$ alkyl, and the two R groups in —NR$_2$ may be the same or different. The two R groups may also form a five- to seven-membered ring.

"Iminoalkyl(ene)" refers to an —R'—N=R" group, where R" represents CH$_2$, CHR, or CR$_2$, where each R is alkyl as defined above, and the two R groups in —CR$_2$ may be the same or different. R$^1$ is alkyl as defined above, i.e. an sp$^2$ hybridized carbon, or alkylene, i.e. an sp$^2$ hybridized carbon forming one member of a double bond. An R in CHR or CR$_2$ taken together with the R$^1$ may form a five- to seven-membered ring.

As used herein, "alkenyl" refers to a branched or unbranched hydrocarbon group of 2 to 15 atoms in length, containing at least one double bond, such as ethenyl, n-propenyl, isopropenyl, n-butenyl, isobutenyl, octenyl, decenyl, tetradecenyl, and the like.

The term "alkynyl" as used herein refers to a branched or unbranched hydrocarbon group of 2 to 15 atoms in length, containing at least one triple bond, ethynyl, n-butynyl, isopentynyl, octynyl, decynyl, and so forth.

"Aliphatic" refers to a group containing carbon and hydrogen which is not aromatic. As used herein, it can refer to linear, branched, or cyclic groups. It can refer to saturated or unsaturated groups, with saturated groups generally being preferred.

"Aryl" means one or more aromatic rings, each of 5 or 6 core carbon atoms. Aryl includes multiple aryl rings that may be fused, as in naphthyl, or unfused, as in biphenyl. Aryl rings may also be fused or unfused with one or more cyclic hydrocarbon, heteroaryl, or heterocyclic rings. As used herein, "aryl" includes heteroaryl. An aromatic moiety (e.g., Ar$^1$, Ar$^2$, and so forth), means a structure containing aryl.

"Heteroaryl" is an aryl group containing from one to four heteroatoms, preferably N, O, or S, or a combination thereof. Heteroaryl rings may also be fused with one or more cyclic hydrocarbon, heterocyclic, aryl, or heteroaryl rings.

"Heterocycle" or "heterocyclic" means one or more rings of 5-12 atoms, preferably 5-7 atoms, with or without unsaturation or aromatic character and having at least one ring atom which is not a carbon. Preferred heteroatoms include sulfur, oxygen, and nitrogen.

"Substituted heteroaryl" is heteroaryl having one or more non-interfering groups as substituents.

"Substituted heterocycle" is a heterocycle having one or more side chains formed from non-interfering substituents.

"Non-interfering substituents" are those groups that, when present in a molecule, are typically non-reactive with other functional groups contained within the molecule. Such groups include: lower alkyl, lower alkoxy, C3-C8 cycloalkyl, e.g., cyclopropyl, cyclobutyl, and the like; halo, e.g., fluoro, chloro, bromo, and iodo; cyano; phenyl; substituted phenyl; and the like. For substitutions on a phenyl ring, the substituents may be in any orientation (i.e., ortho, meta, or para). Preferred non-interfering substituents include lower alkyl, lower alkoxy, cyclopropyl, fluoro, chloro, and cyano.

The term "substituted" as in, for example, "substituted alkyl," refers to a moiety (e.g., an alkyl group) substituted with one or more non-interfering substituents, such as, but not limited to: C$_3$-C$_8$ cycloalkyl, e.g., cyclopropyl, cyclobutyl, and the like; halo, e.g., fluoro, chloro, bromo, and iodo; cyano; alkoxy, lower phenyl (e.g., 0-2 substituted phenyl); substituted phenyl; and the like. "Substituted aryl" is aryl having one or more non-interfering groups as a substituent. For substitutions on a phenyl ring, the substituents may be in any orientation (i.e., ortho, meta, or para).

As used herein, the "halo" designator (e.g., fluoro, chloro, iodo, bromo, and so forth) is generally used when the halogen is attached to a molecule, while the suffix "ide" (e.g., fluoride, chloride, iodide, bromide, and so forth) is used when the halogen exists in its independent ionic form (e.g., such as when a leaving group leaves a molecule).

"Electrophile" refers to an ion or atom or collection of atoms, that may be ionic, having an electrophilic center, i.e., a center that is electron seeking, capable of reacting with a nucleophile.

"Nucleophile" refers to an ion or atom or collection of atoms that may be ionic having a nucleophilic center, i.e., a center that is seeking an electrophilic center or with an electrophile.

A basic or acidic reactant described herein includes neutral, charged, and any corresponding salt forms thereof.

As used herein, the term "ionizable hydrogen atom" ("$H_\alpha$") means a hydrogen atom that can be removed in the presence of a base, often a hydroxide or amine base. Typically, the "ionizable hydrogen atom" ("$H_\alpha$") will be a hydrogen atom attached to a carbon atom that, in turn, is attached to one or more aromatic moieties or another group or groups that in some way stabilize the carbanion that would form from loss of the ionizable hydrogen atom as a proton (or the transition state leading to said carbanion).

As used herein, the term "carboxylic acid" is a moiety having a —C(O)OH functional group, as well as moieties that are derivatives of a carboxylic acid, such derivatives including, for example, protected carboxylic acids. Thus, unless the context clearly dictates otherwise, the term carboxylic acid includes not only the acid form, but corresponding esters and protected forms as well. With regard to protecting groups suited for a carboxylic acid and any other functional group described herein, reference is made to Greene et al., "PROTECTIVE GROUPS IN ORGANIC SYNTHESIS", $3^{rd}$ Edition, John Wiley and Sons, Inc., New York, 1999.

The term "reactive" or "activated" when used in conjunction with a particular functional group, refers to a reactive functional group that reacts readily with an electrophile or a nucleophile on another molecule. This is in contrast to those groups that require strong catalysts or highly impractical reaction conditions in order to react (i.e., a "nonreactive" or "inert" group).

The terms "protected" or "protecting group" or "protective group" refer to the presence of a moiety (i.e., the protecting group) that prevents or blocks reaction of a particular chemically reactive functional group in a molecule under certain reaction conditions. The protecting group will vary depending upon the type of chemically reactive functional group being protected as well as the reaction conditions to be employed and the presence of additional reactive or protecting groups in the molecule, if any. Protecting groups known in the art can be found in Greene et al., supra.

As used herein, the term "functional group" or any synonym thereof is meant to encompass protected forms thereof. In particular, recitation of specific functional groups such as carboxylic acids, aldehydes, or hydroxyl groups encompasses protected forms thereof.

"Multifunctional", in the context of a polymer of the invention, means a polymer having 3 or more functional groups contained therein, where the functional groups may be the same or different. Multifunctional polymers of the invention will typically contain from about 3-100 functional groups, or from 3-50 functional groups, or from 3-25 functional groups, or from 3-15 functional groups, or from 3 to 10 functional groups, or will contain 3, 4, 5, 6, 7, 8, 9 or 10 functional groups within the polymer. A "difunctional" polymer means a polymer having two functional groups contained therein, either the same (i.e., homodifunctional) or different (i.e., heterodifunctional).

"Branched," in reference to the geometry or overall structure of a polymer, refers to polymer having 2 or more polymer "arms." A branched polymer may possess 2 polymer arms, 3 polymer arms, 4 polymer arms, 6 polymer arms, 8 polymer arms or more. One particular type of highly branched polymer is a dendritic polymer or dendrimer, which, for the purposes of the invention, is considered to possess a structure distinct from that of a branched polymer.

A "dendrimer" or dendritic polymer is a globular, size monodisperse polymer in which all bonds emerge radially from a central focal point or core with a regular branching pattern and with repeat units that each contribute a branch point. Dendrimers exhibit certain dendritic state properties such as core encapsulation, making them unique from other types of polymers.

In the context of the present description, the definition of a variable provided with respect to one structure or formula is applicable to the same variable repeated in a different structure, unless the context dictates otherwise. Thus, for example, the definition of "POLY," "a spacer moiety," "$R^{eb}$" and so forth with respect to a polymer can be equally applicable to a water-soluble polymer conjugate provided herein.

The terms "spacer" or "spacer moiety" (which may also be referred to as a linker or linker moiety) are used herein to refer to an atom or a collection of atoms optionally used to link one moiety to another, such as a water-soluble polymer segment to a functional moiety in a polymeric reagent. The spacer moieties of the invention are preferably hydrolytically stable but may include one or more physiologically hydrolyzable or enzymatically degradable linkages. Exemplary spacer moieties are described further below.

A "physiologically cleavable" or "hydrolyzable" bond is a relatively weak bond that reacts with water (i.e., is hydrolyzed) under physiological conditions. The tendency of a bond to hydrolyze in water will depend not only on the general type of linkage connecting two central atoms but also on the substituents attached to these central atoms. Appropriate hydrolytically unstable or weak linkages include, but are not limited to, carboxylate ester, phosphate ester, anhydrides, acetals, ketals, acyloxyalkyl ether, imines, ortho esters, peptides and oligonucleotides.

A "degradable linkage" includes, but is not limited to, a physiologically cleavable bond, a hydrolyzable bond, and an enzymatically degradable linkage. Thus, a "degradable linkage" is a linkage that may undergo either hydrolysis or cleavage by some other mechanism (e.g., enzyme-catalyzed, acid-catalyzed, base-catalyzed, and so forth) under physiological conditions. For example, a "degradable linkage" can involve an elimination reaction that has a base abstraction of a proton, (e.g., an ionizable hydrogen atom, $H_\alpha$), as the driving force.

An "enzymatically degradable linkage" means a linkage that is subject to degradation by one or more enzymes.

A "hydrolytically stable" linkage or bond refers to a chemical bond, typically a covalent bond, that is substantially stable in water, that is to say, does not undergo hydrolysis under physiological conditions to any appreciable extent over an extended period of time. Examples of hydrolytically stable linkages include but are not limited to the following: carbon-carbon bonds (e.g., in aliphatic chains), ethers, amides, urethanes (carbamates), and the like. Generally, a hydrolytically stable linkage is one that exhibits a rate of hydrolysis of less than about 1-2% per day under physiological conditions. Hydrolysis rates of representative chemical bonds can be found in most standard chemistry textbooks. It must be pointed out that some linkages can be hydrolytically stable or hydrolyzable, depending upon (for example) adjacent and neighboring atoms and ambient conditions. One of ordinary skill in the art can determine whether a given linkage or bond is hydrolytically stable or hydrolyzable in a given context by, for example, placing a linkage-containing molecule of interest under conditions of interest and testing for evidence of hydrolysis (e.g., the presence and amount of two molecules resulting from the cleavage of a single molecule). Other approaches known to those of ordinary skill in the art for determining whether a given linkage or bond is hydrolytically stable or hydrolyzable can also be used.

As used herein, "drug release rate" means a rate (stated as a half-life) in which half of the total amount of polymer-active agent conjugates in a system will cleave into the active agent and a polymeric residue.

The terms "active agent," "biologically active agent" and "pharmacologically active agent" are used interchangeably herein and are defined to include any agent, drug, compound, composition of matter or mixture that provides some pharmacologic, often beneficial, effect that can be demonstrated in-vivo or in vitro. This includes foods, food supplements, nutrients, nutriceuticals, drugs, proteins, vaccines, antibodies, vitamins, and other beneficial agents. As used herein, these terms further include any physiologically or pharmacologically active substance that produces a localized or systemic effect in a patient.

"Pharmaceutically acceptable excipient" or "pharmaceutically acceptable carrier" refers to an excipient that can be included in the compositions of the invention and that causes no significant adverse toxicological effects to the patient.

"Pharmacologically effective amount," "physiologically effective amount," and "therapeutically effective amount" are used interchangeably herein to mean the amount of a polymer-active agent conjugate, typically present in a pharmaceutical preparation, that is needed to provide a desired level of active agent and/or conjugate in the bloodstream or in a target tissue. The exact amount will depend upon numerous factors, e.g., the particular active agent, the components and physical characteristics of the pharmaceutical preparation, intended patient population, patient considerations, and the like, and can readily be determined by one of ordinary skill in the art, based upon the information provided herein and available in the relevant literature.

The term "patient" refers to a living organism suffering from or prone to a condition that can be prevented or treated by administration of a conjugate as provided herein, and includes both humans and animals.

II. Carbohydrate-Based Reagents

Because of their very low toxicity and immunogenicity, carbohydrate polymers are attractive candidates for use in conjugating to biologically active molecules for drug delivery. However, because carbohydrates are generally very large polydisperse polymers with hundreds or even thousands of reactive functional groups, controlling the degree of functionality and the polydispersity are important considerations in such applications of carbohydrates.

Carbohydrate polymers, which may also be referred to as polysaccharides, include naturally occurring polysaccharides and materials derived from naturally occurring polysaccharides. Water soluble polymers are preferred. Well known examples are dextran, glycogen, and amylose, as well as chitosan (deacetylated chitin), which is a positively charged carbohydrate. The polymers can be obtained in a large range of molecular weights. For the present application, molecular weights in the range of 200 Da to 2,000,000 Da are contemplated, depending on the intended use of the carbohydrate reagent. Molecular weights such as 5 KDa, 10 KDa, 20 KDa, 40 KDa, and 70 KDa, for example, are typical.

Dextran is one of the most important polysaccharides for medical and industrial applications. It is produced primarily from sucrose by bacterial strains and structurally is a poly (glucose) having an α-(1-6) linked D-glucose main chain. It is commercially available in a variety of molecular weights, though generally with high polydispersity values.

Several existing dextran derivatives, used mainly for modification of small molecular weight drugs, are based on activation of hydroxyl groups present in each repeating unit of the polymer. This type of activation is not suitable for the single point attachment of a drug moiety; thus it is not applicable to protein modification, where a polymer having only one active group on the polymer chain is desired.

Chitosan, a carbohydrate polymer formed by deacetylation of the naturally occurring chitin, is particularly useful in certain drug delivery applications because it is a cationic polymer, having an amine group on each repeating unit.

The present disclosure is directed to monofunctional carbohydrate reagents for drug conjugation, prepared by activation of the reducing end (i.e. the anomeric carbon) of carbohydrates such as dextran. As is well known for aldoses in general, the reducing terminus of dextran can be represented in the closed ring acetal (pyranose) form or the open-chain aldehyde form, as follows:

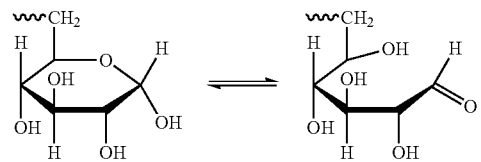

where the aldehyde carbon is the anomeric carbon. A similar conversion between closed ring forms (pyranose or furanose) and open chain (keto) forms exists for ketoses, where the open chain form terminates in —C(O)—CH$_2$OH.

Particular embodiments of the monofunctional carbohydrate polymers of the invention are described in the following sections. The terms "monoderivatized" and "monofunctional" in this context may be used interchangeably and refer to the fact that the carbohydrate polymer is modified such that it may be selectively conjugated at a single location, in this case a single terminus bearing a functional group.

A. Monocarboxylic Acid and Carboxylic Acid Derivatives

In one embodiment, a water soluble carbohydrate polymer terminating in a aldose group, such as dextran, is selectively oxidized at the reductive end of the polymer under mild conditions, effective to produce a single carboxylic acid functionality, without modifying the remaining structure of the polymer. The monoacid dextran reagent is designated (1) herein.

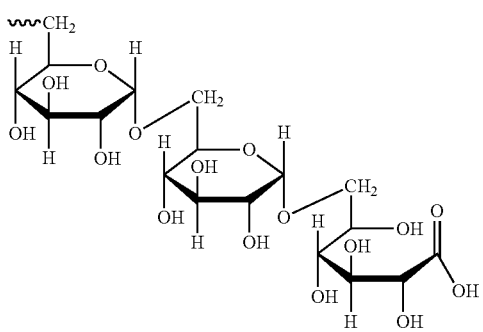

(1)

Suitable oxidation conditions include iodine ($I_2$) and a hydroxide base, e.g. NaOH, such as described in Examples 1, 3, and 5 below. In general, oxidation conditions are such that the ratio of the desired monocarboxylic acid product to over-oxidized side products (such as polymer oxidized at internal sites, including cleaved chain products) is greater than 15:1, preferably greater than 25:1, and more preferably greater than 50:1. Thus, the molecular weight of the oxidized polymer is essentially unchanged. Furthermore, the ratio of desired monocarboxylic acid product to dicarboxylic acid product is preferably greater than 25:1. The total conversion is preferably greater than 70-80%; that is, less than 20-30% of unreacted dextran remains. For example, the conditions described in Example 5 below produced a reaction mixture containing 3.1% of dextran diacid, 83.9% of dextran monoacid, and 13.0% of unreacted dextran. The procedure is effective on higher molecular weight water soluble carbohydrate polymers, as shown for dextran having a molecular weight of 40,000 in Examples 3 and 5.

Further to this embodiment, the polydispersity of a carbohydrate polymer can be significantly reduced by purifying the monocarboxylic product, prepared as described above, by ion exchange chromatography. A demonstration of the process using dextran(40K) monocarboxylic acid, designated herein as (1b), is given in Example 4. In another instance, a dextran monocarboxylic acid having a polydispersity of 2.34 was obtained from a starting dextran (molecular weight 6 KDa) having a polydispersity of 3.27 by mild oxidation, as described herein, followed by ion exchange chromatography.

Preferred polydispersities are less than 2.5, preferably less than 2.0, and more preferably less than 1.5. In some embodiments, polydispersities may be less than 1.35, or less than 1.20.

The low polydispersity carbohydrate monocarboxylic acid also provides access to a range of low polydispersity carbohydrate carboxylic acid derivatives. Such derivatives and their preparation are well known in the art and include functionalities such as ester, activated ester, thioester, anhydride, amide, acid halide, nitrile, carbamate, carbonate, isocyanate, and isothiocyanate. These can of course be further converted to any number of different functionalities by well known methods. Thus, for example, with appropriate linkers, carboxylic acids are readily converted into useful reactive groups such as maleimides, aldehydes, and active disulfides, e.g. orthopyridyl disulfides (OPPS).

B. Monoderivatization with Heterobifunctional Oxyamines or Hydrazines

In a further embodiment, a heterobifunctional reagent comprising, at one terminus, a highly nucleophilic amine such as an oxyamine or hydrazine is selectively reacted with the reductive end of a carbohydrate polymer, preferably the aldehyde end of an aldose. The other terminus of the reagent bears a different functional group (i.e., not an oxyamine or hydrazine) that is either protected or is otherwise unreactive under the conditions of the reaction. Such reactions produce oxyimine or hydrazone linkages, as shown in the scheme below, to the carbohydrate moiety, with a distinct functional group, indicated by $G^1$, where $L^1$ is a linker as described below, at the new terminus. Because of the presence of the heterogroup, X (which may also be sulfur) adjacent the C=N bond, these linkages are generally stable except to certain acid-catalyzed hydrolytic procedures. If more stability is desired, the product may be further converted in a reduction step, as also shown in the scheme below.

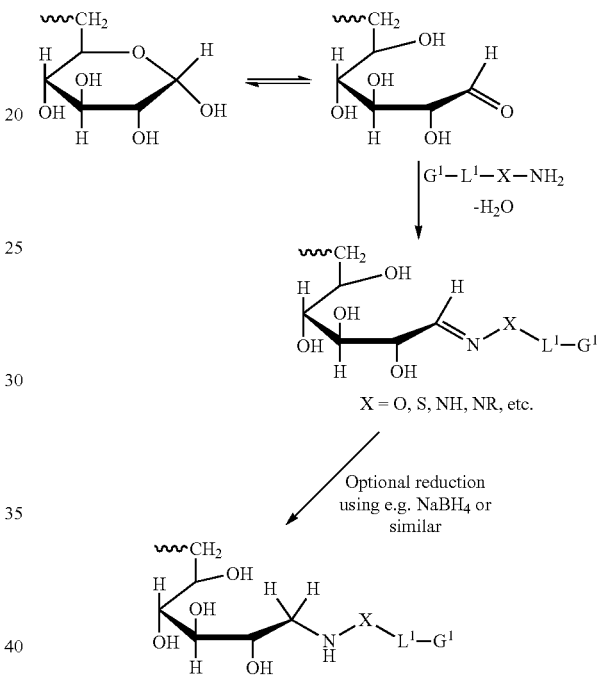

Accordingly, the invention provides a monofunctional water-soluble carbohydrate-based reagent having the structure $$POLY^1\text{-}C^\alpha(H)_x(R^1) \mathrel{\text{---}} N(R^3)_x\text{---}X\text{-}L^1\text{-}G^1 \qquad (IV)$$

where:

POLY$^1$ is a water-soluble carbohydrate polymer having a terminal anomeric carbon atom, where $C^\alpha$ is said terminal anomeric carbon atom;

--- represents a double bond when x=0 and a single bond when x=1;

$R^1$ is H or hydroxymethyl;

X is oxygen or $NR^2$, where $R^2$ is hydrogen, methyl, lower alkyl, cycloalkyl, or aryl, and is preferably H or methyl, and more preferably H;

$R^3$ is H or methyl, and is typically H;

$L^1$ is a linker group, and $G^1$ is a functional group, in reactive or protected form, not selected from oxyamine and hydrazine.

In selected embodiments, the carbohydrate reagent has a double bond represented by --- such that x=0. In other embodiments, e.g. where the double bond is subjected to reduction, the carbohydrate reagent has a single bond represented by --- such that x=1.

In selected embodiments, X is oxygen (an oxyamine reagent) or $NR^2$, e.g. $NH_2$ (a hydrazine reagent). X may also be sulfur.

$R^1$ may be hydroxymethyl, when $POLY^1$ is a ketose, or hydrogen, when $POLY^1$ is an aldose, such as a dextran or a chitosan. $POLY^1$ generally has a molecular weight in the range of 200 Da to 2,000,000 Da. Molecular weights such as 5 KDa, 10 KDa, 20 KDa, 40 KDa, and 70 KDa, for example, are typical.

$L^1$ is a linker as defined further below. Preferably, $L^1$ consists of moieties selected from alkylene, —$CH_2CH_2O$—, amide, carbamate, and combinations thereof; more preferably, $L^1$ consists of alkylene moieties, —$CH_2CH_2O$— moieties, and combinations thereof. Generally, $L^1$ is 1 to about 20 atoms in length, and may be 3-12, or 3-8 atoms in length.

The functional group $G^1$ may be selected from amine, hydroxy, thiol, carboxylic acid, carboxylic acid ester, imide ester, orthoester, carbonate, isocyanate, isothiocyanate, aldehyde, acetal, ketone, ketal, thione, alkenyl, acrylate, methacrylate, acrylamide, sulfone, maleimide, disulfide, iodo, epoxy, sulfonate, thiosulfonate, silane, alkoxysilane, halosilane, and phosphoramidate; and in selected embodiments is selected from amine, hydroxy, thiol, carboxylic acid, carboxylic acid ester, imide ester, orthoester, carbonate, isocyanate, aldehyde, acetal, ketone, ketal, and maleimide.

The preparation method may also include a step of purifying the carbohydrate polymer. In particular, when the heterobifunctional reagent comprises an oxyamine or hydrazine at one terminus and a carboxylic acid or amine group at the other terminus, effective to produce a monoderivatized water-soluble carbohydrate polymer having a single terminal carboxylic acid or amine group, the method may further comprise purifying the amine- or carboxylic acid-terminated carbohydrate polymer by ion exchange chromatography.

A particularly useful embodiment is that in which $G^1$ is a carboxyl group. For example, the reaction of O-(carboxymethyl)hydroxylamine with dextran gives dextran-O-(carboxymethyl)oxyimine, designated herein as (2), as described in Example 6. In this case, $L^1$ is an alkylene(methylene) linker.

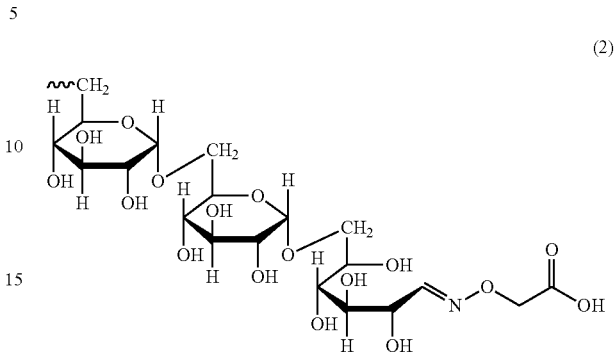

(2)

In another example, a reagent containing an oxyamine group connected by an oligo(ethylene glycol)-alkylene linker to a butanoic acid group can be used to provide a butanoic acid having an extended linker to the polysaccharide, as shown in Example 8 below. The dextran reagent is designated herein as (7). Such reagents can be purified to low polydispersities by ion exchange chromatography.

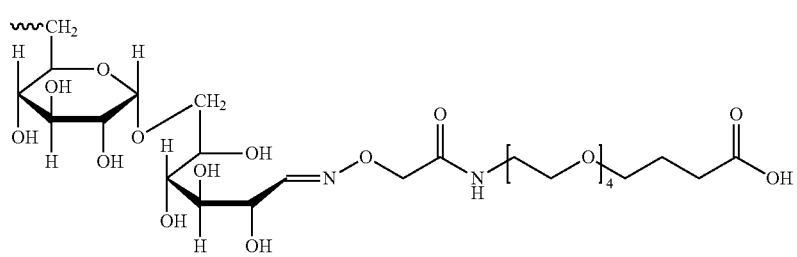

(7)

In further embodiments, additional heterobifunctional reagents having linkers based on oligomers, e.g. tetraethylene glycol, attached to having highly nucleophilic amines, such as hydrazines or oxyamines, are used to prepare a variety of polysaccharide reagents. These reagents include an optionally protected functional group that may ultimately be activated for reaction with a drug moiety. For example, preparation of a protected aldehyde-terminated dextran reagent, oxyimine-linked dextran butyraldehyde (16), is described in Example 13.

The hydroxy-imine moiety in these reagents may rearrange to an amino ketone moiety, as shown in the scheme below.

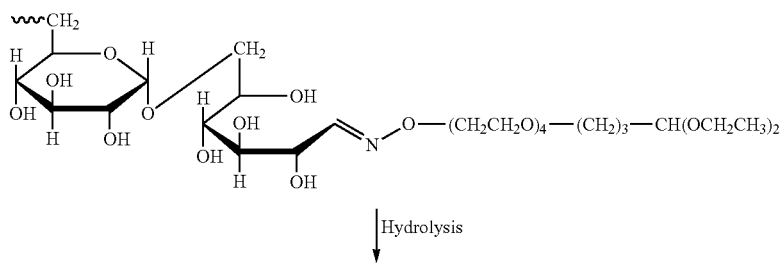

Hydrolysis

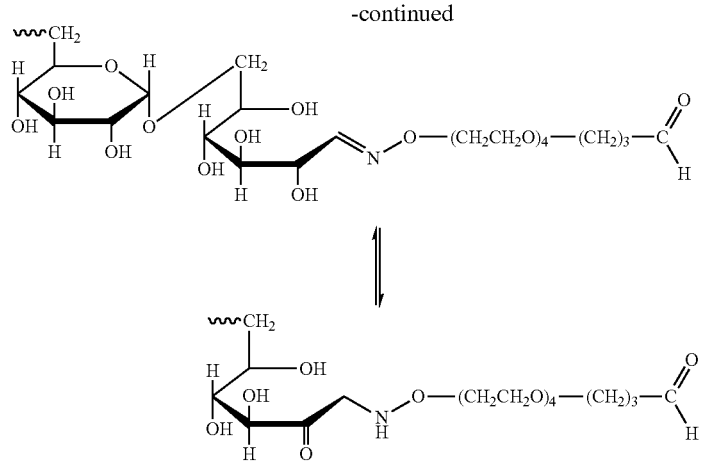

C. Linker Moieties

As described above, the reagents disclosed herein may include a linker moiety, designated L¹. A linker may be used to connect polymer segments making up the component POLY to each other.

A linker is typically but is not necessarily linear in nature. The overall length of the linker will typically range between 1 to about 40 atoms, where by length is meant the number of atoms in a single chain, not counting substituents. For instance, —CH₂— counts as one atom with respect to overall linker length, and —CH₂CH(CH₃)O— counts as 3 atoms in length. Preferably, a linker will have a length of about 1 to about 20 atoms, or, more preferably, from about 2 to about 15 atoms; e.g. 3 to 8 atoms.

Illustrative linkers are those corresponding to either of the following structures: —(CH₂)$_c$-D$_e$-(CH₂)$_f$— or —(CH₂)$_p$-M$_r$-C(O)—K$_s$—(CH₂)$_q$—; where c is 0 to 8; "D" is O, NH, or S; e is 0 or 1; f is 0 to 8; p is 0 to 8; "M" is —NH or O; "K" is NH or O; q is 0 to 8, and r and s are each independently 0 or 1.

Other exemplary linker moieties include, but are not limited to, the following: —O—, —S—, —C(O)—, —S(O₂)—, —S(O)—, —NH—S(O₂)—, —S(O₂)—NH—, —CH=CH—, —O—CH=CH—, —C(O)—NH—, —NH—C(O)—NH—, —O—C(O)—NH—, —C(S)—, —CH₂—, —CH₂—CH₂—, —CH₂—CH₂—CH₂—, —CH₂—CH₂—CH₂—CH₂—, —O—CH₂—, —CH₂—O—, —O—CH₂—CH₂—, —CH₂—O—CH₂—, —CH₂—CH₂—O—, —O—CH₂—CH₂—CH₂—, —CH₂—O—CH₂—CH₂—, —CH₂—CH₂—O—CH₂—, —CH₂—CH₂—CH₂—O—, —O—CH₂—CH₂—CH₂—CH₂—, —CH₂—O—CH₂—CH₂—CH₂—, —CH₂—CH₂—O—CH₂—CH₂—, —CH₂—CH₂—CH₂—O—CH₂—, —CH₂—CH₂—CH₂—CH₂—O—, —S—CH₂—, —CH₂—S—, —S—CH₂—CH₂—, —CH₂—S—CH₂—, —CH₂—CH₂—S—, —S—CH₂—CH₂—CH₂—, —CH₂—S—CH₂—CH₂—, —CH₂—CH₂—S—CH₂—, —CH₂—CH₂—CH₂—S—, —S—CH₂—CH₂—CH₂—CH₂—, —CH₂—S—CH₂—CH₂—CH₂—, —CH₂—CH₂—S—CH₂—CH₂—, —CH₂—CH₂—CH₂—S—CH₂—, —CH₂—CH₂—CH₂—CH₂—S—, —C(O)—NH—CH₂—, —C(O)—NH—CH₂—CH₂—, —CH₂—C(O)—NH—CH₂—, —CH₂—CH₂—C(O)—NH—, —C(O)—NH—CH₂—CH₂—CH₂—, —CH₂—C(O)—NH—CH₂—CH₂—, —CH₂—CH₂—C(O)—NH—CH₂—, —CH₂—CH₂—CH₂—C(O)—NH—, —C(O)—NH—CH₂—CH₂—CH₂—CH₂—, —CH₂—C(O)—NH—CH₂—CH₂—CH₂—, —CH₂—CH₂—C(O)—NH—CH₂—CH₂—, —CH₂—CH₂—CH₂—C(O)—NH—CH₂—, —CH₂—CH₂—CH₂—CH₂—C(O)—NH—, —C(O)—O—CH₂—, —CH₂—C(O)—O—CH₂—, —CH₂—CH₂—C(O)—O—CH₂—, —C(O)—O—CH₂—CH₂—, —NH—C(O)—CH₂—, —CH₂—NH—C(O)—CH₂—, —CH₂—CH₂—NH—C(O)—CH₂—, —NH—C(O)—CH₂—CH₂—, —CH₂—NH—C(O)—CH₂—CH₂—, —CH₂—CH₂—NH—C(O)—CH₂—CH₂—, —C(O)—NH—CH₂—, —C(O)—NH—CH₂—CH₂—, —O—C(O)—NH—CH₂—, —O—C(O)—NH—CH₂—CH₂—, —NH—CH₂—, —NH—CH₂—CH₂—, —CH₂—NH—CH₂—, —CH₂—CH₂—NH—CH₂—, —C(O)—CH₂—, —C(O)—CH₂—CH₂—, —CH₂—C(O)—CH₂—, —CH₂—CH₂—C(O)—CH₂—, —CH₂—CH₂—C(O)—CH₂—CH₂—, —CH₂—CH₂—C(O)—, —CH₂—CH₂—CH₂—C(O)—NH—CH₂—CH₂—NH—, —CH₂—CH₂—CH₂—C(O)—NH—CH₂—CH₂—NH—C(O)—, —CH₂—CH₂—CH₂—C(O)—NH—CH₂—CH₂—NH—C(O)—NH—CH₂—CH₂—NH—C(O)—CH₂—, —CH₂—CH₂—C(O)—NH—CH₂—CH₂—NH—C(O)—CH₂—CH₂—, bivalent cycloalkyl, and amino acids.

Also included are —N(R⁶)—, where R⁶ is H or an organic radical selected from the group consisting of alkyl, substituted alkyl, alkenyl, substituted alkenyl, alkynyl, substituted alkynyl, aryl and substituted aryl; and —NH—C(O)—O—(CH₂)$_h$—(OCH₂CH₂)$_j$— or —O—C(O)—NH—(CH₂)$_h$—(OCH₂CH₂)$_j$—, where (h) is zero to six, and (j) is zero to 20. Other specific spacer moieties have the following structures: —C(O)—NH—(CH₂)$_{1-6}$—NH—C(O)—, —NH—C(O)—NH—(CH₂)$_{1-6}$—NH—C(O)—, and —O—C(O)—NH—(CH₂)$_{1-6}$—NH—C(O)—, wherein the subscript values following each methylene indicate the number of methylenes contained in the structure, e.g., (CH₂)$_{1-6}$ means that the structure can contain 1, 2, 3, 4, 5 or 6 methylenes.

A linker may include combinations of two or more of any of the foregoing.

In the reagents and/or conjugates of structures I-V herein, the linker preferably includes a carbon atom attached to the atom X (generally oxygen or nitrogen), which may be part of, for example, an alkyl or alkylene group, or a carbonyl carbon. A linker can comprise a single functional group such as an amide, an ester, a urethane (carbamate), or a urea, preferably containing contain methylene or other alkylene groups flanking one or both sides of the functional group. Alternatively, a linker may contain a combination of functional groups, which can be the same or different. A linker can be an alkylene chain, optionally containing one or more oxygen or sulfur atoms (i.e., an ether or thioether linkage). Also included are alkylene chains containing a nitrogen atom (i.e. an amine linkage.)

Preferably, the linker is hydrolytically stable, and may contain one or more of the following functional groups: amide, urethane, ether, thioether, or urea. However, hydrolytically degradable linkages, such as carboxylate ester, phosphate ester, orthoester, anhydride, imine, acetal, ketal, oligonucleotide, or peptide, may also be present.

Additionally, any of the above spacer moieties may further include an ethylene oxide oligomer chain comprising 1 to 20 ethylene oxide monomer units (i.e., $-(CH_2CH_2O)_{1-20}$). That is, the ethylene oxide oligomer chain can occur before or after the spacer moiety, and optionally in between any two atoms of a spacer moiety comprised of two or more atoms.

D. Functional Groups

As described above, the reagents of structures I-IV include a functional group $G^1$ which is useful for forming a conjugate of the polymer, e.g., with a pharmacologically active agent, surface, solid support, or the like. The functional group typically comprises an electrophilic or nucleophilic group that provides for covalent attachment of a desired agent to the carbohydrate polymer.

Preferred nucleophilic groups include amine, hydroxy, and thiol, particularly amine.

Examples of electrophilic functional groups include carboxylic acid, carboxylic ester, particularly imide esters, orthoester, carbonate, isocyanate, isothiocyanate, aldehyde, ketone, thione, alkenyl, acrylate, methacrylate, acrylamide, sulfone, maleimide, disulfide, iodo, epoxy, sulfonate, thiosulfonate, silane, alkoxysilane, halosilane, and phosphoramidate. More specific examples of these groups include succinimidyl ester or carbonate, imidazoyl ester or carbonate, benzotriazole ester or carbonate, vinyl sulfone, chloroethylsulfone, vinylpyridine, pyridyl disulfide, iodoacetamide, glyoxal, dione, mesylate, tosylate, and tresylate (2,2,2-trifluoroethanesulfonate).

Also included are sulfur analogs of several of these groups, such as thione, thione hydrate, thioketal, etc., as well as hydrates or protected derivatives of any of the above moieties (e.g. aldehyde hydrate, hemiacetal, acetal, ketone hydrate, hemiketal, ketal, thioketal, thioacetal). Another useful conjugation reagent is 2-thiazolidine thione.

The term "carboxylic acid derivative" encompasses various functional groups that include a carbonyl group with an attached heteroatom, such as ester, thioester, anhydride, amide, acid halide, nitrile, carbamate, carbonate, isocyanate, and isothiocyanate. An "activated derivative" of a carboxylic acid refers to a carboxylic acid derivative which reacts readily with nucleophiles, generally much more readily than the underivatized carboxylic acid. Activated carboxylic acids include, for example, acid halides (such as acid chlorides), anhydrides, carbonates, and esters. Such esters (referred to as active or activated esters) include imide esters, of the general form $-(CO)O-N[(CO)-]_2$; for example, N-hydroxysuccinimidyl (NHS) esters or N-hydroxyphthalimidyl esters. Also preferred are imidazolyl esters and benzotriazole esters. Particularly preferred are activated propionic acid or butanoic acid esters, as described in co-owned U.S. Pat. No. 5,672,662. These include groups of the form $-(CH_2)_{2-3}C(=O)O-Q$, where Q is preferably selected from N-succinimide, N-sulfosuccinimide, N-phthalimide, N-glutarimide, N-tetrahydrophthalimide, N-norbornene-2,3-dicarboximide, benzotriazole, 7-azabenzotriazole, and imidazole.

Other preferred electrophilic groups include succinimidyl carbonate, maleimide, benzotriazole carbonate, glycidyl ether, imidazoyl carbonate, p-nitrophenyl carbonate, acrylate, tresylate, aldehyde, and orthopyridyl disulfide.

These electrophilic groups are subject to reaction with nucleophiles, e.g. hydroxy, thio, or amino groups, to produce various bond types. For example, carboxylic acids and activated derivatives thereof, which include orthoesters, succinimidyl esters, imidazolyl esters, and benzotriazole esters, react with the above types of nucleophiles to form esters, thioesters, and amides, respectively, of which amides are the most hydrolytically stable. Carbonates, including succinimidyl, imidazolyl, and benzotriazole carbonates, will react with hydroxyl or amino groups to form further carbonates or carbamates, respectively. Isocyanates (R—N=C=O) react with hydroxyl or amino groups to form, respectively, carbamate (RNH—C(O)—OR') or urea (RNH—C(O)—NHR') linkages. Phosphoramidites can be reacted with hydroxyl reagents, followed by oxidation, to form phosphate esters (as in conventional oligonucleotide synthesis).

Aldehydes, ketones, glyoxals, diones and their hydrates or alcohol adducts (i.e. aldehyde hydrate, hemiacetal, acetal, ketone hydrate, hemiketal, and ketal) are preferably reacted with amines, followed by reduction of the resulting imine, if desired, to give an amine linkage (reductive amination). Alternatively, these groups can be reacted with hydroxyl containing groups, to form further acetals, ketals, etc. In this cases, the linkages formed are subject to hydrolytic degradation, which may be desirable, as discussed further below.

Several of the electrophilic functional groups include electrophilic double bonds to which nucleophilic groups, such a thiols, can be added, to form, for example, thioether bonds. These groups include maleimides, vinyl sulfones, vinyl pyridine, acrylates, methacrylates, and acrylamides. Other groups comprise leaving groups which can be displaced by a nucleophile; these include chloroethyl sulfone, pyridyl disulfides (which include a cleavable S—S bond), iodoacetamide, mesylate, tosylate, thiosulfonate, and tresylate. Epoxides react by ring opening by a nucleophile, to form, for example, an ether or amine bond. Silanes, including halosilanes and alkoxysilanes, react with hydroxy- or oxide-containing compounds, or surfaces such as glass, to form siloxanes.

III. Conjugation Method

In accordance with the invention, methods of forming stable conjugates of monoderivatized carbohydrate polymers with biologically active molecules (e.g. drugs) are provided. Accordingly, the invention provides a method of conjugating a monoderivatized carbohydrate polymer with a target compound, the method comprising: reacting a reagent of structure (s) I, II or IV, having a terminal functional group $G^1$, or a reagent as described in section IIA above, having a terminal carboxylic acid or carboxylic acid derivative, with a biologically active molecule having a corresponding functional group, which is reactive with $G^1$ or with said carboxylic acid or carboxylic acid derivative, to form a stable covalent bond between the reagent and the biologically active molecule.

Functional groups and corresponding functional group with which they are reactive are known in the art and include those described in section IID above. In one embodiment, the functional group on the biologically active molecule is an amine, as is common in protein conjugations.

In general, preferred embodiments of the method employ preferred embodiments of the reagents as described herein.

A. Reaction Conditions for Conjugation

Suitable solvents for carrying out the conjugation reaction include buffers such as aqueous sodium phosphate, sodium acetate, sodium carbonate, phosphate buffered saline (PBS), sodium borate, and N-(2-hydroxyethyl)piperazine-N'-(2-ethanesulfonic acid) (HEPES). For conjugation to a protein, the polymeric reagent is typically added to the protein-containing solution at an equimolar amount or at a molar excess relative to target protein. Molar excesses of carbohydrate reagent relative to target protein are typically in the range of about 2 to 50, preferably in the range of 2 to 20, and most preferably in the range of 2 to 5. The conjugation reaction is typically carried out at temperatures at or below about room temperature (25° C.), although temperatures may range from about −15° C. to about 100° C., more preferably from about 4° C. to 37° C., for approximately one to 24 hours. Exemplary conjugation reactions are described in Examples 14 and 16-18 below.

Conditions for conjugation to a small molecule, e.g. amphotericin B or other amine-containing molecules as discussed below, will vary according to the small molecule being modified. Typically, however, the conjugation is conducted using a slight molar excess of polymeric reagent relative to small molecule, e.g., about 1.2-1.5, to about a 5 to 10-fold molar excess. In some instances, depending upon the molecule, the small molecule drug may actually be used in excess, such as when the carbohydrate-small molecule conjugate precipitates in the reaction solvent, e.g., ether, while the unreacted drug remains in solution.

The exact reaction time is determined by monitoring the progress of the reaction over time. Progress of the reaction is typically monitored by withdrawing aliquots from the reaction mixture at various time points and analyzing the reaction mixture by SDS-PAGE or MALDI-TOF mass spectrometry or any other suitable analytical method.

B. Characterization and Optional Separation of Conjugates

The strategy for purification of the final conjugate reaction mixture will depend upon a number of factors, such as the molecular weight of the polymer employed, the particular protein, and the residual activity and in vivo properties of the conjugate species.

Conjugates having different molecular weights can be isolated using gel filtration chromatography. Gel filtration columns suitable for carrying out this type of separation include Superdex® and Sephadex® columns available from Amersham Biosciences. Selection of a particular column will depend upon the desired fractionation range desired. Elution is generally carried out using a non-amine based buffer, such as phosphate, acetate, or the like. The collected fractions may be analyzed by a number of different methods, for example, (i) OD at 280 nm for protein content, (ii) BSA protein analysis, (iii) iodine testing for PEG content, or (iv) by running an SDS PAGE gel, followed by staining with barium iodide.

Carbohydrate polymers having carboxylic acid termini, prepared as described herein, can be purified by ion exchange chromatography, as demonstrated in the Examples below. This process can produce reagents having low polydispersities, an important feature for drug delivery.

Separation of positional isomers (i.e. conjugates having polymers attached to different locations on a protein), generally not achievable by molecular weight-based methods, can often be carried out by reverse phase chromatography using e.g. an RP-HPLC C18 column (Amersham Biosciences or Vydac).

C. Conjugation to Proteins: Random and N-Terminal Selective

Generally, the polymeric reagents of the invention can be used to selectively target the modification of the N-terminus of a protein, under conditions that differentiate the reactivity of the α-amine at the N-terminal amino acid. Reaction conditions for preparing an N-terminally modified protein or peptide include (i) dissolving the protein or peptide to be modified in a non-amine-containing buffer (e.g., at a pH range from about 4 to about 6.5, preferably from about 5 to 6.5, most preferably at a pH of about 5 to 5.5), (ii) adding to the protein or peptide solution a polymeric reagent (α-hydroxy aldehyde or ketone) of the invention, and (iii) allowing the protein or peptide and polymeric reagent to react to form the conjugate.

Reaction under conditions of higher pH can be used for random attachment of a polymeric reagent (α-hydroxy aldehyde or ketone). More specifically, to covalently attach a polymeric reagent to any number of lysine residues that are surface accessible, a protein or peptide (such as those exemplary biomolecules provided below) is typically reacted with a polymeric reagent of the invention in a non amine-containing buffer at mild pH, generally ranging from about 5 to 8, more preferably from about 6.5 to 8. Non-amine containing buffers are preferred, since the amino-groups in the buffer can compete with protein amino groups for coupling to the polymeric reagent. A suitable non-amine containing buffer is selected having an appropriate pK for the desired pH range for conducting the conjugation chemistry. The coupling reaction generally takes anywhere from minutes to several hours (e.g., from 5 minutes to 24 hours or more), and on average, coupling is achieved between about 0.2 and 4 hours.

The degree of modification, that is, the number of polymeric reagents that are covalently attached at available sites on the target molecule, can be increased by increasing, either independently or simultaneously, any one or more of: molar ratio of polymeric reagent to protein or peptide, temperature, reaction time, and pH.

IV. Polymeric Conjugates

In accordance with the invention, polymeric conjugates, comprising a reagent as disclosed herein conjugated to a biologically active molecule (e.g. drug), preferably a single such molecule, are provided. (In some cases, multiple carbohydrate polymers may be attached to a single biologically active molecule.) The conjugates are prepared by reaction of a reagent of structure(s) I, II or IV, having a terminal functional group $G^1$, or a reagent as described in section IIA above, having a terminal carboxylic acid or carboxylic acid derivative, with a biologically active molecule having a corresponding functional group, which is reactive with $G^1$ or with said carboxylic acid or carboxylic acid derivative, to form a stable covalent bond between the reagent and the biologically active molecule.

Conjugates formed using reagents of structure IV thereby typically have the structure

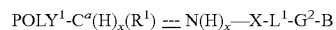

$$POLY^1\text{-}C^\alpha(H)_x(R^1) \mathrel{\text{---}} N(H)_x\text{---}X\text{-}L^1\text{-}G^2\text{-}B$$

where $POLY^1$ is a water-soluble carbohydrate polymer having a terminal anomeric carbon atom, where $C^\alpha$ is said terminal anomeric carbon atom;

--- represents a double bond when x=0 and a single bond when x=1;

$R^1$ is H or hydroxymethyl;

X is oxygen or $NR^2$, where $R^2$ is hydrogen, methyl, lower alkyl, cycloalkyl, or aryl;

$L^1$ is a linker group, and $G^2$ is a covalent bond comprising a residue or converted form of functional group $G^1$, following reaction with a corresponding functional group on biomolecule B.

Conjugates of dextran with several proteins (lysozyme, protegrin-1, C-peptide, and insulin), in accordance with the invention, is described in Examples 14 and 16-18 below. Biological activity of the dextran-insulin conjugate (designated 20b) in vitro and in vivo is described in Examples 19 and 20, respectively. Conjugation of chitosan with a single stranded RNA is described in Example 23.

V. The Conjugated Biologically Active Agent

The biologically active agent conjugated to a polymeric reagent of the invention may fall into one of a number of structural classes, including but not limited to small molecules (including difficultly soluble small molecules), peptides, polypeptides, proteins, polysaccharides, steroids, nucleotides, oligonucleotides, polynucleotides, fats, electrolytes, and the like. In one embodiment, the molecule either possesses a native amino group or is modified to contain at least one reactive amino group. As noted above, the working Examples below describe conjugates of the proteins lysozyme, protegrin-1, C-peptide, and insulin.

The agent may be a therapeutic substance selected from, for example, hypnotics and sedatives, psychic energizers, tranquilizers, respiratory drugs, anticonvulsants, muscle relaxants, antiparkinson agents (dopamine antagonists), analgesics, anti-inflammatories, antianxiety drugs (anxiolytics), appetite suppressants, antimigraine agents, muscle contractants, anti-infectives (antibiotics, antivirals, antifungals, vaccines) antiarthritics, antimalarials, antiemetics, anepileptics, bronchodilators, cytokines, growth factors, anti-cancer agents, antithrombotic agents, antihypertensives, cardiovascular drugs, antiarrhythmics, antioxicants, anti-asthma agents, hormonal agents including contraceptives, sympathomimetics, diuretics, lipid regulating agents, antiandrogenic agents, antiparasitics, anticoagulants, neoplastics, antineoplastics, hypoglycemics, nutritional agents and supplements, growth supplements, antienteritis agents, vaccines, antibodies, diagnostic agents, and contrasting agents.

Specific examples of active agents suitable for covalent attachment to a polymer of the invention include aspariginase, amdoxovir (DAPD), antide, becaplermin, calcitonins, cyanovirin, denileukin diftitox, erythropoietin (EPO), EPO agonists (e.g., peptides from about 10-40 amino acids in length and comprising a particular core sequence as described in WO 96/40749), dornase α, erythropoiesis stimulating protein (NESP), coagulation factors such as Factor V, Factor VII, Factor VIIa, Factor VIII, Factor IX, Factor X, Factor XII, Factor XIII, von Willebrand factor; ceredase, cerezyme, α-glucosidase, collagen, cyclosporin, alpha defensins, beta defensins, exedin-4, granulocyte colony stimulating factor (GCSF), thrombopoietin (TPO), α-1 proteinase inhibitor, elcatonin, granulocyte macrophage colony stimulating factor (GMCSF), fibrinogen, filgrastim, growth hormones human growth hormone (hGH), growth hormone releasing hormone (GHRH), GRO-beta, GRO-beta antibody, bone morphogenic proteins such as bone morphogenic protein-2, bone morphogenic protein-6, OP-1; acidic fibroblast growth factor, basic fibroblast growth factor, CD-40 ligand, heparin, human serum albumin, low molecular weight heparin (LMWH), interferons such as interferon alpha, interferon beta, interferon gamma, interferon omega, interferon tau, consensus interferon; interleukins and interleukin receptors such as interleukin-1 receptor, interleukin-2, interleukin-2 fusion proteins, interleukin-1 receptor antagonist, interleukin-3, interleukin-4, interleukin-4 receptor, interleukin-6, interleukin-8, interleukin-12, interleukin-13 receptor, interleukin-17 receptor; lactoferrin and lactoferrin fragments, luteinizing hormone releasing hormone (LHRH), insulin, pro-insulin, insulin analogues (e.g., mono-acylated insulin as described in U.S. Pat. No. 5,922,675), amylin, C-peptide, somatostatin, somatostatin analogs including octreotide, vasopressin, follicle stimulating hormone (FSH), influenza vaccine, insulin-like growth factor (IGF), insulintropin, macrophage colony stimulating factor (M-CSF), plasminogen activators such as alteplase, urokinase, reteplase, streptokinase, pamiteplase, lanoteplase, and teneteplase; nerve growth factor (NGF), osteoprotegerin, platelet-derived growth factor, tissue growth factors, transforming growth factor-1, vascular endothelial growth factor, leukemia inhibiting factor, keratinocyte growth factor (KGF), glial growth factor (GGF), T Cell receptors, CD molecules/antigens, tumor necrosis factor (TNF), monocyte chemoattractant protein-1, endothelial growth factors, parathyroid hormone (PTH), glucagon-like peptide, somatotropin, thymosin alpha 1, thymosin alpha 1 IIb/IIIa inhibitor, thymosin beta 10, thymosin beta 9, thymosin beta 4, alpha-1 antitrypsin, phosphodiesterase (PDE) compounds, VLA-4 (very late antigen-4), VLA-4 inhibitors, bisphosphonates, respiratory syncytial virus antibody, cystic fibrosis transmembrane regulator (CFTR) gene, deoxyreibonuclease (Dnase), bactericidal/permeability increasing protein (BPI), and anti-CMV antibody. Exemplary monoclonal antibodies include etanercept (a dimeric fusion protein consisting of the extracellular ligand-binding portion of the human 75 kD TNF receptor linked to the Fc portion of IgG1), abciximab, afeliomomab, basiliximab, daclizumab, infliximab, ibritumomab tiuexetan, mitumomab, muromonab-CD3, iodine 131 tositumomab conjugate, olizumab, rituximab, and trastuzumab (herceptin).

Additional agents suitable for covalent attachment to a polymer of the invention include but are not limited to amifostine, amiodarone, aminocaproic acid, aminohippurate sodium, aminoglutethimide, aminolevulinic acid, aminosalicylic acid, amsacrine, anagrelide, anastrozole, asparaginase, anthracyclines, bexarotene, bicalutamide, bleomycin, buserelin, busulfan, cabergoline, capecitabine, carboplatin, carmustine, chlorambucin, cilastatin sodium, cisplatin, cladribine, clodronate, cyclophosphamide, cyproterone, cytarabine, camptothecins, 13-cis retinoic acid, all trans retinoic acid; dacarbazine, dactinomycin, daunorubicin, deferoxamine, dexamethasone, diclofenac, diethylstilbestrol, docetaxel, doxorubicin, epirubicin, estramustine, etoposide, exemestane, fexofenadine, fludarabine, fludrocortisone, fluorouracil, fluoxymesterone, flutamide, gemcitabine, epinephrine, L-Dopa, hydroxyurea, idarubicin, ifosfamide, imatinib, irinotecan, itraconazole, goserelin, letrozole, leucovorin, levamisole, lisinopril, lovothyroxine sodium, lomustine, mechlorethamine, medroxyprogesterone, megestrol, melphalan, mercaptopurine, metaraminol bitartrate, methotrexate, metoclopramide, mexiletine, mitomycin, mitotane, mitoxantrone, naloxone, nicotine, nilutamide, octreotide, oxaliplatin, pamidronate, pentostatin, pilcamycin, porfimer, prednisone, procarbazine, prochlorperazine, ondansetron, raltitrexed, sirolimus, streptozocin, tacrolimus, tamoxifen, temozolomide, teniposide, testosterone, tetrahydrocannabinol, thalidomide, thioguanine, thiotepa, topotecan, tretinoin, valrubicin, vinblastine, vincristine, vindesine, vinorelbine, dolasetron, granisetron; formoterol, fluticasone, leuprolide, midazolam, alprazolam, amphotericin B, podophylotoxins, nucleoside antivirals, aroyl hydrazones, sumatriptan; macrolides such as erythromycin, oleandomycin, troleandomycin, roxithromycin, clarithromycin, davercin, azithromycin, flurithromycin, dirithromycin, josamycin, spiromycin, midecamycin, leucomycin, miocamycin, rokitamycin, andazithromycin, and swinolide A; fluoroquinolones such as ciprofloxacin, ofloxacin, levofloxacin, trovafloxacin, alatrofloxacin, moxifloxacin, norfloxacin, enoxacin, grepafloxacin, gatifloxacin, lomefloxacin, sparfloxacin, temafloxacin, pefloxacin, amifloxacin, fleroxacin, tosufloxacin, prulifloxacin, irloxacin, pazufloxacin, clinafloxacin, and sitafloxacin; aminoglycosides such as gentamicin, netilmicin, paramecin, tobramycin, amikacin, kanamycin, neomycin, streptomycin, vancomycin, teicoplanin, rampolanin, mideplanin, colistin, daptomycin, gramicidin, colistimethate; polymixins such as polymixin B, capreomycin, bacitracin, penems; penicillins including penicllinase-sensitive agents such as penicillin G and penicillin V; penicllinase-resistant agents such as methicillin, oxacillin, cloxacillin, dicloxacillin, floxacillin, and nafcillin; gram negative microorganism active agents such as ampicillin, amoxicillin, and hetacillin, cillin, and galampicillin; antipseudomonal penicillins such as carbenicillin, ticarcillin, azlocillin, mezlocillin, and piperacillin; cephalosporins such as cefpodoxime, cefprozil, ceftbuten, ceftizoxime, ceftriaxone, cephalothin, cephapirin, cephalexin, cephradrine, cefoxitin, cefamandole, cefazolin, cephaloridine, cefaclor, cefadroxil, cephaloglycin, cefuroxime, ceforamide, cefotaxime, cefatrizine, cephacetrile, cefepime, cefixime, cefonicid, cefoperazone, cefotetan, cefinetazole, ceftazidime, loracarbef, and moxalactam; monobactams such as aztreonam; and carbapenems such as imipenem, meropenem, pentamidine isethiouate, albuterol sulfate, lidocaine, metaproterenol sulfate, beclomethasone diprepionate, triamcinolone acetamide, budesonide acetonide, fluticasone, ipratropium bromide, flunisolide, cromolyn sodium, and ergotamine tartrate; taxanes such as paclitaxel; SN-38, and tyrphostines.

Preferred small molecules for coupling to a polymeric reagent of the invention are those having at least one amino group. Preferred molecules include aminohippurate sodium, amphotericin B, doxorubicin, aminocaproic acid, aminolevulinic acid, aminosalicylic acid, metaraminol bitartrate, pamidronate disodium, daunorubicin, levothyroxine sodium, lisinopril, cilastatin sodium, mexiletine, cephalexin, deferoxamine, and amifostine.

Preferred peptides or proteins for coupling to a polymeric reagent of the invention include EPO, IFN-alpha, IFN-beta, IFN-gamma, consensus IFN, Factor VII, Factor VIII, Factor IX, IL-2, remicade (infliximab), Rituxan (rituximab), Enbrel (etanercept), Synagis (palivizumab), Reopro (abciximab), Herceptin (trastuzimab), tPA, Cerizyme (imiglucerase), Hepatitus-B vaccine, rDNAse, alpha-1 proteinase inhibitor, GCSF, GMCSF, hGH, insulin, FSH, an PTH.

TABLE 1

| SEQ ID NO: | Name | Family | Sequence and/or Identifying Information | Therapeutic Activity |
|---|---|---|---|---|
| 1 | carperitide | ANP | SLRRSSCFGGRMDRIGAQSGLGCNSFRY; human alpha-atrial natriuretic peptide; Atriopeptin-28 (human); | Cardiostimulant Respiratory |
| 2 | alpha-neoendorphin | Endorphin | H-Tyr-Gly-Gly-Phe-Leu-Arg-Lys-Tyr-Pro-Lys-OH | Analgesic, other |
| 3 | A-3847 | Insulin | gi\|386828\|gb\|AAA59172.1\| insulin [Homo sapiens] MALWMRLLPLLALLALWGPDPAAAFVNQHLCGSHLVEALYLVCGERGFFY TPKTRREAEDLQVGQVELGGGPGAGSLQPLALEGSLQKRGIVEQCCTSIC SLYQLENYCN | Antidiabetic |
| 4 | A-4114 | Insulin | MALWMRLLPLLALLALWGPDPAAAFVNQHLCGSHLVEALYLVCGERGFFY TPKTRREAEDLQVGQVELGG | Antidiabetic |
| 5 | A-68552 | | GPGAGSLQPLALEGSLQKRGIVEQCCTSICSLYQLENYCN | Anorectic/ Antiobesity |
| 302 and 303 | A-75998 | | [Ac-D-2Nal1-D-4ClPhe2-D-3Pal3-NMeTyr5-D-Lys(Nic)6-Lys(Isp)8-D-Ala10]GnRH; N-acetyl-D-2-naphthylalanyl-D-4-chlorophenylalanyl-D-3-pyridylalanyl-seryl-N-methyltyrosyl-D-N(epsilon)-nicotinyllysyl-leucyl-N(epsilon)-isopropyllysyl-prolyl-alaninamide acetate | Releasing hormone Reproductive/ gonadal, general |
| 6 | AN-1792 | beta-amyloid peptide | gi\|8176533\|gb\|AAB26264.2\| beta-amyloid peptide precursor; beta APP [Homo sapiens] GSGLTNIKTEEISEVKMDAEFRHDSGYEVHHQKLVFFAEDVGSNKGAIIG LMVGGVVIATVIIITLVMLKKQYTSNHHGVVE | Cognition enhancer |
| 7 | AAMP-1 | | MESESESGAAADTPPLETLSFHGDEEIIEVVELDPGPPDPDDLAQEMEDV DFEEEEEEEGNEEGWVLEPQEGVVGSMEGPDDSEVTFALHSASVFCVSLD PKTNTLAVTGGEDDKAFVWRLSDGELLFECAGHKDSVTCAGFSHDSTLVA ATGDMSGLLKVWQVDTKEEVWSFEAGDLEWMEWHPRAPVLLAGTADGNTW MWKVPNGDCKTFQGPNCPATCGRVLPDGKRAVVGYEDGTIRIWDLKQGSP IHVLKGTEGHQGPLTCVAANQDGSLILTGSVDCQAKLVSATTGKVVGVFR PETVASQPSLGEGEESESNSVESLGFCSVMPLAAVGYLDGTLAIYDLATQ TLRHQCQHQSGIVQLLWEAGTAVVYTCSLDGIVRLWDARTGRLLTDYRGH TAEILDFALSKDASLVVTTSGDHKAKVFCVQRPDR | Anticoagulant Anti-inflammatory Immunological Anticancer, other Vulnerary |

TABLE 1-continued

| SEQ ID NO: | Name | Family | Sequence and/or Identifying Information | Therapeutic Activity |
|---|---|---|---|---|
| 8 | Exenatide | GLP-1 | HGEGTFTSDLSKQMEEEAVRLFIEWLKNGGPSSGAPPPS | Antidiabetic Anorectic/ Antiobesity |
| 9 | AC-625 | | Acetyl-ATQRLANELVRLQTYPRTNVGSNTY-NH$_2$ | Antihypertensive, renin system Symptomatic antidiabetic |
| 10 | ACTH | | gi\|80861463\|ref\|NP_001030333.1\| proopiomelanocortin preproprotein [Homo sapiens] MPRSCCSRSGALLLALLLQASMEVRGWCLESSQCQDLTTESNLLECIRAC KPDLSAETPMFPGNGDEQPLTENPRKYVMGHFRWDRFGRRNSSSSGSSGA GQKREDVSAGEDCGPLPEGGPEPRSDGAKGPREGKRSYSMEHFRWGKPVG KKRRPVKVYPNGAEDESAEAFPLEFKRELTQGRLREGDGPDGPADDGAGA QADLEHSLLVAAEKKDEGPYRMEHFRWGSPPKDKRYGGFMTSEKSQTPLV TLFKNAIIKNAYKKGE | Adrenal and pituitary disorders |
| 11 | AIDS therapeutic vaccine | | gi\|288842\|emb\|CAA78890.1\| V3 loop [Human immunodeficiency virus type 1] CTRPSNNTRKSIPVGPGKALYATGAIIGNIRQAHC | Therapeutic vaccine |
| 12 | AIDS therapy | | gi\|5081475\|gb\|AAD39400.1\|AF128998_1 gag [Human immunodeficiency virus type 1] MGARASVLSGGKLDKWEKIRLRPGGKKTYQLKHIVWASRELERFAVNPGL LETGGGCKQILVQLQPSLQTGSEELKSYLNAVATLYCVHQGIEVRDTKEA LDKIEEEQNKSKKKAQQAAADTGNSSQVSQNYPIVQNLQGQMVHQAISPR TLNAWVKVIEEKAFSPEVIPMFSALSEGATPQDLNTMLNTVGGHQAAMQM LKETINEEAAEWDRLHPAHAGPNAPGQMREPRGSDIAGTTSTLQEQIGWM TSNPPVPVGEIYKRWIILGLNKIVRMYSPVSILDIRQGPKEPFEDYVDRF YKTLRAEQASQDVKNWMTETLLVQNANPDCKTILKALGPAATLEEMMTAC QGVGGPSHKARILAEAMSQVTSPANIMMQRGNFRNQRKTIKCFNCGKEGH LARHCRAPRKKGCWKCGREGHQMKDCTERQANFLGKIWPSHKGRPGNFLQ SRPEPTAPPEESFRFGEETTTPPQKQEPLPSQKQETIDKDLYPLASLKSL FGNDPSLQ | Antiviral, anti-HIV |
| 13 and 14 | Allotrap 2702 | | Allotrap 1258; Allotrap 2702; Allotrap E; Allotrap G; RDP58; peptide Bc-1nl; NLRIALR/RLAIRLN | Immuno- suppressant |
| 15 and 16 | Alzheimer's imaging agent | | H-DAEFRHDSGYEVHHQKLVFFAEDVGSNKGAIIGLMVGGVV-OH; or H-DAEFRHDSGYEVHHQKLVFFAEDVGSNKGAIIGLMVGGVVIA-OH | Imaging agent |
| 17 | AM-425 | | gi\|450499\|ref\|NP_002300.1\| leukemia inhibitory factor (cholinergic differentiation factor) [Homo sapiens] MKVLAAGVVPLLLVLHWKHGAGSPLPITPVNATCAIRHPCHNNLMNQIRS QLAQLNGSANAFILYYTAQGEPFPNNLDKLCGPNVTDFPPFHANGTEKAK LVELYRIVVYLGTSLGNITRDQKILNPSALSHSKLNATADILRGLLSNV LCRLCSKYHVGHVDVTYGPDTSGKDVFQKKKLGCQLLGKYKQIIAVLAQA F | Antiarthritic, immunological |
| 304 | AN-238 | | L-Threoninamide, N-[5-[2-[(2S,4S)-1,2,3,4,6,11- hexahydro-2,5,12-trihydroxy-7-methoxy-6,11-dioxo- 4-[[2,3,6-trideoxy-3-(2,3-dihydro-1H-pyrrol-1-yl)- alpha-L-lyxo-hexopyranosyl]oxy]-2-naphthacenyl]- 2-oxoethoxy]-1,5-dioxopentyl]-D-phenylalanyl- L-cysteinyl-L-tyrosyl-D-tryptophyl-L-lysyl-L- valyl-L-cysteinyl-, cyclic (2-7)-disulfide | Somatostatin Anticancer, hormonal |
| 305 | AV-9 | | [D-Arg]9-NH$_2$ | Antiviral, other |
| 8 | AZM-134 | GLP-1 | HGEGTFTSDLSKQMEEEAVRLFIEWLKNGGPSSGAPPPS | Anorectic/ Antiobesity Antidiabetic |
| 18 | Addressin | | gi\|109633022\|ref\|NP_570116.2\| mucosal vascular addressin cell adhesion molecule 1 isoform a precursor [Homo sapiens] MDFGLALLLAGLLGLLLGQSLQVKPLQVEPPEPVVAVALGASRQLTCRLA CADRGASVQWRGLDTSLGAVQSDTGRSVLTVRNASLSAAGTRVCVGSCGG | Recombinant, other Anti- inflammatory |

TABLE 1-continued

| SEQ ID NO: | Name | Family | Sequence and/or Identifying Information | Therapeutic Activity |
|---|---|---|---|---|
| | | | RTFQHTVQLLVYAFPDQLTVSPAALVPGDPEVACTAHKVTPVDPNALSFS LLVGGQELEGAQALGPEVQEEEEPQGDEDVLFRVTERWRLPPLGTPVPP ALYCQATMRLPGLELSHRQAIPVLHSPTSPEPPDTTSPESPDTTSPESPD TTSQEPPDTTSPEPPDKTSPEPAPQQGSTHTPRSPGSTRTRRPEISQAGP TQGEVIPTGSSKPAGDQLPAALWTSSAVLGLLLLALPTYHLWKRCRHLAE DDTHPPASLRLLPQVSAWAGLRGTGQVGISPS | |
| 306 | ambamustine | | L-Methionine, N-[3-[bis(2-chloroethyl)amino]-N-(4-fluoro-L-phenylalanyl)-L-phenylalanyl]-, ether ester | Anticancer, alkylating Anticancer, antimetabollite |
| 19 | amylin antagonists | | DTTVSEPAPSCVTLYQSWRYSQADNGCAETVTVKVVYEDDTEGLCTAVAP GQITTVGDGTIGSHGHARYLARCL | Antidiabetic |
| 20 | anaritide analogues | ANP | gi\|178638\|gb\|AAA35529.1\| atrial natriuretic peptide MSSFSTTTVSFLLLLAFQLLGQTRANPMYNAVSNADLMDFKNLLDHLEEK MPLEDEVPPQVLSDPNEEAGAALSPLPEVPPWTGEVSPAQRDGGALGRGP WDSSDRSALLKSKLRALLTAPRSLRRSSCFGGRMDRIGAQSGLGCNSFRY | Antihypertensive, diuretic |
| 21-28 | antiinflammatory peptide | | As disclosed in U.S. Pat. No. 5,470,831: Thr-Thr-Ser-Gln-Val-Arg-Pro-Arg Val-Lys-Thr-Thr-Ser-Gln-Val-Arg-Pro-Arg. Ser-Gln-Val-Arg-Pro-Arg Val-Arg-Pro-Arg Thr-Thr-Ser-Gln-Val-Arg-Pro-Arg-His-Ile-Thr. Thr-Thr-Ser-Gln-Val Thr-Ser-Gln-Val-Arg Thr-Thr-Ser-Gly-Ile-His-Pro-Lys | Antiinflammatory Immunosuppressant Multiple sclerosis treatment Antiarthritic, other Stomatological Dermatological |
| 307 | antiflammins | | L-Leucine, N-[N-[N-[N-[N2-[N2-[N-(N-L-histidyl-L-alpha-aspartyl)-L-methionyl]-L-asparaginyl]-L-lysyl]-L-valyl]-L-leucyl]-L-alpha-aspartyl]- | Antiinflammatory |
| 308 | antifungal tripeptides | | tripeptides of N3-4-methoxyfumanyl and di- and tripeptides of N3-D-trans 2,3-epoxysuccinamoyl-L-2,3-diaminopropanoic acid | Antifungal |
| 29 | Gastrimmune | | G17-DT; G17DT (vaccine); Gastrimmune; Glu-Gly-Pro-Trp-Leu-Glu-Glu-Glu-Glu-diphtheria toxoid; anti-gastrin 17 immunogen; gastrin 17 vaccine; gastrin-17-diphtheria toxoid conjugate | Anticancer, immunological |
| 30 | antithrombin polypeptides | | gi\|312673\|emb\|CAA51292.1\| Hirudin [*Hirudinaria manillensis*] MFSLKLFVVFLAVCICVSQAVSYTDCTESGQNYCLCVGGNLCGGGKHCEM DGSGNKCVDGEGTPKPKSQTEGDFEEIPDEDILN | Antithrombotic Anticoagulant |
| 31 | antiviral peptides | | NH$_2$-Tyr-Ala-Gly-Ala-Val-Val-Asn-Asp-Leu-COOH | Antiviral, other |
| 32 | apolipoprotein | | gi\|671882\|emb\|CAA28583.1\| apolipoprotein [*Homo sapiens*] MKLLAATVLLLTICSLEGALVRRQAKEPCVESLVSQYFQTVTDYGKDLME KVKSPELQAEAKSYFEKSKEQLTPLIKKAGTELVNFLSYFVELGTHPATQ | Hypolipaemic/ Antiatherosclerosis |
| 33 | arthritis antigen | | gi\|46369603\|gb\|AAS89650.1\| secreted antigen 85A precursor [*Mycobacterium bovis* BCG] MQLVDRVRGAVTGMSRRLVVGAVGAALVSGLVGAVGGTATAGAFSRPGLP VEYLQVPSPSMGRDIKVQFQSGGANSPALYLLDGLRAQDDFSGWDINTPA FEWYDSGLSVVMPVGGQSSFYSDWYQPACGKAGCQTYKWETFLTSELPGW LQANRHVKPTGSAVVGLSMAASSALTLAIYHPQQFVYAGAMSGLLDPSQA MGPTLIGLAMGDAGGYKASDMWGPKEDPAWQRNDPLLNVGKLIANNTRVW VYCGNGKPSDLGGNNLPAKFLEGFVRTSNIKFQDAYNAGGGHNGVFDFPD SGTHSWEYWGAQLNAMKPDLQRALGATPNTGPAPQGA | Recombinant, other Antiarthritic, immunological Immunosuppressant |
| 309 | Avorelin | | 5-Oxo-L-prolyl-L-histidyl-L-tryptophyl-L-seryl-L-tyrosyl-2-methyl-D-tryptophyl-L-leucyl-L-arginyl-N-ethyl-L-prolinamide | Releasing hormone Anticancer, hormonal Menstruation disorders |

TABLE 1-continued

| SEQ ID NO: | Name | Family | Sequence and/or Identifying Information | Therapeutic Activity |
|---|---|---|---|---|
| 310 | B-956 | | N-[8(R)-Amino-2(S)-benzyl-5(S)-isopropyl-9-sulfanyl-3(Z),6(E)-nonadienoyl]-L-methionine | Anticancer, other |
| 311 | BCH-2687 | | L-Tyrosyl-D-arginyl-L-phenylalanyl-L-phenylalaninamide | Analgesic, other |
| 34 | BCH-2763 | | L-Leucine, D-phenylalanyl-L-prolyl-5-aminopentanoyl-5-aminopentanoyl-L-alpha-aspartyl-L-phenylalanyl-L-alpha-glutamyl-L-prolyl-L-isoleucyl-L-prolyl-; BCH-2763; Phe-Pro-(NH(CH$_2$)$_4$CO)$_2$-Asp-Phe-Glu-Pro-Ile-Pro-Leu; phenylalanyl-prolyl-(NH(CH$_2$)$_4$CO)$_2$-aspartyl-phenylalanyl-glutamyl-prolyl-isoleucyl-prolyl-leucine | Anti-thrombotic Anticoagulant |
| 312 | frake-famide | | L-Phenylalaninamide, L-tyrosyl-D-alanyl-4-fluoro-L-phenylalanyl- | Analgesic, other |
| 313 | BIM-22015 | | Glycinamide, D-alanyl-L-glutaminyl-L-tyrosyl-L-phenylalanyl-L-arginyl-L-tryptophyl- | ACTH Neurological |
| 35 | BIM-26028 | | Pyroglutamyl-glutaminyl-arginyl-leucyl-glycyl-asparaginyl-glutaminyl-tryptyl-alanyl-valyl-glycyl-histidinyl-leucyl-leucyl-NH$_2$ | Releasing hormone Respiratory Anorectic/Antiobesity Anticancer, hormonal |
| 314 | BIM-44002 | | L-Tyrosinamide, L-phenylalanyl-L-norleucyl-L-histidyl-L-asparaginyl-L-leucyl-D-tryptophyl-L-lysyl-L-histidyl-L-leucyl-L-seryl-L-seryl-L-norleucyl-L-alpha-glutamyl-L-arginyl-L-valyl-L-.alpha.-glutamyl-L-yryptophyl-L-leucyl-L-arginyl-L-lysyl-L-lysyl-L-leucyl-L-glutaminyl-L-alpha-aspartyl-L-valyl-L-histidyl-L-asparaginyl- | Hormone Osteoporosis treatment |
| 36 | BIO-1211 | | L-Proline, N-((4-((((2-methylphenyl)aminocarbonyl)amino)phenyl)acetyl)-L-leucyl-Lalpha-aspartyl-L-valyl-; BIO-1211; N-((4-((((2-methylphenyl)amino)carbonyl)amino)phenyl) acetyl-leucyl-aspartyl-valyl-proline | Antiasthma GI inflammatory/bowel disorders Multiple sclerosis treatment |
| 37 | BPC-15 | | BPC 15; BPC-15; BPC-157; booly protection compound 15; L-Valine, glycyl-L-alpha-glutamyl-L-prolyl-L-prolyl-L-prolylglycyl-L-lysyl-L-prolyl-L-alanyl-L-alpha-aspartyl-L-alpha-aspartyl-L-alanylglycyl-L-leucyl- | Anti-inflammatory |
| 315 | bivalirudin | | L-Leucine, D-phenylalanyl-L-prolyl-L-arginyl-L-prolylglycylglycylglycylglycyl-L-asparaginylglycyl-L-alpha-aspartyl-L-phenylalanyl-L-alpha-glutamyl-L-alpha-glutamyl-L-isoleucyl-L-prolyl-L-alpha-glutamyl-L-tyrosyl-; D-phenylalanyl-L-prolyl-L-arginyl-L-prolyl-glycylglycyl-glycyl-glycyl-L-asparagyl-glycyl-L-aspartyl-L-phenylalanyl-L-glutamyl-L-glutamyl-L-isoleucyl-Lprolyl-L-glutamyl-L-glutamyl-L-tyrosyl-L-leucine trifluoroacetate (salt) hydrate | Anticoagulant Antianginal |
| 38 | bombesin antagonist | | 5-oxoPro-Gln-Arg-Leu-Gly-Asn-Gln-Trp-Ala-Val-Gly-His-Leu-MetNH$_2$ [CAS], Bombesin 14; Bombesin Dihydrochloride; Dihydrochloride, Bombesin | Anticancer, other |
| 39 | brain natriuretic peptide | BNP | SPKMVQGSGCFGRKMDRISSSSGLGCKVLRRH | COPD treatment, cardiac |
| 41 | C-peptide analogues | C-peptide | Glu-Ala-Glu-Asp-Leu-Gln-Val-Gly-Gln-Val-Glu-Leu-Gly-Gly-Gly-Pro-Gly-Ala-Gly-Ser-Leu-Gln-Pro-Leu-Ala-Leu-Gly-Gly-Ser-Leu-Gln | Symptomatic antidiabetic Ophthalmological Neurological |

TABLE 1-continued

| SEQ ID NO: | Name | Family | Sequence and/or Identifying Information | Therapeutic Activity |
|---|---|---|---|---|
| 316 | C5a antagonist | | Me-Phe-Lys-Pro-D-Cha-L-Cha-D-Phe | Anti-inflammatory |
| 42 | CBT-101 | | L-Cysteinamide, L-asparaginyl-L-leucylglycyl-L-valyl-S-[(acetylamino)methyl]-, monoacetate | Antiglaucoma |
| 43 | CCK(27-32) | | Tyr(SO₃)-Met-Gly-Trp-Met-Asp; CBZ-CCK (27-32)-NH₂; cholecystokinin (27-32) amide, benzoyloxycarbonyl-, D-Trp | Analgesic, obesity, other |
| 44 | CD4 | | CD4 (81-92), D-Ile; CD4 (81-92), D-Tyr; CD4 (81-92) D-Tyr, D-Cys, D-Glu(5); CD4(81-92); TYICEVEDQKEE; Thr-Tyr-Ile-Cys-Glu-Val-Glu-Asp-Gln-Lys-Glu-Glu; threonyl-tyrosyl-isoleucyl-cysteinyl-glutamyl-valyl-glutamyl-aspartyl-glutaminyl-lysyl-glutamyl-glutamic acid | Antiviral, anti-HIV |
| 317 | CEE-04-420 | | Lys-D-Pro-Thr and Lys-D-Pro-Val | Analgesic, other |
| 45 | CEP-079 | | gi\|108796063\|ref\|NP_001007140.2\| insulin-like growth factor 2 isoform 1 precursor [Homo sapiens] MGIPMGKSMLVLLTFLAFASCCIAAYRPSETLCGGELVDTLQFVCGDRGF YFSRPASRVSRRSRGIVEECCFRSCDLALLETYCATPAKSERDVSTPPTV LPDNFPRYPVGKFFQYDTWKQSTQRLRRGLPALLRARRGHVLAKELEAFR EAKRHRPLIALPTQDPAHGGAPPEMASNRK | Ophthalmological |
| 318 | mifa-murtide | | L-Alaninamide, N-(N-acetylmuramoyl)-L-alanyl-D-alpha-glutaminyl-N-[4-hydroxy-10-oxo-7-[(1-oxohexadecyl)oxy]-3,5,9-trioxa-4-phosphapentacos-1-yl]-, P-oxide, monosodium salt, (R)- | Anticancer, immunological |
| 46 | CGRP analogues | CGRP | ACDTATCVTHRLAGLLSRSGGVVKNNFVPTNVGSKAF-NH₂ | Hormone Cardiovascular |
| 47 | rusala-tide acetate | | gi\|4503635\|ref\|NP_000497.1\| coagulation factor II preproprotein [Homo sapiens] MAHVRGLQLPGCLALAALCSLVHSQHVFLAPQQARSLLQRVRRANTFLEE VRKGNLERECVEETCSYEEAFEALESSTATDVFWAKYTACETARTPRDKL AACLEGNCAEGLGTNYRGHVNITRSGIECQLWRSRYPHKPEINSTTHPGA DLQENFCRNPDSSTTGPWCYTTDPTVRRQECSIPVCGQDQVTVAMTPRSE GSSVNLSPPLEQCVPDRGQQYQGRLAVTTHGLPCLAWASAQAKALSKHQD FNSAVQLVEBFCRNPDGDEEGVWCYVAGKPGDFGYCDLNYCEEAVEEETG DGLDEDSDRAIEGRTATSEYQTFFNPRTFGSGEADCGLRPLFEKKSLEDK TERELLESYIDGRIVEGSDAEIGMSPWQVMLFRKSPQELLCGASLISDRW VLTAAHCLLYPPWDKNFTENDLLVRIGKHSRTRYERNIEKISMLEKIYIH PRYNWRENLDRDIALMKLKKPVAFSDYIHPVCLPDRETAASLLQAGYKGR VTGWGNLKETWANVGKGQPSVLQVVNLPIVERPVCKDSTRIRITDNMFCA GYKPDEGKRGDACEGDSGGPFVMKSPFNNRWYQMGIVSWGEGCDRDGKYG FYTHVFRLKKWIQKVIDQFGE | Musculoskeletal Vulnerary Symptomatic antidiabetic Cardiovascular Anti-infective, other Ophthalmological |
| 48 | CKS-17 | | L-Leucine, L-leucyl-L-glutaminyl-L-asparaginyl-L-arginyl-L-arginylglycyl-L-leucyl-L-alpha-aspartyl-L-leucyl-L-leucyl-L-phenylalanyl-L-leucyl-L-lysyl-L-alpha-glutamylglycylglycyl-; CKS-17; CKS-17 peptide | Immuno-suppressant Anticancer, immunological |
| 10 | cortico-relin acetate | cortico-tropin | gi\|80861463\|ref\|NP_001030333.1\| proopiomelanocortin preproprotein [Homo sapiens] MPRSCCSRSGALLLALLLQASMEVRGWCLESSQCQDLTTESNLLECIRAC KPDLSAETPMFPGNGDEQPLTENPRKYVMGHFRWDRFGRRNSSSSGSSGA GQKREDVSAGEDCGPLPEGGPEPRSDGAKPGPREGKRSYSMEHFRWGKPV GKKRRPVKVYPNGAEDESAEAFPLEFKRELTGQRLREGDGPDGPADDGAG AQADLEHSLLVAAEKKDEGPYRMEHFRWGSPPKDKRYGGFMTSEKSQTPL VTLFKNAIIKNAYKKGE | Neuroprotective Antiasthma Anti-inflammatory |
| 49 | CT-112 | | L-Arginine, L-threonyl-L-threonyl-L-seryl-L-glutaminyl-L-valyl-L-arginyl-L-prolyl-; 5-(3-ethoxy-4-pentyloxyphenyl)-2,4-thiazolidinedione | Antiarthritic, immunological |
| 50 | CTAP-III | | phenylalanyl--cysteinyl--tyrosyl-tryptophyl-arginyl-threonyl-penicillaminyl-threoninamide; rCTAP-III-Leu-21 (des 1-15); somatostatin analog CTAP | Vulnerary Antiarthritic, other Musculoskeletal |

TABLE 1-continued

| SEQ ID NO: | Name | Family | Sequence and/or Identifying Information | Therapeutic Activity |
|---|---|---|---|---|
| | | | | Recombinant, other |
| 51 | CVFM | | Cys-Val-Phe-Met | Anticancer, other |
| 52 and 53 | calcitonin | calcitonin | CGNLSTCMLGTYTQDFNKFHTFPQTAIGVGAP (human) H-Cys-Ser-Asn-Leu-Ser-Thr-Cys-Val-Leu-Gly-Lys-Leu-Ser-Gln-Glu-Leu-His-Lys-Leu-Gln-Thr-Tyr-Pro-Arg-Thr-Asn-Thr-Gly-Ser-Gly-Thr-Pro-NH$_2$ (salmon) | Formulation, oral, other Hormone Osteoporosis treatment |
| 54 | calciseptine | | sp\|P22947\|TXCAS_DENPO Calciseptin OS = *Dendroaspis polylepsis polylepsis* PE = 1 SV = 1 RICYIHKASLPRATKTCVENTCYKMFIRTQREYISERGCGCPTAMWPYQT ECCKGDRCNK | Antihypertensive, other |
| 52 and 53 | calcitonin analogues | calcitonin | CGNLSTCMLGTYTQDFNKFHTFPQTAIGVGAP (human) H-Cys-Ser-Asn-Leu-Ser-Thr-Cys-Val-Leu-Gly-Lys-Leu-Ser-Gln-Glu-Leu-His-Lys-Leu-Gln-Thr-Tyr-Pro-Arg-Thr-Asn-Thr-Gly-Ser-Gly-Thr-Pro-NH$_2$ (salmon) | Hormone Osteoporosis treatment |
| 55 | calphobindin I | | gi\|186680508\|ref\|NM_001154.3\| *Homo sapiens* annexin A5 (ANXA5), MAQVLRGTVTDFPGGERADAETLRKAMKGLGTDEESILTLLTSRSNAQRQ EISAAFKTLFGRDLLDDLKSELTGKFEKLIVALMKPSRLYDAYELKHALK GAGTNEKVLTEIIASRTPEELRAIKQVYEEEYGSSLEDDVVGDTSGYYQR MLVVLLQANRDPDAGIDEAQVEQDAQALFQAGELKWGTDEEKFITIFGTR SVSHLRKVFDKYMTISGFQIEETIDRETSGNLEQLLAVVKSIRSIPAYLA ETLYYAMKGAGTDDHTLIRVMVSRSEIDLFNIRKEFRKNFATSLYSMIKG DTSGDYKKALLLLCGEDD | Ophthalmological, Vulnerary |
| 319 | cargutocin | | 1,6-Dicarbaoxytocin, 1-butanoic acid-7-glycine- | Labour inducer |
| 320 | casokefamide | | L-Tyrosinamide, L-tyrosyl-D-alanyl-L-phenylalanyl-D-alanyl- | Antidiarrhoeal |
| 56 | cekropin-P | | sp\|P14661\|CECP1_PIG Cecropin-P1 OS = *Sus scrofa* PE = 1 SV = 1 SWLSKTAKKLENSAKKRISEGIAIAIQGGPR | Antibacterial, other |
| 57 | tasidotin hydrochloride | | N,N-Dimethyl-L-valyl-N-methyl-L-valyl-L-propyl-L-proline-tert-butylamide | Anticancer, other |
| 58 | ceruletide diethylamine | | Pyr-Gln-Asp-Tyr(SO3H)-Thr-Gly-Trp-Met-Asp-Phe-C(O)-NH$_2$ | Analgesic, other Gastroprokinetic |
| 321 | cetrorelix acetate | | D-Alaninamide, N-acetyl-3-(2-naphthalenyl)-D-alanyl-4-chloro-D-phenylalanyl-3-(3-pyridinyl)-D-alanyl-L-seryl-L-tyrosyl-N5-(aminocarbonyl)-D-ol-L-leucyl-L-arginyl-L-prolyl- | Fertility enhancer Prostate disorders Menstruation disorders Anticancer, hormonal |
| 59 | corticoliberin | corticoliberin | SQEPPISLDLTFHLLREVLEMTKADQLAQQAHSNRKLLDIA | Releasing hormone |
| 322 | D-22213 | | L-Histidinamide, N2-[(2,3,4,9-tetrahydro-1H-pyrido[3,4-b]indol-3-yl)carbonyl]-L-glutaminyl-L-tryptophyl-L-alanyl-L-valylglycyl-N-[1-[[[1-(aminocarbonyl)-3-methylbutyl]amino]methyl]-3-methylbutyl]-, [1(R),6S-(R*,R*)]-, monoacetate | Anticancer, other |
| 323 | DAP inhibitors | | L-AP-L-Ala and L-Ala-L-Ala-DL-AP; | Antibacterial, other |
| 60 | DP-640 | insulin | L-Tyrosinamide, β-alanyl-L-arginylglycyl-L-phenylalanyl-L-phenylalanyl-, diacetate (salt) | Insulin Antidiabetic |
| 61 | DP-107 | | L-Leucine, L-methionyl-L-threonyl-L-leucyl-L-threonyl-L-valyl-L-glutaminyl-L-alanyl-L-arginyl-L-glutaminyl-L-leucyl-L-leucyl-L-seryl-L-glutaminyl-L-isoleucyl-L-valyl-L-glutaminyl-L- | Antiviral, anti-HIV |

TABLE 1-continued

| SEQ ID NO: | Name | Family | Sequence and/or Identifying Information | Therapeutic Activity |
|---|---|---|---|---|
| | | | glutaminyl-L-glutaminyl-L-asparaginyl-L-asparginyl-L-leucyl-L-leucyl-L-arginyl-L-alanyl-L-isoleucyl-L-.alpha.-glutamyl-L-alanyl-L-glutaminyl-L-glutaminyl-L-histidyl-L-leucyl-L-leucyl-L-glutaminyl-L-leucyl-L-threonyl-L-valyl-L-tryptophylglycyl-L-isoleucyl-L-lysyl-L-glutaminyl- | |
| 62 | DU-728 | | Arg-Gly-Asp-Ser | Antithrombotic |
| 63 | Dynorphin A | | H-Tyr-Gly-Gly-Phe-Leu-Arg-Arg-Ile-Arg-Pro-Lys-Leu-Lys-Trp-Asp-Asn-Gln-OH | Analgesic, other Neuroprotective Dependence treatment |
| 64 | defensins | | gi\|181535\|gb\|AAA52304.1\| defensin precursor MRTLAILAAILLVALQAQAEPLQARADEVAAAPEQIAADIPEVVVSLAWD ESLAPKHGSRKNMDCYCRIPACIAGERRYGTCIYQGRLWAFCC | Antibiotic, other Antifungal Vulnerary |
| 324 | detirelix | | D-Alaninamide, N-acetyl-3-(2-naphthalenyl)-D-alanyl-4-chloro-D-phenylalanyl-D-tryptophyl-L-seryl-L-tyrosyl-N6-[bis(ethylamino)methylene]-D-lysyl-L-leucyl-L-arginyl-L-prolyl- | Releasing hormone Abortifacient Male contraceptice |
| 65 | disagregin | | gi\|545738\|gb\|AAB30092.1\| disagregin = fibrinogen receptor antagonist [Ornithodoros moubata = tick, salivary gland, Peptide, 60 aa] SDDKCQGRPMYGCREDDDSVFGWTYDSNHGQCWKGSYCKHRRQPSNYFAS QQECRNTCGA | Antithrombotic Cardiovascular |
| 66 and 65 | E-2078 | | D-Leucinamide, N-methyl-L-tyrosylglycylglycyl-L-phenylalanyl-L-leucyl-L-arginyl-N2-methyl-L-arginyl-N-ethyl- SDDKCQGRPMYGCREDDDSVFGWTYDSNHGQCWKGSYCKHRRQPSNYFAS QQECRNTCGA | Analgesic, other |
| | ELS-1 | | Arg-Lys-Glu | Immunostimulant, other |
| 67 | ecal- lantide | | Glu-Ala-Met-His-Ser-Phe-Cys-Ala-Phe-Lys-Ala-Asp-Asp-Gly-Pro-Cys-Arg-Ala-Ala-His-Pro-Arg-Trp-Phe-Phe-Asn-Ile-Phe-Thr-Arg-Gln-Cys-Glu-Glu-Phe-Ile-Tyr-Gly-Gly-Cys-Glu-Gly-Asn-Gln-Asn-Arg-Phe-Glu-Ser-Leu-Glu-Glu-Cys-Lys-Lys-Met-Cys-Thr-Arg-Asp | Angioedema, Anti-inflammatory, Haemostatic, Antiarthritic, other |
| 325 | ES-1005 | | bis(1-naphthyl)methylacetyl-His-Sta-Leu-E-Lys diHCl | Antihypertensive, renin system |
| 326 | efegatran | | L-prolinamide, N-methyl-D-phenylalanyl-n-(4-((aminoiminomethyl)amino)-1-formylbutyl), (S)- | Antithrombotic Antianginal |
| 68 and 69 | elafin deriva- tives | | gi\|999146\|gb\|AAB34627.1\| elafin [Homo sapiens] MRASSFLIVVVFLIAGTLVLE H-Ala-Gln-Glu-Pro-Val-Lys-Gly-Pro-Val-Ser-Thr-Lys-Pro-Gly-Ser-Cys-Pro-Ile-Ile-Leu-Ile-Arg-Cys-Ala-Met-Leu-Asn-Pro-Pro-Asn-Arg-Cys-Leu-Lys-Asp-Thr-Asp-Cys-Pro-Gly-Ile-Lys-Lys-Cys-Cys-Glu-Gly-Ser-Cys-Gly-Met-Ala-Cys-Phe-Val-Pro-Gln-OH (Disulfide bonds between Cys16-Cys45, Cys23-Cys49, Cys32-Cys44, Cys38-Cys53) | Respiratory COPD treatment Antiarthritic, other |
| 70 and 52 | elcatonin | calcitonin | Ser-Asn-Leu-Ser-Thr-Asn-Val-Leu-Gly-Lys-Leu-Ser-Gln-Glu-Leu-His-Lys-Leu-Gln-Thr-Tyr-Pro-Arg-Thr-Asn-Val-Gly-Ala-Gly-Thr-Pro-NH$_2$ CGNLSTCMLGTYTQDFNKFHTFPQTAIGVGAP (human) | Hormone Osteoporosis treatment Analgesic, other |
| 71 | eledoisin | | 5-oxo-L-Pro-L-Pro-L-Ser-L-Lys-L-Asp-L-Ala-L-Phe-L-Ala-L-isoleucylglycyl-L-Leu-L-methionin-amide | Ophthalmological |
| 3 | encapsul- ated | insulin | gi\|386828\|gb\|AAA59172.1\| insulin [Homo sapiens] MALWMRLLPLLALLALWGPDPAAAFVNQHLCGSHLVEALYLVCGERGFFY | Formulation, optimized, |

TABLE 1-continued

| SEQ ID NO: | Name | Family | Sequence and/or Identifying Information | Therapeutic Activity |
|---|---|---|---|---|
| | insulin | | TPKTRREAEDLQVGQVELGGGPGAGSLQPLALEGSLQKRGIVEQCCTSIC SLYQLENYCN | nanoparticles Insulin Antidiabetic |
| 72 | endorphin, β- | | YGGFMTSEKSQTPLVTLFKNAIIKNAYKKGE | Analgesic, other |
| 72 | endorphin, pancreatic | | YGGFMTSEKSQTPLVTLFKNAIIKNAYKKGE | Analgesic, other |
| 73 | endothelial cell growth factor | | gi\|189701\|gb\|AAA60043.1\| endothelial cell growth factor MAALMTPGTGAPPAPGDFSGEGSQGLPDPSPEPKQLPELIRMKRDGGRLS EADIRGFVAAVVNGSAQGAQIGAMLMAIRLRGMDLEETSVLTQALAQSGQ QLEWPEAWRQQLVDKHSTGGVGDKVSLVLAPALAACGCKVPMISGRGLGH TGGTLDKLESIPGFNVIQSPEQMQVLLDQAGCCIVGQSEQLVPADGILYA ARDVTATVDSLPLITASILSKKLVEGLSALVVDVKFGGAAVFPNQEQARE LAKTLVGVGASLGLRVAAALTAMDKPLGRCVGHALEVEEALLCMDGAGPP DLRDLVTTLGGALLWLSGHAGTQAQGAARVAAALDDGSALGRFERMLAAQ GVDPGLARALCSGSPAERRQLLPAREQEELLAPADGTVELVRALPLALV LHELGAGRSRAGEPLRLGVGAELLVDVGQRLRRGTPWLRVHRDGPALSGP QSRALQEALVLSDRAPFAAPSPFAELVLPPQQ | Cardiovascular |
| 74 | epti- fibatide | | MAP-HAR-GLY-ASP-TRP-PRO-CYS-NH$_2$ | Antianginal Cardiovascular |
| 327 | examorelin | GHRP | L-Lysinamide, L-histidyl-2-methyl-D-tyrptophyl-L- alanyl-L-tyrptophyl-D-phenylalanyl- | Releasing hormone Vulnerary Cardiovascular |
| 75 | FG-005 | | SMR1-QHNPR | Male sexual dysfunction |
| 328 | FR-113680 | | L-Phenylalaninamide, N-acetyl-L-threonyl-1- formyl-D-tryptophyl-N-methyl-N-(phenylmethyl)- | Antiasthma |
| 76 | fibro- nectin- related peptide | | Gly-Arg-Gly-Asp-Ser | Anticancer, other |
| 329 | G-4120 | | L-cysteine, N-(mercaptoacetyl)-D-tyrosyl-L- arginylglycyl-L-alpha-aspartyl-, cyclic (1-5)- sulfide, S-oxide | Antithrombotic |
| 330 | EP-51216 | | 2S)-6-amino-2-[[(2S)-2-[[(2R)-2-[[(2R)-2-(4- aminobutanoylamino)-3-(2-methyl-1H-indol-3- yl)propanoyl]amino]-3-(2-methyl-1H-indol-3- yl)propanoyl]amino]-3-(2-methyl-1H-indol-3- yl)propanoyl]amino]hexanamide | GH Releasing hormone Vulnerary, endocrine |
| 8 | GLP-1 + exendin-4 | GLP-1 | HGEGTFTSDLSKQMEEEAVRLFIEWLKNGGPSSGAPPPS | Antidiabetic |
| 77 | GM-1986 | | YYWIGIR | Anti- inflammatory |
| 78 | GnRH- associated peptide | GnRH | gi\|133908612\|ref\|NP_001076580.1\| gonadotropin- releasing hormone 1 precursor [Homo sapiens] MKPIQKLLAGLILLTWCVEGCSSQHWSYGLRPGGKRDAENLIDSFQEIVK EVGQLAETQRFECTTHQPRSPLRDLKGALESLIEEETGQKKI | Antiprolactin Menstruation disorders Fertility enhancer |
| 79 | GRF1-44 | | gi\|11034841\|ref\|NP_066567.1\| growth hormone releasing hormone preproprotein [Homo sapiens] MPLWVFFFVILTLSNSSHCSPPPPLTLRMRRYADAIFTNSYRKV | Musculoskeletal |
| 80 | GRF | GHRF | gi\|337133\|gb\|AAA52609.1\| growth hormone releasing factor MPLWVFFFVILTLSNSSHCSPPPPLTLRMRRYADAIFTNSYRKVLGQLSA RKLLQDIMSRQQGESNQERGARARLGRQVDSMWAEQKQMELESILVALLQ KHRNSQG | Idiopathic growth hormone deficiency; cachexia |

TABLE 1-continued

| SEQ ID NO: | Name | Family | Sequence and/or Identifying Information | Therapeutic Activity |
|---|---|---|---|---|
| 331 | GYKI-14451 | | L-Prolinamide, N-[(1,1-dimethylethoxy)carbonyl]-D-phenylalanyl-N-[4-[(aminoiminomethyl)amino]-1-formylbutyl]-, (S)- | Antithrombotic |
| 81 | galanin | | gi\|1247490\|emb\|CAA01907.1\| galanin [Homo sapiens] MARGSALLLASLLLAAALSASAGLWSPAKEKRGWTLNSAGYLLGPHAVGN HRSFSDKNGLTSKRELRPEDDMKPGSFDRSIPENNIMRTIIEFLSFLHLK EAGALDRLLDLPAAASSEDIERS | Releasing hormone |
| 82 | gastrin antagonists | | (benzyloxycarbonyl)-L-Glu-L-Ala-L-Tyr-Gly-L-Tyr-L-Met-L-aspartic acid amide | Antiulcer |
| 332 | glaspimod | | N2,N2'-[2,7-Bis(pyroglutamyl-glutamyl-aspartylamino)-octanediolyl]bis(lysine) | Immunomodulator, anti-infective Immunostimulant, other Radio/chemoprotective |
| 83 | glicentin | | gi\|125987831\|sp\|P01275.3\|GLUC_HUMAN Glucagon precursor [Contains: Glucentin; Glicentin-related polypeptide (GRPP); Oxyntomodulin (OXY) (OXM); Glucagon; Glucagon-like peptide 1 (GLP-1); Glucagon-like peptide 1(7-37) (GLP-1(7-37)); Glucagon-like peptide 1(7-36) GLP-1(7-36)); Glucagon-like peptide 2 (GLP-2)] MKSIYFVAGLFVMLVQGSWQRSLQDTEEKSRSFSASQADPLSDPDQMNED KRHSQGTFTSDYSKYLDSRRAQDFVQWLMNTKRNRNNIAKRHDEFERHAE GTFTSDVSSYLEGQAAKEFIAWLVKGRGRRDFPEEVAIVEELGRRHADGS FSDEMNTILDNLAARDFINWLIQTKITDRK | Insulin Antiulcer Antidiabetic |
| 84 | glucagon | | $H_2$N-His-Ser-Gln-Gly-Thr-Phe-Thr-Ser-Asp-Tyr-Ser-Lys-Tyr-Leu-Asp-Ser-Arg-Arg-Ala-Gln-Asp-Phe-Val-Gln-Trp-Leu-Met-Asn-Thr-COOH | hypoglycemia Diagnostic |
| 84 | glucagon | glucagon | His-Ser-Gln-Gly-Thr-Phe-Thr-Ser-Asp-Tyr-Ser-Lys-Tyr-Leu-Asp-Ser-Arg-Arg-Ala-Gln-Asp-Phe-Val-Gln-Trp-Leu-Met-Asn-Thr | Hypoglycemia |
| 85 | gonadorelin analogues | gonadorelin | gi\|121522\|sp\|P01148.1\|GON1_HUMAN Progonadoliberin-1 precursor (Progonadoliberin I) [Contains: Gonadoliberin-1 (Gonadoliberin I) (Luteinzing hormone-releasing hormone I) (LH-RH I) (Gonadotropin-releasing hormone I) (GnRH-I) (Luliberin I) (Gonadorelin); GnRH-associated peptide 1 (GnRH-associated peptide I)] MKPIQKLLAGLILLTWCVEGCSSQHWSYGLRPGGKRDAENLIDSFQEIVK EVGQLAETQRFECTTHQPRSPLRDLKGALESLIEEETGQKKI | Female contraceptive; enometiosis, uterine leiomyoma, precocious puberty, prostate and breast cancer |
| 333 | gonadorelin antagonist | | [Ac-DNAL1(2),4FDPhe2,D-Trp3,D-Arg6]-LHRH | Female contraceptive; enometiosis, uterine leiomyoma, precocious puberty, prostate and breast cancer |
| 86 | gonadorelin | gonadorelin | 5-oxo-L-His-L-Trp-L-Ser-L-Tyr-Gly-L-Leu-L-Arg-L-Pro-glycinamide | Female contraceptive; enometiosis, uterine leiomyoma, precocious puberty, prostate and breast cancer |
| 334 | goralatide | | L-Proline, 1-[N2-[N-(N-acetyl-L-seryl)-L-α-aspartyl]-L-lysyl]- | Haematological Immunological Radio/chemoprotective |

TABLE 1-continued

| SEQ ID NO: | Name | Family | Sequence and/or Identifying Information | Therapeutic Activity |
|---|---|---|---|---|
| 335 | H-142 | | L-Lysine, N2[N-[N-[N-[4-methyl-2-[[N-[N-[1-(N-L-prolyl-L-histidyl)-L-prolyl]-L-phenylalanyl]-L-histidyl]amino]pentyl]-L-valyl]-L-isoleucyl]-L-histidyl]-, (S)- | Antihypertensive, renin system |
| 336 | I5B2 | | L-Tyrosinamide, N-methyl-L-valyl-N-[2-(4-hydroxyphenyl)-1-phosphonoethyl]- | Antihypertensive, renin system |
| 87 | iseganan hydro-chloride | | L-Argininamide, L-arginylglycylglycyl-L-leucyl-L-cysteinyl-L-tyrosyl-L-cysteinyl-L-arginylglycyl-L-arginyl-L-phenylalanyl-L-cysteinyl-L-valyl-L-cysteinyl-L-valylglycyl-, cyclic (5-14),(7-12)-bis(disulfide) hydrochloride | Antibacterial, other Antifungal Antiviral, other |
| 88 | netamiftide | | L-Tryptophanamide, 4-fluoro-L-phenylalanyl-(4R)-4-hydroxy-L-propyl-L-arginylglycyl-, bis(trifluoroacetate) (salt) | Antidepressant Anxiolytic |
| 337 | icrocaptide | | L-Arginine, glycyl-N2-ethyl-L-lysyl-L-prolyl- | Cardiovascular Septic shock treatment |
| 338 | icatibant | | L-Arginine, D-arginyl-L-arginyl-L-prolyl-trans-4-hydroxy-L-prolylglycyl-3-(2-thienyl)-L-alanyl-L-seryl-D-1,2,3,4-tetrahydro-3-isoquinolinecarbany-L-(2α,3aβ,7aβ)-octahydro-1H-indole-2-carbonyl- | Cardiovascular Hepatoprotective Vulnerary |
| 339 | AG-1776 | | 3-[2(S)-Hydroxy-3(S)-(3-hydroxy-2-methylbenzamido)-4-phenylbutanoyl]-5,5-dimethyl-N-(2-methylbenzyl)thiazolidine-4(R)-carboxamide | Antiviral, anti-HIV |
| 340 | pralmorelin | | L-Lysinamide, D-alanyl-3-(2-naphthalenyl)-D-alanyl-L-alanyl-L-tyrptophyl-D-phenylalanyl- | Diagnostic Releasing hormone |
| 89 | katacalcin | calci-tonin | gi\|115478\|sp\|P01258.1\|CALC_HUMAN Calcitonin precursor [Contains: Calcitonin; Katacalcin (Calcitonin carboxyl-terminal peptide) (CCP) (PDN-21)] MGFQKFSPFLALSILVLLQAGSLHAAPFRSALESSPADPATLSEDEARLL LAALVQDYVQMKASELEQEQEREGSSLDSPRSKRCGNLSTCMLGTYTQDF NKFHTFPQTAIGVGAPGKKRDMSSDLERDHRPHVSMPQAN | Osteoporosis treatment Hormone Recombinant, other |
| 341 | ketomethyl-ureas | | N-[N-[3-benzoylamino-4-phenyl-2-oxobutyl]-N-methylaminocarbonyl]proline | Antihypertensive, renin system |
| 90 | L-346670 | | N-L-arginine-8-L-methionine-21a-L-phenylalanine-21b-L-arginine-21c-L-tyrosine- | Antihypertensive, diuretic |
| 91 | L-364210 | | N-isovaleryl-L-histidyl-L-prolyl-L-phenylalanyl-L-histidyl-(3S,4S)-4-amino-5-c yclohexyl-3-hydroxypentanoic acid)-L-leucyl-L-phenylalanylamide | Antihypertensive, renin system |
| 342 | L-659837 | | [L-Phenylalanine, N-[2-(3-amino-2-oxo-1-pyrrolidinyl)-4-methyl-1-oxopentyl]-L-methionyl-L-glutaminyl-L-tryptophyl-, cyclic (4-1)-peptide, [S-(R*,S*)]- | Analgesic, other |
| 343 | L-693549 | | 5(S)-(tert-butoxycarbonylamino)-4(S)-hydroxy-N-[2(R)-hydroxyindan-1(S)-yl]-2(R)-[4-(3-hydroxypropyl)benzyl]-6-phenylhexanamide | Antiviral, anti-HIV |
| 344 | L-709049 | | L-Alaninamide, N-acetyl-L-tyrosyl-L-valyl-N-(2-carboxy-1-formylmethyl)-, (S)- | Anti-inflammatory |
| 92 | LDV-containing peptides | | 4-((N'-2-methylphenyl)ureido)phenylalanyl-leucyl-alpha-aspartyl-valyl-prolyl-alanyl-alanyl-lysine | Anticancer, other |
| | Lys-Phe | | L-Phenylalanine, N-L-lysyl- | Haematological Antisickling |
| 93 | lagatide | | D-Alaninamide, L-prolyl-L-valyl-L-threonyl-L-lysyl-L-prolyl-L-glutaminyl- | Antidiarrhoeal |

TABLE 1-continued

| SEQ ID NO: | Name | Family | Sequence and/or Identifying Information | Therapeutic Activity |
|---|---|---|---|---|
| 94 | laminin A peptide | | seryl-isoleucyl-lysyl-valyl-alanyl-valinamide | Anticancer, other Neurological |
| 95 | laminin | | tyrosyl-isoleucyl-glycyl-serylarginine | Anticaner, other |
| 345 | lanreotide | somato-statin | L-Threoninamide, 3-(2-naphthalenyl)-D-alanyl-L-cysteinyl-L-tyrosyl-D-tryptophyl-L-lysyl-L-cysteinyl-, cyclic (2-7)-disulfide; L-Threoninamide, 3-(1-naphthalenyl)-D-alanyl-L-cysteinyl-L-tyrosyl-D-tryptophyl-L-lysyl-L-valyl-L-cysteinyl-, cyclic (2-7)-disulfide | Acromegaly Anticancer, hormonal Cardiovascular Antidiarrhoeal |
| 346 | leuprolide acetate | | Luteinizing hormone-releasing factor (pig), 6-D-leucine-9-(N-ethyl-L-prolinamide)-10-deglycinamide- | Formulation, implant Anticancer, hormonal Menstruation disorders |
| 347 | MCI-826 | | Butanoic acid, 2,2-diethyl-4-[[3-[2-[4-(1-methylethyl)-2-thiazolyl]ethenyl]phenyl]amino]-4-oxo-, (E)- | Antiasthma |
| 96 | omiganan pentahydro-chloride | | L-lysinamide, L-isoleucyl-L-leucyl-L-arginyl-L-tryptophyl-L-prolyl-L-tryptophyl-L-tryptophyl-L-prolyl-L-tryptophyl-L-arginyl-L-arginyl-, pentahydrochloride | Peptide antibiotic |
| 97-100 | MBP | | gi\|68509940\|ref\|NP_001020272.1\| Golli-mbp isoform 1 [Homo sapiens]<br>MGNHAGKRELNAEKASTNSETNRGESEKKRNLGELSRTTSEDNEVFGEAD ANQNNGTSSQDTAVTDSKRTADPKNAWQDAHPADPGSRPHLIRLFSRDAP GREDNTFKDRPSESDELQTIQEDSAATSESLDVMASQKRPSQRHGSKYLA TASTMDHARHGFLPRHRDTGILDSIGRFFGGDRGAPKRGSGKDSHHPART AHYGSLPQKSHGRTQDENPVVHFFKNIVTPRTPPPSQGKGRGLSLSRFSW GAEGQRPGFGYGGRASDYKSAHKGFKGVDAQGTLSKIFKLGGRDSRSGSP MARR<br>gi\|68509938\|ref\|NP_001020271.1\| Golli-mbp isoform 2 [Homo sapiens]<br>MGNHAGKRELNAEKASTNSETNRGESEKKRNLGELSRTTSEDNEVFGEAD ANQNNGTSSQDTAVTDSKRTADPKNAWQDAHPADPGSRPHLIRLFSRDAP GREDNTFKDRPSESDELQTIQEDSAATSESLDVMASQKRPSQRHGSKYLA TASTMDHARGHGFLPRHRDTGILDSIGRFFGGDRGAPKRGSGKVSSEE<br>gi\|68509930\|ref\|NP_001020252.1\| myelin basic protein isoform 1 [Homo sapiens]<br>MASQKRPSQRHGSKYLATASTMDHARHGFLPRHRDTGILDSIGRFFGGDR GAPKRGSGKVPWLKPGRSPLPSHARSQPGLCNMYKDSHHPARTAHYGSLP QKSHGRTQDENPVVHFFKNIVTPRTPPPSQGKGRGLSLSRFSWGAEGQRP GFGYGGRASDYKSAHKGFKGVDAQGTLSKIFKLGGRDSRSGSPMARR<br>gi\|4505123\|ref\|NP_002376.1\| myelin basic protein isoform 2 [Homo sapiens]<br>MASQKRPSQRHGSKYLATASTM | Multiple sclerosis treatment Immuno-suppressant |
| 348 | MDL-104238 | | N-[4-(4-morpholinylcarbonyl)benzoyl]-L-valyl-N'-[3,3,4,4,4-pentafluoro-1-(1-methylethyl)-2-oxobutyl]-L-2-azetamide | Anti-inflammatory |
| 349 | MDL-28050 | | D-Glutamic acid, N-[N-[N-[N-[N-[1-[N-[1-[N-[N-(3-carboxy-1-oxopropyl)-L-tyrosyl]-L-alpha-glutamyl]-L-prolyl]-L-isoleucyl]-L-prolyl]-L-alpha-glutamyl]-L-alpha-glutamyl]-L-alanyl]-3-cyclohexyl-L-alanyl]- | Antithrombotic Anticoagulant |
| 101 | MMP inhibitors | | FN 439; FN-439; H2N—C6H4—CO-Gly-Pro-Leu-Ala-NHOH; MMP-inhibitor I; p-NH2-Bz-Gly-Pro-D-Leu-D-Ala-NHOH | Antiarthritic, Anticancer, Anti-inflammitory |
| 350 | MR-988 | | N-pivaloyl-leucyl-gamma-aminobutyric acid | Antiepileptic |
| 351 | mertiatide | | Glycine, N-[N-[N-(mercaptoacetyl)glycyl]glycyl]- | Diagnostic |
| 352 | metkeph-amide | | L-Methioninamide, L-tyrosyl-D-alanylglycyl-L-phenylalanyl-N2-methyl-, monoacetate (salt) | Analgesic, other |

TABLE 1-continued

| SEQ ID NO: | Name | Family | Sequence and/or Identifying Information | Therapeutic Activity |
|---|---|---|---|---|
| 353 | murabutide | | D-Glutamine, N2-[N-(N-acetylmuramoyl)-L-alanyl]-, butyl ester | Immunomodulator, anti-infective Anticancer, immunological Immunostimulant, other |
| 354 | muramyl dipeptide derivatives | | D-alpha-Glutamine, N2-[N-(N-acetylmuramoyl)-L-alanyl]- | Immunomodulator, anti-infective Anticancer, immunological Immunostimulant, other |
| 355 | NPY24-36 | | N-acetyl[Leu-28Leu-31]NPY24-36 | Antihypotensive |
| 102 | NAGA | | Asn-Ala-Gly-Ala | Analgesic, other |
| 356 | tiplimotide | | L-Proline, D-alanyl-L-lysyl-L-prolyl-L-valyl-L-valyl-L-histidyl-L-leucyl-L-phenylalanyl-L-alanyl-L-asparaginyl-L-isoleucyl-L-valyl-L-threonyl-L-prolyl-L-arginyl-L-threonyl- | Multiple sclerosis treatment |
| 103 | opebecan | | gi\|157276599\|ref\|NP_001716.2\| bactericidal/permeability-increasing protein precursor [Homo sapiens]<br>MRENMARGPCNAPRWASLMVLVAIGTAVTAAVNPGVVVRISQKGLDYASQ<br>QGTAALQKELKRIKIPDYSDSFKIKHLGKGHYSFYSMDIREFQLPSSQIS<br>MVPNVGLKFSISNANIKISGKWKAQKRFLKMSGNFDLSIEGMSISADLKL<br>GSNPTSGKPTITCSSCSSHINSVHVHISKSKVGQLIQLFHKKIESALRNK<br>MNSQVCEKVTNSVSSELQPYFQTLPVMTKIDSVAGINYGLVAPPATTAET<br>LDVQMKGEFYSENHHNPPPFAPPVMEFPAAHDRMVYLGLSDYFFNTAGLV<br>YQEAGVLKMTLRDDMIPKESKFRLTTKFFGTFLPEVAKKFPNMKIQIHVS<br>ASTPPHLSVQPTGLTFYPAVDVQAFAVLPNSSLASLFLIGMHTTGSMEVS<br>AESNRLVGELKLDRLLLELKHSNIGPFPVELLQDIMNYIVPILVLPRVNE<br>KLQKGFPLPTPARVQLYNVVLQPHQNFLLFGADVVYK | Recombinant, other Antibacterial, other GI inflammatory/bowel disorders Vulnerary Anti-inflammatory Symptomatic antidiabetic Ophthalmological |
| 104 and 105 | liraglutide | GLP-1 | Glycine, L-histidyl-L-alanyl-L-alpha-glutamylglycyl-L-threonyl-L-phenylalanyl-L-threonyl-L-seryl-L-alpha-aspartyl-L-valyl-L-seryl-L-seryl-L-tyrosyl-L-leucyl-L-alpha-glutamylglycyl-L-glutaminyl-L-alanyl-L-alanyl-N6-[N-(1-oxohexadecyl)-L-gamma-glutamyl]-L-lysyl-L-alpha-glutamyl-L-phenylalanyl-L-isoleucyl-L-alanyl-L-tryptophyl-L-leucyl-L-valyl-L-arginylglycyl-L-arginyl-<br>SFKIKHLGKGHYSFYSMDIREFQLPSSQISMVPNVGLKFSISNANIKISG<br>KWKAQKRFLKMSGNFDLSIE | Antidiabetic Anorectic/Antiobesity |
| 106 | Nona CCK | | GMSISADLKLGSNPTSGKPTITCSSCSSHINSVHVHISKSKVGWLIQLFH<br>KKIESALRNKMNSQVCEKVT | Diagnostic Neuroleptic Anorectic/Antiobseity Antidepressant |
| 107 and 108 | NP-06 | | Cysteinyl-leucyl-glycyl-valyl-valyl-glycyl-seryl-cysteinyl-asparaginyl-aspartyl-phenylalanyl-alanyl-glycyl-cysteinyl-glycyl-tyrosyl-alanyl-isoleucyl-valyl-cysteinyl-phenylalanyl-tryptophyl S-3.1-S-2.13:S-3.7-S-3.19-bis(disulfide)N-2.1-C-4.9-lactam<br>NSVSSELQPYFQTLPVMTKIDSVAGINYGLVAPPATTAETLDVQMKGEFY<br>SENHHNPPPFAPPVMEFPAA | Antiviral, anti-HIV |
| 109 | NPC-18545 | | Bradykinin, N2-D-arginyl-3-(trans-4-hydroxy-L-proline)-7-(D-1,2,3,4-tetrahydro-3-isoquinolinecarboxylic acid)-8-[L-(2alpha,3aβ,7a.beta.)-octahydro-1H-indole-2-carboxylic acid]-<br>HDRMVYLLGLSDYFFNTAGLVYQEAGVLKMTLRDDMIPKESKFRLTTKFF<br>GTFLPEVAKKFPNMKIQIHVS | Anti-inflammatory |
| 110 | Nva-FMDP | | Nva-N3-4-methoxyfumaroyl-L-2,3-diaminopropanoic acid | Antifungal |

TABLE 1-continued

| SEQ ID NO: | Name | Family | Sequence and/or Identifying Information | Therapeutic Activity |
|---|---|---|---|---|
| | | | ASTPPHLSVQPTGLTFYPAVDVQAFAVLPNSSLASLFLIGMHTTGSMEVS AESNRLVGELKLDRLLLELK | |
| 111 | nacartocin | | 6-Carbaoxytocin, 1-(3-mercaptopropanoic acid)-2-(4-ethyl-L-phenylalanine)- HSNIGPFPVELLQDIMNYIVPILVLPRVNEKLQKGFPLPTPARVQLYNVV LQPHQNFLLFGADVVYK | Hormone Labour inducer Antihypertensive, diuretic |
| 112 | natural peptide | | U.S. Pat. No. 5,288,708 Partial N terminal sequence: H$_2$N-Gly-Glu-Pro-Pro-Pro-Gly-Lys-Pro-Ala-Asp-Asp-Ala-Gly-Leu-Val--. . .--COOH | Antiulcer Hepatoprotective Vulnerary Anti-inflammatory Antiparkinsonian Urological |
| 39 | nesiritide citrate | BNP | SPKMVQGSGCFGRKMDRISSSSGLGCKVLRRH | Cardiostimulant Vasodilator, coronary |
| 113- 141 | neuro-trophic factors | | U.S. Pat. No. 5,545,719; AspLeuGlnValPheVal; GlyGluLysLysAsp; AlaThrHisGluSer; CysLeuProValSerGly; LeuProValSerGlySer; ProCysHisAlaProPro; GlyGlyHisAspLeuGluSerGly; AspAspLeuGlnValPhe 15 ProLeuThrSerGly 15 LeuIleHisPheGluGluGlyVal 15 (2) INFORMATION FOR SEQ ID NO: 11: (i) SEQUENCE CHARACTERISTICS: (A) LENGTH: 7 amino acids (B) TYPE: amino acid (D) TOPOLOGY: linear (ii) MOLECULE TYPE: peptide (v) FRAGMENT TYPE: internal (xi) SEQUENCE DESCRIPTION: SEQ ID NO: 11: GlyGluPheSerTyrAspSer 15 (2) INFORMATION FOR SEQ ID NO: 12: (i) SEQUENCE CHARACTERISTICS: (A) LENGTH: 7 amino acids (B) TYPE: amino acid (D) TOPOLOGY: linear (ii) MOLECULE TYPE: peptide (v) FRAGMENT TYPE: internal (xi) SEQUENCE DESCRIPTION: SEQ ID NO: 12: HisAlaProProLeuThrSer 15 (2) INFORMATION FOR SEQ ID NO: 13: (i) SEQUENCE CHARACTERISTICS: (A) LENGTH: 7 amino acids (B) TYPE: amino acid (D) TOPOLOGY: linear (ii) MOLECULE TYPE: peptide (v) FRAGMENT TYPE: internal (xi) SEQUENCE DESCRIPTION: SEQ ID NO: 13: AspLeuGluSerGlyGluPhe 15 (2) INFORMATION FOR SEQ ID NO: 14: (i) SEQUENCE CHARACTERISTICS: (A) LENGTH: 8 amino acids (B) TYPE: amino acid (D) TOPOLOGY: linear (ii) MOLECULE TYPE: peptide (v) FRAGMENT TYPE: internal (xi) SEQUENCE DESCRIPTION: SEQ ID NO: 14: GlyGluPheSerValCysAspSer 15 (2) INFORMATION FOR SEQ ID NO: 15: (i) SEQUENCE CHARACTERISTICS: (A) LENGTH: 10 amino acids (B) TYPE: amino acid (D) TOPOLOGY: linear (ii) MOLECULE TYPE: peptide (v) FRAGMENT TYPE: internal (xi) SEQUENCE DESCRIPTION: SEQ ID NO: 15: LysLysGlyGluPheSerValAlaAspSer 1510 (2) INFORMATION FOR SEQ ID NO: 16: (i) SEQUENCE CHARACTERISTICS: (A) LENGTH: 9 amino acids (B) TYPE: amino acid (D) TOPOLOGY: linear (ii) MOLECULE TYPE: peptide (v) FRAGMENT TYPE: internal (xi) SEQUENCE DESCRIPTION: SEQ ID NO: 16: LysLysGlyGluPheTyrCysSerArg 15 (2) INFORMATION FOR SEQ ID NO: 17: (i) SEQUENCE CHARACTERISTICS: (A) LENGTH: 13 amino acids (B) TYPE: amino acid (D) TOPOLOGY: linear (ii) MOLECULE TYPE: peptide (v) FRAGMENT TYPE: internal (xi) SEQUENCE DESCRIPTION: SEQ ID NO: 17: GlyLeuArgValArgValTrpAsnGlyLysPheProLys 1510 (2) INFORMATION FOR SEQ ID NO: 18: (i) SEQUENCE CHARACTERISTICS: (A) LENGTH: 16 amino acids (B) TYPE: amino acid (D) TOPOLOGY: linear (ii) MOLECULE TYPE: peptide (v) FRAGMENT TYPE: internal (xi) SEQUENCE DESCRIPTION: SEQ ID NO: 18: GlyValAlaPheGluGluAlaProAspAspHisSerPhePheLeuPhe 151015 (2) INFORMATION FOR SEQ ID NO: 19: (i) SEQUENCE CHARACTERISTICS: (A) LENGTH: 7 amino acids (B) TYPE: amino acid (D) TOPOLOGY: linear (ii) MOLECULE TYPE: peptide (v) FRAGMENT TYPE: | Cognition enhancer Neuroprotective |

TABLE 1-continued

| SEQ ID NO: | Name | Family | Sequence and/or Identifying Information | Therapeutic Activity |
|---|---|---|---|---|
| | | | internal (xi) SEQUENCE DESCRIPTION: SEQ ID NO: 19: GlyGlyHisAspLeuSerGly 15 (2) INFORMATION FOR SEQ ID NO: 20: (i) SEQUENCE CHARACTERISTICS: (A) LENGTH: 8 amino acids (B) TYPE: amino acid (D) TOPOLOGY: linear (ii) MOLECULE TYPE: peptide (v) FRAGMENT TYPE: internal (xi) SEQUENCE DESCRIPTION: SEQ ID NO: 20: GlyGlyHisAspLeuGluSerGly 15 (2) INFORMATION FOR SEQ ID NO: 21: (i) SEQUENCE CHARACTERISTICS: (A) LENGTH: 14 amino acids (B) TYPE: amino acid (D) TOPOLOGY: linear (ii) MOLECULE TYPE: peptide (v) FRAGMENT TYPE: internal (xi) SEQUENCE DESCRIPTION: SEQ ID NO: 21: GlyGlyHisAspLeuGluSerGlyGluPheSerTyrAspSer 1510 (2) INFORMATION FOR SEQ ID NO: 22: (i) SEQUENCE CHARACTERISTCS: (A) LENGTH: 14 amino acids (B) TYPE: amino acid (D) TOPOLOGY: linear (ii) MOLECULE TYPE: peptide (v) FRAGMENT TYPE: internal (xi) SEQUENCE DESCRIPTION: SEQ ID NO: 22: GlyGlySerAspLeuSerGlyGluPheSerValCysAspSer 1510 (2) INFORMATION FOR SEQ ID NO: 23: (i) SEQUENCE CHARACTERISTICS: (A) LENGTH: 15 amino acids (B) TYPE: amino acid (D) TOPOLOGY: linear (ii) MOLECULE TYPE: peptide (v) FRAGMENT TYPE: internal (xi) SEQUENCE DESCRIPTION: SEQ ID NO: 23: GlyGlySerAspLeuSerGlyGlyGluPheSerValCysAspSer 151015 (2) INFORMATION FOR SEQ ID NO: 24: (i) SEQUENCE CHARACTERISTICS: (A) LENGTH: 15 amino acids (B) TYPE: amino acid (D) TOPOLOGY: linear (ii) MOLECULE TYPE: peptide (v) FRAGMENT TYPE: internal (xi) SEQUENCE DESCRIPTION: SEQ ID NO: 24: GlyGlySerAspLeuSerGlyGlyGluPheSerValAlaAspSer 151015 (2) INFORMATION FOR SEQ ID NO: 25: (i) SEQUENCE CHARACTERISTICS: (A) LENGTH: 14 amino acids (B) TYPE: amino acid (D) TOPOLOGY: linear (ii) MOLECULE TYPE: peptide (v) FRAGMENT TYPE: internal (xi) SEQUENCE DESCRIPTION: SEQ ID NO: 25: GlyGlySerAspLeuSerGlyGluPheSerValAlaAspSer 1510 (2) INFORMATION FOR SEQ ID NO: 26: (i) SEQUENCE CHARCATERISTICS: (A) LENGTH: 6 amino acids (B) TYPE: amino acid (D) TOPOLOGY: linear (ii) MOLECULE TYPE: peptide (v) FRAGMENT TYPE: internal (xi) SEQUENCE DESCRIPTION: SEQ ID NO: 26: GluThrLeuGlnPheArg 15 (2) INFORMATION FOR SEQ ID NO: 27: (i) SEQUENCE CHARACTERISTICS: (A) LENGTH: 8 amino acids (B) TYPE: amino acid (D) TOPOLOGY: linear (ii) MOLECULE TYPE: peptide (v) FRAGMENT TYPE: internal (xi) SEQUENCE DESCRIPTION: SEQ ID NO: 27: LysLysGluThrLeuGlnPheArg 15 (2) INFORMATION FOR SEQ ID NO: 28: (i) SEQUENCE CHARACTERISTICS: (A) LENGTH: 8 amino acids (B) TYPE: amino acid (D) TOPOLOGY: linear (ii) MOLECULE TYPE: peptide (v) FRAGMENT TYPE: internal (xi) SEQUENCE DESCRIPTION: SEQ ID NO: 28: GluThrLeuGlnPheArgLysLys 15 (2) INFORMATION FOR SEQ ID NO: 29: (i) SEQUENCE CHARACTERISTICS: (A) LENGTH: 9 amino acids (B) TYPE: amino acid (D) TOPOLOGY: linear (ii) MOLECULE TYPE: peptide (v) FRAGMENT TYPE: internal (xi) SEQUENCE DESCRIPTION: SEQ ID NO: 29: LysAlaSerThrThrThrAsnTyrThr 15 | |
| 357 | nifalatide | | L-Prolinamide, L-tyrosyl-4-(methylsulfinyl)-D-2-aminobutanoylglycyl-4-nitro-L-phenylalanyl- | Antidiarrhoeal Analgesic, other |
| 358 | Org-2766 | | L-Phenylalanine, 4-(methylsulfonyl)-L-2-aminobutanoyl-L-alpha-glutamyl-L-histidyl-L-phenylalanyl-D-lysyl- | ACTH Symptomatic antidiabetic Radio/ chemoprotective Neurological |
| 359 | Org-30035 | | L-Phenylalanine, glycylglycyl-L-phenylalanyl-4-(methylsulfonyl)-L-2-aminobutanoyl-D-lysyl- | Neuroleptic Anxiolytic |
| 360 | octreotide | somato-statin | L-Cysteinamide, D-phenylalanyl-L-cysteinyl-L-phenylalanyl-D-tryptophyl-L-lysyl-L-threonyl-N-[2- | Acromegaly Antidiarrhoeal |

TABLE 1-continued

| SEQ ID NO: | Name | Family | Sequence and/or Identifying Information | Therapeutic Activity |
|---|---|---|---|---|
| | | | hydroxy-1-(hydroxymethyl)propyl]-, cyclic (2-7)-disulfide, [R-(R*,R*)]-; L-cysteinamide, D-phenylalanyl-L-cysteinyl-L-phenylalanyl-D-tryptophyl-L-lysyl-L-threonyl-N-(2-hydroxy-1-(hydroxymethyl)propyl]-, cyclic (2-7)disulfide, (R-(R*,R*))- | Anticancer, hormonal |
| 142 | osteogenic growth peptide | | Glycine, L-alanyl-L-leucyl-L-lysyl-L-arginyl-L-glutaminylglycyl-L-arginyl-L-threonyl-L-leucyl-L-tyrosylglycyl-L-phenylalanylglycyl- | Osteoporosis treatment |
| 143 | P-113 | | Angiotensin II, 1-(N-methylglycine)-5-L-valine-8-L-alanine-[CAS]; (Sar(1),Ala(8))ANGII; (Sar1,Val5,Ala8)Angiotensin II; 1 Sar 8 Ala Angiotensin II; 1 Sarcosine 8 Alanine Angiotensin II; 1-Sar-8-Ala Angiotensin II; 1-Sar-8-Ala-angiotensin II; 1-Sarcosine-8-Alanine Angiotensin II; Acetate, Hydrated Saralasin; Angiotensin II, 1-Sar-8-Ala; Angiotensin II, 1-Sarcosine-8-Alanine; Anhydrous Saralasin Acetate; Hydrated Saralasin Acetate; P-113; P-113 Acetate; Sar Arg Val Tyr Val His Pro Ala; Ser-Arg-Val-Tyr-Val-His-Pro-Ala; Saralasin Acetate; Saralasin Acetate, Anhydrous; Saralasin Acetate, Hydrated; angiotensin II, Sar(1)-Ala(8)-; angiotensin II, sarcosyl(1)-alanine(8)- | Stomatological Antibacterial, other Antifungal |
| 361 | PACAP 27 | | Pituitary adenylate cyclase-activating peptide-27 | Antiviral, anti-HIV |
| 362 | PAPP | | N-(dibenyloxyphosphophionyl)-L-alanyl-L-prolyl-L-proline | Anti-hypersensitive, other |
| 363 | PD-83176 | | CBZ-his-tyr(OBn)-ser(OBn)-trp-D-ala-NH$_2$ | Anticancer, other |
| 364 | PD-122264 | | N-[(1,1-dimethylethoxy)carbonyl]-alpha-methyltryptophyl-L-phenylalaninamide | Anorectic/Antiobesity Analgesic, other |
| 365 | PD-132002 | | DL-Serinamide, N-(4-morpholinylsulfonyl)-L-phenylalanyl-N-[1-(cyclohexylmethyl)-2,3-dihydro-5-methylhexyl]-O-methyl-3-oxo-, [1S-(1R*,2S*,3R*)]- | Antihypertensive, renin system |
| 144 | Penetratin | | U.S. Pat. Nos. 5,888,762 and 6,080,762; PCT Pub. Nos. WO/2000/29427 and WO/2000/01417; NH2-Arg Lys Arg Gly Arg Gln Thr Tyr Thr Arg Tyr Gln Thr Leu Glu Leu Glu Lys Glu Phe His Phe Asn Arg Tyr Leu Thr Arg Arg Arg Arg Ile Glu Ile Ala His Ala Leu Cys Leu Thr Glu Arg Gln Ile Lus Ile Trp Phe Gln Asn Arg Arg Met Lys Trp Lys Lys Glu Asn-COOH. | Formulation technology |
| 366 | PL-030 | | Glycinamide, L-tyrosyl-L-prolyl-N-methyl-L-phenylalanyl-D-prolyl- | Analgesic, other |
| 367 | POL-443 | | Z-prolyl-leucyl-tryptophan | Antihypertensive, renin system |
| 368 | POL-509 | | L-Tryptophan, N-[N-(5-oxo-L-prolyl)-L-leucyl]-, methyl ester- | Immunostimulant, other |
| 369 | PPA | | D-phenylalanine-L-proline-L-arginylchloromethane | Anticoagulant Diagnostic Antithrombotic |
| 145 | PR-39 | | L-Prolinamide, L-arginyl-L-arginyl-L-arginyl-L-prolyl-L-arginyl-L-prolyl-L-prolyl-L-tyrosyl-L-leucyl-L-prolyl-L-arginyl-L-prolyl-L-arginyl-L-prolyl-L-prolyl-L-prolyl-L-phenylalanyl-L-phenylalanyl-L-prolyl-L-prolyl-L-arginyl-L-leucyl-L-prolyl-L-prolyl-L-arginyl-L-isoleucyl-L-prolyl- | Antibacterial, other |

TABLE 1-continued

| SEQ ID NO: | Name | Family | Sequence and/or Identifying Information | Therapeutic Activity |
|---|---|---|---|---|
| | | | L-prolylglycyl-L-phenylalanyl-L-prolyl-L-prolyl-L-arginyl-L-phenylalanyl-L-prolyl-L-prolyl-L-arginyl-L-phenylalanyl- | |
| 146 | tigapotide triflutate | | L-Threonine, L-alpha-glutamyl-L-tryptophyl-L-glutaminyl-L-threonyl-L-alpha-aspartyl-L-asparaginyl-S-[(acetylamino)methyl]-L-cysteinyl-L-alpha-glutamyl-L-threonyl-S-[(acetylamino)methyl]-L-cysteinyl-L-threonyl-S-[(acetylamino)methyl]-L-cysteinyl-L-tyrosyl-L-alpha-glutamyl-, mono(trifluoroacetate) | Anticancer, other |
| 370 | PT-14 | | L-Lysinamide, N-acetyl-L-norleucyl-L-alpha-aspartyl-L-histidyl-D-phenylalanyl-L-arginyl-L-tryptophyl-, cyclic (2-7)-peptide | Male sexual dysfunction Female sexual dysfunction |
| 147 | PT-5 | somato-statin | gi\|21619156\|gb\|AAH32625.1\| Somatostatin [Homo sapiens] MLSCRLQCALAALSIVLALGCVTGAPSDPRLRQFLQKSLAAAAGKQELAK YFLAELLSEPNQTENDALEPEDLSQAAEQDEMRLELQRSANSNPAMAPRE RKAGCKNFFWKTFTSC | Anticancer, other |
| 148 | sempara-tide | PTHrP | gi\|131542\|sp\|P12272.1\|PTHR_HUMAN Parathyroid hormone-related protein precursor (PTH-rP) (PTHrP) [Contains: PTHrP[1-36]; PTHrP[38-94]; Osteostatin (PTHrP[107-139])] MQRRLVQQWSVAVFLLSYAVPSCGRSVEGLSRRLKRAVSEHQLLHDKGKS IQDLRRRFFLHHLIAEIHTAEIRATSEVSPNSKPSPNTKNHPVFGSDDEG RYLTQETNKVETYKEQPLKTPGKKKKGKPGKRKEQEKKKRRTRSAWLDSG VTGSGLEGDHLSDTSTTSLELDSRRH | Hormone Osteoporosis treatment |
| 149 | parathyroid hormone fragments | PTH | SVSEIQLMHNLGKHLNSMERVEWLRKKLQDVHNF | Osteoporosis treatment |
| 150 | enfuvitide | | L-Phenylalaninamide, N-acetyl-L-tyrosyl-L-threonyl-L-seryl-L-leucyl-L-isoleucyl-L-histidyl-L-seryl-L-leucyl-L-isoleucyl-L-alpha-glutamyl-L-alpha-glutamyl-L-seryl-L-glutaminyl-L-asparaginyl-L-glutaminyl-L-glutaminyl-L-alpha-glutamyl-L-lysyl-L-asparaginyl-L-alpha-glutamyl-L-glutaminyl-L-alpha-glutamyl-L-leucyl-L-leucyl-L-alpha-glutamyl-L-leuvyl-L-alpha-aspartyl-L-lysyl-L-tryptophyl-L-alanyl-L-seryl-L-leucyl-L-tryptophyl-L-asparaginyl-L-tryptophyl- | Antiviral, anti-HIV |
| 151 | pentapeptide 6A | | Ala-Arg-Pro-Ala-Lys | Vasodilator, coronary |
| 371 | pentigetide | | L-Arginine, N2-[1-[N-(N-L-alpha-aspartyl-L-seryl)-L-alpha-aspartyl]-L-prolyl]- | Antiallergic, non-asthma Ophthalmological Antiasthma |
| 372 | peptide analogues | | N1,N3-bis(2,3-dihydroxypropyl)-2,4,6-triiodo-5-(2-methoxyacetamido)-N1-methylisophthalamide | Ophthalmological Antiarthritic, other Antiulcer Antihypertensive, other Multiple sclerosis treatment COPD treatment |
| 373 | peptide G | | [Arg(6),D-Trp(7,9),MePhe(8)]substance P | Anticancer, other |
| 374 | peptide T analogue | | D-Ala1-peptide T | Antiviral, anti-HIV |
| 375 | peptide T | | L-Threonine, N-[N-[N2-[N-[N-(N-L-alanyl-L-seryl)-L-threonyl]-L-threonyl]-L-threonyl]-L-asparginyl]-L-tyrosyl]- | Analgesic, other Antiviral, other |

TABLE 1-continued

| SEQ ID NO: | Name | Family | Sequence and/or Identifying Information | Therapeutic Activity |
|---|---|---|---|---|
| | | | | Antiarthritic, other GI inflammatory/ bowel disorders Anti-inflammatory |
| 152 | pramlinitide | | 1,2-Dithia-5,8,11,14,17-pentaazacycloeicosane, cyclic peptide derivative U.S. Pat. No. 5,998,367 gi\|10066209\|gb\|AAE39671.1\| Sequence 1 from patent U.S. 5998367 KCNTATCATQRLANFLVHSSNNFGAILSSTNVGSNTY; | Antidiabetic Anorectic/ Antiobesity |
| 376 | pranlukast | | Benzamide, N-[4-oxo-2-(1H-tetrazol-5-yl)-4H-1-benzopyran-8-yl]-4-(4-phenylbutoxy)-; 8-(4 (4-phenylbutoxy)benzoyl)amino-2-(tetrazol-5'-yl)-4-oxo-4H-1-benzopyran | Antiasthma Antiallergic, non-asthma |
| 3 | proinsulin | proinsulin | gi\|59036749\|gb\|AAW83741.1\| proinsulin [Homo sapiens] MALWMRLLPLLALLALWGPDPAAAFVNQHLCGSHLVEALYLVCGERGFFY TPKTRREAEDLQVGQVELGGGPGAGSLQPLALEGSLQKRGIVEQCCTSIC SLYQLENCYN | Antidiabetic |
| 377 | protirelin | TRH | L-Prolinamide, 5-oxo-L-prolyl-L-histidyl-; 2-Nle-3-Prot-protirelin; TRH, Nle(2)-Prot(3)-; pyroglutamyl-norleucyl-proline thioamide | Releasing hormone Diagnostic |
| 378 | protirelin | TRH | prolinamide, 5-oxo-L-prolyl-L-histidyl- | Releasing hormone Cognition enhancer |
| 153 | Ro-25-1553 | | L-Threoninammide, N-acetyl-L-histidyl-L-seryl-L-alpha-aspartyl-L-alanyl-L-valyl-L-phenylalanyl-L-threonyl-L-alpha-glutamyl-L-asparaginyl-L-tyrosyl-L-threonyl-L-lysyl-L-leucyl-L-arginyl-L-lysyl-L-glutaminyl-L-norleucyl-L-alanyl-L-alanyl-L-lysyl-L-lysyl-L-tyrosyl-L-leucyl-L-asparaginyl-L-alpha-aspartyl-L-leucyl-L-lysyl-L-lysylglycylglycyl-, (25-21)-lactam | Antiasthma Anti-inflammatory |
| 379 | RWJ-51438 | | N-methylphenylalanyl-N-(4-((aminoiminomethyl)amino)-1-((6-carboxy-2-benzothiazolyl)carbonyl)butyl)prolinamide | Antithrombotic |
| 380 | TRH | TRH | L-Prolinamide, 5-oxo-L-prolyl-L-histidyl-3,3-dimethyl-; pyroGlu-His-Pro-NH$_2$ (or 5-oxo-L-prolyl-L-histidyl-L-prolinamide) | Diagnostic Thyroid hormone Releasing hormone |
| 154 | renin inhibitors | | Boc-Leu-Lys-Arg-Met-Pro-OMe | Antihypertensive, |
| 381 | romurtide | | L-Lysine, N2-[N2-[N-(N-acetylmuramoyl)-L-alanyl]-D-alpha-glutaminyl]-N6-(1-oxooctadecyl)-; L-lysine, N2-(N2-(N-(N-acetylnuramoyl)-L-alanyl)-D-alpha-glutaminyl)-N6-(1-oxooctadecyl)- | Radio/ chemoprotective Immunostimulant, other |
| 382 | S-17162 | | L-Tryptophan, N-[(2,3-dihydroxypropoxy)hydroxyphosphinyl]-L-leucyl, disodium salt | Urological |
| 383 | S-2441 | | L-Argininamide, D-prolyl-L-phenylalanyl-N-heptyl- | Antimigraine Antigout Septic shock treatment |
| 384 | SDZ-CO-611 | somato-statin | L-Cysteinamide, N-(1-deoxy-4-O-.alpha.-D-glucopyranosyl-D-fructopyranos-1-yl)-D-phenylalanyl-L-cysteinyl-L-phenylalanyl-D-tryptophyl-L-lysyl-L-threonyl-N-[2-hydroxy-1- | Somatostatin |

TABLE 1-continued

| SEQ ID NO: | Name | Family | Sequence and/or Identifying Information | Therapeutic Activity |
|---|---|---|---|---|
| | | | (hydroxymethyl)propyl]-, cyclic (2.fwdarw.7)-disulfide, [R-(R*,R*)]- | |
| 385 | SK&F-101926 | | L-Argininamide, O-ethyl-N-[(1-mercaptocyclohexyl)acetyl]-D-tyrosyl-L-phenylalanyl-L-valyl-L-asparaginyl-L-cysteinyl-L-prolyl-, cyclic (1-5)-disulfide | Antihypertensive, diuretic |
| 386 | SK&F-110679 | | His-D-Trp-Ala-Trp-D-Phe-LysNH$_2$ | Releasing hormone Vulnerary |
| 387 | edotreotide | | [N-[2-[4,7-Bis[(carboxy-kappaO)methyl]-10-(carboxymethyl)-1,4,7,10-tetraazacyclododec-1-yl-kappaN1,kappaN4,kappaN10]acetyl]-D-phenylalanyl-L-cysteinyl-L-tyrosyl-D-tryptophyl-L-lysyl-L-threonyl-L-cysteinyl-L-threoninol cyclic (2-7)-disulfidato(3-)]yttrium | Anticancer, hormonal |
| 155 | SP-1 | | pGlu-Glu-Asp-Cys-Lys | Anticancer, other |
| 156 | SPAAT | | L-Lysine, L-methionyl-L-phenylalanyl-L-leucyl-L-alpha-glutamyl-L-alanyl-L-isoleucyl-L-prolyl-L-methionyl-L-seryl-L-isoleucyl-L-prolyl-L-prolyl-L-alpha-glutamyl-L-valyl-L-lysyl-L-phenylalanyl-L-asparaginyl-L-lysyl-L-prolyl-L-phenylalanyl-L-valyl-L-phenylalanyl-L-leucyl-L-methionyl-L-isoleucyl-L-alpha-glutamyl-L-glutaminyl-L-asparaginyl-L-threonyl-L-lysyl-L-seryl-L-prolyl-L-leucyl-L-phenylalanyl-L-methionylglycyl-L-lysyl-L-valyl-L-valyl-L-asparaginyl-L-prolyl-L-threonyl-L-glutamminyl- | COPD treatment |
| 388 | SR-41476 | | Z-Tyr-Val-Sta-Ala-Sta-OMe | Antiviral, anti-HIV |
| 389 | SR-42128 | | 1-[N-(3-methyl-1-oxobutyl)-L-phenylalanine]-2-L-norleucine- | Antihypertensive, renin system |
| 157 | SR-42654 | | isoval-phe-norleu-sta-ala-sta-lys | Antihypertensive, renin system |
| 147 | SRIF-A | somato-statin | gi|21619156|gb|AAH32625.1| Somatostatin [Homo sapiens] MLSCRLQCALAALSIVLALGCVTGAPSDPRLRQFLQKSLAAAAGKQELAK YFLAELLSEPNQTENDALEPEDLSQAAEQDEMRLELQRSANSNPAMAPRE RKAGCKNFFWKTFTSC 8-D-tryptophan-14-D-cysteinesomatostatin (sheep) | Somatostatin Haemostatic Alimentary/ Metabolic, other |
| 158 | calcitonin | calcitonin | CSNLSTCVLGKLSQELHKLQTYPRTNTGSGTP | Osteoporosis treatment |
| 390 | salmon calcitonin | calcitonin | 11,18-Arg-14-Lys-salmon calcitonin; 11,18-arginyl-14-lysine-salmon calcitonin; Arg-Lys-Arg-CT; calcitonin, salmon, arginyl(11,18)-lysine(14)- | Osteoporosis treatment |
| 159 | sermorelin | | Tyr-Ala-Asp-Ala-Ile-Phe-Thr-Asn-Ser-Tyr-Arg-Lys-Val-Leu-Gly-Gln-Leu-Ser-Ala-Arg-Lys-Leu-Leu-Gln-Asp-Ile-Met-Ser-Arg-NH$_2$ | Idiopathic growth hormone deficiency Imaging agent |
| 391 | saralasin acetate | | 1-Sar-8-Ala-angiotensin; Angiotensin II, 1-(N-methylglycine)-5-L-valine-8-L-alanine- | Antihypertensive, renin system |
| 160 | secretin | | His-Ser-Asp-Gly-Thr-Phe-OMe; histidyl-seryl-aspartyl-glycyl-threonyl-phenylalanine-O-methyl- | Haemostatic; pancreatic dysfunction (diagnostic), asthma, COPD, others |
| 159 | sermorelin acetate | | Tyr-Ala-Asp-Ala-Ile-Phe-Thr-Asn-Ser-Tyr-Arg-Lys-Val-Leu-Gly-Gln-Leu-Ser-Ala-Arg-Lys-Leu-Leu-Gln-Asp-Ile-Met-Ser-Arg-NH$_2$ | Releasing hormone Diagnostic |

TABLE 1-continued

| SEQ ID NO: | Name | Family | Sequence and/or Identifying Information | Therapeutic Activity |
|---|---|---|---|---|
| 159 | sermorelin | | Tyr-Ala-Asp-Ala-Ile-Phe-Thr-Asn-Ser-Tyr-Arg-Lys-Val-Leu-Gly-Gln-Leu-Ser-Ala-Arg-Lys-Leu-Leu-Gln-Asp-Ile-Met-Ser-Arg-NH₂ | |
| 161 | sinapultide | | L-Lysine, L-lysyl-L-leucyl-L-leucyl-L-leucyl-L-leucyl-L-lysyl-L-leucyl-L-leucyl-L-leucyl-L-leucyl-L-lysyl-L-leucyl-L-leucyl-L-leucyl-L-leucyl-L-lysyl-L-leucyl-L-leucyl-L-leucyl-L-leucyl- | Lung Surfactant |
| 162 | sleep inducing peptide | | Trp-Ala-Gly-Asp-Ala-Ser-Gly-Glu | Hypnotic/ Sedative Dependence treatment |
| 163 | somato-liberin | | gi|11034841|ref|NP_066567.1| growth hormone releasing hormone preproprotein [Homo sapiens] MPLWVFFFVILTLSNSSHCSPPPPLTLRMRRYADAIFTNSYRKVLGQLSARKLLQDIMSRQQGESNQERGARARLGRQVDSMWAEQKQMELESILVALLQKHSRNSQG | Growth hormone Releasing hormone |
| 164 | PTR-3173 | somato-statin | Cyclic[(R)-βMeNphe-Phe-DTrp-Lys-Thr-Phe], MPLWVFFFVILTLSNSSHCSPPPPLTLRMRRYADAIFTNSYRKVLGQLSARKLLQDIMSRQQGESNQERG | Acoegaly Symptomatic antidiabetic Ophthalmological Urological Anticancer, hormonal |
| 165 | somato-statin analogue | somato-statin | des-(Ala1,Gly2)-(D-Trp8,D-Asu(3,14))-somatostatin, ARARLGRQVDSMWAEQKQMELESILVALLQKHSRNSQG | Acromegaly Antidiabetic Diagnostic |
| 392 | somato-statin analogues | somato-statin | cyclo-(N-Me-Ala-Tyr-D-Trp-Lys-Val-Phe)- somatostatin | Acromegaly Antidiabetic |
| 393 | somato-statin | somato-statin | 3,14-Dicarbasomatostatin, 1-de-L-alanine-2-deglycine-3-butanoic acid-11-L-tyrosine- | Acromegaly |
| 394 | somato-statin | somato-statin | 3,14-Dicarbasomatostatin, 1-de-L-alanine-2-deglycine-3-butanoic acid-11-L-tyrosine- | Acromegaly |
| 395 | syndy-phalin | | Glycinamide, L-tyrosyl-4-(methylsulfinyl)-D-2-aminobutanoyl-N-methyl-N-(2-phenylethyl)- | Analgesic, other |
| 166 | synthetic peptide BPC | | gi|109948285|ref|NP_001035971.1| poly(A) binding protein, cytoplasmic 1-like 2B [Homo sapiens] MASLYVGDLHPEVTEAMLYEKFSPAGPILSIRICRDKITRRSLGYAYVNYQQPVDAKRALETLNFDVIKGRPVRIMWSQRDPSLRKSGVGNVFIKNLGKTIDNKALYNIFSAFGNILSCKVACDEKGPKGYGFVHFQKQESAERAIDVMNGMFLNYRKIFVGRFKSHKEREAERGAWARQSTSADVKDFEEDTDEEATLR | Antiulcer Hepatoprotective Vulnerary Anti-inflammatory Antiparkinsonian Musculoskeletal |
| 167 | T22 | | L-Argininamide, L-arginyl-L-arginyl-L-tryptophyl-L-cysteinyl-L-tyrosyl-L-arginyl-L-lysyl-L-cysteinyl-L-tyrosyl-L-lysylglycyl-L-tyrosyl-L-cysteinyl-L-tyrosyl-L-arginyl-L-lysyl-L-cysteinyl-, cyclic (4-17),(8-13)-bis(disulfide) | Antiviral, anti-HIV |
| 396 | Tc-99m depreotide | | Technetium-99Tc, (cyclo(L-homocysteinyl-N-methyl-L-phenylalanyl-L-tyrosyl-D-tryptophyl-L-lysyl-L-valyl) (1-1')-thioether with 3-((mercaptoacetyl)amino)-L-alanyl-L-lysyl-L-cysteinyl-L-lysinamidato(3-))oxo-, (SP-5-24)- | Imaging agent |
| 397 | Tc-99m-P280 | | 13, 13'-[Oxybis[methylene(2,5-dioxo-1,3-pyrrolidinediyl)]]bis[N-(mercaptoacetyl)-D-tyrosyl-S-(3-aminopropyl)-L-cysteinylglycyl-L-alpha-aspartyl-L-cysteinylglycyl-S-[(acetylamino)mehtyl]-L-cysteinylglycyl-S-[(acetylamino)methyl-L-cysteinylglycylglycyl-L-cysteinamide], cyclic (1 --> 5), (1' --> 5'), -bis(sulfide) | Imaging agent Antithrombotic |

TABLE 1-continued

| SEQ ID NO: | Name | Family | Sequence and/or Identifying Information | Therapeutic Activity |
|---|---|---|---|---|
| 398 | TEI-1345 | | (7E)-8-(2-naphthyl)-5,6-trans-5,6-methano-7-octenyl 3-(3,4-dimethoxyphenyl)-2-propenoate | Anti-inflammatory |
| 168 | THF | | Leu-Glu-Asp-Gly-Pro-Lys-Phe-Leu; leucyl-glutamyl-aspartyl-glycyl-prolyl-lysyl-phenylalanyl-leucine | Immunomodulator, anti-infective, Immunostimulant, anti-AIDS |
| 169 | Theradigm-HBV | | Dipalmitoyl-Lys-Ser-Ser-Gln-Tyr-Ile-Lys-Ala-Asn-Ser-Lys-Phe-Ile-Gly-Ile-Thr-Glu-Ala-Ala-Ala-Phe-Leu-Pro-Ser-Asp-Phe-Phe-Pro-Ser-Val-OH | Immunomodulator, anti-infective Immunostimulant |
| 80 | tesamorelin acetate | GHRF | gi\|337133\|gb\|AAA52609.1\| growth hormone releasing factor MPLWVFFFVILTLSNSSHCSPPPPLTLRMRRYADAIFTNSYRKVLGQLSA RKLLQDIMSRQQGESNQERGARARLGRQVDSMWAEQKQMELESILVALLQ KHRNSQG (3E)-Hex-3-enoylsomatoliberin (human) acetate (salt) | Musculoskeletal, COPD, Hypnotic/Sedative, Immunostimulant, Antidiabetic, Anabolic, Symptomatic antidiabetic, Vulnerary |
| 170 | TP-9201 | | L-Cysteinamide, N-acetyl-L-cysteinyl-L-asparaginyl-L-prolyl-L-arginylglycyl-L-alpha-aspartyl-O-methyl-L-tyrosyl-L-arginyl-, cyclic (1-9)-disulfide | Neuroprotective, Antithrombotic, Antianginal, Cardiovascular |
| 399 | TRH analogues | TRH | pyroGlu-His-Pro-NH$_2$ (or 5-oxo-L-prolyl-L-histidyl-L-prolinamide) | Cognition enhancer |
| 400 | TT-235 | | [β,β-(3-Thiapentamethylene)-β-sulfanylpropionic acid, D-Trp2,Pen6,Arg8]-oxytocin acetate | Labour inhibitor |
| 401 | tabilautide | | L-Lysinamide, 6-carboxy-N6-[N-[N-(1-oxododecyl)-L-alanyl]-D-gamma-glutamyl]-, (S)- | Immunomodulator, anti-infective Radio/chemoprotective Immunostimulant, other |
| 171 and 172 | terlipressin | | N-[N-(N-glycylglycyl)glycyl]-8-L-lysine; Gly-Gly-Gly-8-Lys-vasopressin; N-(alpha)-glycyl-glycyl-glycyl-8-lysinevasopressin; Gly-Gly-Gly-c[Cys-Tyr-Phe-Gln-Asn-Cys]-Pro-Lys-Gly-NH$_2$; N-(N-(N-glycylglycyl)glycyl)-8-L-lysinevasopressin | Haemostatic; GI bleeding |
| 171 and 172 | terlipressin | | N-[N-(N-glycylglycyl)glycyl]-8-L-lysine-; Gly-Gly-Gly-8-Lys-vasopressin; N-(alpha)-glycyl-glycyl-glycyl-8-lysine vasopressin; Gly-Gly-Gly-c[Cys-Tyr-Phe-Gln-Asn-Cys]-Pro-Lys-Gly-NH$_2$ | Haemostatic; GI bleeding |
| 402 | teverelix | | D-Alaninamide, N-acetyl-3-(2-naphthalenyl)-D-alanyl-4-chloro-D-phenylalanyl-3-(3-pyridinyl)-D-alanyl-L-seryl-L-tyrosyl-N6-(aminocarbonyl)-D-lysyl-L-leucyl-N6-(1-methylethyl)-L-lysyl-L-prolyl- | Anticancer, hormonal Prostate disorders Menstruation disorders Fertility enhancer Male contraceptive |
| 403 | thymopentin | | L-Tyrosine, N-[N-[N-(N2-L-arginyl-L-lysyl)-L-alpha-aspartyl]-L-valyl]-; L-Tyrosine, N-(N-(N-(N2-L-arginyl-L-lysyl)-L-alpha-aspartyl)-L-valyl)- | Immunostimulant, other Immunomodulator, anti-infective |
| 404 | triletide | | L-Histidine, N-[N-(N-acetyl-L-phenylalanyl)-L-phenylalanyl]-, methylester | Antiulcer |
| 405 | tuftsin | | L-Arginine, N2-[1-(N2-L-threonyl-L-lysyl)-L-prolyl]- | Anticancer, immunological Immunostimulant, other |

TABLE 1-continued

| SEQ ID NO: | Name | Family | Sequence and/or Identifying Information | Therapeutic Activity |
|---|---|---|---|---|
| 173 | Uro-guanylin | | Guanylin (rat reduced), 1-L-glutamine-2-L-glutamic acid-3-L-aspartic acid-6-L-leucine-8-L-isoleucine-9-L-asparagine-10-L-valine- | Alimentary/Metabolic, other Antidiarrhoeal Diagnostic |
| 174 | VIC | | gi\|6681267\|ref\|NP_031929.1\| endothelial 3 [Mus musculus]<br>MEPGLWLLLGLTVTSAAGLVPCPQSGDSGRASVSQGPPEAGSERGCEETV<br>AGPGERIVSPTVALPAQPESAGQERAPGRSGKQEDKGLPAHHRPRRCTCF<br>TYKDKECVYYCHLDIIWINTPEQTVPYGLSNYRESLRGKRSLGPVPESSQ<br>PSPWTRLRCTCMGADDKACAHFCARTRDVTSTSGRAERPAAEEMRETGGP<br>RQRLMSRTDKAHRP | Gastroprokinetic |
| 175 | VIP derivative | | gi\|5803023\|ref\|NP_006807.1\| lectin, mannose-binding 2 [Homo sapiens]<br>MAAEGWIWRWGWGRRCLGRPGLLGPGPGPTTPLFLLLLLGSVTADITDGN<br>SEHLKREHSLIKPYQGVGSSSMPLWDFQGSTMLTSQYVRLTPDERSKEGS<br>IWNHQPCFLKDWEMHVHFKVHGTGKKNLHGDGIALWYTRDRLVPGPVFGS<br>KDNFHGLAIFLDTYPNDETTERVFPYISVMVNNGSLSYDHSKDGRWTELA<br>GCTADFRNRDHDTFLAVRYSRGRLTVMTDLEDKNEWKNCIDITGVRLPTG<br>YYFGASAGTGDLSDNHDIISMKLFQLMVEHTPDEESIDWTKIEPSVNFLK<br>SPKDNVDDPTGNFRSGPLTGWRVFLLLLCALLGIVVCAVVGAVVFQKRQE<br>RNKRFY | Antiasthma Vasodilator, preipheral |
| 147 | vapreotide, immediate-release | somato-statin | gi\|21619156\|gb\|AAH32625.1\| Somatostatin [Homo sapiens]<br>MLSCRLQCALAALSIVLALGCVTGAPSDPRLRQFLQKSLAAAAGKQELAK<br>YFLAELLSEPNQTENDALEPEDLSQAAEDQEMRLELQRSANSNPAMAPRE<br>RKAGCKNFFWKTFTSC<br>L-Tryptophanamide, D-phenylalanyl-L-cysteinyl-L-tyrosyl-D-tryptophyl-L-lysyl-L-valyl-L-cysteinyl-, cyclic (2-7)-disulfide- | Formulation, modified-release, immediate Somatostatin Haemostatic Anticancer, hormonal Antidiarrhoeal GI inflammatory/bowel disorders |
| 406 | Pharma-projects No. 1269 | | L-Proline, 1-[N-[N-[1-[4-(4-hydroxyphenyl)-1-oxobutyl]-L-prolyl]-.alpha.-methyl-DL-phenylalanyl]glycyl]- | Vasodilator, renal |
| 407 | Pharma-projects No. 1583 | | N($\alpha$)-((3S)-1-oxo-1,2,3,4-tetrahydroisoquinoline-3-carbonyl)-L-histidyl-L-prol inamide | Neuroleptic Antiparkinsonian |
| 408 | Pharma-projects No. 1626 | | D-2-phenylglycyl-D-2-phenylglycine | Anticancer, immunological Immunostimulant, other |
| 409 | Pharma-projects No. 1779 | | N-acyl-D-glutamyl-1-meso-diaminopimelyl-1-lysine tripeptide derivatives | Immunomodulator, anti-infective Immunostimulant, other |
| 176 | Pharma-projects No. 1876 | | Thr-Asp-Ser-Phe-Val-Gly-Leu-Methionylamide | Antihypertensive, other |
| 410 | Pharma-projects No. 1913 | | L-leucyl-D-methionyl-glucyl-N-(2-adamantyl)-L-phenylalanylamide | Antihypertensive, renin system |
| 177 | Pharma-projects No. 1939 | | Lys-Pro-Gly-Glu-Pro-Gly-Pro-Lys | Anticoagulant |
| 178-182, 178, 183-185 and 178 | Pharma-projects No. 2063 | | U.S. Pat. No. 4,461,724 and European Patent No. EP0078228: GSHK; ASHK; A$_D$SHK; LSHK; TSHK; YSHK; GSHKCH$_3$COOH•H$_2$O; SAR-SHK; PSHK; (PYR)ESHK; ESHK; GSHK•2TosOH | Antiulcer Antithrombotic |

TABLE 1-continued

| SEQ ID NO: | Name | Family | Sequence and/or Identifying Information | Therapeutic Activity |
|---|---|---|---|---|
| 411 | Pharma-projects No. 2363 | | N-methyl-D-Phe-Pro-Arg-H | Antithrombotic |
| 186 | Pharma-projects No. 2388 | | N-3-(4-hydroxyphenyl)propionyl-Pro-Hyp-Gly-Ala-Gly | Antiarrhythmic |
| 412 | Pharma-projects No. 2425 | | Glp-lys-NH$_2$-L-mandelate | Anticancer, immunological Immunostimulant, other |
| 413 | Pharma-projects No. 3341 | | D-1-Tiq-Pro-Arg-H-sulfate | Antithrombotic |
| 414 | Pharma-projects No. 3415 | | (2R,4S,5S,1'S)-5-(t-butoxycarbonyl)amino-4-hydroxy-N-[1'-isopropyl-1'-(4-isopropylcarbonylimidazol-2-yl]methyl-6-phenyl-2-phenylmethyl-hexanamide | Antiviral, anti-HIV |
| 415 | Pharma-projects No. 4004 | | Piv-1-Ser-Leu-GABA, and Piv-Ser-Leu-GABA | Neurological |
| 416 | Pharma-projects No. 4323 | | (1R,4aR,8aR)-1,2,3,4,5,6,7,8-perhydroisoquinolin-1-carbonyl-(L)-prolinyl-(L)-arinine aldehyde | Antithrombotic Anticoagulant |
| 187, and 417 | Pharma-projects No. 491 | | H-Trp-Ala-Ser-Gly-L-Asn-OH & H-Trp-D-Ala-Ser-Gly-Asp(OH)$_2$ | Hypnotic/Sedative Antidepressant Neuroprotective |
| 188 | Pharma-projects No. 4975 | | H$_2$N-Asp-Ala-Asp-Pro-Arg-Gln-Tyr-Ala-COOH | Anti-inflammatory |
| 418 | Pharma-projects No. 5200 | | 2-Amino-N-{1-(R)-benzyloxymethyl-2-[4-(morpholine-4-carbonyl)-4-phenyl-piperidine-1-yl]-2-oxo-ethyl}-isobutyramide | Osteoporosis treatment |
| 419 | Pharma-projects No. 5336 | | 4-chloro-phenylcarbamoyl-thienylalanyl-leucyl-phenylalanine | Anti-inflammatory Anti-infective, other |
| 420 | DMP-444 | | synthetic cyclic pentapeptide (cyclo(D-Val-NMeArg-Gly-Asp-Mamb)) with a tethered hydrazinonicotinyl (HYNIC) chelator for radiolabelling with 99mTc | Imaging agent |
| 189 | RIP-3 | | MSCVKLWPSGAPAPLVSIEELENQELVGKGGFGTVFRAQHRKWGYDVAVK IVNSKAISREVKAMASLDNEFVLRLEGVIEKVNWDQDPKPALVTKFMENG SLSGLLQSQCPRPWPLLCRLLKEVVLGMFYLHDQNPVLLHRDLKPSNVLL DPELHVKLADFGLSTFQGGSQSGTGSGEPGGTLGYLAPELFVNVNRKAST ASDVYSFGILMWAVLAGREVELPTEPSLVYEAVCNRQNRPSLAELPQAGP ETPGLEGLKELMQLCWSSEPKDRPSFQECLPKTDEVFQMVENNMNAAVST VKDFLSQLRSSNRRFSIPESGQGGTEMDGFRRTIENQHSRNDVMVSEWLN KLNLEEPPSSVPKKCPSLTKRSRAQEEQVPQAWTAGTSSDSMAQPPQTPE TSTFRNQMPSPTSTGTPSPGPRGNQGAERQGMNWSCRTPEPNPVTGRPLV NIYNCSGVQVGDNNYLTMQQTTALPTWGLAPSGKGRGLQHPPPVGSQEGP KDPEAWSRPQGWYNHSGK | Anticancer, other |
| 421 | Pharma-projects No. 955 | | N-(N-acetyl-1-isoleucyl-L-tyrosyl)-(-)-1-amino-2-(4-hydroxyphenyl)ethylphosphonic acid | Antihypertensive, other |
| 422 | leuprolide | | 6-D-leucine-9-(N-ethyl-L-prolinamide)-10-deglycinamide- | Formulation, modified-release, Anticancer |
| 190 | edratide | | L-glycyl-L-tyrosyl-L-tyrosyl-L-tryptophyl-L-seryl-L-tryptophyl-L-isoleucyl-L-arginyl-L-glutaminyl-Lprolyl-L-prolyl-L-glycyl-L-lysyl-L-glycyl-L- | Immunosuppresant |

TABLE 1-continued

| SEQ ID NO: | Name | Family | Sequence and/or Identifying Information | Therapeutic Activity |
|---|---|---|---|---|
| | | | glutamyl-L-glutamyl-L-tryptophyl-L-isoleucyl-L-glycine | |
| 423 | Prosaptide TX14(A) | | H-Thr-D-Ala-Leu-Ile-Asp-Asn-Asn-Ala-Thr-Glu-Glu-Ile-Leu-Tyr-OH | Symptomatic antidiabetic Neurological Analgesic, other |
| 8 | GLP-1 | GLP-1 | HGEGTFTSDLSKQMEEEAVRLFIEWLKNGGPSSGAPPPS | Antidiabetic |
| 160 | secretin | | His-Ser-Asp-Gly-Thr-Phe-OMe; histidyl-seryl-aspartyl-glycyl-threonyl-phenylalanine-O-methyl- | Hormone, Diagnostic, GI inflammatory/bowel disorders, Neurological, Neuroleptic |
| 147 | BIM-23190 | somato-statin | gi\|21619156\|gb\|AAH32625.1\| Somatostatin [Homo sapiens] MLSCRLQCALAALSIVLALGCVTGAPSDPRLRQFLQKSLAAAAGKQELAK YFLAELLSEPNQTENDALEPEDLSQAAEQDEMRLELQRSANSNPAMAPRE RKAGCKNFFWKTFTSC L-Threoninamide, N-[[4-(2-hydroxyethyl)-1-piperazinyl]acetyl]-D-phenylalanyl-L-cysteinyl-L-tyrosyl-D-tryptophyl-L-lysyl-(2S)-2-aminobutanoyl-L-cysteinyl-, cyclic (2-7)-disulfide | Acromegaly Antidiabetic |
| 424 | leuprorelin | | 6-D-leucine-9-(N-ethyl-L-prolinamide)-10-deglycinamide | Formula, Anticancer |
| 191 | β-amyloid peptides | beta-amyloid peptide | gi\|8176533\|gb\|AAB26264.2\| beta-amyloid peptide precursor; beta AAP [Homo sapiens] GSGLTNIKTEEISEVKMDAEFRHDSGYEVHHQKLVFFAEDVGSNKGAIIG LMVGGVVIATVIIITLVMLKKQYTSNHHGVVE | Cognition enhancer |
| 425 | oglufanide disodium | | L-tryptophan, L-alpha-glutamyl-, disodium salt | Immunomodulator, anti-infective Anticancer, immunological |
| 192 | HAV peptide matrix | | leucyl-arginyl-alanyl-histidyl-alanyl-valyl-aspartly-valyl-asparaginyl-glycinamide | Neurological |
| 149 | PTH 1-34 leuprorelin | PTH | SVSEIQLMHNLGKHLNSMERVEWLRKKLQDVHNF 6-D-leucine-9-(N-ethyl-L-prolinamide)-10-deglycinamide- | Hormone Anticancer |
| 193 | TRP-2 | | H-Leu-Leu-Pro-Gly-Gly-Arg-Pro-Tyr-Arg-OH | Anticancer, immunological |
| 426 | golotimod | | (2R)-2-amino-5-[[(1S)-1-carboxy-2-(1H-indol-3-yl)ethyl]amino]-5- oxopentanoic acid | Immunostimulant, other Immunomodulator, anti-infective Anticancer, immunological Stomatological |
| 194 | angiotensin-II | Angio-tensin II | gi\|28710\|emb\|CAA77513.1\| angiotensin II [Homo sapiens] MILNSSTEDGIKRIQDDCPKAGRHNYIFVMIPTLYSIIFVVGIFGNSLVV IVIYFYMKLKTVASVFLLNLALADLCFLLTLPLWAVYTAMEYRWPFGNYL CKIASASVSFNLYASVFLLTCLSIDRYLAIVHPMKSRLRRTMLVAKVTCI IIWLLAGLASLPAIIHRNVFFIENTNITVCAFHYESQNSTLPIGLGLTKN ILGFLFPFLIILTSYTLIWKALKKAYEIQKNKPRNDDIFKIIMAIVLFFF FSWIPHQIFTFLDVLIQLGIIRDCRIADIVDTAMPITICIAYFNNCLNPL FYGFLGKKFKRYFLQLLKYIPPKAKSHSNLSTKMSTLSYRPSDNVSSSTK KPAPCFEVE | Vulnerary Symptomatic antidiabetic |
| 195 | omiganan | | L-lysinamide, L-isoleucyl-L-leucyl-L-arginyl-L-tryptophyl-L-prolyl-L-tryptophyl-L-tryptophyl-L-prolyl-L-tryptophyl-L-arginyl-L-arginyl-, | Formulation, dermal, topical |

TABLE 1-continued

| SEQ ID NO: | Name | Family | Sequence and/or Identifying Information | Therapeutic Activity |
|---|---|---|---|---|
| | | | pentahydrochloride | Peptide antibiotic Antiacne |
| 427 | leuprorelin | | 6-D-leucine-9-(N-ethyl-L-prolinamide)-10-deglycinamide- | Transmucosal, nasal, Menstruation disorders, Anticancer, hormonal, Fertility enhancer |
| 428 | delmitide acetate | | D-Tyrosinamide, D-arginyl-D-norleucyl-D-norleucyl-D-norleucyl-D-arginyl-D-norleucyl-D-norleucyl-D-norleucylglycyl-, monoacetate | GI inflammatory/bowel disorders, Radio/chemoprotective, Antipsoriasis, Antipruritic/inflamm, allergic, Multiple sclerosis treatment, Alimentary/Metabolic, other, Antiviral, anti-HIV, Antiasthma, COPD treatment, Respiratory Stomatological |
| 196 | cat PAD | | MRGALLVLALLVTQALGVKMAETCPIFYDVFFAVANGNELLLDLSLTKVN ATEPERTAMKKIQDCYVENGLISRVLDGLVMTTISSSKDCMGEAVQNTVE DLKLNTLGR | Antiasthma Antiallergic, non-asthma |
| 429 | NOV-002 | | bis-(gamma-L-glutamyl)-L-cysteinyl-bis-glycin disodium salt | Anticancer, immunological Radio/chemosensitizer Antidote |
| 430 | GPG-NH2 | | glycyl-prolyl-glycine amide | Antiviral, anti-HIV |
| 431 | ABT-510 | | NAc-Sar-Gly-ValDalloIleThrNValIle/ArgProNHE | Anticancer, other |
| 8 | CJC-1131 | GLP-1 | HGEGTFTSDLSKQMEEEAVRLFIEWLKNGGPSSGAPPPS | Antidiabetic |
| 432 | desmopressin | | Vasopressin, 1-(3-mercaptopropanoic acid)-8-D-arginine- | Formulation, oral, Hormone, Antidiabetic, Urological |
| 197 | metastin | | MNSLVSWQLLLFLCATHFGEPLEKVASVGNSRPTGQQLESLGLLAPGEQS LPCTERKPAATARLSRRGTSLSPPPESSGSPQQPGLSAPHSRQIPAPQGA VLVQREKDLPNYNWNSFGLRFGKREAAPGNHGRSAGRG | Anticancer, other |
| 433 | leuprorelin | | 5-Oxo-L-prolyl-L-histidyl-L-tryptophyl-L-seryl-L-tyrosyl-D-leucyl-L-leucyl-L-arginyl-N-ethyl-L-prolinamide acetate (salt) | Anticancer |
| 434 | SGS-111 | | N-phenylacetylprolylglycine ethyl ester | Cognition enhancer Neuroprotective |
| 435 | taltobulin | | (4S)-4-[[(2S)-3,3-dimethyl-2-[[(2S)-3-methyl-2-(methylamino)-3- | Anticancer, other |

TABLE 1-continued

| SEQ ID NO: | Name | Family | Sequence and/or Identifying Information | Therapeutic Activity |
|---|---|---|---|---|
| | | | phenylbutanoyl]amino]butanoyl]methylamino]-2,5-dimethylhex-2-enoic acid | |
| 436 | leuprolide | | 6-D-leucine-9-(N-ethyl-L-prolinamide)-10-deglycinamide- | inhalable, systemic, Anticancer, Menstruation disorders |
| 103 | XOMA-629 | | gi\|157276599\|ref\|NP_001716.2\| bactericidal/permeability-increasing protein precursor [Homo sapiens] MRENMARGPCNAPRWASLMVLVAIGTAVTAAVNPGVVVRISQKGLDYASQ QGTAALQKELKRIKIODYSDSFKIKHLGKGHYSFYSMDIREFQLPSSQIS MVPNVGLKFSISNANIKISGKWKAQKRFLKMSGNFDLSIEGMSISADLKL GSNPTSGKPTITCSSCSSHINSVHVHISKSKVGWLIQLFHKKIESALRNK MNSQVCEKVTNSVSSELQPYFQTLPVMTKIDSVAGINYGLVAPPATTAET LDVQMKGEFYSENHHNPPPFAPPVMEFPAAHDRMVYLGLSDYFFNTAGLV YQEAGVLKMTLRDDMIPKESKFRLTTKFFGTFLPEVAKKFPNMKIQIHVS ASTPPHLSVQPTGLTFYPAVDVQAFAVLPNSSLASLFLIGMHTTGSMEVS AESNRLVGELKLDRLLLELKHSNIGPFPVELLQDIMNYIVPILVLPRVNE KLQKGFPLPTPARVQLYNVVLQPHQNFLLFGADVVYK | Antiacne Anti-infective, other |
| 198 | synthetic eryhtro-poiesis pro | | gi\|8393713\|ref\|NP_058651.1\|Sep (O-phosphoserine) tRNA:Sec (selenocysteine) tRNA synthase isoform 1 [Homo sapiens] MSTSYGCFWRRFIHGIGRSGDISAVQPKAAGSSLLNKITNSLVLDIIKLA GVHTVANCFVVPMATGMSLTLCFLTLRHKRPKAKYIIWPRIDQKSCFKSM ITAGFEPVVIENVLEGDELRTDLKAVEAKVQELGPDCILCIHSTTSCFAP RVPDRLEELAVICANYDIPHIVNNAYGVQSSKCMHLIQQGARVGRIDAFV QSLDKNFMVPVGGAIIAGFNDSFIQEISKMYPGRASASPSLDVLITLLSL GSNGYKKLLKERKEMFSYLSNQIKKLSEAYNERLLHTPHNPISLAMTLKT LDEHRDKAVTQLGSMLFTKQVSGARVVPLGSMQTVSGYTFRGFMSHTNNY PCAYLNAASAIGMKMQDVDLFINRLDRCLKAVRKERSKESDDNYDKTEDV DIEEMALKLDNVLLDTYQDASS | Antiranaemic Radio/chemoprotective |
| 191 | β-amyloid vaccine | beta-amyloid peptide | gi\|8176533\|gb\|AAB26264.2\| beta-amyloid peptide precursor, beta APP [Homo sapiens] GSGLTNIKTEEISEVKMDAEFRHDSGYEVHHQKLVFFAEDVGSNKGAIIG LMVGGVVIATVIIITLVMLKKQYTSNHHGVVE | Cognition enhancer |
| 437 | sincalide | | 1-De-(5-oxo-L-proline)-2-de-L-glutamine-5-L-methioninecaerulein | Imaging agent Alimentary/Metabolic |
| 438 | albiglutide | | ([8-glycine]human glucagon-like peptide 1-(7-36)-peptidyl)([8-glycine]human glucagon-like peptide 1-(7-36)-peptidyl)(human serum albumin (585 residues)) | Antidiabetic Anorectic/Antiobesity |
| 199 | SB-144 | | gi\|13899257\|ref\|NP_113622.1\| transmembrane and ubiquitin-like domain containing 1 [Homo sapiens] MTLIEGVGDEVTVLFSVLACLLVLALAWVSTHTAEGGDPLPQPSGTPTPS QPSAAMAATDSMRGEAPGAETPSLRHRGQAAQPEPSTGFTATPPAPDSPQ EPLVLRLKFLNDSEQVARAWPHDTIGSLKRTQFPFREQQVRLIYQGQLLG DDTQTLGSLHLPPNCVLHCHVSTRVGPPNPPCPPGSEPGPSGLEIGSLLL PLLLLLLLLLWYCQIQYRPFFPLTATLGLAGFTLLLSLLAFAMYRP | Anticancer, other Radio/chemosensitizer |
| 200 | exenatide LAR | | L-histidylglycyl-L-glutamylglycyl-L-threonyl-L-phenylalanyl-L-threonyl-L-seryl-L-aspartyl-L-leucyl-L-seryl-L-lysyl-L-glutaminyl-L-methionyl-L-glutamyl-L-glutamyl-L-glutamyl-L-alanyl-L-valyl-L-arginyl-L-leucyl-L-phenylalanyl-L-isoleucyl-L-glutamyl-L-tryptophyl-L-leucyl-L-lysyl-L-asparaginylglycylglycyl-L-prolyl-L-seryl-L-serylglycyl-L-alanyl-L-prolyl-L-prolyl-L-prolyl-L-serinamide | Antidiabetic |
| 201 | BA-058 | PTHrP | gi\|131542\|sp\|P12272.1\|PTHR_HUMAN Parathyroid hormone-related protein precursor (PTH-rP) (PTHrP) [Contains: PTHrP[1-36]; PTHrP[38-94]; Osteostatin (PTHrP[1107-139])] MQRRLVQQWSVAVFLLSYAVPSCGRSVEGLSRRLKRAVSEHQLLHDKGKS IQDLRRRFFLHHLIAEIHTAEIRATSEVSPNSKPSPNTKNHPVRFGSDDE GRYLTQETNKVETYKEQPLKTPGKKKKGKPGKRKEQEKKKRRTRSAWLDS SGVTGSGLEGDHLSDTSTTSLELDSRRH | Osteoporosis treatment |

TABLE 1-continued

| SEQ ID NO: | Name | Family | Sequence and/or Identifying Information | Therapeutic Activity |
|---|---|---|---|---|
| 8 | BIM-51077 | GLP-1 | HGEGTFTSDLSKQMEEEAVRLFIEWLKNGGPSSGAPPPS [(aminoisobutyric acid) 8,35]hGLP- 1(1-36)NH 2, has the same amino acid sequence as human GLP-1(7-36 amide) except for the replacement of amino acids 8 and 35 with α-aminoisobutyric acid (Aib) to reduce protease susceptibility. | Antidiabetic |
| 202 | TM-701 | | H-Met-Cys-Met-Pro-Cys-Phe-Thr-Thr-Asp-His-Gln-Met-Ala-Arg-Lys-Cys-Asp-Asp-Cys-Cys-Gly-Gly-Lys-Gly-Arg-Gly-Lys-Cys-Tyr-Gly-Pro-Gln-Cys-Leu-Cys-Arg-NH$_2$ (Disulfide bridge: 2-19, 5-28, 16-33, 20-35) | Anticancer, other Radio/chemosensitizer |
| 439 | CZEN-002 | | [dNal(2')-7, Phe-12]-α-MSH 6-13 | Antifungal, Antibacterial, other, Antiviral, anti-HIV, Immunosuppressant, Metabolic and enzyme disorders, Anti-inflammatory, Antiarhtritic, other GI inflammatory/bowel disorders |
| 203 | ZP-120 | | Ac-RYYRWKKKKKKK-NH$_2$ | Cardiostimulant |
| 204 | CTT | | H-Cys-Thr-Thr-His-Trp-Gly-Phe-Thr-Leu-Cys-OH | Formulation technology |
| 205 | PYY3-36 | | gi\|71361686\|ref\|NP_004151.2\| peptide YY [Homo sapiens] MVFVRRPWPALTTVLLALLVCLGALVDAYPIKPEAPREDASPEELNRYYA SLRHYLNLVTRQRYGKRDGPDTLLSKTFFPDGEDRPVRSRSEGPDLW | Anorectic/Antiobseity |
| | AEZS-130 | | EP1572 UMV1843 [Aib-DTrp-DgTrp-CHO] | Growth hormone Anabolic Musculoskeletal |
| 206 | AL-108 | | H-Asn-Ala-Pro-Val-Ser-Ile-Pro-Gln-OH | Neuroprotective Cognition enhancer Antiparkinsonian Ophthalmological |
| 202 | TM-801 | | H-Met-Cys-Met-Pro-Cys-Phe-Thr-Thr-Asp-His-Gln-Met-Ala-Arg-Lys-Cys-Asp-Asp-Cys-Cys-Gly-Gly-Lys-Gly-Arg-Gly-Lys-Cys-Tyr-Gly-Pro-Gln-Cys-Leu-Cys-Arg-NH$_2$ (Disulfide bridge: 2-19, 5-28, 16-33, 20-35) | Imaging agent |
| 202 | TM-901 | | H-Met-Cys-Met-Pro-Cys-Phe-Thr-Thr-Asp-His-Gln-Met-Ala-Arg-Lys-Cys-Asp-Asp-Cys-Cys-Gly-Gly-Lys-Gly-GArg-ly-Lys-Cys-Tyr-Gly-Pro-Gln-Cys-Leu-Cys-Arg-NH$_2$ (Disulfide bridge: 2-19, 5-28, 16-33, 20-35) | Anticancer, other Imaging agent |
| 440 | S-0373 | TRH | pyroGlu-His-Pro-NH$_2$ (or 5-oxo-L-prolyl-L-histidyl-L-prolinamide) | Neurological Psychostimulant Antiparkinsonian |
| 205 | PYY3-36 | | gi\|71361686\|ref\|NP_004151.2\| peptide YY [Homo sapiens] MVFVRRPWPALTTVLLALLVCLGALVDAYPIKPEAPREDASPEELNRYYA SLRHYLNLVTRQRYGKRDGPDTLLSKTFFPDGEDRPVRSRSEGPDLW | Formulation, oral, other Anorectic/Antiobseity |
| 207 | XG-101 | | gi\|4885433\|ref\|NP_005447.1\| mitogen-activated protein kinase 8 interacting protein 1 [Homo sapiens] MAERESGGLGGGAASPPAASPFLGLHIASPPNFRLTHDISLEEFEDEDLS EITDECGISLQCKDTLSLRPPRAGLLSAGGGGAGSRLQAEMLQMDLIDAT GDTPGAEDDEEDDDEERAARRPGAGPPKAESGQEPASRGQGQSQGQSQGP GSGDTYRPKRPTTLNLFPQVPRSQDTLNNNSLGKKHSWQDRVSRSSSPLK TGEQTPPHEHICLSDELPPQSGPAPTTDRGTSTDSPCRRSTATQMAPPGG PPAAPPGGRGDSHRDRIHYQADVRLEATEEIYLTPVQRPPDAAEPTSAFL PPTESRMSVSSDPDPAAYPSTAGRPHPSISEEEEGFDCLSSPERAEPPGG GWRGSLGEPPPPPPRASLSSDTSALSYDSVKYTLVVDEHAQLELVSLRPCF | Immunological Cardiovascular Neuroprotective Immunosuppressant |

TABLE 1-continued

| SEQ ID NO: | Name | Family | Sequence and/or Identifying Information | Therapeutic Activity |
|---|---|---|---|---|
| | | | GDYSDESDSATVYDNCASVSSPYESAIGEEYEEAPRPQPPACLSEDSTPD EPDVHFSKKFLNVFMSGRSRSSSAESFGLFSCIINGEEQEQTHRAIFRFV PRHEDELELEVDDPLLVELQAEDYWYEAYNMRTGARGVFPAYYAIEVTKE PEHMAALAKNSDWVDQFRVKFLGSVQVPYHKGNDVLCAAMQKIATTRRLT VHFNPPSSCVLEISVRGVKIGVKADDSQEAKGNKCSHFFQLKNISFCGYH PKNNKYFGFITKHPADHRFACHVFSEDSTKALAESVGRAFQQFYKQFVE YTCPTEDIYLE | |
| 208 | XG-102 | | gi\|4885433\|ref\|NP_005447.1\| mitogen-activated proteinkinase 8 interacting protein 1 [Homo sapiens] MAERESGGLGGGAASPPAASPFLGLHIASPPNFRLTHDISLEEFEDEDLS EITDECGISLQCKDTLSLRPPRAGLLSAGGGGAGSRLQAEMLQMDLIDAT GDTPGAEDDEEDDDEERAARRPGAGPPKAESGQEPASRGQGQSQGQSQGP GSGDTYRPKRPTTLNLFPQVPRSQDTLNNNSLGKKHSWQDRVSRSSSPLK TGEQTPPHEHICLSDELPPQSGPAPTTDRGTSTDSPCRRSTATQMAPPGG PPAAPPGGRGHSHRDRIHYQADVRLEATEEIYLTPVQRPPDAAEPTSAFL PPTESRMSVSSDPDPAAYPSTAGRPHPSISEEEEGFDCLSSPERAEPPGG GWRGSLGEPPPPPRASLSSDTSALSYDSVKYTLVVDEHAQLELVSLRPCF GDYSDESDSATVYDNCASVSSPYESAIGEEYEEAPRPQPPACLSEDSTPD EPDVHFSKKFLNVFMSGRSRSSSAESFGLFSCIINGEEQEQTHRAIFRFV PRHEDELELEVDDPLLVELQAEDYWYEAYNMRTGARGVFPAYYAIEVTKE PEHMAALAKNSDWVDQFRVKFLGSVQVPYHKGNDVLCAAMQKIATTRRLT VHFNPPSSCVLEISVRGVKGVKADDSQEAKGNKCSHFFQLKNISFCGYHP KNNKYFGFITKHPADHRFACHVFSEDSTKALAESVGRAFQQFYKQFVEY TCPTEDIYLE | Neuroprotective Cardiovascular Otological Ophthalmological Antiparkinsonian Immunosuppressant |
| 441 | lanreotide SR | | L-Threonamide,3-(2-naaphtalenyl)-D-alanyl-L-cysteinyl-L-tyrosyl-D-tryptophyl-L-lysyl-L-valyl-L-cysteinyl-, cyclic (2-7)-disulfide | Formulation, modified-release, other Somatostatin Antihypertensive, other |
| 209 | OGP-(10-14)-L | | H-Tyrosine-Glycine-Phenylalanine-Glycine-Glycine-OH | Haematological Musculoskeletal |
| 210 | WP9QY | | cyclo(Tyr-Cys-Trp-Ser-Gln-Tyr-Leu-Cys-Tyr); cyclo(tyrosyl-cysteinyl-tryptophyl-seryl-glutaminyl-tyrosyl-leucyl-cysteinyl-tyrosyl) | Antiarthritic, other Anti-inflammatory |
| 211 | aviptadil | | His-Ser-Asp-Ala-Val-Phe-Thr-Asp-Asn-Tyr-Thr-Arg-Leu-Arg-Lys-Gln-Met-Ala-Val-Lys-Lys-Tyr-Leu-Asn-Ser-Ile-Leu-Asn | Antihypertensive, other Respiratory Immunosuppressant |
| 212 | AL-209 | | Ser-Ala-Leu-Leu-Arg-Ser-Ile-Pro-Ala | Neuroprotective Cognition enhancer Ophthalmological |
| 442 | octreotide | | L-Cysteinamide, D-phenylalanyl-L-cysteinyl-L-phenylalanyl-D-tryptophyl-L-lysyl-L-threonyl-N-[2-hydroxy-1-(hydroxymethyl)propyl], cyclic (2-7)-disulfide, [R-(R*,R*)]- | Formulation, implant Formulation, modified-release, >24 hr Somastatin |
| 213 | CDX-110 | | Leu-Glu-Glu-Lys-Lys-Gly-Asn-Tyr-Val-Val-Thr-Asp-His-Cys-KLH | Recombinant vaccine Anticancer, immunological |
| 444 | des-mospressin | | Vasopressin, 1-(3-mercaptopropanoic acid)-8-D-arginine- | Hormone, Urological, Reproductive/gonadal, general |
| 445 | obinepitide Insulin | | [34-L-glutamine]pancreatic hormone (human) Insulin (ox), 8A-L-threonine-10A-L-isoleucine-30B-L-threonine- | Anorectic/Antiobesity solubility-enhanced Insulin |

TABLE 1-continued

| SEQ ID NO: | Name | Family | Sequence and/or Identifying Information | Therapeutic Activity |
|---|---|---|---|---|
| 171 | terlipressin | | N-(N-(N-glycylglycyl)glycyl)-8-L-lysinevasopressin [CAS]; Gly-Gly-Gly-8-Lys-vasopressin; N-(alpha)-glycyl-glycyl-glycyl-8-lysine vasopressin; Remestyp; TGLVP; glipressin; glycylpressin; glypressin; terlypressin; triglycyl lysine vasopressin; triglycyl-(8-lysine)vasopressin; triglycylvasopressin; vasopressin, tri-Gly-8-Lys- | Hepatoprotective, Urological, Gi bleeding |
| 214 | ZT-153 | | Asn-Phe-Gly-Ala-Ile-Leu; NFGAIL; asparagyl-phenylalanyl-glycyl-alanyl-isoleucyl-leucine; islet amyloid polypeptide (22-27) | Antidiabetic |
| 215, 215 and 216 | FGLL | | gi\|42544189\|ref\|NP_004458.3\| fibrinogen-like 1 precursor [Homo sapiens]<br>MAKVFSFILVTTALTMGREISALEDCAQEQMRLRAQVRLLETRVKQQQVK<br>IKQLLQENEVQFLDKGDENTVIDLGSKRQYADCSEIFNDGYKLSGFYKIK<br>PLQSPAEFSVYCDMSDGGGWTVIQRRSDGSENFNRGWKDYENGFGNFVQK<br>HGEYWLGNKNLHFLTTQEDYTLKIDLADFEKNSRYAQYKNFKVGDEKNFY<br>ELNIGEYSGTAGDSLAGNFHPEVQWWASHQRMKFSTWDRDHDNYEGNCAE<br>EDQSGWWFNRCHSANLNGVYYSGPYTAKTDNGIVWYTWHGWWYSLKSVVM<br>KIRPNDFIPNVI<br>gi\|42544200\|ref\|NP_063846.1\| fibrinogen-like 1 precursor [Homo sapiens]<br>MAKVFSFILVTTALTMGREISALEDCAQEQMRLRAQVRLLETRVKQQQVK<br>IKQLLQENEVQFLDKGDENTVIDLGSKRQYADCSEIFNDGYKLSGFYKIK<br>PLQSPAEFSVYCDMSDGGGWTVIQRRSDGSENFNRGWKDYENGFGNFVQK<br>HGEYWLGNKNLHFLTTQEDYTLKIDLADFEKNSRYAQYKNFKVGDEKNFY<br>ELNIGEYSGTAGDSLAGNFHPEVQWWASHQRMKFSTWDRDHDNYEGNCAE<br>EDQSGWWFNRCHSANLNGVYYSGPYTAKTDNGIVWYTWHGWWYSLKSVVM<br>KIRPNDFIPNVI<br>gi\|42544198\|ref\|NP_671736.2\| fibrinogen-like 1 precursor [Homo sapiens]<br>MAKVFSFILVTTALTMGREISALEDCAQEQMRLRAQVRLLETRVKQQQVK<br>IKQLLQENEVQFLD | Cognition enhancer Neurological |
| 217 | ST-03 | | gi\|386634\|gb\|AAB27460.1\| 01-ST-3=heat-stable enterotoxin [Vibrio cholerae, 01, Peptide, 19 aa]<br>NLIDCCEICCNPACFGCLN | Recombinant growth factor Musculoskeletal Osteoporosis treatment |
| 446 | cetrorelix acetate | | D-Alaninamide, N-acetyl-3-(2-naphthalenyl)-D-alanyl-4-chloro-D-phenylalanyl-3-(3-pyridinyl)-D-alanyl-L-seryl-L-tyrosyl-N5-(aminocarbonyl)-D-ol-L-leucyl-L-arginyl-L-prolyl- | Formulation, modified-release, >24 hr Menstruation disorders |
| 218 | neurodegenerative ther | | alpha toxin, Naja; cobra alpha toxin; cobra toxin alpha; toxin alpha, cobra;<br>gi\|64054\|emb\|CAA26373.1\| unnamed protein product [Laticauda semifasciata]<br>MKTLLLTLVVVTIVCLDLGYTRICFNHQSSPQYYKTCSPGESSCYNKQW<br>SDFRGTIIERGCGCPTVKPGIKLSCCESEVCNN<br>gi\|4519816\|dbj\|BAA57552.1\| short chain neurotoxin [Laticauda semifasciata]<br>MKTLLLTLVVVTIVCLDLGYTRICFNHQSSPQTTKTCSPGESSCYNKQW<br>SDFRGTIIERGCGCPTVKPGIKLSCCESEVCNN<br>gi\|32140561\|dbj\|BAC78199.1\| erabutoxin a[Laticauda semifasciata]<br>MKTLLLTLVVVTIVCLDLGYTRICFNHQSSPQTTKTCSPGESSCYNKQW<br>SDFRGTIIERGCGCPTVKPGIKLSCCESEVCNN<br>gi\|32140563\|dbj\|BAC78200.1\| erabutoxin a [Laticauda semifasciata]<br>MKTLLLTLVVVTIVCLDLGYTRICFNHQSSPQTTKTCSPGESSCYNKQW<br>SDFRGTIIERGCGCPTVKPGIKLSCCESEVCNN | Cognition enhancer |
| 219 | CT-319 | | MSNKKIIKIIKLQIPGGKANPAPPIGPALGAAGVNIMGF<br>CKEFNAATQDRPGDLLPVVIT<br>VYSDKTFSFVMKQSPVSSLIKKALGLESGSKIPNRNKV<br>GKLTRAQITVIAEQKMKDMDVV<br>LLESAERMVEGTARSMGVDVE | Antiviral, anti-HIV |
| 447 | Peptide T | | L-Threonine, N-(N-(N2-(N-(N-(N-D-alanyl-L-seryl)-L-threonyl)-L-threonyl)-L-threonyl)-L-asparaginyl)-L-tyrosyl)-[CAS]; HIV Peptide T; | Antipsoriasis Multiple sclerosis |

TABLE 1-continued

| SEQ ID NO: | Name | Family | Sequence and/or Identifying Information | Therapeutic Activity |
|---|---|---|---|---|
| | | | Peptide T, HIV | treatment Cognition enhancer Musculoskeletal |
| 220 and 221 | APP-018 | | pallidin [Mus musculus]<br>gi\|9790039\|ref\|NP_062762.1\|[9790039]<br>MSVPEPPPPDGVLTGPSDSLEAGEPTPGLSDTSPDEGLIEDFPVDDRAVE<br>HLVGGLLSHYLPDLQRSKRALQELTQNQVVLLDTLEQEISKFKECHSMLD<br>INALFTEAKHYHAKLVTIRKEMLLLHEKTSKLKKRALKLQQKRQREELER<br>EQQREKEFEREKQLTAKPAKRT<br>envelope glycoprotein [Human immunodeficiency virus type 1]<br>gi\|4205319\|gb\|AAD11044.1\|[4205319]<br>KLTPLCVTLNCTDLDLRNTTNNTTTEERGEMKNCSFNITTNIRDRYQKEY<br>ALFYKLDVIPIKEDNTSDNTSYRLISCNTSVITQACPKIS | Hypolipaemic/ Anti-atherosclerosis |
| 222 | somatropin | | gi\|60651145\|gb\|AAX31661.1\| somatotropin [Bubalus bubalis]<br>AFPAMSLSSLFANAVLRAQHLHQLAADTFKEFERTYIPEGQRYSIQNTQV<br>AFCFSETIPAPTGKNEAQQKSDLELLRISLLLIQSWLGPLQFLSRVFTNS<br>LVFGTSDRVYEKLKDLEEGILALMRELEDGTPRAGQILKRTYDKFDTNMR<br>SDDALLKNYGLLSCFRKDLHKTETYLRVMKCRRFGEASCAF | Formulation, transmucosal, nasal Growth hormone Anabolic Reproductive/ gonadal, general |
| 448 | heparin | | 6-[5-acetamido-4,6-dihydroxy-2-(sulfooxymethyl)oxan-3-yl]oxy-3-[5-(6-carboxy-4,5-dihydroxy-3-sulfooxyoxan-2-yl)oxy-6-(hydroxymethyl)-3-(sulfoamino)-4-sulfooxyoxan-2-yl]oxy-4-hydroxy-5-sulfooxyoxane-2-carboxylic acid | Formulation, transmucosal, nasal Anticoagulant |
| 46 | CGRP | CGRP | ACDTATCVTHRLAGLLSRSGGVVKNNFVPTNVGSKAF-NH$_2$ | Cardiovascular Cardiostimulant |
| 449 | YM-216391 | | A concise total synthesis of the usual oxazole-based cyclopeptide structure YM-216391, which also establishes the stereochemistry of the natural product i.e., 1, is described. The unusual polyoxazole-thiazole-based cyclopeptide 1, designated YM-216391, was recently isolated from Streptomyces nobilis.1 It shares both a structural and biological homology with the potent telomerase inhibitor telomestatin 2 which is showing promise in cancer chemotherapy.2 The structure YM-216391 comprises a continuum of five azoles which have their origins in serine, cysteine and phenylalanine, linked via a glycine- valine-isoleucine tripeptide tether. The complete stereochemical assignment of YM-216391 has not been established. In this communication we described a concise total synthesis of the cyclopeptide, which not only confirms its unique structure but also allows the assignment of its stereochemistry, shown in formula 1. Thus, the 2,4-disubstituted oxazoles 3 and 4 and the trisubstituted oxazole 5 were first elaborated | Anticancer, other |
| 223 | FGLm | | LSENDEWTQDRAKP | Cognition enhancer Neurological |
| 224 | prohanin | | NPFPTWRKRPG | Analgesic, other |
| 225 | heart failure therapy | NP | gi\|189079\|gb\|AAA36355.1\| natriuretic peptide<br>MDPQTAPSRALLLLLFLHLAFLGGRSHPLGSPGSASDLETSGLQEQRNHL<br>QGKLSELQVEQTSLEPLQESPRPTGVWKSREVATEGIRGHRKMVLYTLRA<br>PRSPKMVQGSGCFGRKMDRISSSSGLGCKVLRRH | Cardiostimulant |
| 450 | SEN-034 | | D-[(chG)Y-(chG)(chG)(MeL)]-NH$_2$, where chG is R-cyclohexylglycine | Cognition enhancer Anti-inflammatory |

TABLE 1-continued

| SEQ ID NO: | Name | Family | Sequence and/or Identifying Information | Therapeutic Activity |
|---|---|---|---|---|
| 451 | Primacoll | | Synthetic growth factor | Musculoskeletal |
| 452 | Octreotide | | L-Cysteinamide, D-phenylalanyl-L-cysteinyl-L-phenylalanyl-D-tryptophyl-L-lysyl-L-threonyl-N-[2-hydroxy-1-(hydroxymethyl)propyl]-, cyclic (2-7)-disulfide, [R-(R*,R*)]- | Formulation, modified-release, >24 hr Symptomatic antidiabetic Ophthalmological Somatostatin |
| 453 | ALS-02 | | Glycine, N-(aminoiminomethyl)-N-methyl- | Neuroprotective |
| 200 | exendin-4, PC-DAC | GLP-1 | L-histidylglycyl-L-glutamylglycyl-L-threonyl-L-phenylalanyl-L-threonyl-L-seryl-L-aspartyl-L-leucyl-L-seryl-L-lysyl-L-glutaminyl-L-methionyl-L-glutamyl-L-glutamyl-L-glutamyl-L-alanyl-L-valyl-L-arginyl-L-leucyl-L-phenylalanyl-L-isoleucyl-L-glutamyl-L-tryptophyl-L-leucyl-L-lysyl-L-asparaginylglycylglycyl-L-propyl-L-seryl-L-serylglycyl-L-alanyl-L-prolyl-L-prolyl-L-prolyl-L-serinamide | Antidiabetic |
| 226 | Exenatide | | gi\|1916067\|gb\|AAB51130.1\|exendin 4 [*Heloderma suspectum*] MKIILWLCVFGLFLATLFPISWQMPVESGLSSEDSASSESFASKIKRHGE GTFTSDLSKQMEEEAVRLFIEWLKNGGPSSGAPPPSG | Formulation, transmucosal, nasal Antidiabetic |
| 225 | Cardeva | BNP | gi\|113836\|sp\|p16860.1\|ANFB_HUMAN Natriuretic peptides B precursor [Contains: Gamma-brain natriuretic peptide; Brain natriuretic peptide 32 (BNP-32)] MDPQTAPSRALLLLLFLHLAFLGGRSHPLGSPGSASDLETSGLQEQRNHL QGKLSELQVEQTSLEPLQESPRPTGVWKSREVATEGIRGHRKMVLYTLRA PRSPKMVQGSGCFGRKMDRISSSSGLGCKVLRRH | Cardiostimulant |
| 227 | Alloferon | | H-His-Gly-Val-Ser-Gly-His-Gly-Gln-His-Gly-Val-His-Gly-OH | Immunomodulator, anti-infective |
| 454 | PAC-G31P | | AMCF-1; Alveolar Macrophage Chemotactic Factor I; Alveolar Macrophage Chemotactic Factor-I; Anionic Neutrophil Activating Peptide; Anionic Neutrophil-Activating Peptide; CXCL9 Chemokine; CXCL8 Chemokines; CXCL8, Chemokine; Chemokine CXCL8; Chemokine, CXCL8; Chemokines, CXCl8; Chemotactic Factor, Macrophage Derived; Chemotactic Factor, Macrophage-Derived; Chemotactic Factor, Neutrophil; Chemotactic Factor, Neutrophil, Monocyte-Derived; Chemotactic Peptide-Interleukin-8, Granulocyte; Granulocyte Chemotactic Peptide Interleukin 8; Granulocyte Chemotactic Peptide-Interleukin-8; IL-8; IL8; Interleukin 8; Lymphocyte-Derived Neutrophil-Activating Peptide; Macrophage-Derived Chemotactic Factor; Monocyte-Derived Neutrophil Chemotactic Factor; Monocyte-Derived Neutrophil-Activating Peptide; Neutrophil Activating Peptide, Lymphocyte Derived; Neutrophil Activating Peptide, Monocyte Derived; Neutrophil Activatoion Factor; Neutrophil Chemotactic Factor; Neutrophil-Activating Peptide, Anionic; Neutrophil-Activating Peptide | Recombinant interleukin Respiratory Antiasthma COPD treatment |
| 228 | PAC-525 | | Ac-KWRRWVRWI-NH$_2$ | Antibacterial, other |
| 229, 229 and 230 | PAC-113 | | Lys-Phe-His-Glu-Lys-His-His-Ser-His-Arg-Gly-Tyr histatin 10, human; histatin 11, human; histatin 12, human; histatin 3, human; histatin 4, human; histatin 5, human; histatin 6, human; histatin 7, human; histatin 8, human; histatin 9, human; histatin-3 (12-24), human; histatin-3 (12-25), human; histatin-3 (12-24), human; histatin-3 (12-25), human; histatin-3 (12-32), human; histatin-3 (13-25), human; histatin-3 (5-11), human; histatin-3 (5-12), human; lysyl-phenylalanyl-histidyl-glutamyl-lysyl-histidyl-histidyl-seryl-histidyl-arginyl-glycyl-tyrosine | Antifungal |

TABLE 1-continued

| SEQ ID NO: | Name | Family | Sequence and/or Identifying Information | Therapeutic Activity |
|---|---|---|---|---|
| | | | gi|4557653|ref|NP_000191.1| histatin 3 [Homo sapiens] MKFFVFALILALMLSMTGADSHAKRHHGYKRKFHEKHHSHRGYRSNYLYDN | |
| 231 | MLIF | | Met-Gln-Cys-Asn-Ser U.S. Pat. No. 6,524,591 | Anti-inflammatory |
| 454 | carfilzomib | | L-Phenylalaninamide, (alphaS)-alpha-[(4-morpholinylacetyl)amino]benzenebutanoyl-L-leucyl-N-[(1S)-3-methyl-1-[[(2R)-2-methyloxiranyl]carbonyl]butyl]- | Anticancer, other |
| 232 | NAFB001 | | gi|63025222|ref|NP_000651.3| transforming growth factor, beta 1 [Homo sapiens] MPPSGLRLLPLLLPLLWLLVLTPGRPAAGLSTCKTIDMELVKRKRIEAIR GQILSKLRLASPPSQGEVPPGPLPEAVLALYNSTRDTVAGESAEPEPEPE ADYYAKEVTRVLMVETHNEIYDKFKQSTHSIYMFFNTSELREAVPEPVLL SRAELRLLRLKLKVEQHVELYQKYSNNSWRYLSNRLLAPSDSPEWLSFDV TGVVRQWLSRGGEIEGFRLSAHCSCDSRDNTLQVDINGFTTGRRGDLATI HGMNRPFLLLMATPLERAQHLQSSRHRRALDTNYCFSSTEKNCCVRQLYI DFRKDLGWKWIHEPKGYHANFCLGPCPYIWSLDTQYSKVLALYNQHNPGA SAAPCCVPQALEPLPIVYYVGRKPKVEQLSNMIVRSCKCS [PIR] | Ophthalmological Heptaprotective |
| 233 | IL12-NGR | | H-Cys-Asn-Gly-Arg-Cys-Gly-OH (Disulfide bridge: 1-5) | Recombinant, other Cytokine Anticancer, immunological |
| 234 and 235 | enterostatin | | Val-Pro-Val-Asp; Val-Pro-Asp-Pro-Arg | Anorectic/ Antiobseity |
| 455 | octreotide | | L-Cysteinamide, D-phenylalanyl-L-cysteinyl-L-phenylalanyl-D-tryptophyl-L-lysyl-L-threonyl-L-N-[2-hydroxy-1-(hydroxymethyl)propyl]-, cyclic (2-7)-disulfide, [R-(R*,R*)]- | Formulation, modified-release, >24 hr Somatostatin |
| 150 | enfuviritide | | L-Phenylalaninamide, N-acetyl-L-tyrosyl-L-threonyl-L-seryl-L-leucyl-L-isoleucyl-L-histidyl-L-seryl-L-leucyl-L-isoleucyl-L-alpha-glutamyl-L-alpha-glutamyl-L-seryl-L-glutaminyl-L-asparaginyl-L-glutaminyl-L-glutaminyl-L-alpha-glutaminyl-L-lysyl-L-asparaginyl-L-alpha-glutamyl-L-glutaminyl-L-alpha-glutamyl-L-leucyl-L-leucyl-L-alpha-glutamyl-L-leucyl-L-alpha-aspartyl-L-lysyl-L-tryptophyl-L-alanyl-L-seryl-L-leucyl-L-tryptophyl-L-asparaginyl-L-tryptophyl- | Formulation, parenaral, needle-free Antiviral, anti-HIV |
| 236 | PR-21 | | gi|2213924|gb|AAB61615.1| neural cell adhesion molecule [Homo sapiens] MLQTKDLIWTLFFLGTAVSLQVDIVPSQGEISVGESKFFLCQVAGDAKDK DISWFSPNGEKLTPNQQRISVVVWNDDSSSTKTIYNANIDDAGIYKCVVT GEDGSESEATVNVKIFQKLMFKNAPTPQEFREGEDAVIVCDVVSSLPPTI IWKHKGRDVILKKDVRFIFLSNNYLPIPGIKKTDEGTYRCEGRILARGEI NFNDIQVIVNVPPTIQARQNIVNATANLGQSVTLVCDAEGFPGPTMSWTK DGEQIEQEEHDEKYLFSDDSSHLTIKKVDKNHEAENICIAENKVGEQDAT IHLKVFAKPQITYVEDQTAMELAEQVILTVEASGDHIPYITWWTSTWQI | Neurological Cognition enhancer |
| 237 | AC-163794 | GIP | gi|183221|gb|SSS53192.1| gastric inhibitory polypeptide precursor MVATKTFALLLLSLFLAVGLGEKKEGHFSALPSLPVGSHAKVSSPQPRGP RYAEGTFISDYSIAMDKIHQQDFVNWLLAQKGKKNDWKHNITQREARALE LASQANRKEEEAVEPQSSPAKNPSDEDLLRDLLIQELLACLLDQTNLCRL RSR; | Antidiabetic |
| 456 | glucagon | | Glucagon (1-29); Glukagon; HG Factor; HG-Factor; Hyperglycemic Glycogenolytic Factor; Hyperglycemic-Glycogenolytic Factor; Proglucagon (33-61) | Formulation, transdermal, systemic hypoglycemia |
| 457 | Insulin | | Insulin (ox), 8A-L-threonine-10A-L-isoleucine-30B-L-threonine- | Formulation, oral, other Formulation, optimized, |

TABLE 1-continued

| SEQ ID NO: | Name | Family | Sequence and/or Identifying Information | Therapeutic Activity |
|---|---|---|---|---|
| | | | | nanoparticles Antidiabetic |
| 458 | Dekafin-2 | | DNA Synthesis Factor; Fibroblast Growth Factor; Fibroblast Growth Regulatory Factor; Growth Factor, Fibroblast; Growth Factors, Fibroblast | Anticancer, other |
| 238 and 239 | relaxin | | (1) Glu-Leu-Tyr-Ser-Ala-Leu-Ala.Asn-Lys-Cys-Cys-His-Val-Gly-Cys-Thr-Lys-Arg-Ser-Leu-Ala-Arg-Phe-Cys<br>(2) H-Asp-Ser-Trp-Met-Glu-Glu-Val-Ile-Lys-Leu-Cys-Gly-Arg-Glu-Leu-Val-Arg-Ala-Gln-Ile-Ala-Ile-Cys-Gly-Met-Ser-Thr-Ser<br>Cys 11 of each chain form disulfide bond; cys 24 of the first chain forms disulfide bond with cys 23 of chain 2 | Recombinant hormone Hormone Labour inducer Antihypertensive, other |
| 459 | rhNRG-1 | | Differentiation Factor, neu; GGF Protein; Glial Growth Factor; Heregulin; NDF Protein; NRG1 Protein; Neuregulin 1; neu Differentiation Factor | Recombinant, other Cardiostimulant |
| 240 | c-peptide analogue | C-peptide | Glu-Ala-Glu-Asp-Leu-Gln-Val-Gly-Gln-Val-Glu-Leu-Gly-Gly-Gly-Pro-Gly-Ala-Gly-Ser-Leu-Gln-Pro-Leu-Ala-Leu-Glu-Gly-Ser-Leu-Gln | Symptomatic antidiabetic |
| 241 | SB-101 | | gi\|30353933\|gb\|AAH52287.1\| CD44 protein [Homo sapiens]<br>MDKFWWHAAWGLCLVPLSLAQIDLNITCRFAGVFHVEKNGRYSISRTEAA DLCKAFNSTLPTMAQMEKALSIGFETCSST | Recombinant, other Anticancer, other |
| 242 | Britistatin | | gi\|66270695\|gb\|AAY43681.1\| disintegrin isoform D-1 [Bitis arietans]<br>SPPVCGNKILEQGEDCDCGSPANCQDRCCNAATCKLTPGSQCNYGECCDQ CRFKKAGTVCRIARGDWNDDYCTGKSSDCPWNH | Antithrombotic |
| 243 | echistatin | | gi\|208338\|gb\|AAA72777.1\| echistatin<br>MECESGPCCRNCKFLKEGTICKRARGDDLDDYCNGKTCDCPRNPHKGPAT | Antithrombotic |
| 244 | gastrin | | gi\|4503923:20-101 gastrin preprotein [Homo sapiens]<br>EASWKPRSQQPDAPLGTGANRDLELPWLEQQGPASHHRRQLGPQGPPHLV ADPSKKQGPWLEEEEEATGWMDFGRRSAEDEN | diabetes |
| 245 | herpes simplex vaccine | | gi\|9629447:1-23 envelope glycoprotein D [Human herpesvirus 1]<br>MGGAAARLGAVILFVVIVGLHGV | Propylactic vaccine |
| 246 | neurostatin | | gi\|5453816:1520163 neurotensin/neuromedin N preprotein [Homo sapiens]<br>LYENKPRRPYIL | Analgesic, other |
| 247 | nociceptin | | gi\|5453922\|ref\|NP_006219.1\| prepronociceptin [Homo sapiens]<br>MKVLLCDLLLLSLFSSVFSSCQRDCLTCQEKLHPALDSFDLEVCILECEE KVFPSPLWTPCTKVMARSSWQLSPAAPEHVAAALYQPRASEMQHLRRMPR VRSLFQEQEEPEPGMEEAGEMEQKQLQKRFGGFTGARKSARKLANQKRFS EFMRQYLVLSMQSSQRRRTLHQNGNV | Neurological Cognition enhancer Analgesic, other |
| 248 | oxynto-modulin | | sp\|P01275.3\|GLUC_HUMAN:53-89 Glucagon precursor [Contains: Glicentin; Glicentin-related polypeptide (GRPP);Oxyntomodulin (OXY) (OXM)]<br>HSQGTFTSDYSKYLDSRRAQDFVQWLMNTKRNRNNIA | Obesity; Antiulcer |
| 249 | pancreastatin | | gi\|164417:256-304 chromogranin A precursor<br>GWPQAPAMDGAGKTGAEEAQPPEGKGAREHSRQEEEEETAGAPGQLFRG | Antidiabetic |
| 250 | relaxin | Relaxin | gi\|5902052\|ref\|NP_008842.1\| relaxin 1 preproprotein [Homo sapiens]<br>MPRLFLFHLLEFCLLLNQFSRAVAAKWKDDVIKLCGRELVRAQIAICGMS TWSKRSLSQEDAPQTPRPVAEIVPSFINKDTETIIMLEFIANLPPELKA ALSERQPSLPELQQYVPALKDSNLSFEEFKKLIRNRQSEAADSNPSELKY LGLDTHSQKKRRPYVALFEKCCLIGCTKRSLAKYC | Recombinant hormone Hormone Labour inducer |
| 251 | secretin | | gi\|11345450:28-54 secretin preprotein [Homo sapiens]<br>HSDGTFTSELSRLREGARLQRLLQGLV | Haemostatic; diagnostic of pancreatic |

TABLE 1-continued

| SEQ ID NO: | Name | Family | Sequence and/or Identifying Information | Therapeutic Activity |
|---|---|---|---|---|
| | | | | dysfunction, asthma, COPD, others |
| 252 | TIMP | | MAPFEPLASGILLLLWLIAPSRACTCVPPHPQTAFCNSDLVIRAKFVGTP EVNQTTLYQRYEIKMTKMIKGFQALGDAADIRFVYTPAMESVCGYFHRSH NRSEEFLIAGKLQDGLLHITTCSFVAPWNSLSLAQRRGFTKTYTVGCEEC TVFPCLSIPCKLQSGTHCLWTDQLLQGSEKGFQSRHLACLPREPGLCTWQ SLRSQIA | Recombinant, other Vulnerary Antiarthritic, other Stomatological |
| 252 | TIMP | | MAPFEPLASGILLLLWLIAPSRACTCVPPHPQTAFCNSDLVIRAKFVGTP EVNQTTLYQRYEIKMTKMYKGFQALGAADIRFVYTPAMESVCGYFHRSDH NRSEEFLIAGKLQDGLLHITTCSFCAPWNSLSLAQRRGFTKTYTVGCEEC TVFPCLSIPCKLQSGTHCLWTDQLLQGSEKGFQSRHLACLPREPGLCTWQ SLRSQIA | Recombinant, other Antiarthritic, other Stomatological |
| 253 | tendamistat | | Asp-Thr-Thr-Val-Ser-Glu-Pro-Ala-Pro-Ser-Cys-Val-Thr-Leu-Tyr-Gln-Ser-Trp-Arg-Tyr-Ser-Gln-Ala-Asp-Asn-Gly-Cys-Ala-Gln-Thr-Val-Thr-Val-Lys-Val-Val-Tyr-Glu-Asp-Asp-Thr-Glu-Gly-Leu-Cys-Tyr-Ala-Val-Ala-Pro-Gly-Gln-Ile-Thr-Thr-Val-Gly-Asp-Gly-Tyr-Ile-Gly-Ser-His-Gly-His-Ala-Arg-Tyr-Leu-Ala-Arg-Cys-Leu | Antidiabetic |
| 254 | thymosin β4 | | gi\|11056061\|ref\|NP_066932.1\| thymosin, beta 4 [Homo sapiens] MSDKPDMAEIEKFDKSKLKKTETQEKNPLPSKETIEQEKQAGES | Vulnerary Ophthalmological Symptomatic antidiabetic Dermatological Cardiovascular Septic shock treatment Antiasthma |
| 255 | urodilatin | | Thr-Ala-Pro-Arg-Ser-Leu-Arg-Arg-Ser-Ser-Cys-Phe-Gly-Gly-Arg-Met-Asp-Arg-Ile-Gly-Ala-Gln-Ser-Gly-Leu-Gly-Cys-Asn-Ser-Phe-Arg-Tyr | Cardiostimulant Urological Antiasthma |
| 256 | Pharma-projects No. 6236 | | Gly-Ser-Arg-Ala-His-Ser-Ser-His-Leu-Lys | Anticancer, other Antiarrhythmitic Antiparkinsonian Cognition enhancer Neuroprotective |
| 257 | ANUP-1 | | Glu-Leu-Lys-Cys-Tyr-Thr-Cys-Lys-Glu-Pro-Met-Thr-Ser-Ala-Ala-Cys | Anticancer, other |
| 258 | DMI-4983 | | Asp-Ala-His-Lys | Cardiovascular |
| 460 | Glypromate | | Gly-Pro-Glu | Neuroprotective |
| 259 | CD-NP | | Lys Met Val Gln Gly Ser Gly Cys Phe Gly Arg Lys Met Asp Ile Ser Ser Ser Ser Gly Leu Gly Cys Pro Ser Leu Arg Asp Pro Arg Pro Asn Ala Pro Ser Thr Ser Ala | Cardiostimulant |
| 260 | Kisspeptin-54 | | GTSLSPPPESSFSPQQPGLSAPHSRQIPAPQGAVLVQREKDLPNYNWNSF GLRF-NH2 | Cancer metastasis, angiogenesis |
| 261 | Kisspeptin-14 | | DLPNYNWNSFGLRF-NH2 | Cancer metastasis, angiogenesis |
| 262 | Kisspeptin-13 | | LPNYNWNSFGLRF-NH2 | Cancer metastasis, angiogenesis |
| 263 | Kisspeptin-10 | | YNWNSFGLRF-NH2 | Cancer metastasis, angiogenesis |
| 264 | Ziconotide | | CKGKGAKCSRLMYDCCTGSCRSGKC | |

TABLE 1-continued

| SEQ ID NO: | Name | Family | Sequence and/or Identifying Information | Therapeutic Activity |
|---|---|---|---|---|
| 461 | Biphalin | | Tyr-D-Ala-Gly-Phe-NH-NH-Phe-Gly-D-Ala-Tyr | |
| 39 | Nesiritide | Brain Netri- uritic peptide (BNP) | SPKMVQGSGCFGRKMDRISSSSGLGCKVLRRH | |
| 40 | CD-NP | | GLSKGCFGLKLDRIGSMSGLGCPSLRDPRPNAPSTSA | |
| 265 | Protegrin-1 | Cytolytic | RGGRLCYCRRRFCVCVGR-NH2 | antibiotic |
| 266 | V681 | | Ac-KWKSFLKTFKSAVKTVLHTALKAISS-NH2 | |
| 462 | V681 (V13A$_D$) | | Ac-KWKSFLKTFKSA(AD)KTVLHTALKAISS-NH2 | '(AD)' discloses the D- configuration of Alanine |
| 267 | V681 des A12 | | KWKSFLKTFKSVKTVLHTALKAISS | |
| 268 | V681 V13K | | KWKSFLKTFKSVKTVLHTALKAISS | |
| 269 | V681 V13K, T15K | | KWKSFLKTFKSVKTVLHTALKAISS | |
| 270 | GLP-2 | GLP | HADGSFSDEMNTILDNLAARDFINWLIQTKITD | |
| 271 | GLP-2 (A2G) | GLP | HGDGSFSDEMNTILDNLAARDFINWLIQTKITD | |
| 272 | GLP-2 (A2G/C34) | GLP | HGDGSFSDEMNTILDNLAARDFINWLIQTKITDC | |
| 273 | AOD-9604 | Human Growth Hormone | LRIVQCASVEGSCGFY | Musculoskeletal, COPD, Hypnotic/ Sedative, Immunostimulant, Antidiabetic, Anabolic, Symptomatic antidiabetic, Vulnerary |
| 274 | Ac-AOD- 9604(S8K) | Human Growth Hormone | Ac-LRIVQCAKVEGSCGFY | Musculoskeletal, COPD, Hypnotic/ Sedative, Immunostimulant, Antidiabetic, Anabolic, Symptomatic antidiabetic, Vulnerary |
| 275 | Ac-AOD- 9604(K17) | Human Growth Hormone | Ac-LRIVQCASVEGSCGFYK | Musculoskeletal, COPD, Hypnotic/ Sedative, Immunostimulant, Antidiabetic, Anabolic, Symptomatic antidiabetic, Vulnerary |
| 276 | C-peptide | Insulin | EAEDLQVGQVELGGGPGAGSLQPLALEGSLQ | |

TABLE 1-continued

| SEQ ID NO: | Name | Family | Sequence and/or Identifying Information | Therapeutic Activity |
|---|---|---|---|---|
| 463 | CR845 | Opioids | peripherally-selective kappa 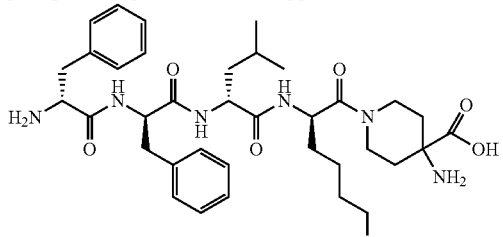 opioid receptor agonists D-Phe-D-Phe-D-Leu-D-Lys-[☐(4-aminopiperidine-4-carboxylic acid)]-OH | acute and chronic pain of visceral, inflammatory and neuropathic origin, and for the treatment of pruritis (itch) |
| 277 | Protegrin-2 | Cytolytic | RGGRLCYCRRRFCICV | antibiotic |
| 278 | Protegrin-3 | Cytolytic | RGGGLCYCRRRFCVCVGRG | antibiotic |
| 279 | Protegrin-4 | Cytolytic | RGGGLCYCRRRFCVCVGRG | antibiotic |
| 280 | Protegrin-5 | Cytolytic | RGGGLCYCRRRFCVCVGRG | antibiotic |
| 281 | Preprotegrin | Cytolytic | METQRASLCLGRWSLWLLLLGLVVPSASAQALSYREAVLRAVDRLNEQSS EANLYRLLELDQPPKADEDPGTPKPVSFTVKETVVPRPTRQPPELCDFKE NGRVKQCVGTVTLDQIKDPLDITCNEVQGVRGGRLCYCRPRFCVCVGRG | antibiotic |
| 248 | Oxyntomodulin | | HSQGTFTSDYSKYLDSRRAQDFVQWLMNTKRNRNNIA | |
| 276 | C-peptide | | EAEDLQVGQVELGGGPGAGSLQPLALEGSLQ | |
| 282 | C-peptide mutant | | EGSLC | |
| 283 | Human Opioid Growth Factor | Enkephalin | Tyr-Gly-Gly-Phe-Met | |
| 284 | cholecystokinin | | RDY(SO3-)TGW(Nle)DF | |
| 285 | Dynorphin A (1-13) | | YGGFLRRIRPKLK | |
| 464 | Pralmorelin (GHRFA) | | D-Ala-D-2-Nal-Ala-Trp-D-Phe-Lys-NH$_2$ | |
| 286 | Aniritide | | RSSCFGGRMDRIGAQSGLGCNSFRY | |
| 287 | Vessel dilator proANP31-67 | | EVVPPQVLSDPNEEAGAALSPLPEVPPWTGEVSPAQR | |
| 465 | Peptide G | | Arg-Pro-Lys-Pro-Gln-Arg-D-Trp-MePhe-D-Trp-Leu-Met | |
| 466 | Tiplimotide | | D-Ala-lys-pro-val-val-his-leu-phe-ala-asp-ile-val-thr-pro-arg-thr-pro | |
| 288 | Desirudin (63-desulfohirudin) | | VVYTDCTESGQNLCLCEGSNVCGQGNKCILGSDGEKNQCVTGEGTPKPQS HNDGDFEEIPEEYLQ | |
| 467 | Examorelin | | His-DTrp(2-Me)-Ala-Trp-DPhe-Lys-NH2 | |
| 172 | Terlipressin | Vesopressin | Gly-Gly-Gly-c[Cys-Tyr-Phe-Gln-Asn-Cys]-Pro-Lys-Gly-NH2 | |
| 289 | Osteogenic Growth Factor (WT) | | ALKRQGRTLYGFGG | |

TABLE 1-continued

| SEQ ID NO: | Name | Family | Sequence and/or Identifying Information | Therapeutic Activity |
|---|---|---|---|---|
| 290 | Osteogenic Growth Factor (10-14) | | YGFGG | |
| 291 | Myelin Basic Protein peptide | | Ac-ASQKRPSQRHG | |
| 292 | Myelin Basic Protein peptide Ac1-11[4Y] | | Ac-ASQYRPSQRHG | |
| 293 | Gonadorelin (24-33) | | pyroGlu-His-Trp-Ser-Tyr-Gly-Leu-Arg-Pro-Gly CONH2 | |
| 468 | Bremelano-tide | Alpha-MSH | Ac-Nle-cyclo[Asp-His-D-Phe-Arg-Trp-Lys]-OH | |
| 294 | Islet Neogenesis associated peptide (INGAP) | | GLHDPSHGTLPNGSG | Diabetes |
| 295 | Urocortin II | | IVLSLDVPIGLLQILLEQARARAAREQATTNARILARVGHC | |
| 296 | A6 (anti-angiogenic peptide) | | CH3CO-NH2-KPSSPPEE-CONH2 | |
| 297 | Obestatin | | H-Phe-Asn-Ala-Pro-Phe-Asp-Val-Gly-Ile-Lys-Leu-Ser-Gly-Val-Gln-Tyr-Gln-Gln-His-Ser-Gln-Ala-Leu-NH2 | |
| 298 | ITF-1697 | | Gly-Lys(Et)-Pro-Arg | |
| 299 | CNP (C-type netriuretic peptide | | GLSKGCFGLKLDRIGSMSGLGC | |
| 300 301 | Osteocalcin | | YLYQWLGAPVPYPDPLEPRREVCELNPDCDELADHIGFQEAYRRFYGPV EAEDLQVGQVELGGGPGAGCLQPLALEGSLQ | Diabetes |
| 469 | D4F-APO1 mimetic peptide | | Ac-D-W-F-K-A-F-Y-D-K-V-A-E-K-F-K-E-A-F-NH$_2$ | |

This table lists the SEQ ID NOs., names, sequences, and known or suspected therapeutic activities of various peptides described herein. The SEQ ID NOs. 1-301 describe sequences that are required to be provided with the Sequence Listing and are therefore appended with the instant Specification. In some instances, these peptides contain features that are either inconsistent with or not amenable to inclusion in the Sequence Listing. For example, a sequence with less than four-amino acids; a sequence with D-amino acid; or certain modification that cannot be described in the Sequence Listing presently, and therefore are not provided in the Sequence Listing. However, for the ease of use and description, a SEQ ID NO. has been provided to these peptides (i.e., SEQ ID NOs: 302-469).
(—NH$_2$ indicates amidation at the C-terminus; Ac indicates acetylation; other modifications are as described herein and in the specification; SIN indicates Sequence Identification Number)

The above exemplary biologically active agents are meant to encompass, where applicable, analogues, agonists, antagonists, inhibitors, isomers, and pharmaceutically acceptable salt forms thereof. In reference to peptides and proteins, the invention is intended to encompass synthetic, recombinant, native, glycosylated, and non-glycosylated forms, as well as biologically active fragments thereof. The above biologically active proteins are additionally meant to encompass variants having one or more amino acids substituted, deleted, or the like, as long as the resulting variant protein possesses at least a certain degree of activity of the parent (native) protein.

The reactive polymeric reagents of the invention may be attached, either covalently or non-covalently, to a number of solid entities including films, chemical separation and purification surfaces, solid supports, metal/metal oxide surfaces, such as gold, titanium, tantalum, niobium, aluminum, steel, and their oxides, and silicon oxide. Additionally, the polymers of the invention may also be used in biochemical sensors, bioelectronic switches, and gates. The polymeric reagents of the invention may also be employed as carriers for peptide synthesis, for the preparation of polymer-coated surfaces and polymer grafts, to prepare polymer-ligand conjugates for affinity partitioning, to prepare cross-linked or non-cross-linked hydrogels, and to prepare polymer-cofactor adducts for bioreactors.

VI. Pharmaceutical Compositions and Administration Methods

The invention also includes pharmaceutical preparations comprising a conjugate as provided herein in combination with a pharmaceutical excipient. Generally, the conjugate itself will be in a solid form (e.g., a precipitate), which can be combined with a suitable pharmaceutical excipient that can be in either solid or liquid form. The pharmaceutical preparations encompass all types of formulations and in particular those that are suited for injection, e.g., powders that can be reconstituted as well as suspensions and solutions.

Exemplary excipients include, without limitation, those selected from the group consisting of carbohydrates, inorganic salts, antimicrobial agents, antioxidants, surfactants, buffers, acids, bases, and combinations thereof.

A carbohydrate such as a sugar, a derivatized sugar such as an alditol, aldonic acid, an esterified sugar, and/or a sugar polymer may be present as an excipient. Specific carbohydrate excipients include, for example: monosaccharides, such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol, sorbitol (glucitol), pyranosyl sorbitol, myoinositol, and the like.

The excipient can also include an inorganic salt or buffer such as citric acid, sodium chloride, potassium chloride, sodium sulfate, potassium nitrate, sodium phosphate monobasic, sodium phosphate dibasic, and combinations thereof.

The preparation may also include an antimicrobial agent for preventing or deterring microbial growth. Nonlimiting examples of antimicrobial agents suitable for the present invention include benzalkonium chloride, benzethonium chloride, benzyl alcohol, cetylpyridinium chloride, chlorobutanol, phenol, phenylethyl alcohol, phenylmercuric nitrate, thimersol, and combinations thereof.

An antioxidant can be present in the preparation as well. Antioxidants are used to prevent oxidation, thereby preventing the deterioration of the conjugate or other components of the preparation. Suitable antioxidants for use in the present invention include, for example, ascorbyl palmitate, butylated hydroxyanisole, butylated hydroxytoluene, hypophosphorous acid, monothioglycerol, propyl gallate, sodium bisulfite, sodium formaldehyde sulfoxylate, sodium metabisulfite, and combinations thereof.

A surfactant may be present as an excipient. Exemplary surfactants include: polysorbates, such as "Tween 20" and "Tween 80," and pluronics such as F68 and F88 (both of which are available from BASF, Mount Olive, N.J.); sorbitan esters; lipids, such as phospholipids such as lecithin and other phosphatidylcholines, phosphatidylethanolamines (although preferably not in liposomal form), fatty acids and fatty esters; steroids, such as cholesterol; and chelating agents, such as EDTA, zinc and other such suitable cations.

Acids or bases may be present as an excipient in the preparation. Nonlimiting examples of acids that can be used include those acids selected from the group consisting of hydrochloric acid, acetic acid, phosphoric acid, citric acid, malic acid, lactic acid, formic acid, trichloroacetic acid, nitric acid, perchloric acid, phosphoric acid, sulfuric acid, fumaric acid, and combinations thereof. Examples of suitable bases include, without limitation, bases selected from the group consisting of sodium hydroxide, sodium acetate, ammonium hydroxide, potassium hydroxide, ammonium acetate, potassium acetate, sodium phosphate, potassium phosphate, sodium citrate, sodium formate, sodium sulfate, potassium sulfate, potassium fumerate, and combinations thereof.

The amount of the conjugate (i.e., the conjugate formed between the active agent and the polymer described herein) in the composition will vary depending on a number of factors, but will optimally be a therapeutically effective dose when the composition is stored in a unit dose container (e.g., a vial). In addition, the pharmaceutical preparation can be housed in a syringe. A therapeutically effective dose can be determined experimentally by repeated administration of increasing amounts of the conjugate in order to determine which amount produces a clinically desired endpoint.

The amount of any individual excipient in the composition will vary depending on the activity of the excipient and particular needs of the composition. Typically, the optimal amount of any individual excipient is determined through routine experimentation, i.e., by preparing compositions containing varying amounts of the excipient (ranging from low to high), examining the stability and other parameters, and then determining the range at which optimal performance is attained with no significant adverse effects. Generally, however, the excipient will be present in the composition in an amount of about 1% to about 99% by weight, preferably from about 5%-98% by weight, more preferably from about 15-95% by weight of the excipient, with concentrations less than 30% by weight most preferred.

These foregoing pharmaceutical excipients along with other excipients are described in "Remington: The Science & Practice of Pharmacy", 19th ed., Williams & Williams, (1995), the "Physician's Desk Reference", 52nd ed., Medical Economics, Montvale, N.J. (1998), and Kibbe, A. H., Handbook of Pharmaceutical Excipients, 3rd Edition, American Pharmaceutical Association, Washington, D.C., 2000.

The pharmaceutical preparations of the present invention are typically, although not necessarily, administered via injection and are therefore generally liquid solutions or suspensions immediately prior to administration. The conjugates can be administered injected parenterally by intravenous injection, or less preferably by intramuscular or by subcutaneous injection. Suitable formulation types for parenteral administration include ready-for-injection solutions, dry powders for combination with a solvent prior to use, suspensions ready for injection, dry insoluble compositions for combination with a vehicle prior to use, and emulsions and liquid concentrates for dilution prior to administration, among others.

The pharmaceutical preparation can also take other forms such as syrups, creams, ointments, tablets, powders, and the like. Other modes of administration are also included, such as pulmonary, rectal, transdermal, transmucosal, oral, intrathecal, subcutaneous, intra-arterial, and so forth.

The invention also provides methods for administering a conjugate as provided herein to a patient suffering from a condition that is responsive to treatment with the conjugated agent. The method comprises administering, generally via injection, a therapeutically effective amount of the conjugate (preferably provided as part of a pharmaceutical preparation). The actual dose to be administered will vary depend upon the age, weight, and general condition of the subject, as well as the severity of the condition being treated, the judgment of the health care professional, and conjugate being administered. Therapeutically effective amounts are known to those skilled in the art and/or are described in the pertinent reference texts and literature. Generally, a therapeutically effective amount will range from about 0.001 mg to 100 mg, preferably in doses from 0.01 mg/day to 75 mg/day, and more preferably in doses from 0.10 mg/day to 50 mg/day.

Optimally, cleavage of the water-soluble polymer portion, which may be desirable to facilitate clearance from the body, can be facilitated through the incorporation of one or more physiologically cleavable and/or enzymatically degradable linkages such as urethane, amide, carbonate or ester-containing linkages, as described above, into the polymer component. In this way, clearance of the conjugate (via cleavage of individual water-soluble polymer portions) can be modulated by selecting the polymer molecular size and the type of linkage that would provide the desired clearance properties. One of ordinary skill in the art can determine the proper molecular size of the polymer as well as the cleavable functional group. Clearance properties can be evaluated by preparing a series of polymer derivatives with different polymer weights and cleavable functional groups, and then obtaining clearance profiles (e.g., through periodic blood or urine sampling) by administering the polymer derivatives to a patient and taking periodic blood and/or urine sampling.

EXPERIMENTAL

Materials

Dextran obtained from *Leuconostoc* ssp., having a molecular weight ~6,000, was purchased from Fluka Chemical Corp. and used for exploratory experiments. For drug delivery applications, where higher molecular weights are desired, dextran having molecular weights of 40 and 70 kDa was obtained from Pharmacosmos, located in Holbaek, Denmark. These higher molecular weight starting materials had polydispersity (PDI) values of 1.25-1.35.

Example 1

Preparation of Dextran(6K)-Monocarboxylic Acid (1a) by Mild Oxidation

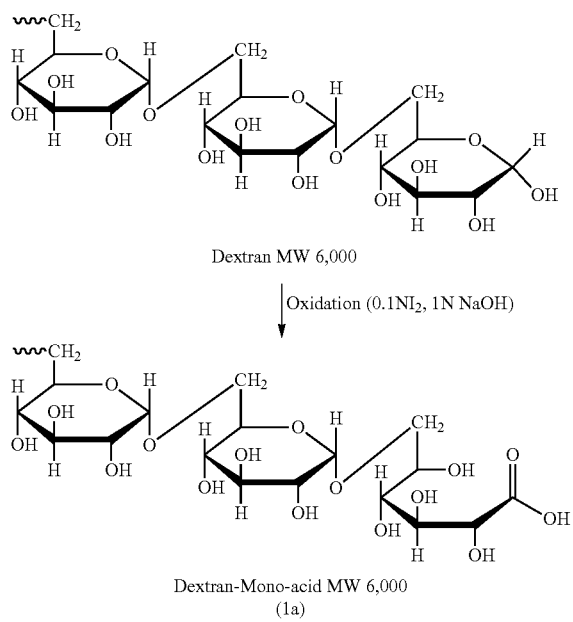

To a solution of Dextran 6 (10.0 g; Mw=6353, Mn=2,717, Mw/Mn=2.34; Fluka, product number 31388) in deionized water (12.0 ml) was added 0.1N iodine solution (2.0 ml) followed by slow addition of 1.0N sodium hydroxide solution until the solution became clear. This addition of iodine solution followed by slow addition of sodium hydroxide solution was repeated 18 times. The total amounts of added iodine solution and sodium hydroxide solution were 40.0 ml and 5.0 ml, respectively. The reaction mixture was dialyzed against deionized water using dialysis cassettes having a 3500 kD cutoff (Pierce). Water was distilled off under reduced pressure, and the wet product was dried under vacuum overnight. Yield 9.2 g. Anion exchange chromatography showed that the product contained 46.1% of dextran monocarboxylic acid (1) and 51.9% of unreacted dextran.

Example 2

Purification of Dextran(6K)-Monocarboxylic Acid (1a) by Anion Exchange Chromatography A sample of the product from Example 1 (1.0 g; containing 46.1% of dextran acid and 51.9% of unreacted dextran) was dissolved in deionized water (100 ml) and applied to a DEAE Sepharose FF column (10 ml). The column was then washed with deionized water. The product adsorbed on the column was eluted with 10% ammonia. Ammonia and water were distilled off from the eluate under reduced pressure, and the residue was dried under vacuum, giving 0.2 g of white solid product. Anion exchange chromatography showed that the product contained 99.1% of dextran monocarboxylic acid (1a) and 0.9% of dextran.

Example 3

Preparation of Dextran(40K)-Monocarboxylic Acid (1b) by Mild Oxidation

To a solution of Dextran 40 (10.0 g; Mw=46,021, Mn=22,617, Mw/Mn=2.03; Sigma-Aldrich) in deionized water (12.0 ml) was added 0.1N iodine solution (2.0 ml) followed by slow addition of 1.0N sodium hydroxide solution until the solution became clear. This addition of iodine solution followed by slow addition of sodium hydroxide solution was repeated several times. The total amounts of added iodine solution and sodium hydroxide solution were 34.0 ml and 5.1 ml, respectively. The reaction mixture was dialyzed against deionized water using dialysis cassettes having a 3500 MW cutoff (Pierce). Water was then distilled off under reduced pressure, and the wet product was dried under vacuum overnight. Yield 9.3 g. Anion exchange chromatography showed that the product contained 36.4% of dextran-diacid, 59.3% of dextran-monoacid (1b), and 4.3% of unreacted dextran.

Example 4

Purification of Dextran(40K)-Monocarboxylic Acid (1b) by Anion Exchange Chromatography A sample of the product from Example 3 (5.0 g) was dissolved in deionized water (250 ml) and applied to a DEAE Sepharose FF column (50 ml). The column was then washed with deionized water. The following fractions were collected:

| Fraction # | Volume (ml) | Dextran-Diacid, % | Dextran-Monoacid (1b), % | Dextran, % |
|---|---|---|---|---|
| 1 | 25 | 0 | 0 | 0 |
| 2 | 25 | 0 | 0 | 100 |
| 3 | 25 | 0 | 0 | 100 |
| 4 | 25 | 0 | 0 | 100 |
| 5 | 25 | 0 | 36.0 | 64.0 |
| 6 | 25 | 4.1 | 81.4 | 14.5 |
| 7 | 25 | 8.9 | 79.6 | 11.5 |
| 8 | 25 | 14.4 | 80.3 | 5.3 |

-continued

| Fraction # | Volume (ml) | Dextran-Diacid, % | Dextran-Monoacid (1b), % | Dextran, % |
|---|---|---|---|---|
| 9 | 25 | 12.7 | 82.1 | 5.2 |
| 10 | 25 | 15.3 | 80.0 | 4.7 |
| 11 | 25 | 0 | 100 | 0 |

Example 5

Preparation of Dextran(40K)-Monocarboxylic Acid (1b) by Controlled Oxidation of Dextran Monitored by Ion Exchange Chromatography To a solution of Dextran 40 (10.0 g; Mw=46,021, Mn=22,617, Mw/Mn=2.03; Sigma-Aldrich) in deionized water (12.0 ml) was added 0.1N iodine solution (2.0 ml) followed by slow addition of 1.0N sodium hydroxide solution (~0.25 ml) until the solution became clear. Ion exchange chromatography showed that the reaction mixture at that point contained 25.3% of dextran monoacid and 74.7% of unreacted dextran. The addition of iodine solution (2.0 ml) followed by slow addition of sodium hydroxide solution was repeated two more times. At this stage, ion exchange chromatography showed that the reaction mixture contained 50.7% of dextran monoacid and 49.3% of unreacted dextran. After addition of a fourth portion of iodine solution (2.0 ml) followed by slow addition of sodium hydroxide, ion exchange chromatography showed that the reaction mixture contained 84.9% of dextran monoacid and 15.1% of unreacted Dextran. A fifth addition of iodine solution (2.0 ml) followed by slow addition of sodium hydroxide produced a reaction mixture containing 3.1% of dextran diacid, 83.9% of dextran monoacid, and 13.0% of unreacted dextran. This final reaction mixture was diluted with deionized water (500 ml) and the obtained solution was filtered through a desalting column containing 120 ml of Amberlite IR-120 and 120 ml of Amberlite IRA-67 ion exchange resin. Water was then distilled off under reduced pressure from the filtrate, and the wet product was dried under vacuum overnight. Yield 8.5 g.

Example 6

Preparation of Dextran(40K)-O-(Carboxymethyl)Oxyimine (2)

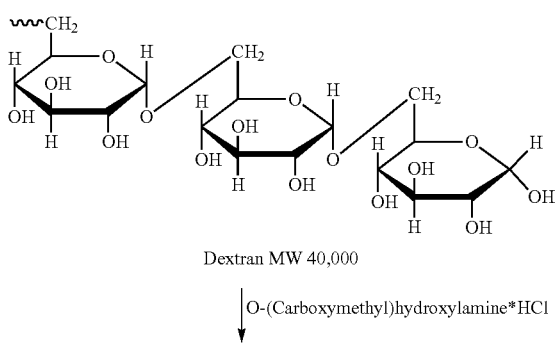

Dextran MW 40,000

↓ O-(Carboxymethyl)hydroxylamine*HCl

-continued

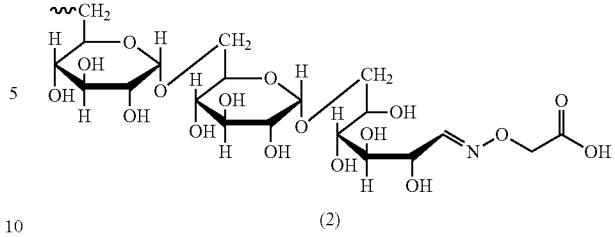

(2)

To a solution of Dextran 40 (2.5 g; Mw=46,021, Mn=22,617, Mw/Mn=2.03; Sigma-Aldrich) in 0.1M sodium acetate buffer (pH=5.5) was added O-(carboxymethyl) hydroxylamine hemihydrochloride (0.1 g; Sigma-Aldrich). The pH was readjusted to 5.2 and the mixture was stirred overnight at room temperature. Ion exchange chromatography showed that the product contained 77.1% of dextran(40K)-O-(carboxymethyl)oxyimine (2) and 22.9% of unreacted dextran.

Example 7

Preparation of Tetra(Ethylene Glycol)-α-Amino-ω-Butanoic Acid, Orthoester (5)

This reagent can be used to prepare a carboxy-terminated carbohydrate derivative, as shown in Example 8 below.

A. Tetra(Ethylene Glycol)-Monobutanoic Acid, Orthoester (3)

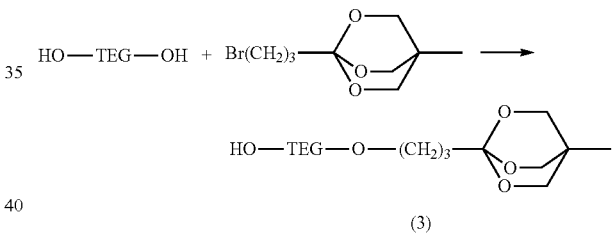

(3)

A solution of tetra(ethylene glycol) (97.1 g, 0.5 mole) in toluene (200 ml) was azeotropically dried by distilling off toluene under reduced pressure. The dried tetra(ethylene glycol) was dissolved in anhydrous toluene (180 ml), and 1.0 M solution of potassium tert-butoxide in tert-butanol (120 ml, 0.12 moles) and 1-(3-bromopropyl)-4-methyl-3,6,7-trioxabicyclo[2,2,2]octane (25.1 g, 0.1 mole) were added. The mixture was placed under an argon atmosphere, heated to 70° C. and stirred overnight. After cooling to room temperature, the mixture was filtered and the solvents were distilled off under reduced pressure. The crude product was dissolved in 1000 ml of deionized water and the disubstituted product was removed by extraction with ethyl acetate (2×100 ml). Sodium chloride (100 g) was added and the product was extracted with dichloromethane (200, 100, and 100 ml). The extract was dried (MgSO$_4$) and the solvent was distilled off under reduced pressure. The crude product (3) (26.6 g) was dissolved in 300 ml of deionized water and extracted with dichloromethane (200, 100, and 50 ml). The extract was dried (MgSO$_4$) and the solvent was distilled off under reduced pressure. Yield: 23.4 g. NMR (d$_6$-DMSO): 0.74 ppm (s, —CH$_3$, orthoester) 1.56 μm (m, —CH$_2$—CH$_2$-orthoester), 3.51 ppm (bm, —OCH$_2$CH$_2$O—), 3.80 ppm (s, —CH$_2$, orthoester), 4.58 ppm (t, —OH). Purity: ~100%.

B. Tetra(Ethylene Glycol)-α-Mesylate-ω-Butanoic Acid, Orthoester (4)

C. Tetra(Ethylene Glycol)-α-Amine-ω-Butanoic Acid, Orthoester (5)

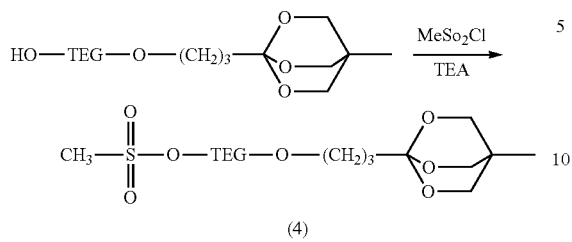

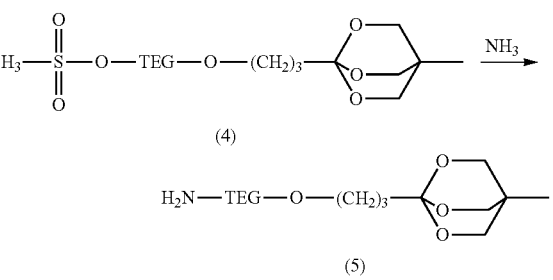

A mixture of tetra(ethylene glycol) monobutanoic acid orthoester (3) (20 g, 0.0549 moles), prepared in step A above, and toluene (200 ml) was azeotropically dried by distilling off toluene under reduced pressure. The dried tetra(ethylene glycol) monobutanoic acid orthoester was dissolved in anhydrous toluene (200 ml). Then, 40 ml of anhydrous dichloromethane and 15.4 ml of triethylamine (0.1105 moles) were added to the solution followed by the dropwise addition of 7.4 g of methanesulfonyl chloride (0.0646 moles) dissolved in dichloromethane (80 ml) while maintaining the solution temperature at 0-5° C. The solution was stirred an additional 2 h at room temperature under argon atmosphere. The resulting mixture was filtered, sodium carbonate (2 g) was added, and the mixture was stirred 1.0 h. Finally the solution was filtered and the solvents distilled off under reduced pressure. Yield: 23.2 g. NMR (d$_6$-DMSO): 0.74 ppm (s, —CH$_3$, orthoester) 1.56 ppm (m, —CH$_2$—CH$_2$-orthoester), 3.18 ppm (s, CH$_3$-methanesulfonate), 3.51 ppm (bm, —OCH$_2$CH$_2$O—), 3.67 ppm (m, —CH$_2$—CH$_2$-methanesulfonate), 3.80 ppm (s, —CH$_2$, orthoester), 4.31 ppm (m, —CH$_2$-methanesulfonate). Purity: ~100%.

A mixture of tetra(ethylene glycol)-α-mesylate-ω-butanoic acid orthoester (4) (23.2 g), prepared in step B above, ethyl alcohol (100 ml), and concentrated ammonia (1000 ml) was stirred for 88 h at room temperature. The reaction mixture was extracted with dichloromethane (600, 400, and 400 ml), the extract was dried (MgSO$_4$), and the solvent was distilled off under reduced pressure. Yield 19.5 g. NMR (D$_2$O): 0.74 ppm (s, —CH$_3$, orthoester) 1.63 ppm (m, —CH$_2$—CH$_2$-orthoester), 2.71 ppm (t, —CH$_2$-amine), 3.58 ppm (bm, —OCH$_2$CH$_2$O—), 3.67 ppm (m, —CH$_2$—CH$_2$— methanesulfonate), 3.89 ppm (s, —CH$_2$, orthoester). Purity: ~100%.

Example 8

Preparation of Oxyimine-Linked Dextran(40K)-Butanoic Acid (7)

This reagent was prepared according to the following scheme, described in greater detail below:

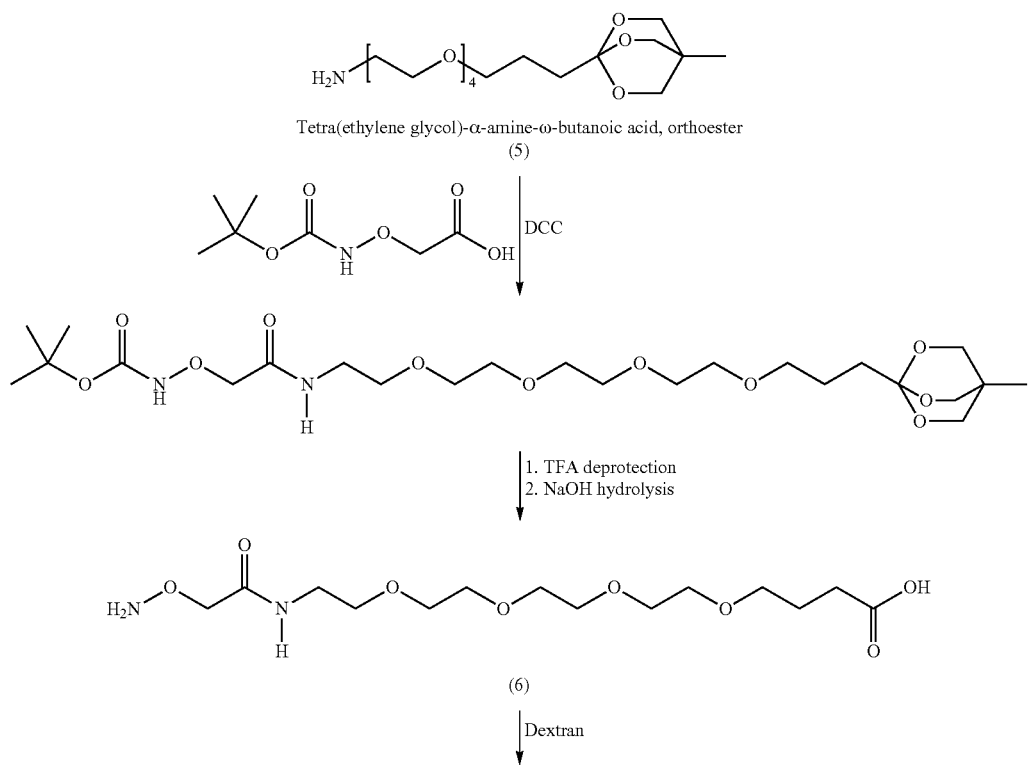

-continued

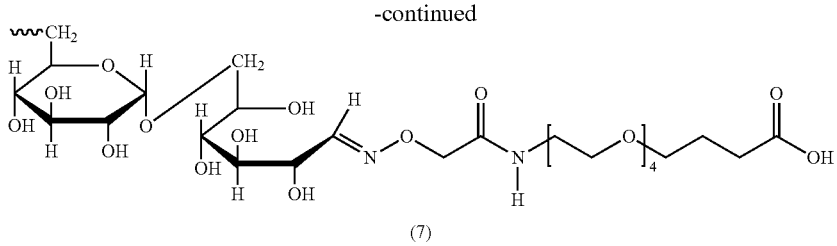

(7)

A. Preparation of Tetra(Ethylene Glycol)-α-Aminooxyacetamide-ω-Butanoic Acid (6)

To a solution of (Boc-aminooxy)acetic acid (2.0 g, 0.0105 moles; Sigma-Aldrich), N-hydroxysuccinimide (1.20 g, 0.0105 moles), 1-hydroxybenzotriazole (0.30 g, 0.0022 moles) in anhydrous $CH_2Cl_2$ (100 ml) cooled to ~5° C., N,N-dicyclohexylcarbodiimide (1.70 g, 0.0115 moles) dissolved in anhydrous $CH_2Cl_2$ (30 ml) was added and the mixture was stirred 1 h at 5-15° C. Tetra(ethylene glycol)-α-amine-ω-butanoic acid orthoester (5), prepared as described in Example 7 (4.0 g, 0.0109 moles), and triethylamine (3.80 ml) were then added, and the mixture was stirred overnight at room temperature under nitrogen atmosphere. The mixture was filtered and the solvent was distilled off. The residue was dissolved in deionized water (80 ml) and the product was extracted with dichloromethane. The extract was dried and the solvent was distilled off under reduced pressure, giving 4.8 of the Boc- and orthoester-protected linker as a liquid product.

The Boc- and orthoester-protected linker, prepared as described above (4.8 g), was dissolved in a mixture of trifluoroacetic acid (30 ml) and anhydrous dichloromethane (30 ml). The resulting solution was stirred 2 h at room temperature, after which time the dichloromethane and trifluoroacetic acid were distilled off under reduced pressure. The residue was dissolved in deionized water (40 ml) and 1.0M sodium hydroxide was added to adjust the pH to 12.2. The mixture was stirred 2 h, keeping the pH 12.1-12.3 by periodical addition of 0.1M sodium hydroxide. The pH was then adjusted to 7.5, and a portion of water was distilled off under reduced pressure, giving 12.2 g of concentrated solution of tetra(ethylene glycol) linker (6) containing terminal oxyamine and butanoic acid groups.

B. Reaction of Heterobifunctional Reagent (6) with Dextran(40K)

To a solution of Dextran 40 (2.5 g; Mw=46,021, Mn=22,617, Mw/Mn=2.03; Sigma-Aldrich) in 0.1M sodium acetate buffer, pH=5.5, a solution of tetra(ethylene glycol)-α-aminooxyacetamide-ω-butanoic acid (6) (from part A above) was added. The pH was readjusted to 5.2 with acetic acid and the mixture was stirred overnight at room temperature. The solution was dialyzed 3 times against DI water using Dialysis Cassette MW CO 3.5K (Pierce). The water was then distilled off under reduced pressure. The wet crude product (7) was dried under vacuum overnight, giving 2.2 g of white solid. NMR analysis performed in $D_2O$ showed that the substitution of end groups of dextran with butanoic acid groups was 38.6%.

Example 9

Purification of Oxyimine-Linked Dextran(40K)-Butanoic Acid (7)

The crude functionalized dextran(7) from step B (1.8 g) was dissolved in deionized water (180 ml) and applied to a DEAE Sepharose FF column (50 ml). The column was then washed with deionized water. The material adsorbed on the column product was eluted with 10% NaCl solution. The eluate (100 ml) was dialyzed 4 times against DI water using Dialysis Cassette MW CO 3.5K (Pierce). The water was distilled off under reduced pressure, and the wet product was dried under vacuum overnight, giving 0.5 g of purified (7) as a white solid. NMR analysis performed in $D_2O$ showed that the substitution of end groups of dextran with butanoic acid groups in the purified product was ~100%.

Example 10

Preparation of Dextran(6K)-Hexamethylenediamine (8)

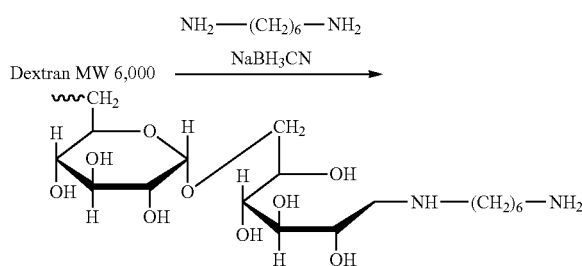

A mixture of hexamethylenediamine (1.8 g), sodium cyanoborohydride (1.2 g), acetic acid (0.44 ml) and DMSO (12 ml) was warmed to 85° C. Dextran 40 (1.5 g; Mw=46,021, Mn=22,617, Mw/Mn=2.03; Sigma-Aldrich) was added slowly during 3 h, and the mixture was stirred 24 h at 85° C. After cooling to room temperature, the reaction mixture was dialyzed 3 times against DI water using Dialysis Cassette MW CO 3.5K (Pierce). The water was distilled off under reduced pressure, and the wet product (8) was dried under vacuum overnight. The product was purified using cation exchange chromatography. NMR analysis performed in $D_2O$ showed that the substitution of end groups of dextran with amine groups was 38.6%.

Example 11

Preparation of Heterobifunctional Reagent Di(Ethylene Glycol)-α-Amino-ω-Oxyamine (11)

A. Preparation of CBZ—NH—CH$_2$—CH$_2$—OCH$_2$CH$_2$—OH (9)

To 2-(2-aminoethoxy)ethanol (20 g) dissolved in dichloromethane (200 ml) was added stepwise triethylamine (26.5 ml) and benzyloxy(carbonyloxy)succinimide (47.47 g). The reaction mixture was stirred overnight at room temperature. The solvent was distilled off under reduced pressure and the residue was dissolved in deionized water (500 ml). The insoluble layer was separated, and the aqueous layer was mixed with 50 g of NaCl and the pH adjusted to 5.0 with 5% $H_3PO_4$. The product was extracted with dichloromethane (100 ml, 50 ml, and 50 ml) and the extract was dried with $MgSO_4$, filtered, and evaporated to dryness under reduced pressure. The residue was dried under vacuum overnight, then combined with the previously separated insoluble layer and dissolved in dichloromethane (300 ml). The solution was washed with 5-% aqueous NaCl solution (3×50 ml) and dried with $MgSO_4$. The solvent was distilled under reduced pressure, and the residue was dried overnight under vacuum, giving 40 g of the desired product.

B. Preparation of $CBZ—NH—CH_2CH_2OCH_2CH_2—O(SO_2)CH_3$ (10)

CBZ-Methanesulfonyl chloride (7.1 ml) dissolved in anhydrous dichloromethane (70 ml) was slowly added to the product (9) of step A, and the mixture was stirred overnight at room temperature under nitrogen atmosphere. The mixture was filtered, stirred 1 h with solid $Na_2CO_3$ (26.6 g), and refiltered. The filtrate was concentrated under reduced pressure, the residue was re-dissolved in toluene (150 ml), and the resulting solution was filtered and concentrated by distillation under reduced pressure. The residue was dried overnight under vacuum, giving 24 g of the desired product (10).

C. Preparation of $CBZ—NH—CH_2CH_2OCH_2CH_2—ONH_2$ (11)

$CBZ—NH—CH_2CH_2OCH_2CH_2—O(SO_2)CH_3$ (10) (24 g), prepared as described in step B, was dissolved in $CH_3CN$ (240 ml), and endo-N-hydroxy-5-norbornene-2,3-dicarboximide (20.5 g) followed by diisopropylethylamine (39.5 ml) was added. The reaction mixture was refluxed at 93° C. overnight under nitrogen atmosphere. After cooling to room temperature, the mixture was filtered and the solvent distilled off under reduced pressure. The residue was dissolved in dichloromethane (200 ml), and the solution was washed with 0.1 M phosphate buffer (pH 5.0, 2×100 ml) and dried with ($MgSO_4$). The solvent was distilled off under reduced pressure, the residue was dissolved in ethyl alcohol (150 ml), and butylamine (28.0 ml) was added. The mixture was stirred overnight at 90° C. under nitrogen atmosphere. The solution was filtered and the solvent was distilled off under reduced pressure. The crude product was dissolved in 100 mM phosphate buffer, pH=4.5 (120 ml), and the solution was filtered. The impurities were removed by extraction with ethyl ether (3×20 ml). NaCl (15 g) was added, the pH was readjusted to 9 with 1.0 M NaOH, and the product was extracted with dichloromethane (3×50 ml). The extract was dried with anhydrous magnesium sulfate and the solvent was distilled off under reduced pressure giving (11) as a clear liquid product.

Example 12

Preparation of Tetra(Ethylene Glycol)-α-Oxyamino-ω-Butyraldehyde, Diethyl Acetal (14)

This reagent can be used to prepare an aldehyde-terminated carbohydrate derivative, as shown in Example 13 below.

A. Tetra(Ethylene Glycol)Mono-Butyraldehyde, Diethyl Acetal (12)

A mixture of tetra(ethylene glycol) (97.1 g, 0.500 moles) and toluene (200 ml) was azeotropically dried by distilling off toluene under reduced pressure. The dried tetra(ethylene glycol) was dissolved in anhydrous toluene (180 ml), and a 1.0 M solution of potassium tert-butoxide in tert-butanol (120.0 ml, 0.120 moles) and 4-chlorobutyraldehyde diethyl acetal (18.1 g, 0.100 moles) were added. The mixture was stirred at 90° C. overnight under argon atmosphere. After cooling to room temperature, the mixture was filtered and the solvents were distilled off under reduced pressure. The crude product was dissolved in 1000 ml deionized water and the resulting solution was filtered through activated carbon. Sodium chloride (10 g) was added and the product was extracted with dichloromethane (250, 200, and 150 ml). The extract was dried ($MgSO_4$) and the solvent was distilled off under reduced pressure. Yield: 20.3 g. NMR ($d_6$-DMSO): 1.10 ppm (t, $CH_3—C—$) 1.51 ppm (m, $C—CH_2—CH_2—$), 3.49 ppm (bm, $—OCH_2CH_2O—$), 4.46 ppm (t, —CH, acetal), 4.58 ppm (t, —OH). Purity: ~100%.

B. Tetra(Ethylene Glycol)-α-Mesylate-ω-Butyraldehyde Diethyl Acetal (13)

A mixture of tetra(ethylene glycol) mono-butyraldehyde diethyl acetal (12) (12.5 g, 0.037 moles), prepared in step A above, and toluene (120 ml) was azeotropically dried by distilling off toluene under reduced pressure. The dried tetra(ethylene glycol) mono-butyraldehyde, diethyl acetal was dissolved in anhydrous toluene (100 ml). To the solution was added 20 ml of anhydrous dichloromethane and 5.7 ml of triethylamine (0.041 moles). Then 4.5 g of methanesulfonyl chloride (0.039 moles) was added dropwise. The solution was stirred at room temperature under nitrogen atmosphere overnight. Sodium carbonate (5 g) was added, and the mixture was stirred 1 h. The solution was filtered and solvents were distilled off under reduced pressure. NMR ($d_6$-DMSO): 1.10 ppm (t, $CH_3—C—$) 1.51 ppm (m, $C—CH_2—CH_2—$), 3.17 ppm (s, $CH_3—$ methanesulfonate), 3.49 ppm (bm, $—OCH_2CH_2O—$), 4.30 ppm (m, $—CH_2$-methanesulfonate), 4.46 ppm (t, —CH, acetal). Purity: ~100%.

C. Tetra(Ethylene Glycol)-α-Oxyamino-ω-Butyraldehyde Diethyl Acetal (14)

To a solution of tetra(ethylene glycol)-α-mesylate-ω-butyraldehyde diethyl acetal (13) (20.0 g), prepared in step B above, in anhydrous acetonitrile (200 ml), endo-N-hydroxy-5-norbornene-2,3-dicarboximide (13.0 g) and diisopropylethylamine (21.0 ml) was added and the mixture was stirred at 90° C. overnight under nitrogen atmosphere. The solution was filtered and the solvent was distilled off under reduced pressure. The residue was dissolved in ethyl alcohol (100 ml) and butylamine (26.0 ml) was added. The mixture was stirred 6 h at 90° C. under nitrogen atmosphere. The solution was filtered and the solvent was distilled off under reduced pressure. The crude product was dissolved in 100 mM phosphate buffer, pH=5.0 (200 ml), and the solution was filtered. The impurities were removed by extraction with ethyl ether (3×25 ml). NaCl (20 g) was then added, the pH was readjusted to 9 with 1.0 M NaOH, and the product was extracted with dichloromethane (3×50 ml). The extract was dried with anhydrous magnesium sulfate and the solvent was distilled off under reduced pressure, giving 18 g of clear viscous water white liquid product. NMR (DMSO-$d_6$): 1.11 ppm (t, $CH_3—C—$) 1.51 ppm (m, $C—CH_2—CH_2—$), 3.47 ppm (bm, $—OCH_2CH_2O—$), 4.56 ppm (t, —CH, acetal), 5.97 ppm (s, $H_2N—O—$). Purity: ~100%.

Example 13

Preparation of Oxyimine-Linked Dextran(40K)-Butyraldehyde (16)

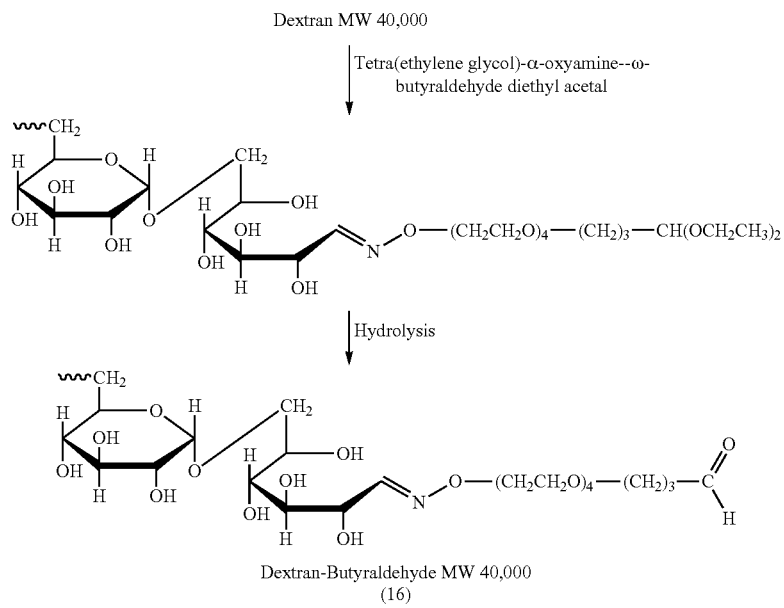

A. Oxyimine-Linked Dextran(40K)-Butyraldehyde Diethyl Acetal (15)

To a solution of Dextran 40 (2.5 g; Mw=46,021, Mn=22,617, Mw/Mn=2.03; Sigma-Aldrich) in 0.1M sodium acetate buffer, pH=5.2 (20 ml), tetra(ethylene glycol)-α-oxyamino-ω-butyraldehyde diethyl acetal (14) (0.30 g), prepared as described in Example 12, was added. The pH was readjusted to 5.2 and the mixture was stirred overnight at room temperature. The solution was dialyzed 3 times against DI water using Dialysis Cassette MW CO 3.5K (Pierce). The water was then distilled off under reduced pressure. The wet product was dried under vacuum overnight, giving 2.3 g of a white solid. NMR analysis performed in $D_2O$ showed that the substitution of end groups of dextran with butyraldehyde diethyl acetal groups was 78.9%.

B. Oxyimine-Linked Dextran(40K)-Butyraldehyde (16)

Dextran(40K)-butyraldehyde diethyl acetal (0.336 g), prepared in step A above, was dissolved in 2 ml of 10 mM phosphate buffer (pH=7.2), and the pH was adjusted to 2.0 with 5% phosphoric acid. The mixture was stirred 1.5 h. The pH was then readjusted to 6.5 with 1.0 N sodium hydroxide. The obtained solution of (16) was used directly for the dextran modification of lysozyme.

Example 14

Reaction of oxyimine-Linked Dextran(40K)-Butyraldehyde (16) with Lysozyme

To the solution of oxyimine-linked dextran(40K)-butyraldehyde (16) obtained as described in Example 13 above, lysozyme (6 mg; Sigma-Aldrich) was added, and the mixture was stirred for 15 min, followed by addition of 0.21 ml of 0.1 M aqueous solution of sodium cyanoborohydride (Sigma-Aldrich). The mixture was stirred overnight at room temperature. HPLC analysis showed that Dextran-Lysozyme conjugate (17) was formed.

Example 15

Larger Scale Preparation of Oxyimine-Linked Dextran(40K)-Butyraldehyde (16)

A. Oxyimine-Linked Dextran(40K)Butyraldehyde Diethyl Acetal (15)

To a solution of Dextran 40 (130 g; Mw=40,210, Mn=30,931, Mw/Mn=1.3; Pharmacosmos A/S, Denmark) in 0.1M sodium acetate buffer, pH=5.2 (780 ml), tetra(ethylene glycol)-α-oxyamino-ω-butyraldehyde diethyl acetal (14) (20.3 g), prepared as described in Example 12 above, was added. The pH was readjusted to 5.2 with acetic acid and the mixture was stirred overnight at room temperature. The crude product was precipitated with isopropyl alcohol, collected by vacuum filtration and dried. The precipitation process was repeated two more times to remove all unreacted reagent. The yield of the solid dry product (15) was 114 g. NMR analysis performed in $D_2O$ showed that the substitution of end groups of dextran with butyraldehyde diethyl acetal groups was ~85%.

B. Oxyimine-Linked Dextran(40K)-Butyraldehyde (16)

Dextran(40K)-butyraldehyde diethyl acetal (114 g), prepared in step A above, was dissolved in 1100 ml of deionized water and the pH was adjusted to 3.0 with 10% phosphoric acid, and the mixture was stirred for 1 h. The pH was then readjusted to 6.8 with 1.0 N sodium hydroxide. The solution was concentrated to dryness under reduced pressure, the crude product was redissolved in 600 ml of deionized water, and the solution was lyophilized, giving 108 g of white solid product. NMR analysis performed in D$_2$O showed that the substitution of end groups of dextran with butyraldehyde groups was ~80%.

Example 16

Conjugation of Protegrin-1 with Oxyimine-Linked Dextran$_{40K}$ Tetraethylene Glycol Butyraldehyde (16)

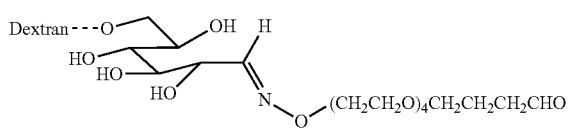

(16)

Stock solutions of 0.3 mg/mL protegrin-1 and 55 mg/mL dextran tetraethylene glycol (TEG) butyraldehyde 40K (16), both in 50 mM HEPES, pH 7.0, were prepared. To initiate a reaction, both stock solutions were brought to 25° C. and then mixed in equal volumes. The reaction mixture was stirred at 25° C. After 1 hour reaction, 100 µM sodium cyanoborohydride (final concentration) was added and the reaction was allowed to proceed for an additional 4 hours.

The dextran-protegrin-1 conjugate (18) was purified from the reaction mixture by cation-exchange chromatography using CM Sepharose (GE Healthcare). Thus, upon completion of the conjugation reaction, the reaction mixture was diluted 10-fold with water and loaded onto a column packed with CM Sepharose resin. The resin was washed with buffer B (10 mM HEPES, pH 7, 1M NaCl) and equilibrated with buffer A (10 mM HEPES, pH 7) prior to sample loading. After loading, the column was washed with 2 column volumes buffer A. Conjugated and nonconjugated peptides were eluted in a linear gradient of 0-100% buffer B in 10 column volumes at a flow rate of 7 mL/min.

Fractions containing dextran-butyraldehyde-40K-protegrin-1 were pooled, dialyzed against water, lyophilized and stored at –80° C. SDS-PAGE analysis (4-12% gel) of the purified dextran-butryaldehyde-40K-protegrin-1 conjugate (18) is shown in FIG. 1. Dextran perturbs the gel migration of the dextran-peptide conjugate; the conjugate's band location is not indicative of its size.

Example 17

Conjugation of C-Peptide (S20C) with Oxyimine-Linked Dextran$_{40K}$ Tetraethylene Glycol Butyraldehyde (16)

Stock solutions of 2 mg/mL C-peptide (S20C) and 200 mg/mL oxyimine-linked_dextran tetraethylene glycol (TEG)-butyraldehyde 40K (16), both in 500 mM HEPES, pH 7.0, were prepared. To initiate a reaction, both stock solutions were brought to 25° C. and then mixed in equal volumes. The reaction mixture was stirred at 25° C. After 1 hour reaction, 10 mM sodium cyanoborohydride (final concentration) was added, and the reaction was allowed to proceed for an additional 16 hours.

The dextran-C-peptide (S20C) conjugate (19) was purified from the reaction mixture by anion-exchange chromatography using Q HP Sepharose resin (GE Healthcare). Thus, upon completion of the conjugation reaction, the reaction mixture was diluted 2-fold with water and loaded onto a column packed with the Sepharose resin. The resin was washed with buffer B (10 mM HEPES, pH 7, 1M NaCl) and equilibrated with buffer A (10 mM HEPES, pH 7) prior to sample loading. After loading, the column was washed with 2 CV buffer A. Conjugated and nonconjugated peptides were eluted in a linear gradient of 0-100% buffer B in 10 CV at a flow rate of 8 mL/min. A conjugate-containing fraction collected during chromatography with Q HP Sepharose was diluted 10-fold with water and re-loaded onto the Q column in order to concentrate the conjugate. The conjugate (19) was eluted with 100% buffer B.

Fractions collected during both anion exchange chromatography runs were analyzed using reversed-phase HPLC. An Agilent Poroshell 300-SB-C8 column was used with a flow rate of 0.2 ml/min and a column temperature of 50° C. Detection was carried out at 215 nm. The column was equilibrated in 0% Mobile Phase B, and conjugate separation was achieved using the gradient timetable shown below:

| Time (min) | % Mobile phase A (0.1% TFA in water) | % Mobile phase B (0.85% TFA in CH$_3$CN) |
| --- | --- | --- |
| 0.00 | 100.0 | 0.0 |
| 5.00 | 70.0 | 30.0 |
| 15.00 | 40.0 | 60.0 |
| 20.00 | 20.0 | 80.0 |

Figure 2:
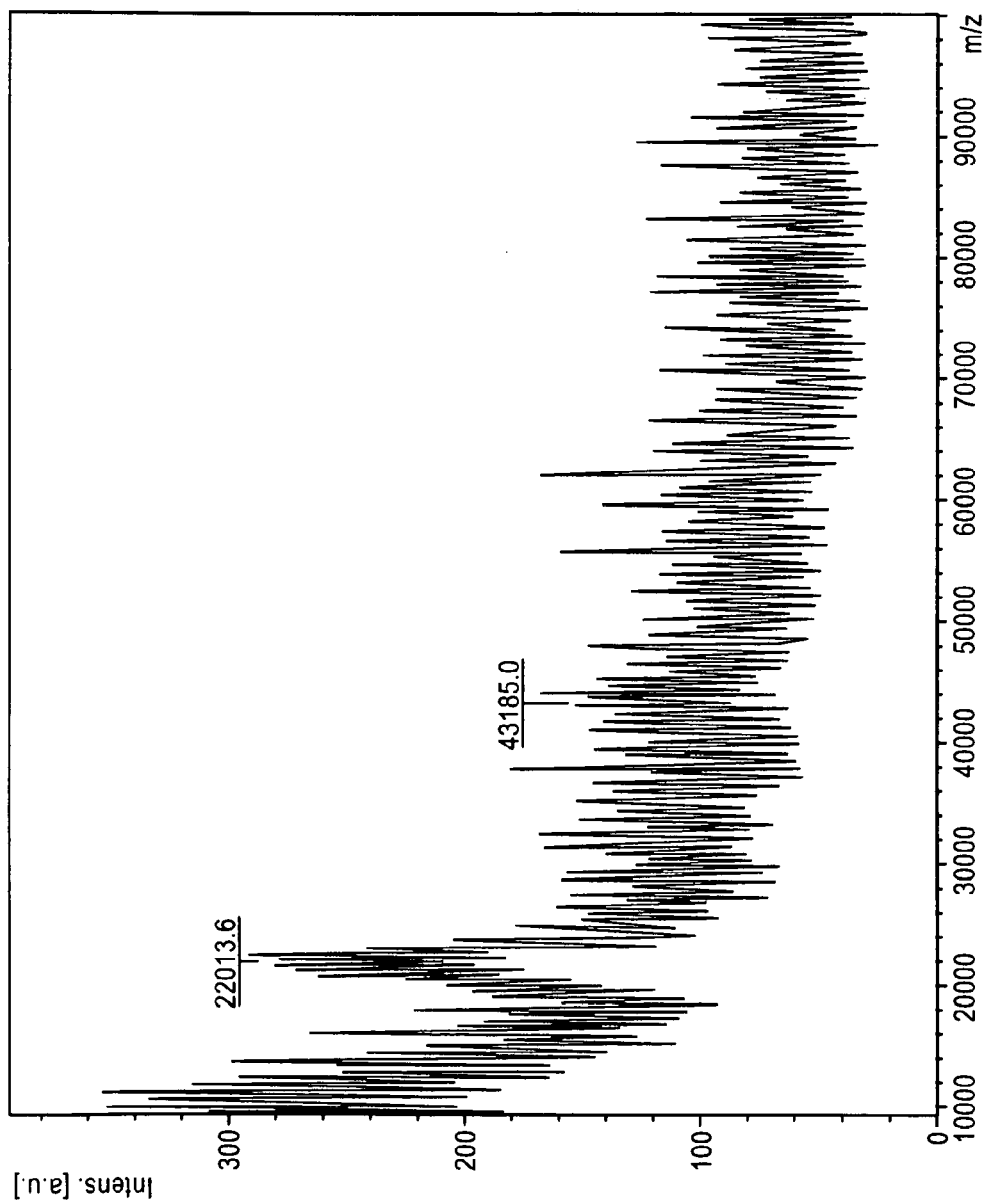
FIG. 2 shows a MALDI-TOF spectrum for mono-Dextran$_{40K}$-C-peptide (S20C) conjugate, prepared as described in Example 17. The peaks at 43.2 kDa and 22.0 kDa agree with molecular weights of the singly and doubly charged forms of the conjugated peptide.

The concentrated purified conjugate (19) collected from the second anion exchange chromatography run was dialyzed against water and frozen at –80° C. The purity of the mono-dextran conjugate (19) was >93% by RP-HPLC analysis, and the mass as determined by MALDI-TOF was within the expected range (FIG. 2).

Example 18

Conjugation of Insulin with Oxyimine-Linked Dextran$_{40K}$ Tetraethylene Glycol butyraldehyde (16)

Insulin contains three primary amine groups, all of which can undergo a reductive amination reaction with an aldehyde. Reactions of insulin with oxyimine-linked dextran$_{40K}$ tetraethylene glycol butyraldehyde (16) therefore produce a mixture of mono-, di- and tri-conjugated peptides. The relative yields of these products depend primarily on the molar ratios of insulin and the dextran reagent used in the reactions, and the reaction conditions (e.g., reaction time and temperature). The relative yield of the mono-conjugated peptide was determined to be very low unless reaction conditions were selected in which the majority of the insulin remained unreacted. Thus, in order to increase the relative and absolute yields of mono-conjugated insulin, a fraction of the amine groups on the peptide were blocked by acetylation prior to reacting the peptide and the dextran reagent. This example will describe the conjugation of both non-acetylated and partially acetylated insulin.

A. Conjugation of Non-Acetylated Insulin with Oxyimine-Linked Dextran$_{40K}$ Tetraethylene Glycol Butyraldehyde (16)

Stock solutions of 2 mg/ml insulin and 42/mL oxyimine-linked dextran-butyrALD-40K (16) were prepared in DMSO/TEA (95%:5%, v/v). To initiate a reaction, both stock solutions were brought to ambient temperature and then mixed in equal volumes. After 5 min reaction with stirring at ambient temperature, 1 M sodium cyanoborohydride was added, to a final concentration of 20 mM, and the reaction was allowed to proceed with continued stirring for 22 hours at ambient temperature.

The product dextran-butyrALD-40K-insulin (20a) was purified from the reaction mixture by anion-exchange chromatography using Q Sepharose FF (GE Healthcare). Thus, upon completion of the conjugation reaction, the reaction mixture was diluted 15-fold with 20 mM HEPES (pH 7) and the mixture was loaded onto a column packed with Q Sepharose FF resin. The resin was washed with Buffer B (20 mM HEPES, 1.0 M sodium chloride, pH 7) and equilibrated with Buffer A (20 mM HEPES, pH 7) prior to sample loading. After loading, the resin was washed with 5 column volumes Buffer A. Conjugated and nonconjugated peptides were eluted using a linear gradient of 0-100% Buffer B over 10 column volumes at a flow rate of 150 cm/h.

B. Conjugation of Partially Acetylated Insulin with Oxyimine-Linked Dextran$_{40K}$ Tetraethylene Glycol Butyraldehyde (16)

Stock solutions of 2.5 mg/mL (430 μM) insulin, 2.24 mg/mL (8.62 mM) sulfo-N-hydroxysuccinimide (NHS)-acetate, and 138 mg/mL (3.45 mM) oxyimine-linked dextran-butyrALD-40K were prepared in DMSO/TEA (95%:5%, v/v), DMSO, and DMSO/TEA (99.35%:0.65%, v/v), respectively. To initiate an acetylation reaction of insulin, in which a fraction of the amine groups on the peptide are acetylated, the insulin and sulfo-NHS-acetate stock solutions were brought to ambient temperature and mixed at a 4:1 ratio (v/v).

After 30 min acetylation reaction with stirring, conjugation of the peptide with dextran-butyrALD-40K (16) was initiated by the drop-wise addition of an equal volume of stock solution of (16) to the acetylation reaction mixture under vigorous stirring. Tween-20 was then added, to a final concentration of 0.05% (v/v), and the reaction mixture was brought to 37° C. with stirring. After 20 minutes, 1 M sodium cyanoborohydride was added, to a final concentration of 17 mM, and the reaction was allowed to proceed with continued stirring for an additional 20 hours at 37° C.

The product dextran-butyrALD-40K-insulin was purified from the reaction mixture by anion-exchange chromatography using Q Sepharose FF (GE Healthcare). Thus, upon completion of the conjugation reaction, the reaction mixture was diluted 1:3 with 20 mM HEPES (pH 7) and the mixture was loaded onto a column packed with Q Sepharose FF resin. The resin was washed with Buffer B (20 mM HEPES, 1.0 M sodium chloride, pH 7) and equilibrated with Buffer A (20 mM HEPES, pH 7) prior to sample loading. After loading, the resin was washed with 10 column volumes Buffer A. Conjugated and nonconjugated peptides were eluted using a two-step gradient consisting of 0 to 25% Buffer B over 25 column volumes and 25% to 75% Buffer B over 5 column volumes at a flow rate of 90 cm/h.

Fractions containing lower molecular weight, less substituted conjugates were identified by SDS-PAGE. These fractions were pooled, diluted 10-fold with 20 mM HEPES, pH 7 (Buffer A), and applied to a second column packed with Q Sepharose FF resin for sample concentration. The resin was washed with Buffer B and equilibrated with Buffer A prior to sample loading. Dextran-butyrALD-40K-insulin was eluted using a linear gradient of 0-75% Buffer B over 3 column volumes at a flow rate of 90 cm/h.

Figure 3:
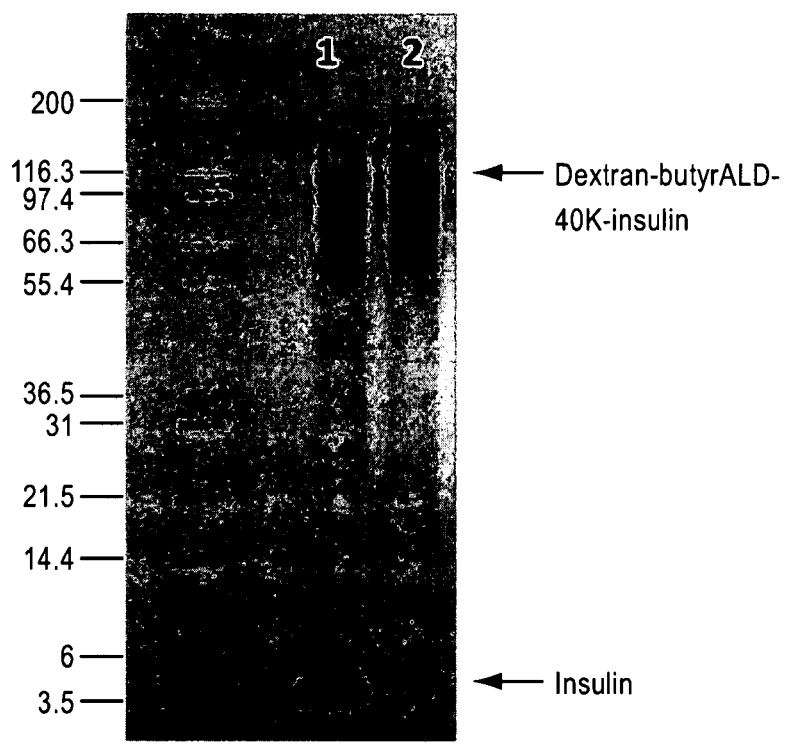
FIG. 3 shows gels produced by SDS-PAGE (4-12% Bis-Tris-Nu-PAGE, Invitrogen) analysis of purified dextran-butyrALD-40K-insulin, produced by conjugation of Dextran$_{40K}$ tetraethylene glycol butyraldehyde (16) with acetylated insulin, as described in Example 18B. Lane 1: Dextran-butyrALD-40K-insulin purified and concentrated by anion-exchange chromatography; Lane 2: Purified and concentrated dextran-butyrALD-40K-insulin after precipitation from water/DMSO with acetonitrile.

Fractions containing dextran-butyrALD-40K-insulin were pooled and lyophilized. These fractions were shown SDS-PAGE analysis of the pooled fractions to contain a significant amount of nonconjugated insulin (FIG. 3, Lane 1). The nonconjugated insulin can be removed by selective precipitation of the conjugate from a water/DMSO solution (50/50, v/v) through the addition of an organic solvent (for example, acetonitrile). Dextran-butyrALD-40K-insulin is less soluble than nonconjugated insulin in organic solvents and precipitates upon addition of an organic solvent. Thus, lyophilized dextran-butyrALD-40K-insulin was dissolved in water, to a peptide concentration of 2 mg/mL, and an equal volume of DMSO was added to the solution. After thorough mixing, acetonitrile was added drop-wise until the composition of the mixture was 25% water, 25% DMSO, and 50% acetonitrile (v/v/v). Precipitated conjugated insulin was collected by centrifugation and re-dissolved in water. SDS-PAGE analysis showed that the final concentration of nonconjugated insulin in this product was less than 1% of the total peptide amount (FIG. 3, Lane 2). The redissolved conjugate (20b) was lyophilized and stored at −80° C.

Example 19

Receptor Binding: In Vitro Binding of the Insulin-Dextran Conjugate

The in vitro affinity for the insulin receptor of the insulin-dextran conjugate (20b), prepared as described in Example 18, was evaluated using radioligand binding assays in CHO cells that stably express the recombinant human insulin receptor (CHO-hIR). CHO-hIR cells were plated in 24 well plates and washed with assay buffer containing 120 mM NaCl, 5 mM KCl, 1.2 mM MgSO$_4$, 9 mM Glucose, 10 mM HEPES, 0.5% BSA, pH 8.0. The insulin-dextran conjugate was 98% pure and contained unto 2% of free and acetylated insulin.

Competition binding assays were conducted by incubating CHO-hIR cells with increasing concentrations of insulin, insulin-dextran conjugate (20b), and glycine dextran and a fixed concentration (100 μM) of $^{125}$I-labelled recombinant human insulin for 4 hours at 4° C. Cells were washed to remove unbound ligands and solubilized with 0.2 N NaOH, and bound radioactivity was counted using a gamma counter. Non-specific binding was measured in the presence of excess cold insulin, and subtraction of this value from the total binding yielded the specific binding at each test compound concentration. IC$_{50}$ values were obtained from non-linear regression analysis of specific binding versus concentration curves.

Figure 4:
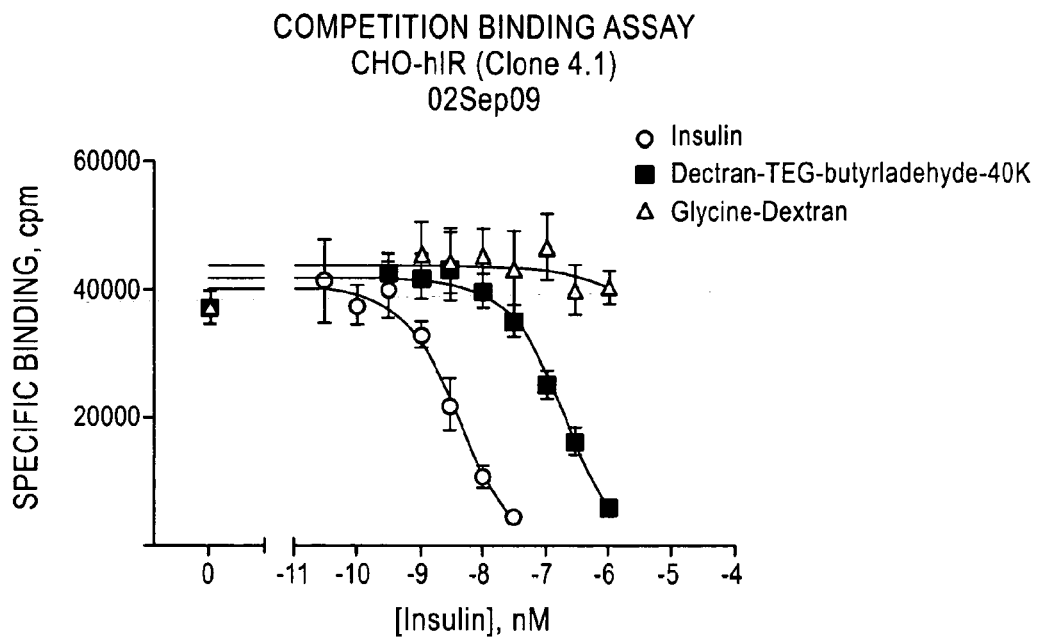
FIG. 4 shows the results of the in vitro competition binding assay described in Example 19, where the in vitro affinity for the insulin receptor of the insulin-dextran conjugate (20b) was evaluated.

The results of the in vitro competition binding assay are shown in FIG. 4. Insulin and the Dextran-TEG-butyrlaldehyde-40K acetyl insulin conjugate (20b) bound to the insulin receptor with IC$_{50}$ values of 4.3 nM and 174.9 nM respectively. Dextran conjugation thus resulted in a 40-fold reduction in the binding affinity of insulin. The dextran itself did not display specific binding to the insulin receptor at concentrations up to 1 μM.

Example 20

In Vivo Effect of Dextran-Conjugated Insulin on Blood Glucose Levels in db/db Diabetic Mice Summary: Dextran conjugated insulin (20b) (250 μg/mouse) was administered by i.p. injection into diabetic mice having elevated blood glucose levels. Blood glucose levels were measured At different time points after dosing. PBS saline solution and Dextran equivalent doses were administrated as negative controls, and insulin (50 μg/mouse) was injected as positive control. Insulin (5 μg/mouse) was also given to a group of db/db mice to determine whether the presence of ~2% free insulin in the 250 μg Dextran-insulin prep (i.e. ~5 μg) would have an effect.

Study Procedure: Animals were acclimated to researcher's handling procedures. Baseline glucose levels were measured prior to drug administration. Outlier animals with glucose level <300 or >600 mg/dL were excluded from the study. Animals were assigned randomly to different groups, as follows:

| Group | Test Article | Route | Dose | Dose Volume | # Animals |
|---|---|---|---|---|---|
| 1 | PBS | ip | — | 100 ul | 4 |
| 2 | Dextran-Insulin | ip | 250 ug/mouse | 100 ul | 5 |
| 3 | Insulin | ip | 50 ug/mouse | 100 ul | 5 |
| 4 | Insulin | ip | 5 ug/mouse | 100 ul | 5 |
| 5 | Dextran | ip | 1.75 mg/mouse | 100 ul | 5 |

At different time points (1, 2, 4, 8, and 24 hrs), blood was collected by tail clipping, and glucose level was measured using a One Touch® Ultra glucometer (Johnson & Johnson; Life Scan Ltd.)

Figure 5:
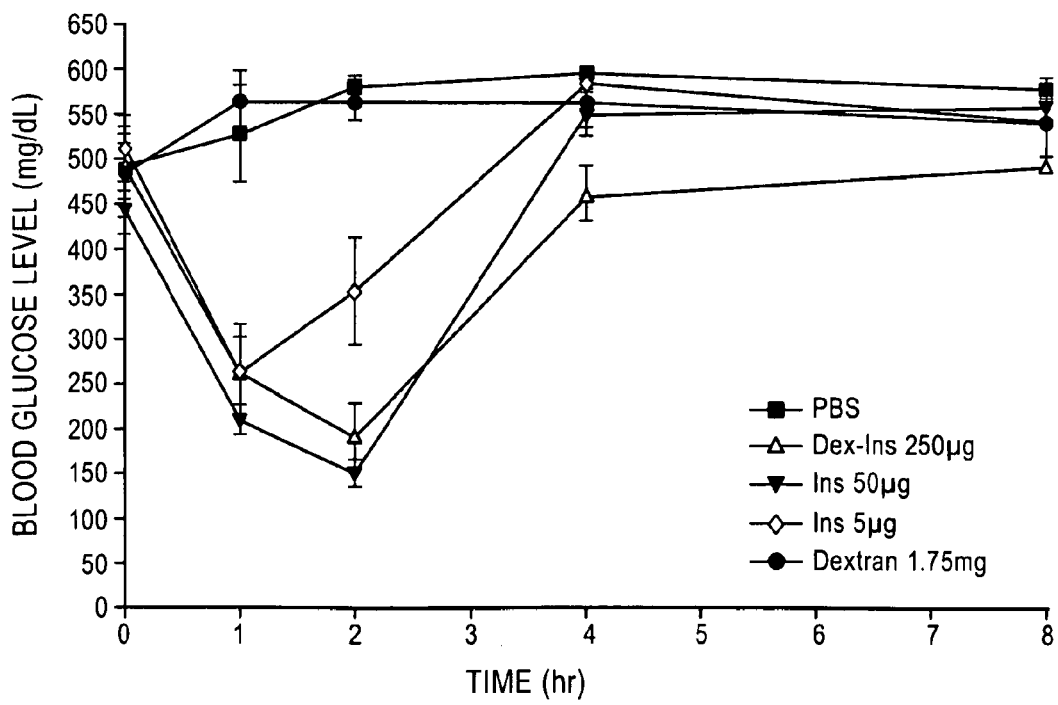
FIG. 5 shows the effect of insulin and dextran-conjugated insulin on blood glucose levels in db/db diabetic mice, as described in Example 20.

Results: Glucose levels in db/db mice after drug administration are listed in Table 1 and plotted in FIG. 5. As shown, Dextran-Insulin conjugate (20b) (250 ug/mouse) reduced glucose level from 495±32 mg/dL at time 0 to 263±39 mg/dL at 1 hr (47% reduction) and to 192±36 mg/dL at 2 hrs after administration (61% reduction). Insulin (50 ug/mouse) produced a 53% and 67% reduction at 1 and 2 hrs, respectively, after injection; and insulin (5 ug/mouse) produced a 48% and 31% reduction at 1 and 2 hrs, respectively, after injection.

PBS and Dextran injections were not observed to decrease db/db mice glucose levels throughout the course of the study.

The data shows that the Dextran-Insulin conjugate produced a prolonged effect in comparison with the 5 μg/mouse insulin injections (i.e. 61% vs. 31% reduction at 2 hr).

Example 21

Preparation of Oxyimine-Linked Chitosan (3-5K) Tetra(Ethylene Glycol) Maleimidopropionamide (22)

A. Preparation of α-Oxyaminoacetamide-Tetra(Ethylene Glycol)-ω-Maleimidopropionamide (21)

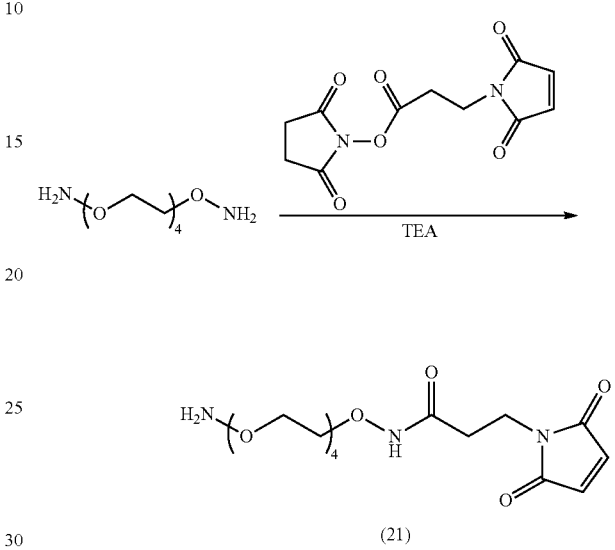

To a solution of α,ω-bis-oxyaminotetra(ethylene glycol) (2.0 g) and triethylamine (1.0 ml) in acetonitrile (20 ml) was added dropwise a ten-fold excess of 3-maleimidopropionic acid, N-succinimidyl ester (Pierce) while stirring and maintaining the liquid temperature at ~25° C. After stirring for an additional 2 hours, the solids were filtered off and the solvent was removed by vacuum distillation. The residue was dissolved in $CH_2Cl_2$ and extracted with water. The $CH_2Cl_2$ extract was evaporated and distilled water was added to dissolve the residue. This solution, containing a mixture of the desired product and a large amount of bis-TEG-maleimide, was chromatographed on a POROS cation exchange resin to provide 0.26 g of the desired product 21. This product was used directly in the next step.

B. Preparation of Oxyimine-Linked Chitosan (3-5K) Tetra (Ethylene Glycol) Maleimidopropionamide (22)

TABLE 1

| | | | Glucose levels in db/db mice after compound administration. | | | | | | |
|---|---|---|---|---|---|---|---|---|---|
| Time | PBS (N = 4) | | Dex-Ins 250 ug (N = 4) | | Ins 50 ug (N = 5) | | Ins 5 ug (N = 5) | | Dextran 1.75 mg (N = 5) |
| (hr) | Mean | SEM | Mean | SEM | Mean | SEM | Mean | SEM | Mean | SEM |
| 0 | 486 | 51 | 495 | 32 | 445 | 29 | 510 | 37 | 485 | 31 |
| 1 | 528 | 54 | 263 | 39 | 210 | 16 | 265 | 51 | 565 | 32 |
| 2 | 582 | 9 | 192 | 36 | 150 | 15 | 352 | 60 | 565 | 22 |
| 4 | 597 | 1 | 462 | 30 | 550 | 25 | 587 | 9 | 562 | 27 |
| 8 | 577 | 14 | 494 | 10 | 558 | 23 | 538 | 30 | 540 | 36 |
| 24 | 560 | 24 | 517 | 24 | 541 | 19 | 538 | 36 | 531 | 40 |

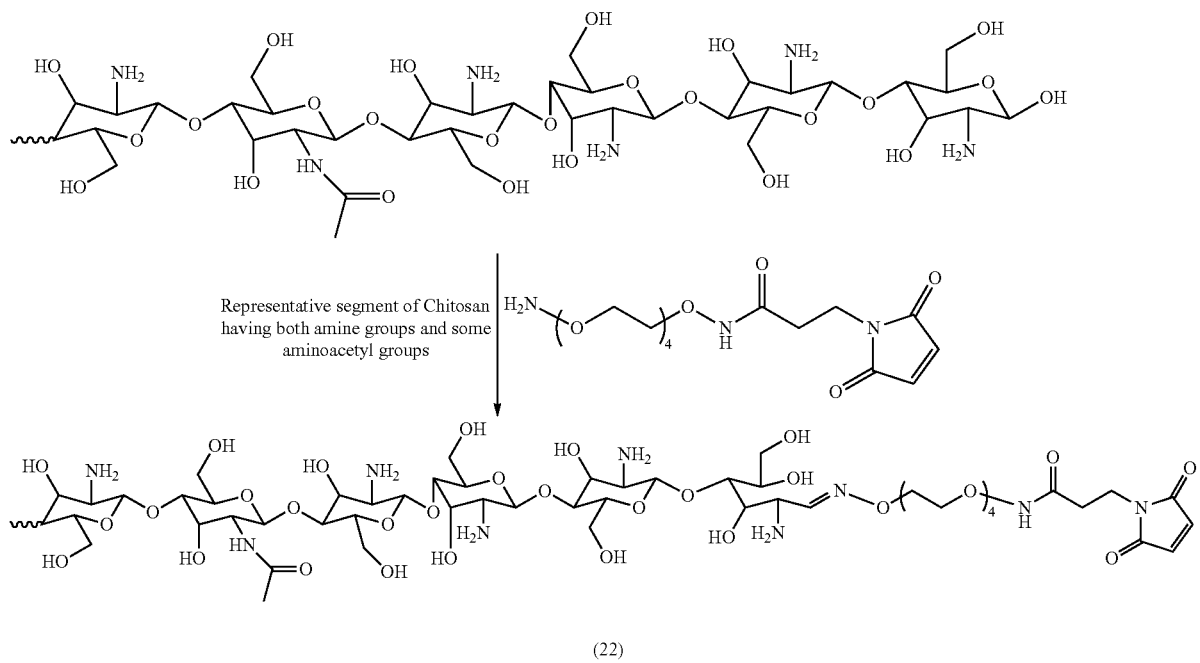

(22)

To a solution of chitosan 3-5K (Kitto Life, Kyongki-Do, Korea, 0.1 g; MW=3000-5000 by GPC) in 0.5M sodium phosphate buffer, pH=5 (2 mL), α-oxyaminoacetamide-tetra (ethylene glycol)-ω-maleimidopropionamide (prepared in step A above, 0.060 g) was added. Slowly to the solution, acetonitrile (2 mL) was added. The mixture was stirred overnight at 70° C. The reaction mixture was cooled to room temperature and dialyzed for 3 hours against DI water using Dialysis Cassette MWCO 3500 (Pierce). The water was distilled off under reduced pressure. The wet product was dried under vacuum overnight giving 0.13 g of 22 as a yellowish solid. NMR analysis performed in $D_2O$ showed that the substitution of end groups of chitosan with maleimide substitution was ≥90%.

Example 22

Preparation of Oxyimine-Linked Chitosan (10K)-Butanoic Acid (23)

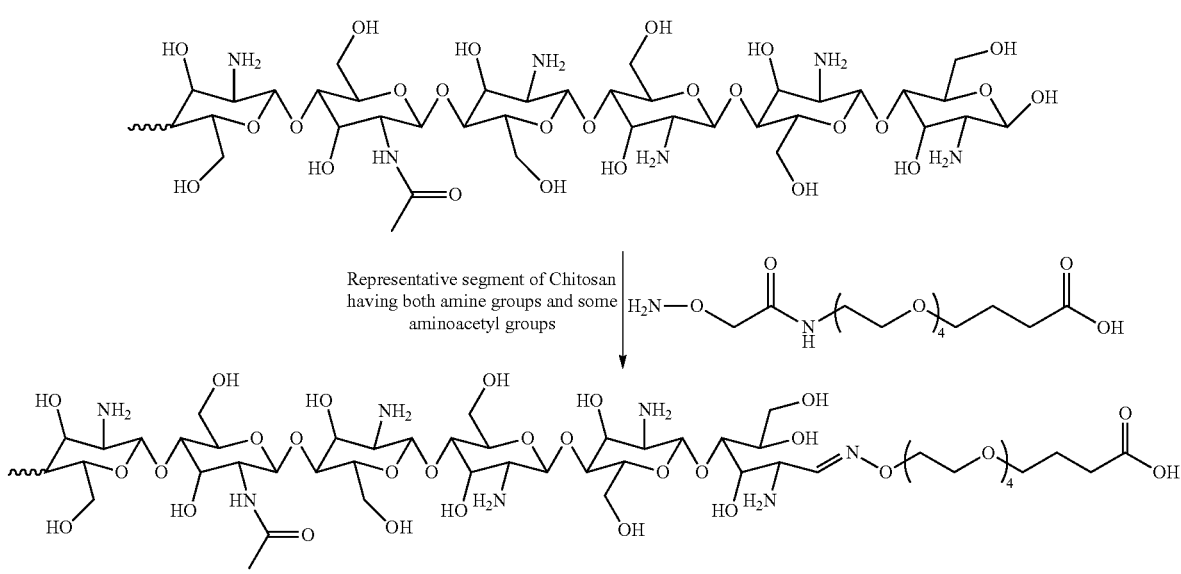

To a solution of chitosan (10K) (0.2 g, Kitto Life, Kyongki-Do, Korea, containing ~15% acetyl groups, ave. MW=10000 by GPC) in 0.1M sodium acetate buffer, pH=5.5, a solution of tetra(ethylene glycol) linker containing oxyamine group and butanoic acid group (from Example 8 above) was added. The pH was readjusted to 5.2 with acetic acid and the mixture was stirred overnight at room temperature. The solution was dialyzed 3 times against DI water using Dialysis Cassette MW CO 10000K (Pierce). The water was distilled off under reduced pressure. The wet product was dried under vacuum overnight giving 2.2 g of 23 as a white solid. NMR analysis performed in $D_2O$ showed that the substitution of end groups of chitosan with butanoic acid groups was ~26%.

Example 23 ssRNA-C$_6$-SS-Mal-TEG-Chitosan Conjugate (24)

The title conjugate was produced by the reduction of 5'capped-RNA (5'-C6-S-SC6-AmCAmACmAGmACmUU-mUAmAUmGUmAA-3', Tri-Link BioTechnologies, San Diego, Calif.) with Tris(2-Carboxyethyl)phosphine Hydrochloride (TCEP.HCl) followed by the coupling with chitosan (3-5K) tetra(ethylene glycol)maleimidopropionamide 22, produced in Example 21. To reduce 5'-capped-RNA, a 0.015 mL solution containing 0.003 mL 5' capped-RNA, 0.003 mL, 1 M, EPPS, pH 8.5 and 0.007 mL 64 mM TCEP.HCl was incubated at 25° C. without stirring for 60 minutes. After 60 minutes incubation, 0.015 mL reaction mixture was loaded on a desalting column (pre-equilibrated with 20 mM HEPES, 50 mM NaCl, pH 7.4) and rinsed with 0.045 mL buffer (20 mM HEPES, 50 mM NaCl, pH 7.4). A total of 0.06 mL solution containing RNA with free thiol group (5'-HSC6-AmCAmACmAGmACmUUmUAmAUmGUmAA-3') was collected.

To couple reduced RNA with the maleimide, 0.005-mL of reduced oligo from the above reaction was mixed with 0.005-ML solution containing the maleimide. The reaction mixture was incubated at 25° C. without stirring for three hours. Analysis of the reaction mixture by ion-exchange HPLC revealed a new peak attributable to the title conjugate.

---

The invention claimed is:

1. A monofunctional water-soluble carbohydrate-based reagent having a structure selected from

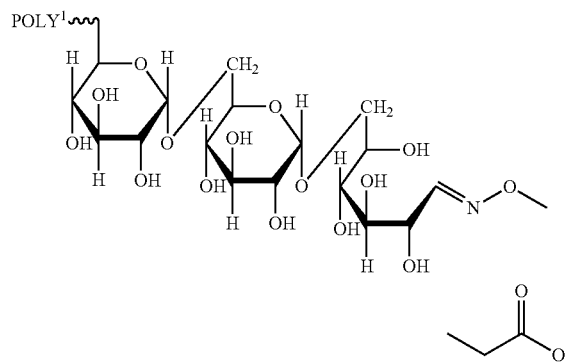

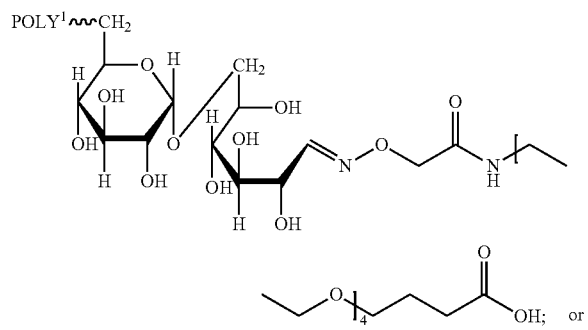

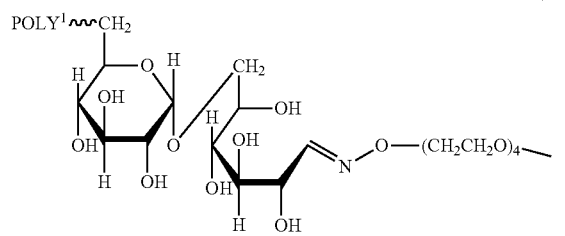

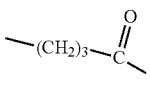

where:

POLY$^1$ is a dextran polymer.

2. The reagent of claim 1, wherein POLY$^1$ has a molecular weight of 200 Da to 2,000,000 Da.

3. The reagent of claim 1, wherein POLY$^1$ has a molecular weight of 5,000 Da to 70,000 Da.

4. The reagent of claim 1, wherein POLY$^1$ has a molecular weight of about 5,000 Da.

5. The reagent of claim 1, wherein POLY$^1$ has a molecular weight of about 10,000 Da.

6. The reagent of claim 1, wherein POLY$^1$ has a molecular weight of about 20,000 Da.

7. The reagent of claim 1, wherein POLY$^1$ has a molecular weight of about 40,000 Da.

8. The reagent of claim 1, wherein POLY$^1$ has a molecular weight of about 70,000 Da.

9. The reagent of claim 1, wherein the reagent has the structure

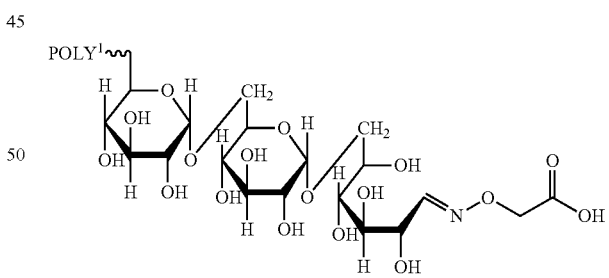

where POLY$^1$ is a dextran polymer having a molecular weight of 200 Da to 2,000,000 Da.

10. The reagent of claim 9, wherein POLY$^1$ has a molecular weight of 5,000 Da to 70,000 Da.

11. The reagent of claim 9, wherein POLY$^1$ has a molecular weight of about 20,000 Da.

12. The reagent of claim 9, wherein POLY$^1$ has a molecular weight of about 40,000 Da.

13. The reagent of claim 1, wherein the reagent has the structure

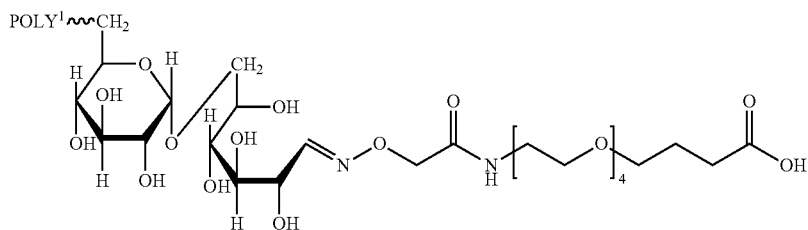

where POLY$^1$ is a dextran polymer having a molecular weight of 200 Da to 2,000,000 Da.

14. The reagent of claim 13, wherein POLY$^1$ has a molecular weight of 5,000 Da to 70,000 Da.

15. The reagent of claim 13, wherein POLY$^1$ has a molecular weight of about 20,000 Da.

16. The reagent of claim 13, wherein POLY$^1$ has a molecular weight of about 40,000 Da.

17. The reagent of claim 1, wherein the reagent has the structure

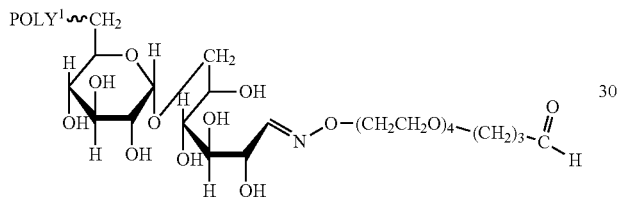

where POLY$^1$ is a dextran polymer having a molecular weight of 200 Da to 2,000,000 Da.

18. The reagent of claim 17, wherein POLY$^1$ has a molecular weight of 5,000 Da to 70,000 Da.

19. The reagent of claim 17, wherein POLY$^1$ has a molecular weight of about 20,000 Da.

20. The reagent of claim 17, wherein POLY$^1$ has a molecular weight of about 40,000 Da.

* * * * *